US012649748B2

(12) United States Patent
Song et al.

(10) Patent No.: US 12,649,748 B2
(45) Date of Patent: Jun. 9, 2026

(54) WEE1 INHIBITOR AND USE THEREOF

(71) Applicant: JIANGSU TASLY DIYI PHARMACEUTICAL CO., LTD., Huai'an (CN)

(72) Inventors: Li Song, Huai'an (CN); Hai Tang, Huai'an (CN); Xiaohui Ma, Huai'an (CN); Shuiping Zhou, Huai'an (CN); Jinyong Cai, Huai'an (CN); Liming Dong, Huai'an (CN); Zhuang Song, Huai'an (CN)

(73) Assignee: JIANGSU TASLY DIYI PHARMACEUTICAL CO., LTD., Jiangsu (CN)

( * ) Notice: Subject to any disclaimer, the term of this patent is extended or adjusted under 35 U.S.C. 154(b) by 393 days.

(21) Appl. No.: 18/282,872

(22) PCT Filed: May 12, 2022

(86) PCT No.: PCT/CN2022/092348

§ 371 (c)(1),
(2) Date: Sep. 19, 2023

(87) PCT Pub. No.: WO2022/247641

PCT Pub. Date: Dec. 1, 2022

(65) Prior Publication Data

US 2024/0199619 A1 Jun. 20, 2024

(30) Foreign Application Priority Data

May 28, 2021 (CN) ......................... 202110587790.8

(51) Int. Cl.

| | |
|---|---|
| ***C07D 487/04*** | (2006.01) |
| ***A61K 31/519*** | (2006.01) |
| ***A61K 31/5377*** | (2006.01) |
| ***A61K 31/538*** | (2006.01) |
| ***C07D 519/00*** | (2006.01) |

(52) U.S. Cl.

CPC .......... *C07D 487/04* (2013.01); *A61K 31/519* (2013.01); *A61K 31/5377* (2013.01); *A61K 31/538* (2013.01); *C07D 519/00* (2013.01)

(58) Field of Classification Search

CPC ................ C07D 487/04; C07D 519/00; A61K 31/519; A61K 31/5377; A61K 31/538

See application file for complete search history.

(56) References Cited

U.S. PATENT DOCUMENTS

2019/0084985 A1* 3/2019 Reigan ................. A61K 31/519

FOREIGN PATENT DOCUMENTS

| | | | |
|---|---|---|---|
| CN | 101616920 | A | 12/2009 |
| CN | 101616921 | A | 12/2009 |
| CN | 107613769 | A | 1/2018 |
| WO | 2008/094575 | A2 | 8/2008 |
| WO | 2011156698 | A2 | 12/2011 |
| WO | 2017/075629 | A2 | 5/2017 |
| WO | 2017/075629 | S2 | 5/2017 |
| WO | 2018/011569 | A1 | 1/2018 |
| WO | 2019/037678 | A1 | 2/2019 |
| WO | 2019/074979 | A1 | 4/2019 |
| WO | 2019/169065 | A2 | 9/2019 |
| WO | 2020/210320 | A1 | 10/2020 |
| WO | 2021/043152 | A1 | 3/2021 |
| WO | 2020/074251 | S1 | 4/2021 |
| WO | 2022/082174 | A1 | 4/2022 |

OTHER PUBLICATIONS

Matheson Christopher J. et al: "Development of Potent Pyrazolopyrimidinone-Based WEE1 Inhibitors with Limited Single-Agent Cytotoxicity for Cancer Therapy", Chemmedchem Communications, vol. 13, No. 16, Aug. 20, 2018 (Aug. 20, 2018), pp. 1681-1694, XP055850405, DE ISSN: 1860-7179, DOI:10.1002/cmdc.201800188.

Supplementary Partial European Search Report in European Application No. 22810368.5 dated Apr. 24, 2025.

* cited by examiner

*Primary Examiner* — Timothy R Rozof
(74) *Attorney, Agent, or Firm* — Dilworth & Barrese, LLP

(57) ABSTRACT

Provided are a new class of compounds having a WEE1 inhibitory effect and as represented by formula I, and the use thereof in the preparation of a drug.

I

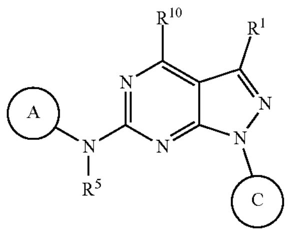

24 Claims, No Drawings

WEE1 INHIBITOR AND USE THEREOF

TECHNICAL FIELD

The present invention is related to a class of novel compounds having a Wee1 inhibitory effect, and the use thereof in the manufacture of a medicament.

BACKGROUND ART

Cell cycle is a highly regulated and controlled process, which aims to make cells proliferate only according to specific stimuli and appropriate conditions. A normal cell cycle will go through G1, S (DNA synthesis phase), G2 and M (cell division phase) in turn. There are several cycle arrest checkpoints during G1-S transition, S phase and G2-M transition, etc., which are used to maintain the integrity of the genome and provide time for repairing damaged DNA before entering mitosis.

Wee1 protein is a tyrosine kinase, which is a key component of G2-M cell cycle checkpoint, and can prevent cellular DNA damage from entering mitosis. CDK1 (Cyclin-dependent kinase 1) is maintained in an inactive state by phosphorylation of tyrosine 15 by Wee1, and then CDK1 is phosphorylated by myelin transcription factor (MYT1) in threonine 14. Therefore, Wee1 is a negative regulator of mitosis entry during the G2-M transition and plays an important monitoring role. Wee1 is overexpressed in many malignant tumors, such as liver cancer, breast cancer, malignant glioma, melanoma, adult and child brain tumors. Among them, the G1 checkpoint of some tumor cells is abnormal, and if Wee1 activity is inhibited, it will lead to G2 checkpoint failure, which will eventually lead to the death of cells with damaged DNA that have not been repaired. Therefore, Wee1 inhibitor plays a key role in anti-cancer treatment and has become a hot spot in the research and development of anti-cancer drugs.

At present, there have been reports of Wee1 inhibitor (WO2007126128, WO2004007499, etc.), but no Wee1 inhibitor has been approved. At present, the compound with the fastest development progress is AZD-1775, which has entered the phase II clinical trial, but the incidence of adverse reactions in clinical experiments is high, and it is necessary to develop new Wee1 inhibitor drugs with better activity and higher safety.

SUMMARY OF THE INVENTION

The present invention provides a compound represented by formula I, or a deuterated compound thereof, or a stereoisomer thereof, or a pharmaceutically acceptable salt thereof:

I

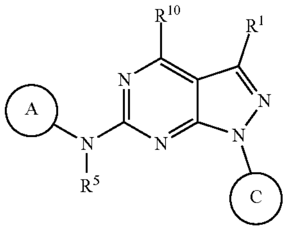

wherein, $R^1$ is selected from a group consisting of H (hydrogen), halogen, cyano, $-C_{1\sim6}$ alkyl, $-C_{2\sim6}$ alkenyl, $-C_{2\sim6}$ alkynyl, halogen substituted $-C_{1\sim6}$ alkyl, halogen substituted $-C_{2\sim6}$ alkenyl, halogen substituted $-C_{2\sim6}$ alkynyl, $-C_{0\sim4}$ alkylene-$OR^{11}$, $-C_{0\sim4}$ alkylene-$NR^{12}R^{12}$;

$R^{11}$ is selected from a group consisting of $-C_{1\sim6}$ alkyl, $-C_{2\sim6}$ alkenyl, $-C_{2\sim6}$ alkynyl, halogen substituted $-C_{1\sim6}$ alkyl, halogen substituted $-C_{2\sim6}$ alkenyl, halogen substituted $-C_{2\sim6}$ alkynyl;

each $R^{12}$ is independently selected from a group consisting of H, $-C_{1\sim6}$ alkyl, $-C_{2\sim6}$ alkenyl, $-C_{2\sim6}$ alkynyl, halogen substituted $-C_{1\sim6}$ alkyl, halogen substituted $-C_{2\sim6}$ alkenyl, halogen substituted $-C_{2\sim6}$ alkynyl;

C-ring is selected from a group consisting of

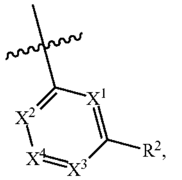

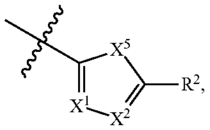

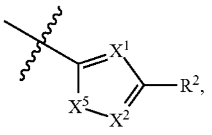

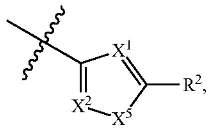

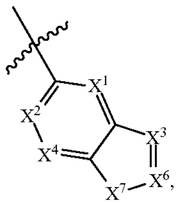

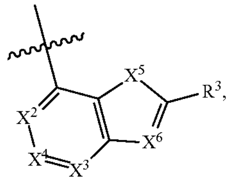

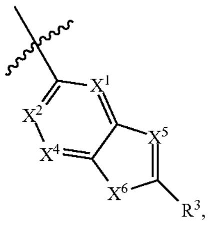

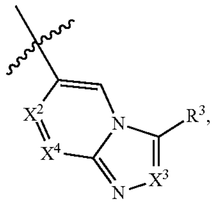

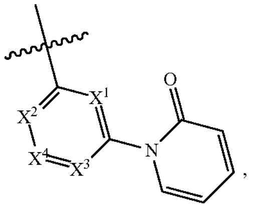

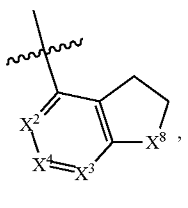

-continued

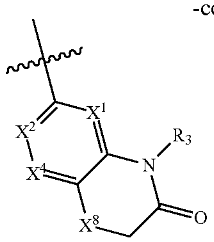 or 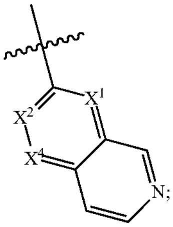

$X^1$, $X^2$, $X^4$ is independently selected from a group consisting of N or $CR^4$;

$X^3$ is selected from a group consisting of N or $CR^3$;

$X^5$ is selected from a group consisting of O, S or $NR^4$;

$X^6$ is selected from a group consisting of $CR^4$ or N;

$X^8$ is selected from a group consisting of $CR^4R^4$, O;

$X^7$ is selected from a group consisting of S, $NR^4$; $R^2$ is selected from a group consisting of

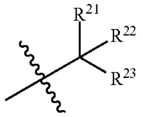 or 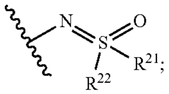

$R^{21}$, $R^{22}$ is independently selected from a group consisting of H, halogen, cyano, —$C_{1\sim6}$ alkyl, —$C_{2\sim6}$ alkenyl, —$C_{2\sim6}$ alkynyl, halogen substituted —$C_{1\sim6}$ alkyl, halogen substituted —$C_{2\sim6}$ alkenyl, halogen substituted —$C_{2\sim6}$ alkynyl, —$C_{0\sim4}$ alkylene-$OR^{24}$, —$C_{0\sim4}$ alkylene-$NR^{24}R^{24}$;

each $R^{24}$ is independently selected from a group consisting of H, —$C_{1\sim6}$ alkyl, —$C_{2\sim6}$ alkenyl, —$C_{2\sim6}$ alkynyl, halogen substituted —$C_{1\sim6}$ alkyl, halogen substituted —$C_{2\sim6}$ alkenyl, halogen substituted —$C_{2\sim6}$ alkynyl;

or, $R^{21}$, $R^{22}$ together with the atom adjacent therewith form 3~8-membered carbocyclyl, 4~8-membered heterocylcylalkyl,

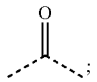

$R^{23}$ is selected from a group consisting of H, halogen, cyano, —$C_{1\sim6}$ alkyl, —$C_{2\sim6}$ alkenyl, —$C_{2\sim6}$ alkynyl, halogen substituted —$C_{1\sim6}$ alkyl, halogen substituted —$C_{2\sim6}$ alkenyl, halogen substituted —$C_{2\sim6}$ alkynyl, —$C_{0\sim4}$ alkylene-C(O)$R^{25}$, —$C_{0\sim4}$ alkylene-C(O)$NR^{25}R^{25}$, —$C_{0\sim4}$ alkylene-C(O)$OR^{25}$, —$C_{0\sim4}$ alkylene-$S(O)_2R^{25}$, —$C_{0\sim4}$ alkylene-S(O)$R^{25}$, —$C_{0\sim4}$ alkylene-S(O)(NH)$R^{25}$, —$C_{0\sim4}$ alkylene-$S(NH)_2R^{25}$, —$C_{0\sim4}$ alkylene-$S(O)_2NR^{25}R^{25}$, —$C_{0\sim4}$ alkylene-S(O)$NR^{25}R^{25}$, —$C_{0\sim4}$ alkylene-S(O)(NH)$NR^{25}R^{25}$, —$C_{0\sim4}$ alkylene-$S(NH)_2NR^{25}R^{25}$, —$C_{0\sim4}$ alkylene-$OR^{25}$, —$C_{0\sim4}$ alkylene-OC(O)$R^{25}$, —$C_{0\sim4}$ alkylene-$OS(O)_2R^{25}$, —$C_{0\sim4}$ alkylene-OS(O)$R^{25}$, —$C_{0\sim4}$ alkylene-$NR^{25}R^{25}$, —$C_{0\sim4}$ alkylene-$NR^{25}C(O)R^{25}$, —$C_{0\sim4}$ alkylene-$NR^{25}S(O)_2R^{25}$, —$C_{0\sim4}$ alkylene-$NR^{25}S(O)R^{25}$, —$C_{0\sim4}$ alkylene-$NR^{25}S(O)(NH)R^{25}$, —$C_{0\sim4}$ alkylene-$NR^{25}S(NH)_2R^{25}$;

each $R^{25}$ is independently selected from a group consisting of H, —$C_{1\sim6}$ alkyl, —$C_{2\sim6}$ alkenyl, —$C_{2\sim6}$ alkynyl, halogen substituted —$C_{1\sim6}$ alkyl, halogen substituted —$C_{2\sim6}$ alkenyl, halogen substituted —$C_{2\sim6}$ alkynyl;

or, $R^{23}$, $R^3$ together with the atom adjacent therewith form 4~8-membered carbocyclyl, 4~8-membered heterocylcylalkyl;

$R^3$ is selected from a group consisting of H, halogen, cyano, —$C_{1\sim6}$ alkyl, —$C_{2\sim6}$ alkenyl, —$C_{2\sim6}$ alkynyl, hydroxy substituted —$C_{1\sim6}$ alkyl, halogen substituted —$C_{1\sim6}$ alkyl, halogen substituted —$C_{2\sim6}$ alkenyl, halogen substituted —$C_{2\sim6}$ alkynyl, —$C_{0\sim4}$ alkylene-OH, —$C_{0\sim4}$ alkylene-O($C_{1\sim6}$ alkyl), —$C_{0\sim4}$ alkylene-$NH_2$, —$C_{0\sim4}$ alkylene-NH($C_{1\sim6}$ alkyl), —$C_{0\sim4}$ alkylene-N($C_{1\sim6}$ alkyl)($C_{1\sim6}$ alkyl);

each $R^4$ is independently selected from a group consisting of H, halogen, cyano, —$C_{1\sim6}$ alkyl, —$C_{2\sim6}$ alkenyl, —$C_{2\sim6}$ alkynyl, halogen substituted —$C_{1\sim6}$ alkyl, halogen substituted —$C_{2\sim6}$ alkenyl, halogen substituted —$C_{2\sim6}$ alkynyl, —$C_{0\sim4}$ alkylene-OH, —$C_{0\sim4}$ alkylene-O($C_{1\sim6}$ alkyl), —$C_{0\sim4}$ alkylene-$NH_2$, —$C_{0\sim4}$ alkylene-NH($C_{1\sim6}$ alkyl), —$C_{0\sim4}$ alkylene-N($C_{1\sim6}$ alkyl)($C_{1\sim6}$ alkyl);

$R^5$ is selected from a group consisting of H, —$C_{1\sim6}$ alkyl;

A-ring is selected from a group consisting of

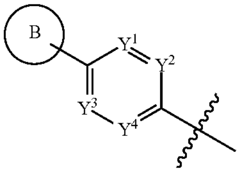,

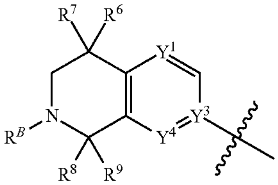,

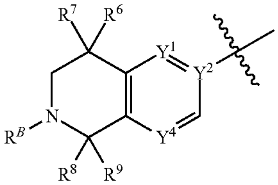,

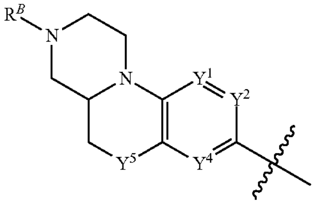,

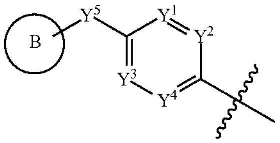,

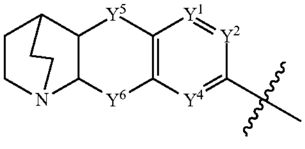,

-continued

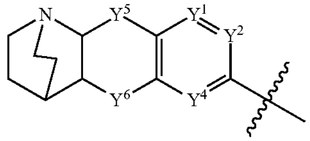

,

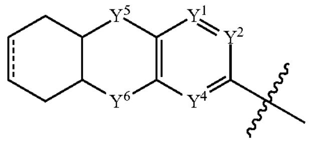

,

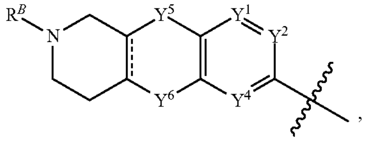

,

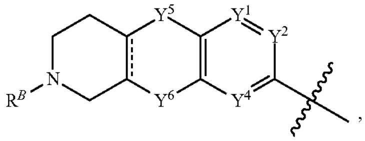

,

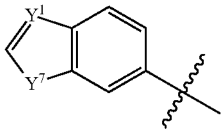

,

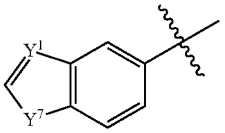

,

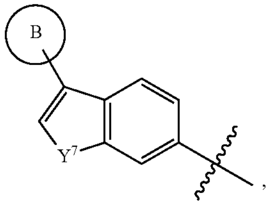

,

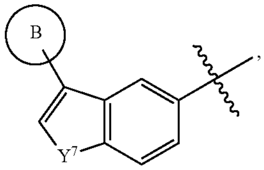

,

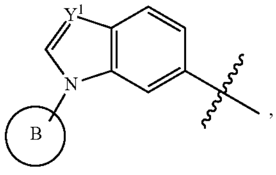

,

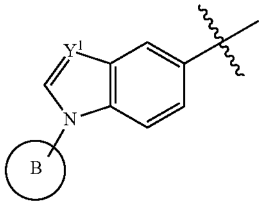

;

$\overline{\underline{---}}$ represents a single bond or double bond;

$Y^1$, $Y^2$, $Y^3$, $Y^4$ is independently selected from a group consisting of N or $CR^Y$;

each $R^Y$ is independently selected from a group consisting of H, halogen, cyano, —$C_{1\sim6}$ alkyl, —$C_{2\sim6}$ alkenyl, —$C_{2\sim6}$ alkynyl, halogen substituted —$C_{1\sim6}$ alkyl, halogen substituted —$C_{2\text{-}6}$ alkenyl, halogen substituted —$C_{2\sim6}$ alkynyl, —$C_{0\sim4}$ alkylene-OH, —$C_{0\sim4}$ alkylene-O($C_{1\sim6}$ alkyl), —$C_{0\sim4}$ alkylene-$NH_2$, —$C_{0\sim4}$ alkylene-NH($C_{1\sim6}$ alkyl), —$C_{0\sim4}$ alkylene-N($C_{1\sim6}$ alkyl)($C_{1\sim6}$ alkyl);

B-ring is selected from a group consisting of 3~12-membered carbocyclyl, 4~12-membered heterocylcylalkyl; said carbocyclyl, heterocylcylalkyl is optionally substituted by one, two, three, four or five $R^B$;

each $R^B$ is independently selected from a group consisting of H, halogen, cyano, —$C_{1\sim6}$ alkyl, —$C_{2\sim6}$ alkenyl, —$C_{2\sim6}$ alkynyl, halogen substituted —$C_{1\sim6}$ alkyl, halogen substituted —$C_{2\sim6}$ alkenyl, halogen substituted —$C_{2\sim6}$ alkynyl, —$C_{0\sim4}$ alkylene-$OR^{B1}$, —$C_{0\sim4}$ alkylene-OC(O)$R^{B1}$, —$C_{0\sim4}$ alkylene-$SR^{B1}$, —$C_{0\sim4}$ alkylene-S(O)$_2R^{B1}$, —$C_{0\sim4}$ alkylene-S(O)$R^{B1}$, —$C_{0\sim4}$ alkylene-S(O)$_2NR^{B1}R^{B1}$, —$C_{0\sim4}$ alkylene-S(O)$NR^{B1}R^{B1}$, —$C_{0\sim4}$ alkylene-C(O)$R^{B1}$, —$C_{0\sim4}$ alkylene-C(O)$OR^{B1}$, —$C_{0\sim4}$ alkylene-C(O)$NR^{B1}R^{B1}$, —$C_{0\sim4}$ alkylene-$NR^{B1}R^{B1}$, —$C_{0\sim4}$ alkylene-$NR^{B1}$C(O)$R^{B1}$, 3~12-membered carbocyclyl, 4~12-membered heterocylcylalkyl; said carbocyclyl, heterocylcylalkyl is optionally substituted by one, two, three, four or five $R^{B1}$;

or, two independent $R^B$ together with the atom adjacent therewith form

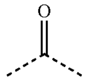, 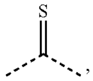, 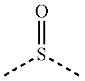, 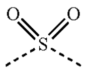, each $R^{B1}$ is independently selected from a group consisting of H, —$C_{1\sim6}$ alkyl, —$C_{2\sim6}$ alkenyl, —$C_{2\sim6}$ alkynyl, halogen substituted —$C_{1\sim6}$ alkyl, halogen substituted —$C_{2\sim6}$ alkenyl, halogen substituted —$C_{2\sim6}$ alkynyl;

$R^6$, $R^7$, $R^8$, $R^9$ is independently selected from a group consisting of H, halogen, cyano, —$C_{1\sim6}$ alkyl, —$C_{2\sim6}$ alkenyl, —$C_{2\sim6}$ alkynyl, halogen substituted —$C_{1\sim6}$ alkyl, halogen substituted —$C_{2\sim6}$ alkenyl, halogen substituted —$C_{2\sim6}$ alkynyl, —$C_{0\sim4}$ alkylene-OH, —$C_{0\sim4}$ alkylene-O($C_{1\sim6}$ alkyl), —$C_{0\sim4}$ alkylene-$NH_2$, —$C_{0\sim4}$ alkylene-NH($C_{1\sim6}$ alkyl), —$C_{0\sim4}$ alkylene-N($C_{1\sim6}$ alkyl)($C_{1\sim6}$ alkyl);

or, $R^6$, $R^7$ together with the atom adjacent therewith form 3~8-membered carbocyclyl, 4~8-membered heterocylcylalkyl; or, $R^8$, $R^9$ together with the atom adjacent therewith form 3~8-membered carbocyclyl, 4~8-membered heterocylcylalkyl;

$Y^5$, $Y^6$ is independently selected from a group consisting of chemical bond, —$C_{0\sim4}$ alkylene-O—, —$C_{0\sim4}$ alkylene-S—, —$C_{0\sim4}$ alkylene-$NR^{Y51}$—, $CR^{Y51}R^{Y51}$;

each $R^{Y51}$ is independently selected from a group consisting of H, —$C_{1\sim6}$ alkyl, —$C_{2\sim6}$ alkenyl, —$C_{2\sim6}$ alkynyl, halogen substituted —$C_{1\sim6}$ alkyl, halogen substituted —$C_{2\sim6}$ alkenyl, halogen substituted —$C_{2\sim6}$ alkynyl, —$C_{0\sim4}$ alkylene-OH, —$C_{0\sim4}$ alkylene-O($C_{1\sim6}$ alkyl), —$C_{0\sim4}$ alkylene-$NH_2$, —$C_{0\sim4}$ alkylene-NH ($C_{1\sim6}$ alkyl), —$C_{0\sim4}$ alkylene-N($C_{1\sim6}$ alkyl)($C_{1\sim6}$ alkyl);

$Y^7$ is selected from a group consisting of O, S or $NR^{Y71}$;

$R^{Y71}$ is selected from a group consisting of H, —$C_{1\sim6}$ alkyl, —$C_{2\sim6}$ alkenyl, —$C_{2\sim6}$ alkynyl, halogen substituted —$C_{1\sim6}$ alkyl, halogen substituted —$C_{2\sim6}$ alkenyl, halogen substituted —$C_{2\sim6}$ alkynyl, —$C_{0\sim4}$ alkylene-OH, —$C_{0\sim4}$ alkylene-O($C_{1\sim6}$ alkyl), —$C_{0\sim4}$ alkylene-$NH_2$, —$C_{0\sim4}$ alkylene-NH($C_{1\sim6}$ alkyl), —$C_{0\sim4}$ alkylene-N($C_{1\sim6}$ alkyl)($C_{1\sim6}$ alkyl);

$R^{10}$ is selected from a group consisting of H, halogen, cyano, —$C_{1\sim6}$ alkyl, —$C_{2\sim6}$ alkenyl, —$C_{2\sim6}$ alkynyl, halogen substituted —$C_{1\sim6}$ alkyl, halogen substituted —$C_{2\sim6}$ alkenyl, halogen substituted —$C_{2\sim6}$ alkynyl, —$C_{0\sim4}$ alkylene-OH, —$C_{0\sim4}$ alkylene-O($C_{1\sim6}$ alkyl), —$C_{0\sim4}$ alkylene-$NH_2$, —$C_{0\sim4}$ alkylene-NH($C_{1\sim6}$ alkyl), —$C_{0\sim4}$ alkylene-N($C_{1\sim6}$ alkyl)($C_{1\sim6}$ alkyl).

Preferably, $R^1$ is selected from a group consisting of H, halogen, cyano, —$C_{1\sim6}$ alkyl, halogen substituted —$C_{1\sim6}$ alkyl, —$OR^{11}$, —$NR^{12}R^{12}$;

$R^{11}$ is selected from a group consisting of —$C_{1\sim6}$ alkyl, —$C_{2\sim6}$ alkenyl, —$C_{2\sim6}$ alkynyl, halogen substituted —$C_{1\sim6}$ alkyl;

each $R^{12}$ is independently selected from a group consisting of H, —$C_{1\sim6}$ alkyl, halogen substituted —$C_{1\sim6}$ alkyl;

$R^{10}$ is selected from a group consisting of H, halogen, cyano, —$C_{1\sim6}$ alkyl, halogen substituted —$C_{1\sim6}$ alkyl, —OH, —O($C_{1\sim6}$ alkyl), —$NH_2$, —NH($C_{1\sim6}$ alkyl), —N($C_{1\sim6}$ alkyl)($C_{1\sim6}$ alkyl).

More preferably, $R^1$ is selected from a group consisting of H, halogen, cyano, —$C_{1\sim6}$ alkyl, trifluoromethyl, —O($C_{1\sim6}$ alkyl), —O($C_{2\sim6}$ alkenyl), —O(trifluoromethyl), —$NH_2$, —NH($C_{1\sim6}$ alkyl), —N($C_{1\sim6}$ alkyl)($C_{1\sim6}$ alkyl);

$R^{10}$ is selected from a group consisting of H, halogen, —$C_{1\sim6}$ alkyl, —O($C_{1\sim6}$ alkyl).

Preferably,

C-ring is selected from a group consisting of

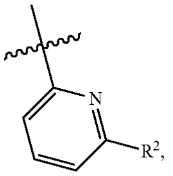
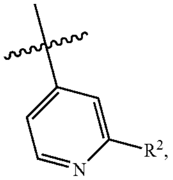
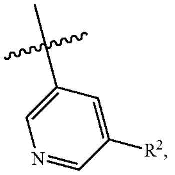
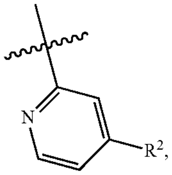
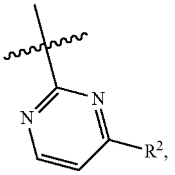
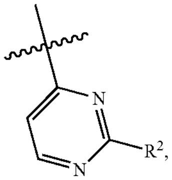
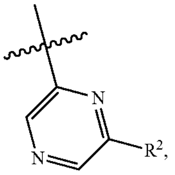
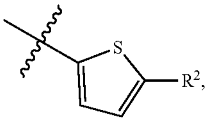
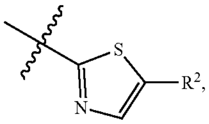
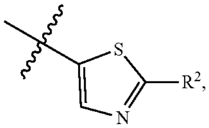

-continued

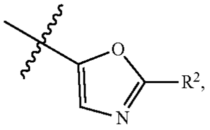
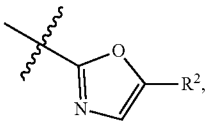
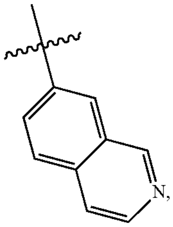
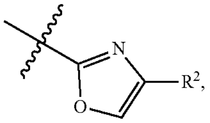
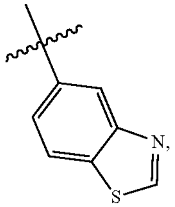
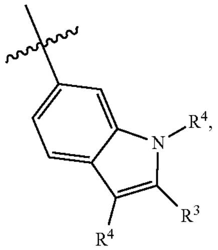
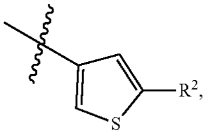
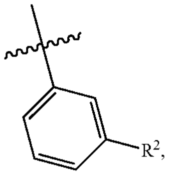
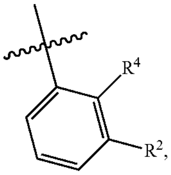
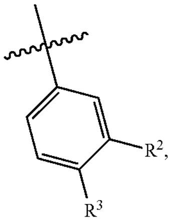
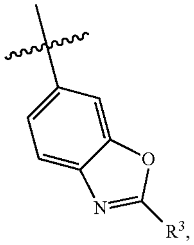
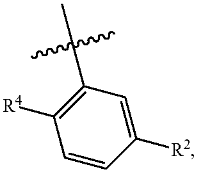
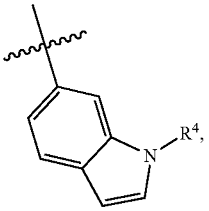
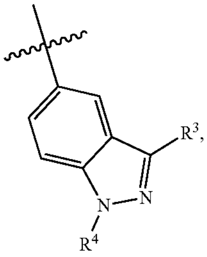

-continued

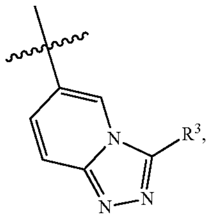

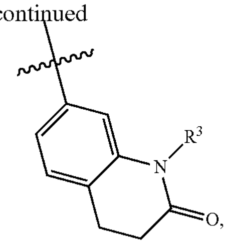

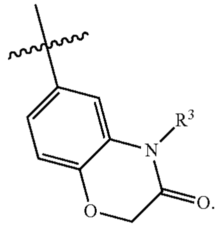

More preferably, $R^2$ is selected from a group consisting of

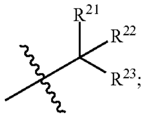

$R^{21}$, $R^{22}$ is independently selected from a group consisting of H, halogen, cyano, —$C_{1\sim6}$ alkyl, halogen substituted —$C_{1\sim6}$ alkyl, —$OR^{24}$;

each $R^{24}$ is independently selected from a group consisting of H, —$C_{1\sim6}$ alkyl; or, $R^{21}$, $R^{22}$ together with the atom adjacent therewith form carbonyl, 3-membered carbocyclyl, 4-membered carbocyclyl, 5-membered carbocyclyl, 6-membered carbocyclyl, 4-membered heterocylcylalkyl, 5-membered heterocylcylalkyl, 6-membered heterocylcylalkyl; said heteroatom in the heterocylcylalkyl is selected from a group consisting of N, O, S;

$R^{23}$ is selected from a group consisting of H, halogen, cyano, —$C_{1\sim6}$ alkyl, halogen substituted —$C_{1\sim6}$ alkyl, —$S(O)_2R^{25}$, —$S(O)R^{25}$, —$S(O)(NH)R^{25}$, —$S(NH)_2R^{25}$;

each $R^{25}$ is independently selected from a group consisting of H, —$C_{1\sim6}$ alkyl.

More preferably, specifically, $R^2$ is selected from a group consisting of

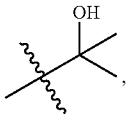
,
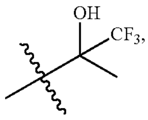
,
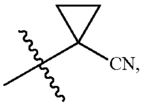
,
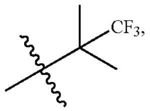
,
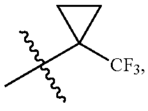
,
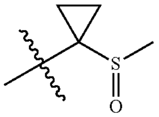
,

-continued

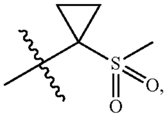
,
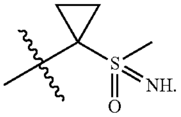
.

Preferably,

C-ring is selected from a group consisting of

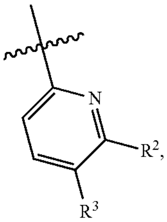
,
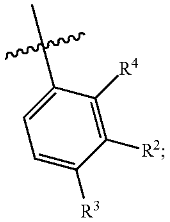
;

$R^2$ is selected from a group consisting of

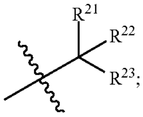

$R^{21}$, $R^{22}$ is independently selected from a group consisting of H, halogen, cyano, —$C_{1\sim6}$ alkyl, halogen substituted —$C_{1\sim6}$ alkyl, —$OR^{24}$;

each $R^{24}$ is independently selected from a group consisting of H, —$C_{1\sim6}$ alkyl;

$R^{23}$, $R^3$ together with the atom adjacent therewith form 4-membered carbocyclyl, 5-membered carbocyclyl, 6-membered carbocyclyl, 7-membered carbocyclyl, 5-membered heterocylcylalkyl, 6-membered heterocylcylalkyl.

More preferably,

C-ring is selected from a group consisting of

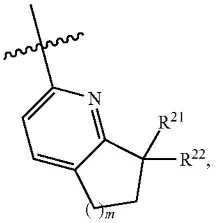
,
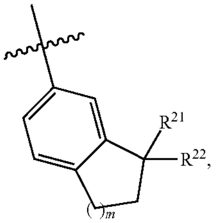
,
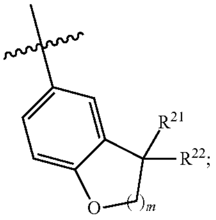
;

wherein, m is selected from a group consisting of 0, 1, 2, 3.

More preferably, $R^2$ is selected from a group consisting of

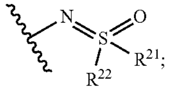

$R^{21}$, $R^{22}$ is independently selected from a group consisting of H, —$C_{1\sim6}$ alkyl.

Preferably,

A-ring is selected from a group consisting of

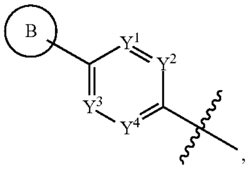

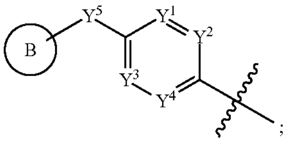

$Y^1$, $Y^2$, $Y^3$, $Y^4$ is independently selected from a group consisting of N or $CR^Y$;

each $R^Y$ is independently selected from a group consisting of H, halogen, cyano, —$C_{1\sim6}$ alkyl, halogen substituted —$C_{1\sim6}$ alkyl, —$C_{0\sim4}$ alkylene-OH, —$C_{0\sim4}$ alkylene-O($C_{1\sim6}$ alkyl), —$C_{0\sim4}$ alkylene-$NH_2$, —$C_{0\sim4}$ alkylene-NH($C_{1\sim6}$ alkyl), —$C_{0\sim4}$ alkylene-N($C_{1\sim6}$ alkyl)($C_{1\sim6}$ alkyl);

B-ring is selected from a group consisting of 3~8-membered monocyclic-carbocyclyl, 4~8-membered monocyclic heterocylcylalkyl, 5~10-membered bridged-carbocyclyl, 5~10-membered bridged-heterocylcylalkyl, 5~10-membered spiro-carbocyclyl, 5~10-membered spiro-heterocylcylalkyl, 8~12-membered fused-carbocyclyl, 8~12-membered fused-heterocylcylalkyl; said monocyclic-carbocyclyl, monocyclic heterocylcylalkyl, bridged-carbocyclyl, bridged-heterocylcylalkyl, spiro-carbocyclyl, spiro-heterocylcylalkyl, fused-carbocyclyl, fused-heterocylcylalkyl is optionally substituted by one, two, three, four or five $R^B$;

each $R^B$ is independently selected from a group consisting of H, halogen, cyano, —$C_{1\sim6}$ alkyl, halogen substituted —$C_{1\sim6}$ alkyl, —$OR^{B1}$, —$SR^{B1}$, —$S(O)_2R^{B1}$, —S(O)$R^{B1}$, —C(O)$R^{B1}$, —C(O)O$R^{B1}$, —$NR^{B1}R^{B1}$, 3~12-membered carbocyclyl, 4~12-membered heterocylcylalkyl; said carbocyclyl, heterocylcylalkyl is optionally substituted by one, two, three, four or five $R^{B1}$; or, two independent $R^B$ together with the atom adjacent therewith form

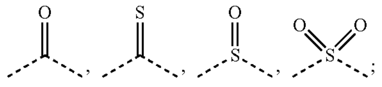

each $R^{B1}$ is independently selected from a group consisting of H, —$C_{1\sim6}$ alkyl, halogen substituted —$C_{1\sim6}$ alkyl;

$Y^5$ is selected from a group consisting of O, S, $NR^{Y51}$, $CR^{Y51}R^{Y51}$;

each $R^{Y51}$ is independently selected from a group consisting of H, —$C_{1\sim6}$ alkyl.

More preferably,

B-ring is selected from a group consisting of

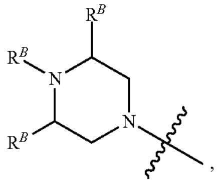

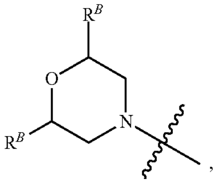

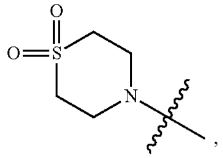

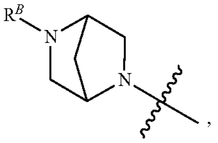

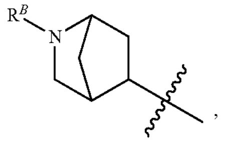

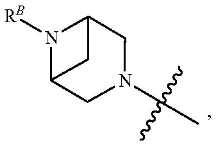

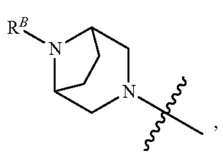

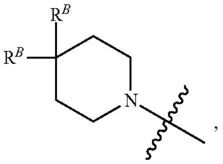

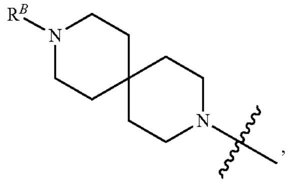

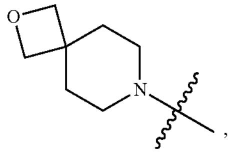

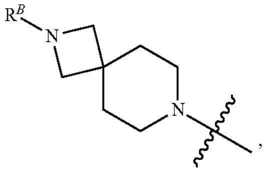

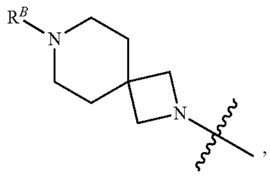

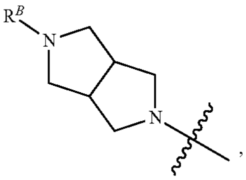

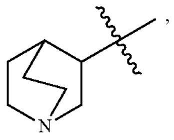

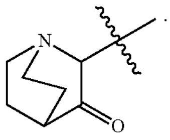

More preferably, specifically,

B-ring is selected from a group consisting of

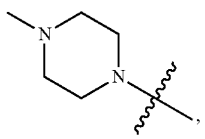

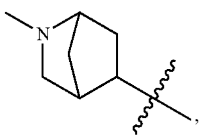

-continued

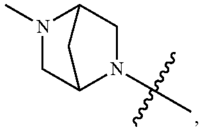,
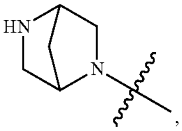,
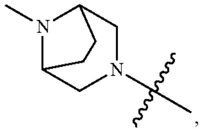,
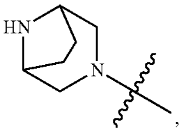,
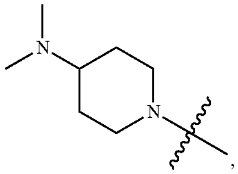,
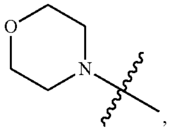,
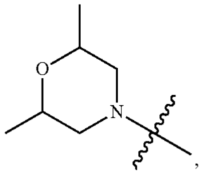,
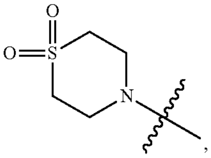,
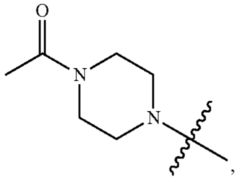,
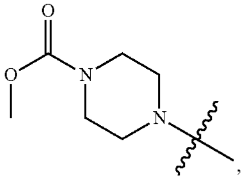,
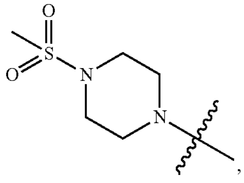,
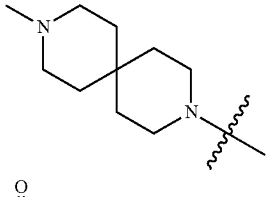,
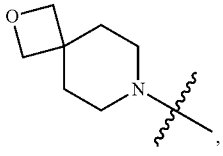,
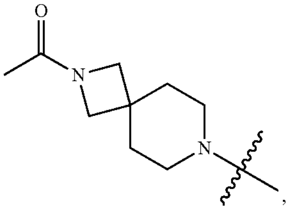,
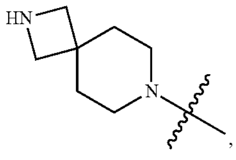,
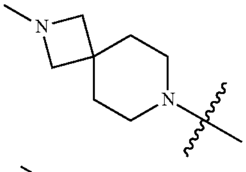,
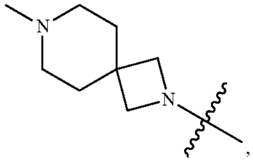,
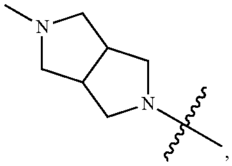,
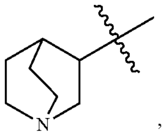,
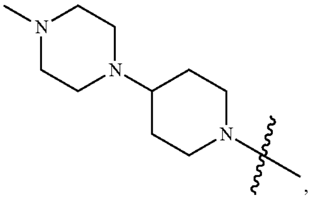, -continued

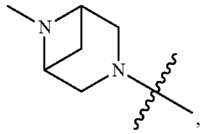,
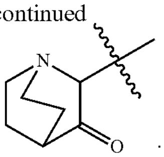.

Preferably,

A-ring is selected from a group consisting of

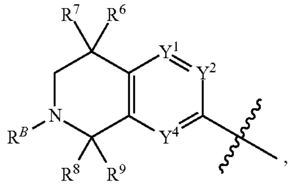,
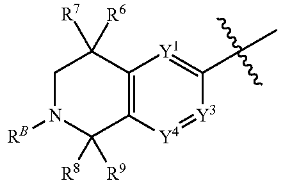;

$Y^1$, $Y^2$, $Y^3$, $Y^4$ is independently selected from a group consisting of N or $CR^Y$;

each $R^Y$ is independently selected from a group consisting of H, halogen, cyano, —$C_{1\sim6}$ alkyl, halogen substituted —$C_{1\sim6}$ alkyl, —$C_{0\sim4}$ alkylene-OH, —$C_{0\sim4}$ alkylene-O($C_{1\sim6}$ alkyl), —$C_{0\sim4}$ alkylene-$NH_2$, —$C_{0\sim4}$ alkylene-NH($C_{1\sim6}$ alkyl), —$C_{0\sim4}$ alkylene-N($C_{1\sim6}$ alkyl)($C_{1\sim6}$ alkyl);

$R^6$, $R^7$, $R^8$, $R^9$ is independently selected from a group consisting of H, —$C_{1_}$alkyl;

or, $R^6$, $R^7$ together with the atom adjacent therewith form 3-membered carbocyclyl, 4-membered carbocyclyl, 5-membered carbocyclyl, 6-membered carbocyclyl, 4-membered heterocylcylalkyl, 5-membered heterocylcylalkyl, 6-membered heterocylcylalkyl; or, $R^8$, $R^9$ together with the atom adjacent therewith form 3-membered carbocyclyl, 4-membered carbocyclyl, 5-membered carbocyclyl, 6-membered carbocyclyl, 4-membered heterocylcylalkyl, 5-membered heterocylcylalkyl, 6-membered heterocylcylalkyl; $R^B$ is selected from a group consisting of H, —$C_{1\sim6}$ alkyl, halogen substituted —$C_{1\sim6}$ alkyl, —$S(O)_2R^{B1}$, —S(O)$R^{B1}$, —C(O)$R^{B1}$, —C(O)O$R^{B1}$.

each $R^{B1}$ is independently selected from a group consisting of H, —$C_{1\sim6}$ alkyl, halogen substituted —$C_{1\sim6}$ alkyl.

More preferably,

A-ring is selected from a group consisting of

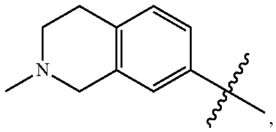,
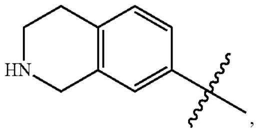,
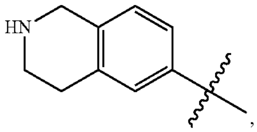,
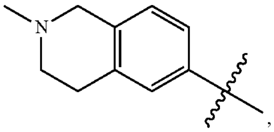,

-continued

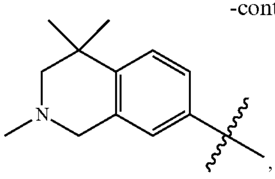
,
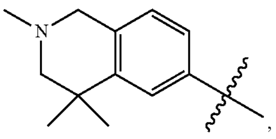
,
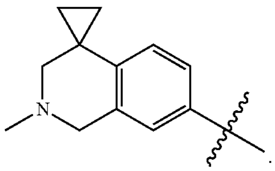
.

Preferably,

A-ring is selected from a group consisting of

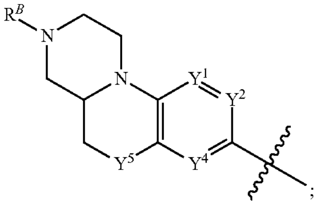
;

$Y^1$, $Y^2$, $Y^4$ is independently selected from a group consisting of N or $CR^Y$;

each $R^Y$ is independently selected from a group consisting of H, halogen, cyano, —$C_{1\sim6}$ alkyl, halogen substituted —$C_{1\sim6}$ alkyl, —$C_{0\sim4}$ alkylene-OH, —$C_{0\sim4}$ alkylene-O($C_{1\sim6}$ alkyl), —$C_{0\sim4}$ alkylene-$NH_2$, —$C_{0\sim4}$ alkylene-NH($C_{1\sim6}$ alkyl), —$C_{0\sim4}$ alkylene-N($C_{1\sim6}$ alkyl)($C_{1\sim6}$ alkyl);

$R^B$ is selected from a group consisting of H, —$C_{1\sim6}$ alkyl, halogen substituted —$C_{1\sim6}$ alkyl, —$S(O)_2R^{B1}$, —S(O)$R^{B1}$, —C(O)$R^{B1}$, —C(O)O$R^{B1}$.

each $R^{B1}$ is independently selected from a group consisting of H, —$C_{1\sim6}$ alkyl, halogen substituted —$C_{1\sim6}$ alkyl;

$Y^5$ is selected from a group consisting of chemical bond, O, S, $NR^{Y51}$, $CR^{Y51}R^{Y51}$;

each $R^{Y51}$ is independently selected from a group consisting of H, —$C_{1\sim6}$ alkyl.

More preferably,

A-ring is selected from a group consisting of

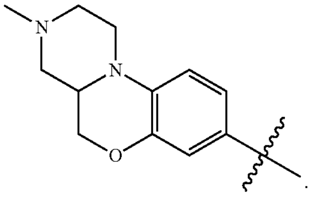 [SMILES: *c1ccc2c(c1)OCC1CN(C)CCN21]
.

Preferably,

A-ring is selected from a group consisting of,

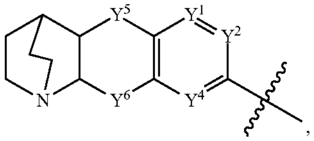
,
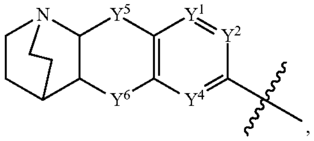
,
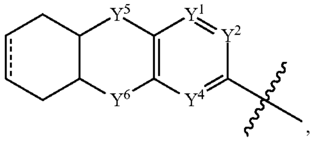
,
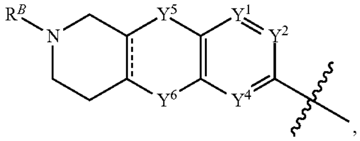
,
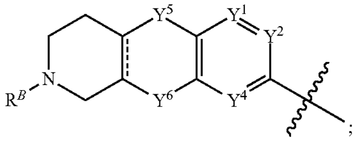
;

$\overline{\text{- - -}}$ represents a single bond or double bond;

$Y^1$, $Y^2$, $Y^4$ is independently selected from a group consisting of N or $CR^Y$;

each $R^Y$ is independently selected from a group consisting of H, halogen, cyano, —$C_{1\sim6}$ alkyl, halogen substituted —$C_{1\sim6}$ alkyl, —$C_{0\sim4}$ alkylene-OH, —$C_{0\sim4}$ alkylene-O($C_{1\sim6}$ alkyl), —$C_{0\sim4}$ alkylene-$NH_2$, —$C_{0\sim4}$ alkylene-NH($C_{1\sim6}$ alkyl), —$C_{0\sim4}$ alkylene-N($C_{1\sim6}$ alkyl)($C_{1\sim6}$ alkyl);

$R^B$ is selected from a group consisting of H, —$C_{1\sim6}$ alkyl, halogen substituted —$C_{1\sim6}$ alkyl, —$S(O)_2R^{B1}$, —S(O)$R^{B1}$, —C(O)$R^{B1}$, —C(O)O$R^{B1}$;

each $R^{B1}$ is independently selected from a group consisting of H, —$C_{1\sim6}$ alkyl, halogen substituted —$C_{1\sim6}$ alkyl;

$Y^5$, $Y^6$ is independently selected from a group consisting of chemical bond, —$C_{0\sim1}$ alkylene-O—, —$C_{0\sim1}$ alkylene-S—, —$C_{0\sim1}$ alkylene-$NR^{Y51}$—, $CR^{Y51}R^{Y51}$;

each $R^{Y51}$ is independently selected from a group consisting of H, —$C_{1\sim6}$ alkyl.

More preferably,

A-ring is selected from a group consisting of

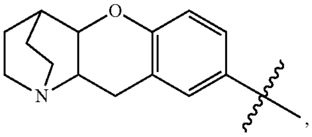
,
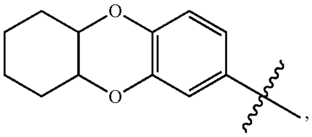
,

-continued

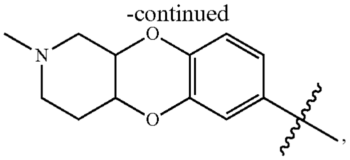,

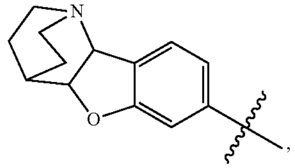,

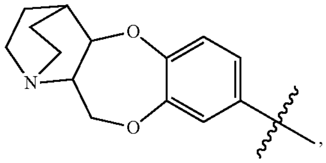,

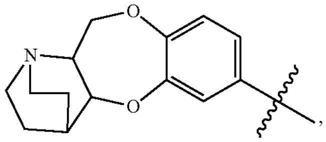,

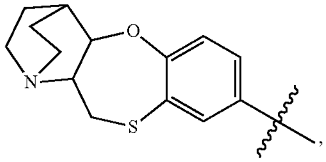,

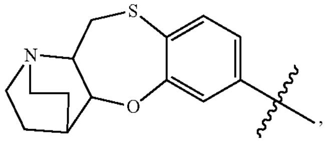,

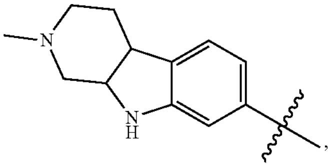,

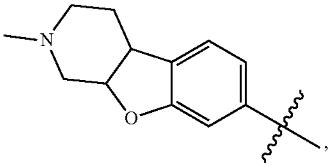,

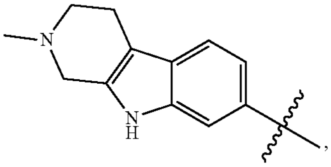,

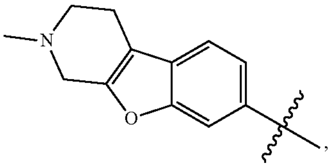,

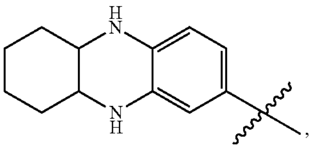,

-continued

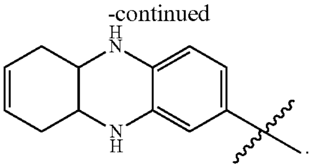.

Preferably,

A-ring is selected from a group consisting of

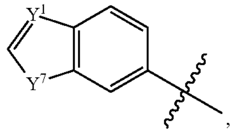, 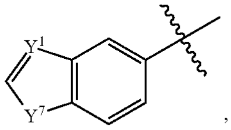,

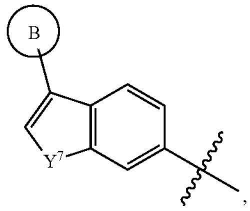, 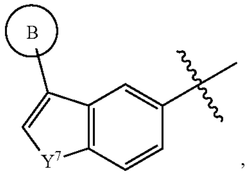,

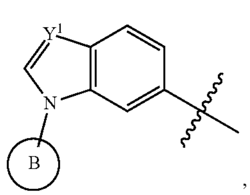, 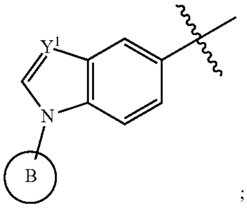;

$Y^1$ is selected from a group consisting of N or $CR^Y$;

$R^Y$ is selected from a group consisting of H, halogen, cyano, —$C_{1\sim6}$ alkyl, halogen substituted —$C_{1\sim6}$ alkyl, —$C_{0\sim4}$ alkylene-OH, —$C_{0\sim4}$ alkylene-O($C_{1\sim6}$ alkyl), —$C_{0\sim4}$ alkylene-$NH_2$, —$C_{0\sim4}$ alkylene-NH($C_{1\sim6}$ alkyl), —$C_{0\sim4}$ alkylene-N($C_{1\sim6}$ alkyl)($C_{1\sim6}$ alkyl);

B-ring is selected from a group consisting of 3~8-membered monocyclic-carbocyclyl, 4~8-membered monocyclic heterocylcylalkyl; said monocyclic-carbocyclyl, monocyclic heterocylcylalkyl is optionally substituted by one, two, three, four or five $R^B$.

each $R^B$ is independently selected from a group consisting of H, halogen, cyano, —$C_{1\sim6}$ alkyl, halogen substituted —$C_{1\sim6}$ alkyl, —$OR^{B1}$, —$SR^{B1}$, —$S(O)_2R^{B1}$, —S(O)$R^{B1}$, —C(O)$R^{B1}$, —C(O)O$R^{B1}$, —$NR^{B1}R^{B1}$; or, two independent $R^B$ together with the atom adjacent therewith form

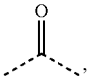, 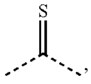, 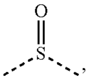, 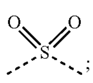;

each $R^{B1}$ is independently selected from a group consisting of H, —$C_{1\sim6}$ alkyl, halogen substituted —$C_{1\sim6}$ alkyl;

$Y^7$ is selected from a group consisting of O, S or $NR^{Y71}$;

$R^{Y71}$ is selected from a group consisting of H, —$C_{1\sim6}$ alkyl, halogen substituted —$C_{1\sim6}$ alkyl, —$C_{1\sim4}$ alkylene-OH, —$C_{1\sim4}$ alkylene-O($C_{1\sim6}$ alkyl), —$C_{1\sim4}$ alkylene-$NH_2$, —$C_{1\sim4}$ alkylene-NH($C_{1\sim6}$ alkyl), —$C_{1\sim4}$ alkylene-N($C_{1\sim6}$ alkyl)($C_{1\sim6}$ alkyl).

More preferably,
A-ring is selected from a group consisting of
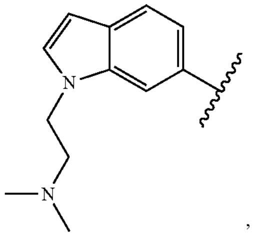
,
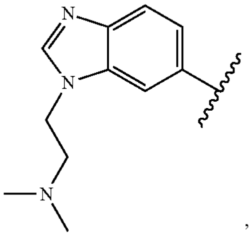
,
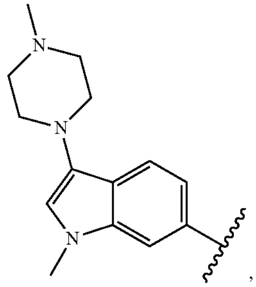
,
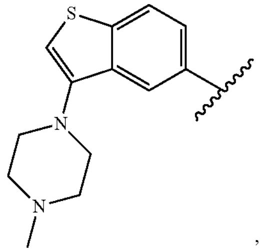
,
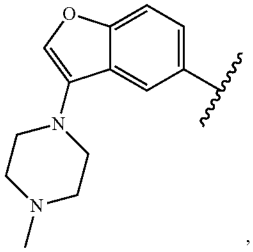
,
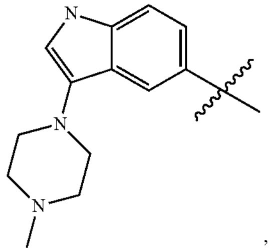
,
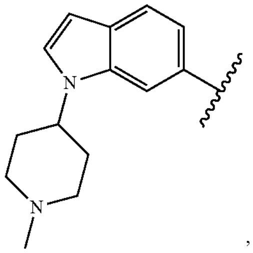
,
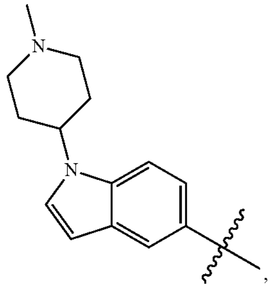
,
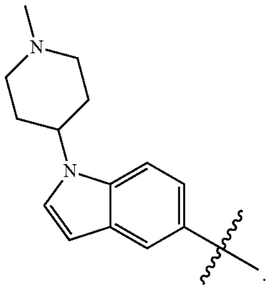
.
More preferably,
C-ring is selected from a group consisting of
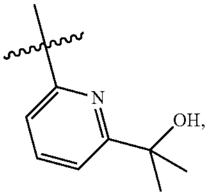
,
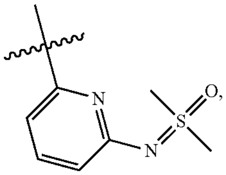
,
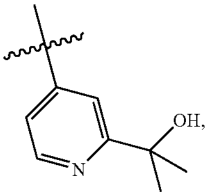
,
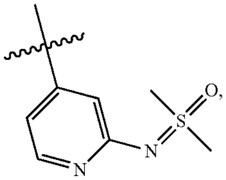
,
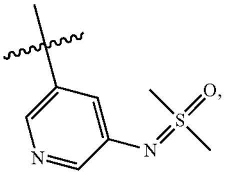
,
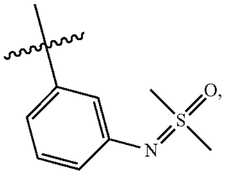
,
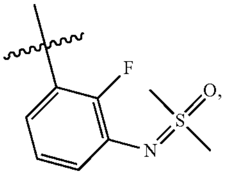
,
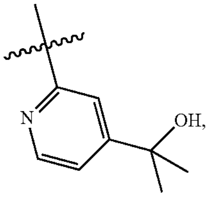
,
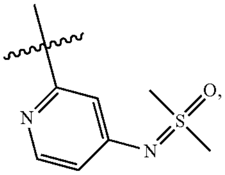
,
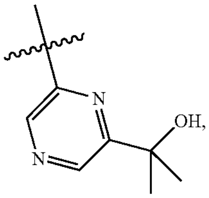
,
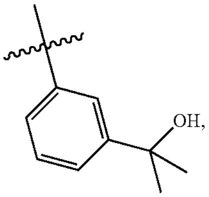
,
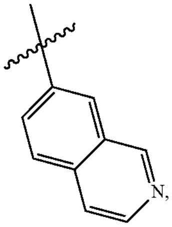
,
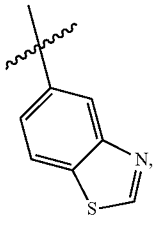
,
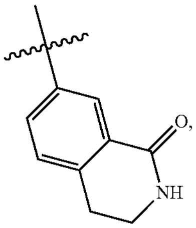
, -continued
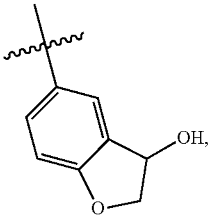
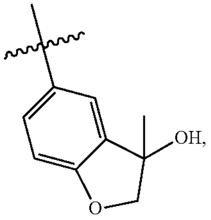
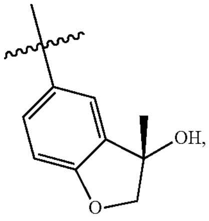
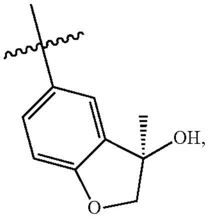
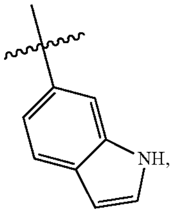
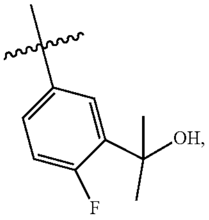
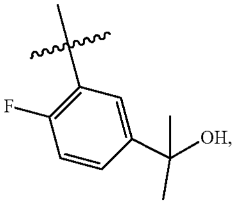
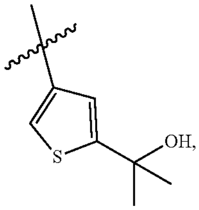
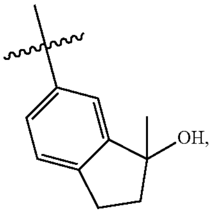
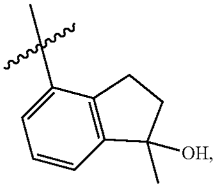
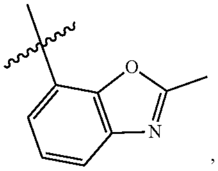
,
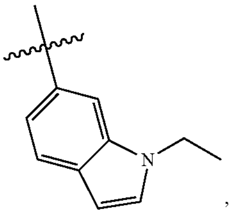
,
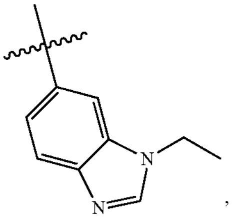
,
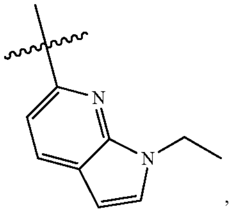
,
-continued
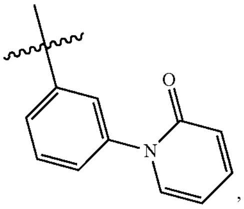
,
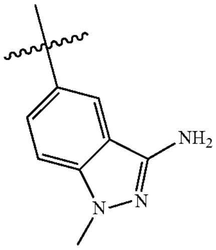
,
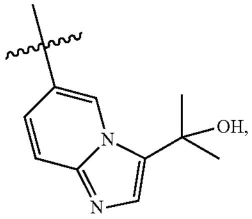
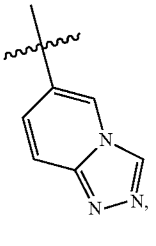
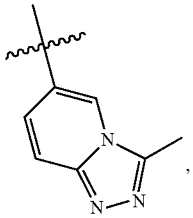
,
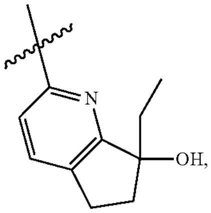
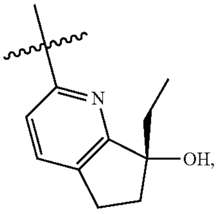
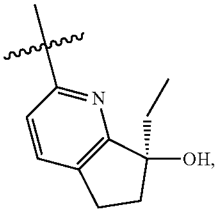
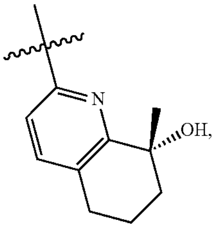
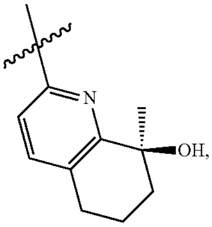
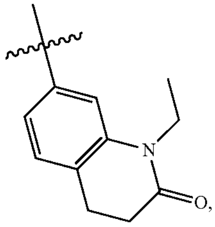
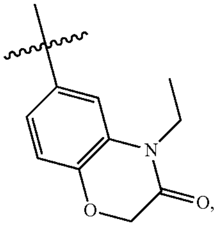
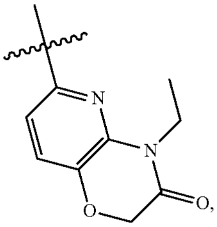
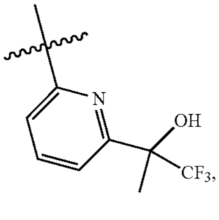

-continued
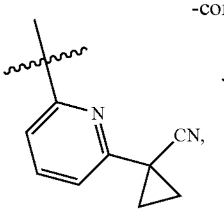 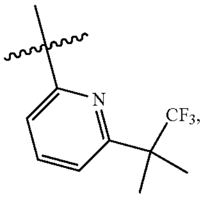
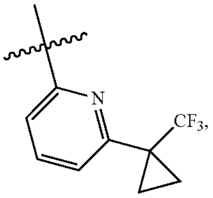 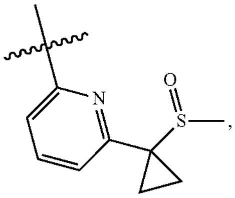,
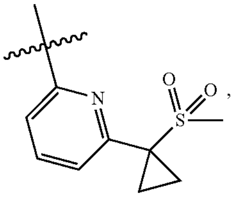, 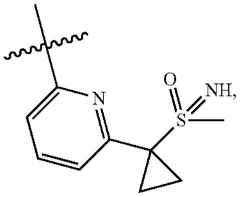 or
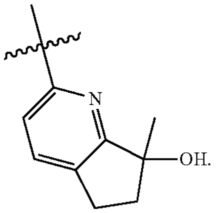
More preferably,
A-ring is selected from a group consisting of
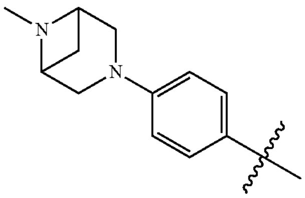,
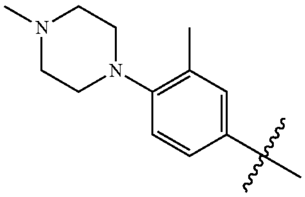,
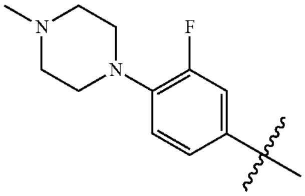,
-continued
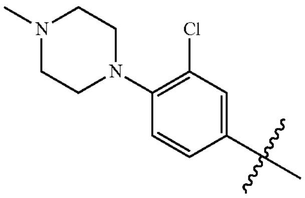,
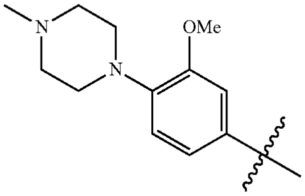,
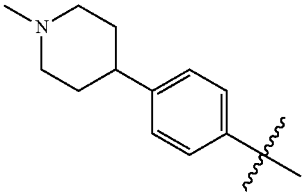,
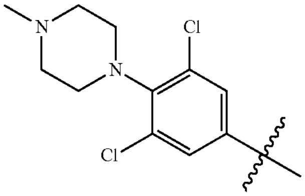,
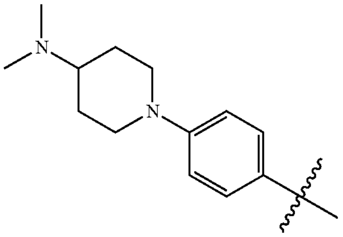,
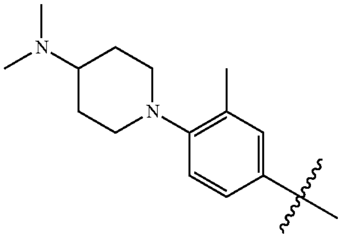,
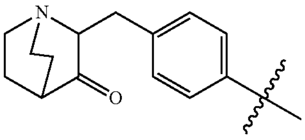,
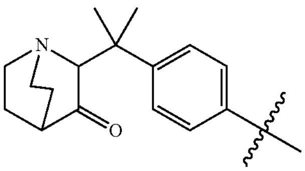, -continued
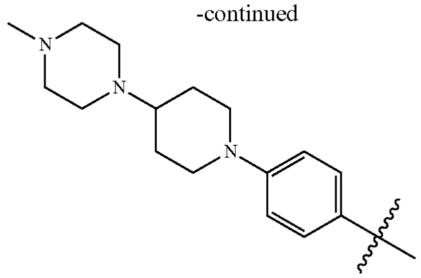
,
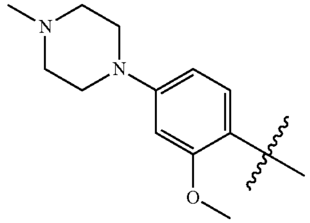
,
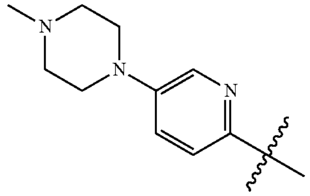
,
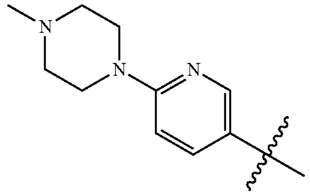
or
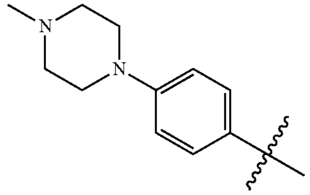
.
In some specific embodiments of the present invention, the compound represented by formula I is specifically:
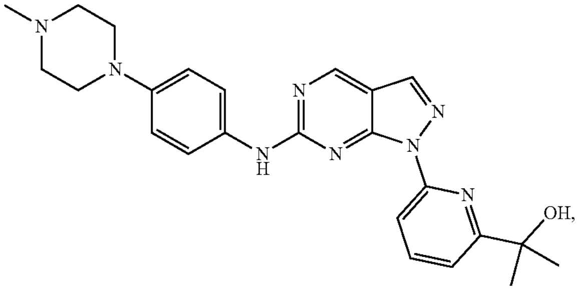
-continued
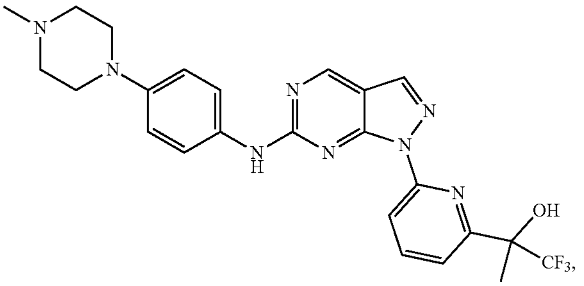
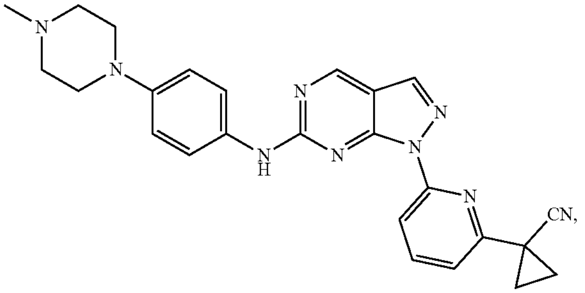
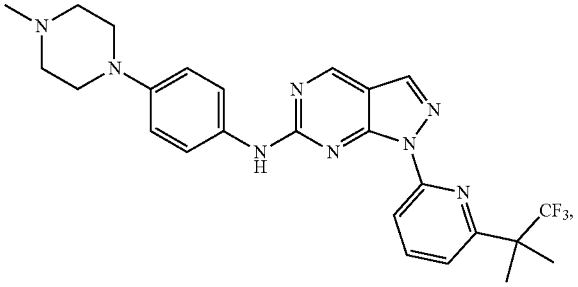
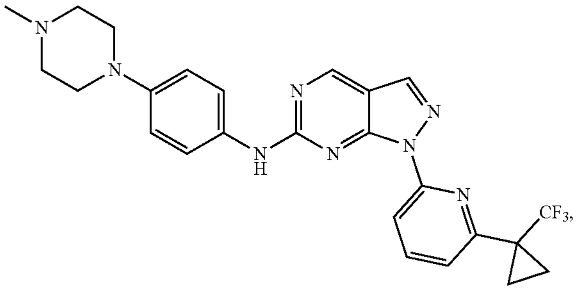
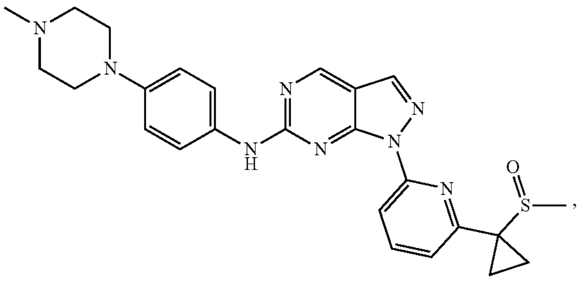
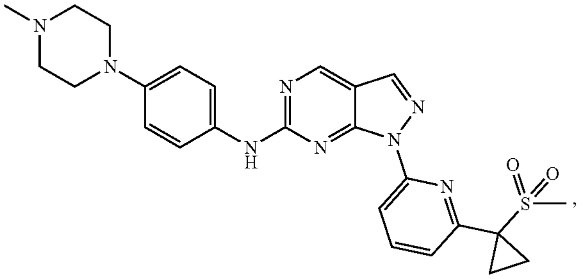

-continued
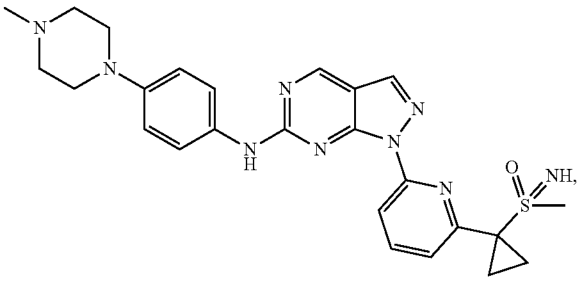
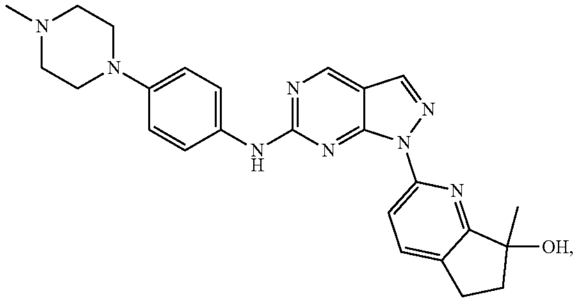
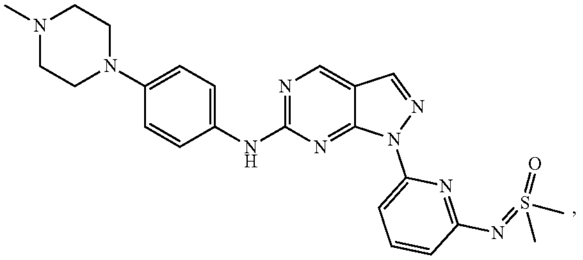
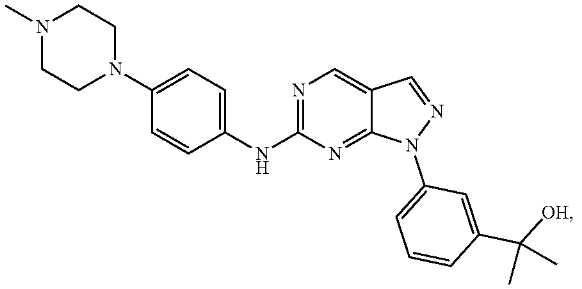
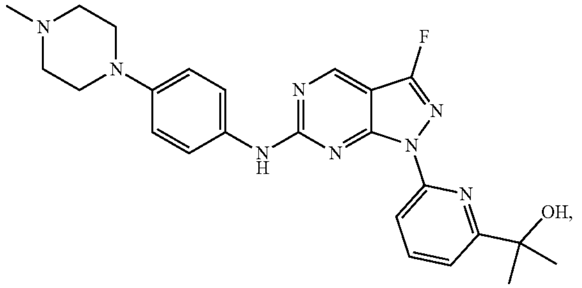
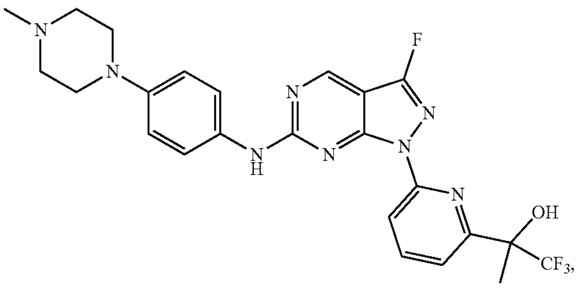
-continued
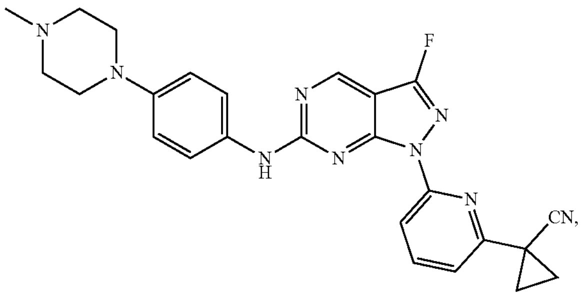
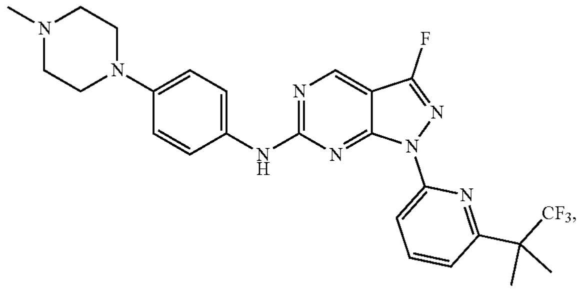
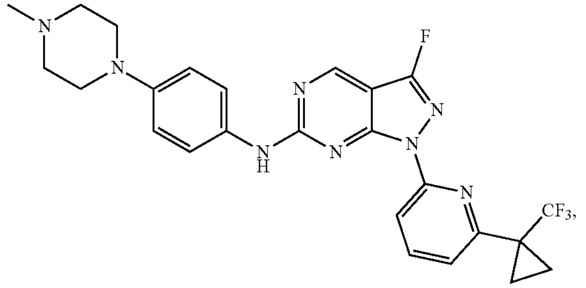
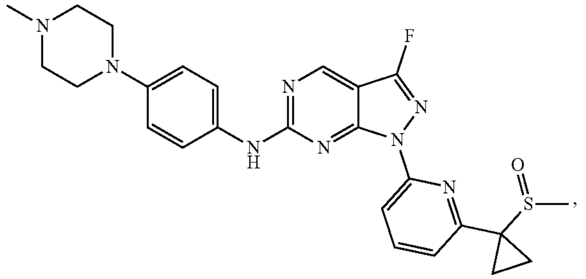
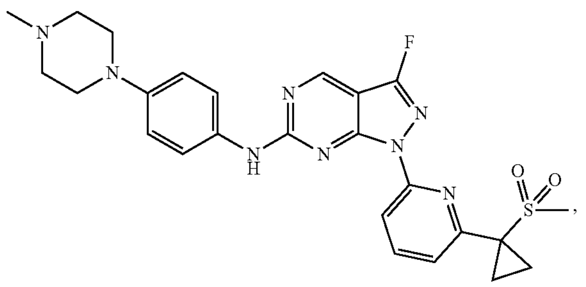
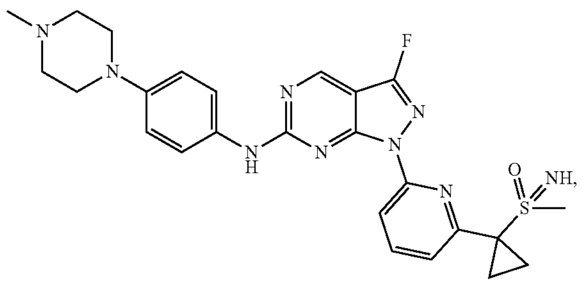

-continued
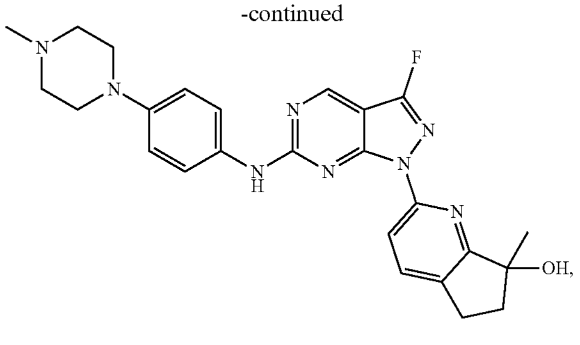
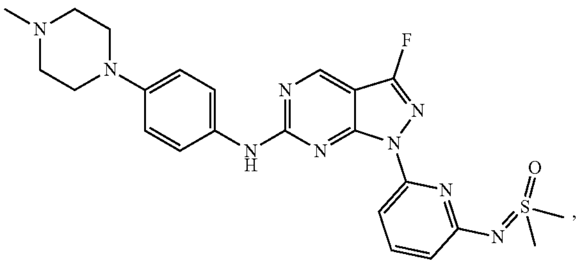
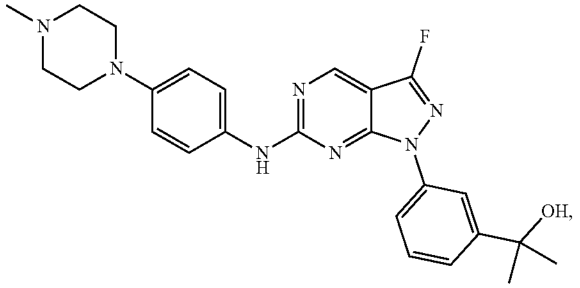
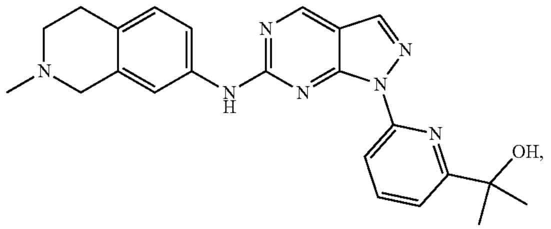
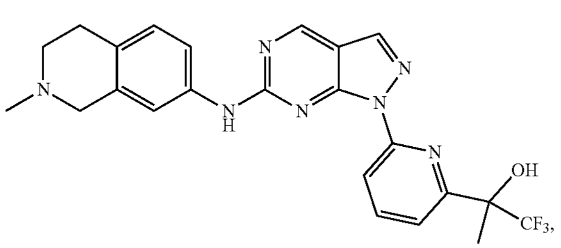
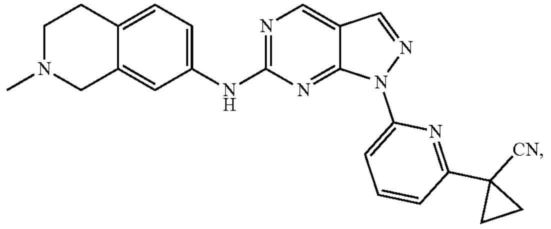
-continued
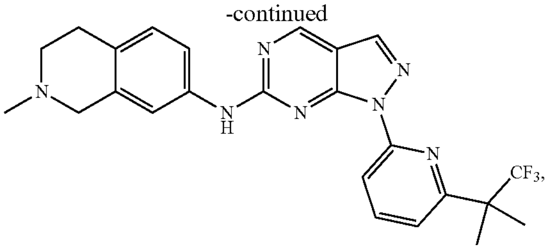
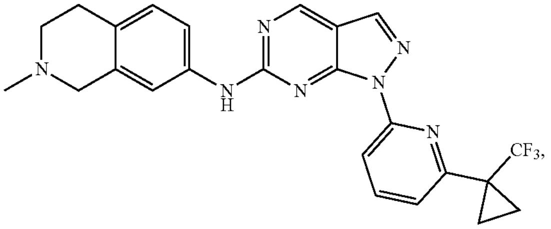
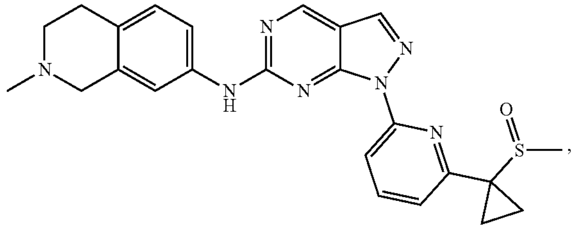
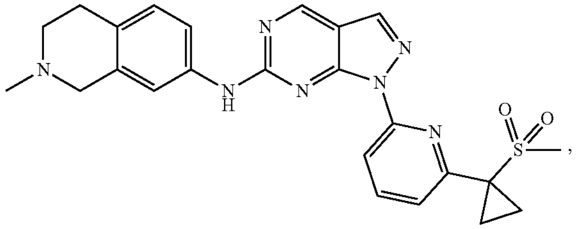
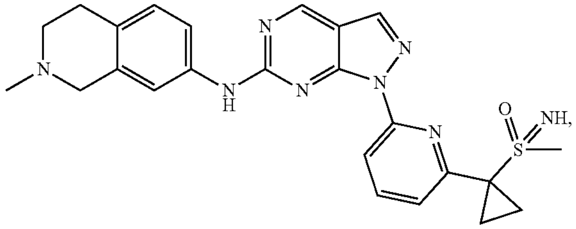
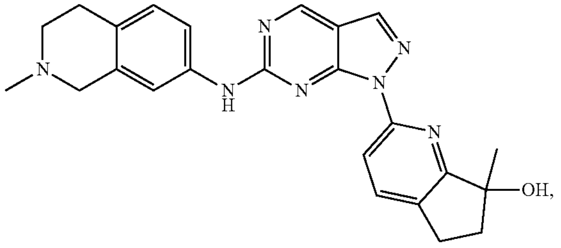
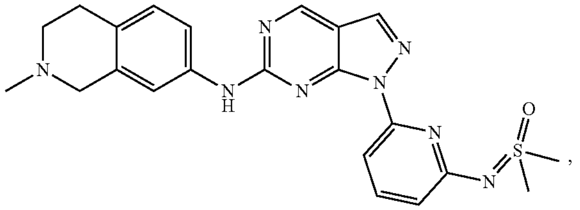

-continued
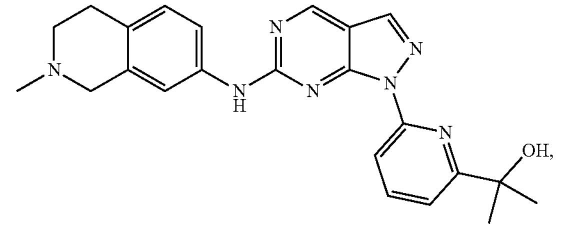
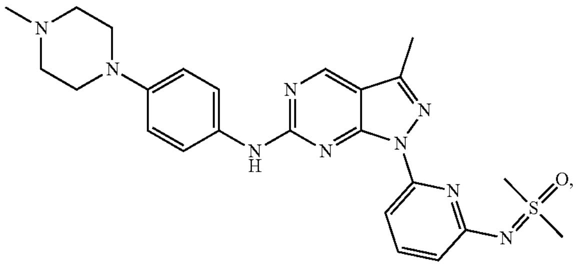
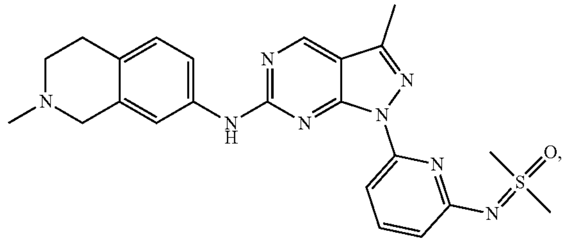
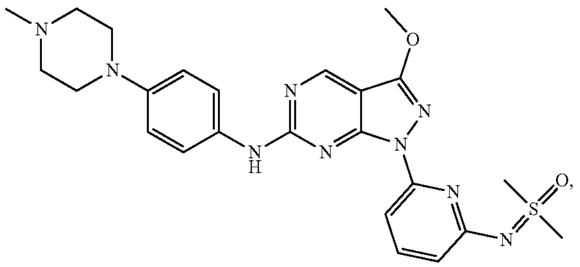
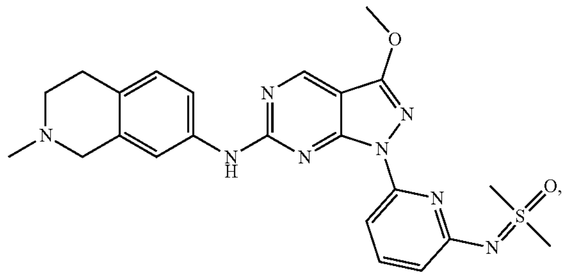
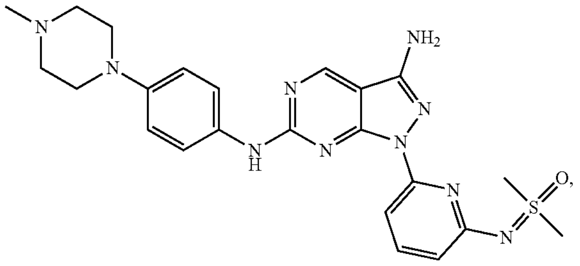
-continued
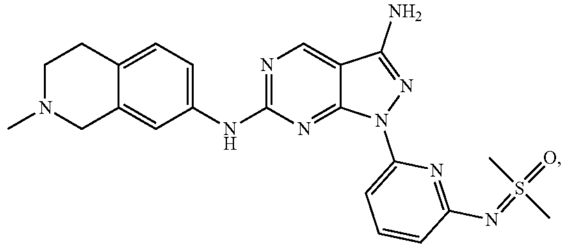
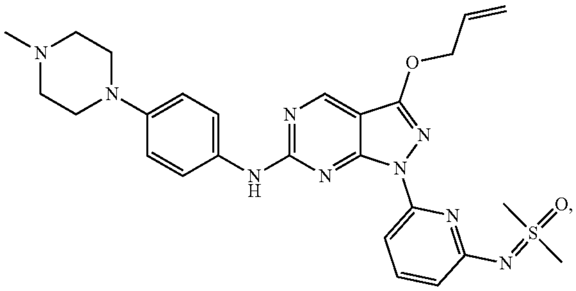
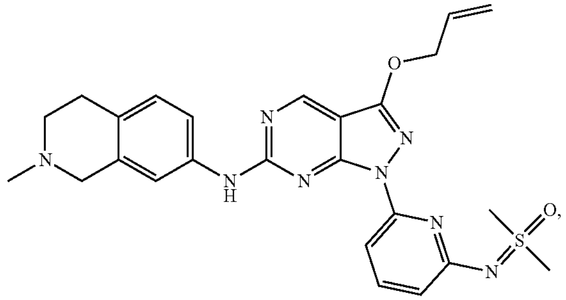
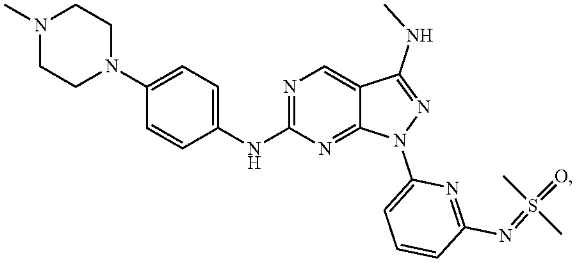
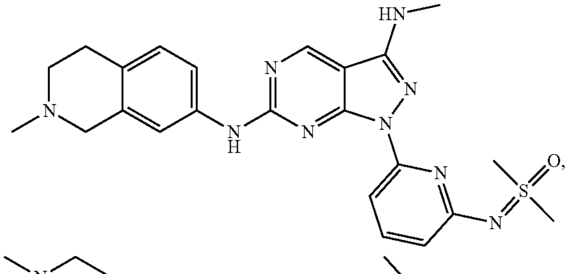
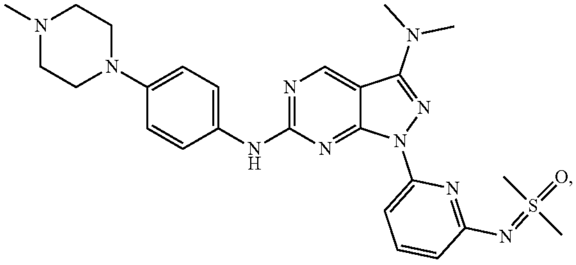

-continued
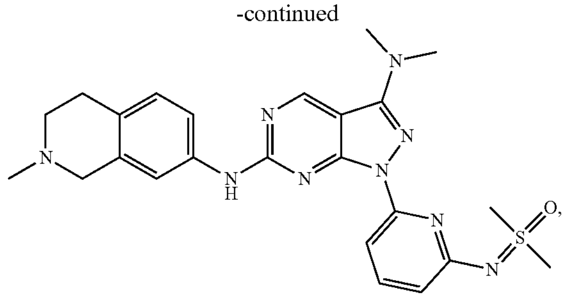
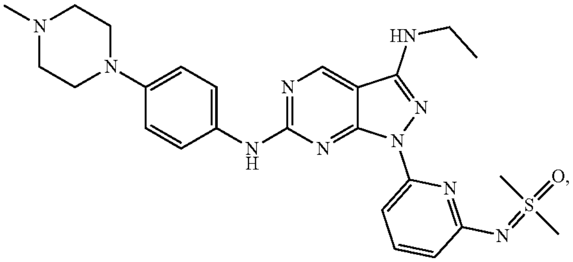
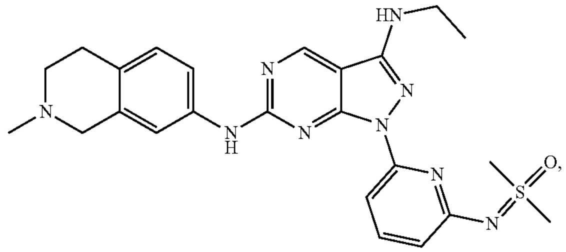
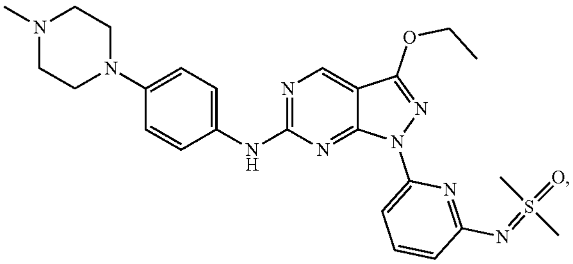
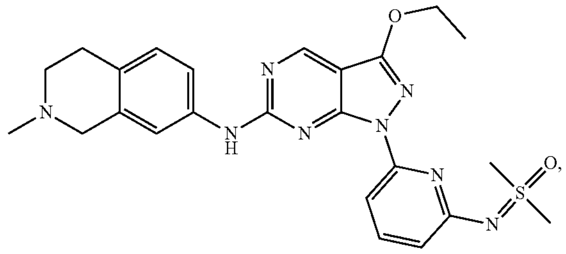
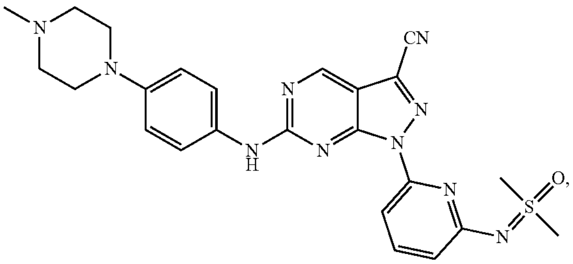
-continued
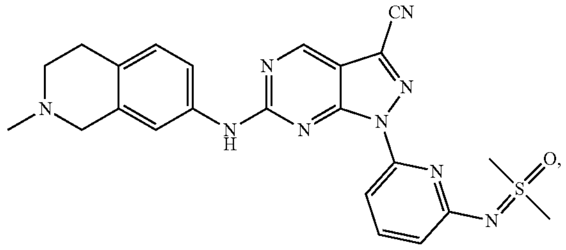
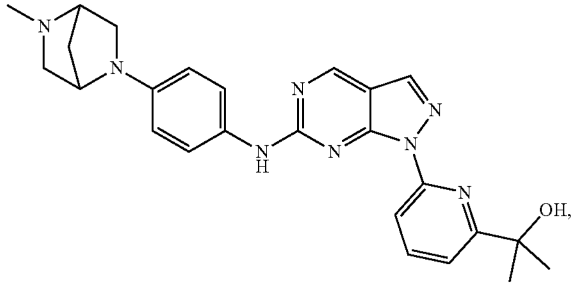
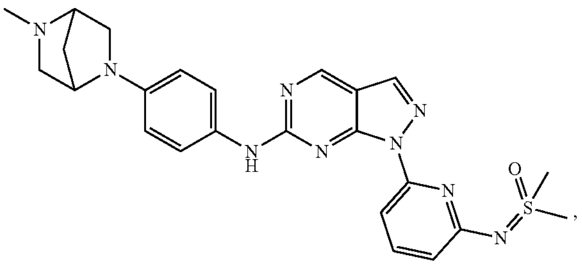
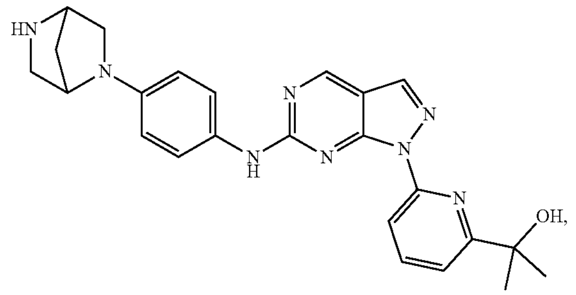
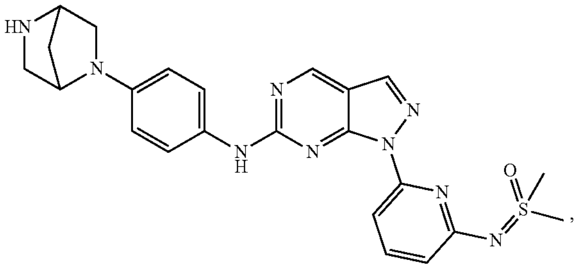
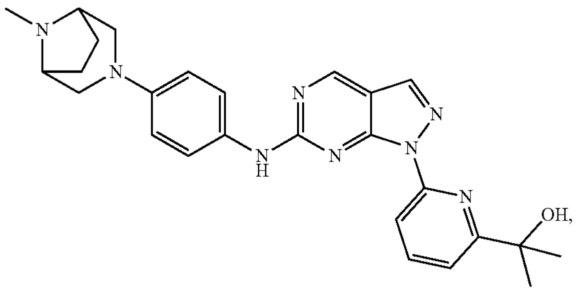

-continued
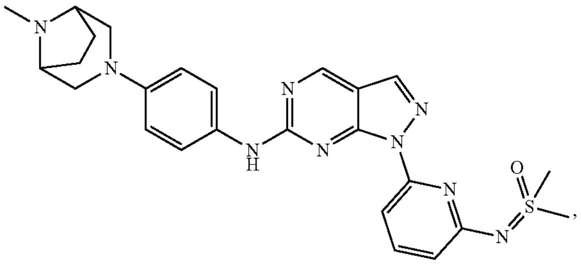
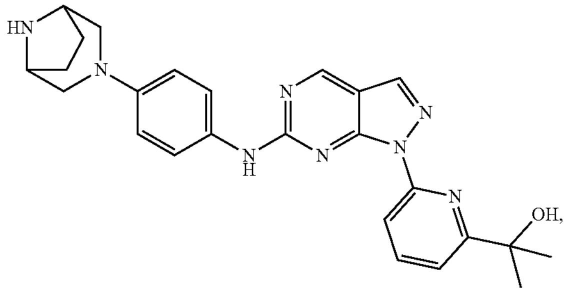
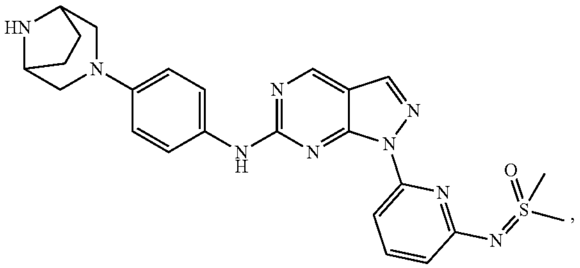
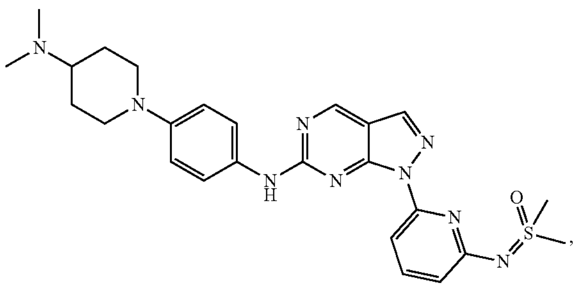
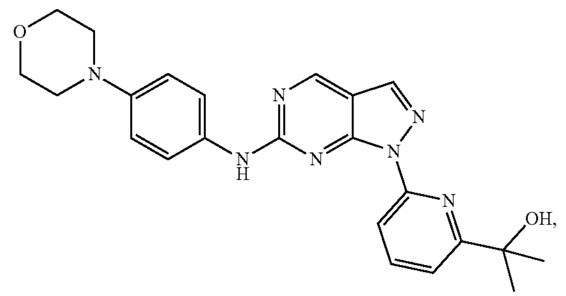
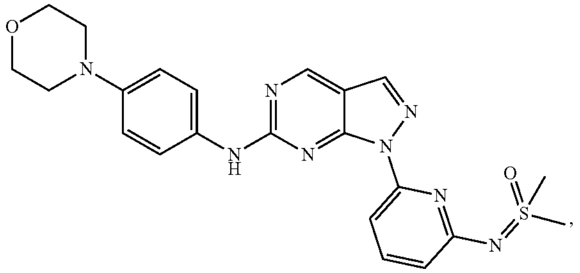
-continued
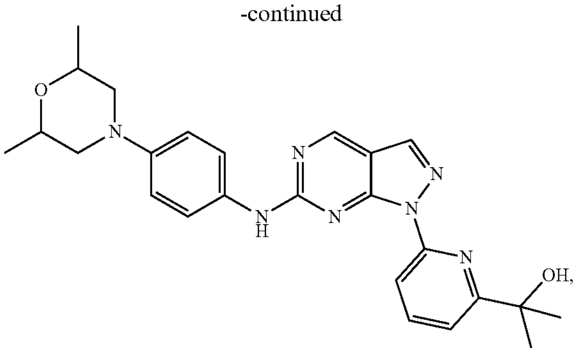
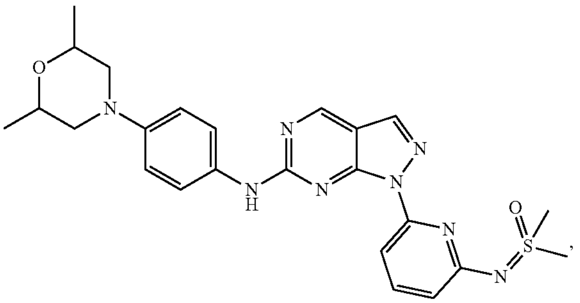
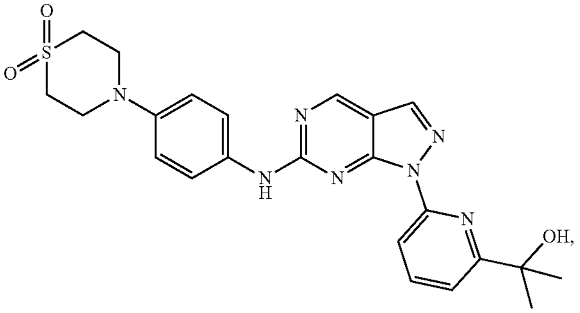
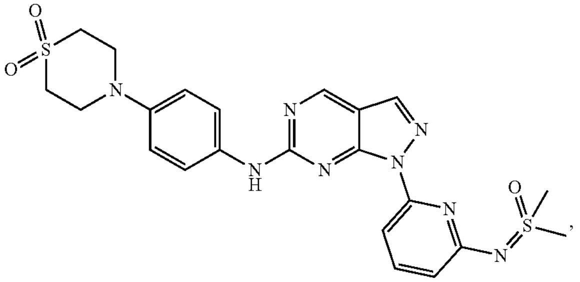
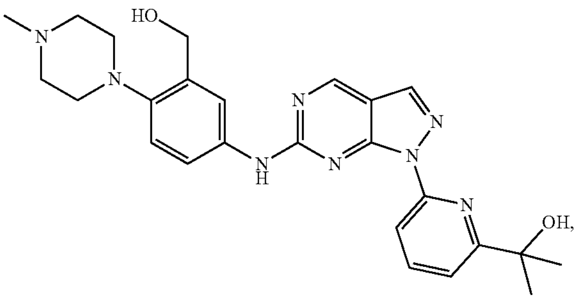

-continued
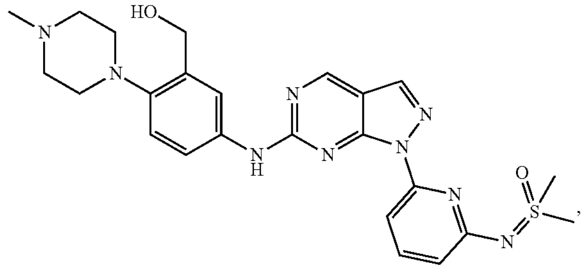
,
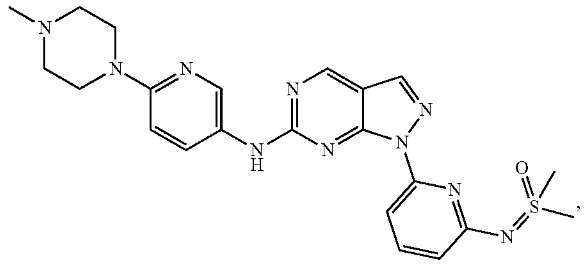
,
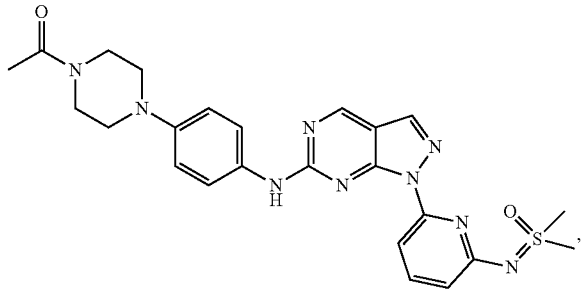
,
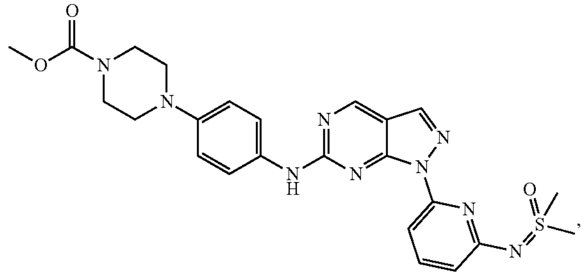
,
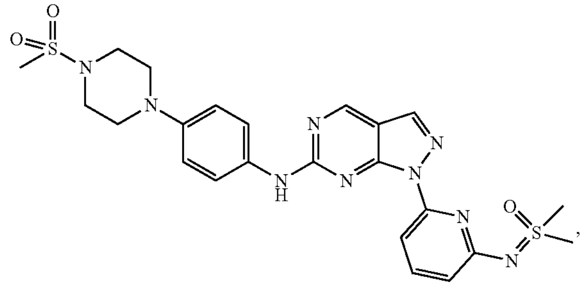
,
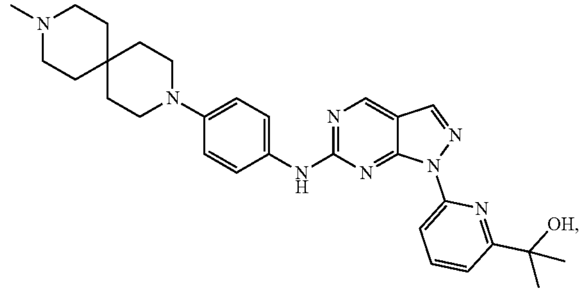
,
-continued
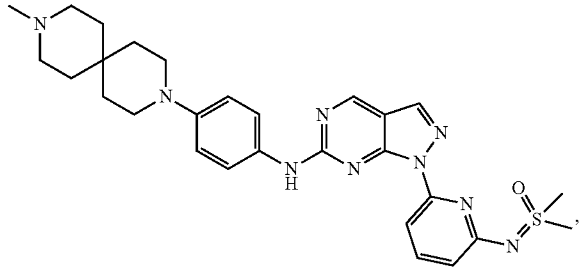
,
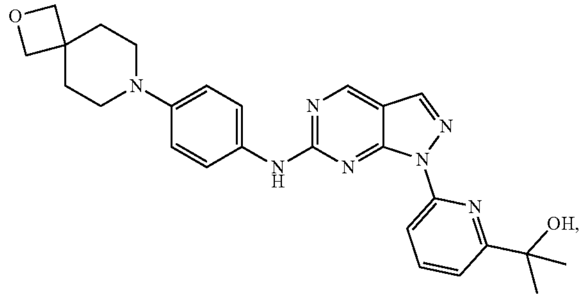
,
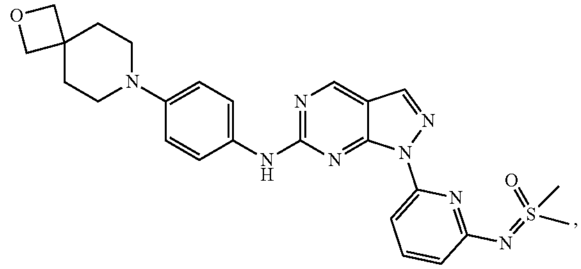
,
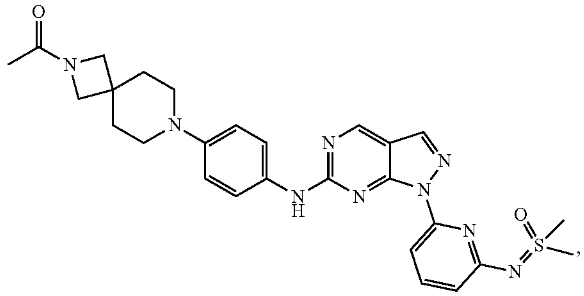
,
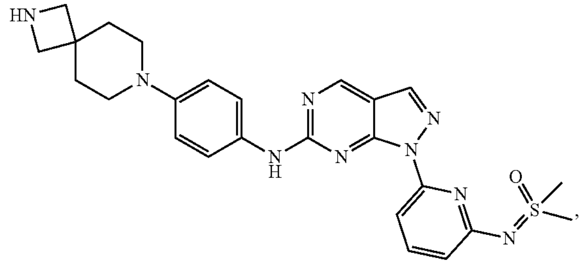
,
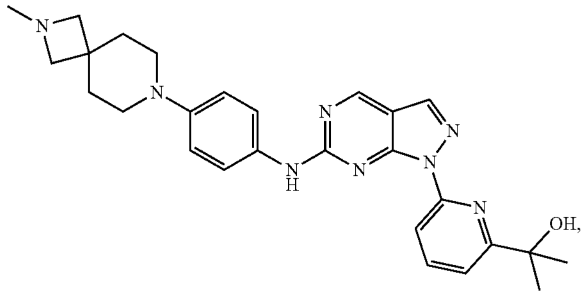
, -continued
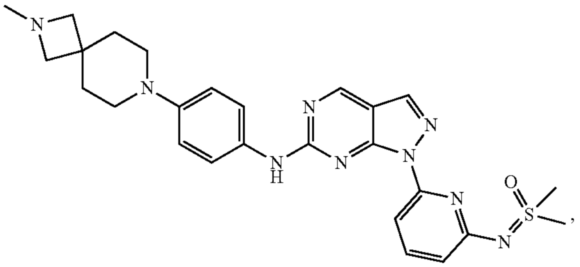
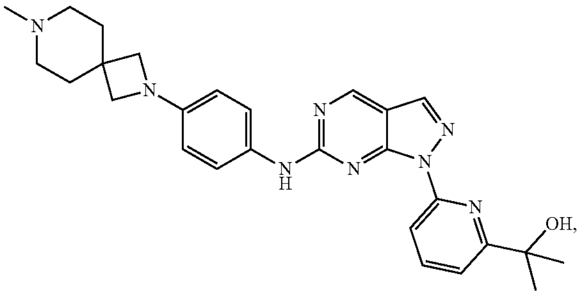
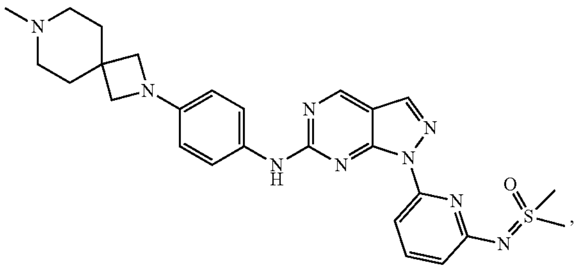
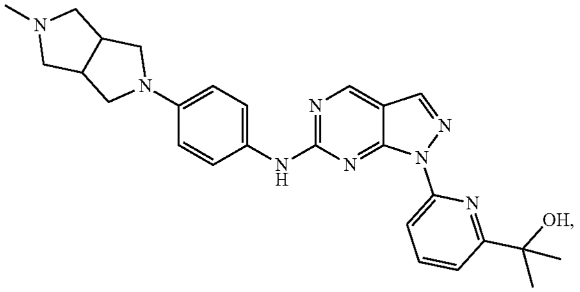
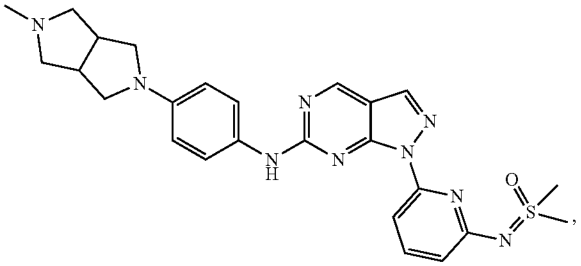
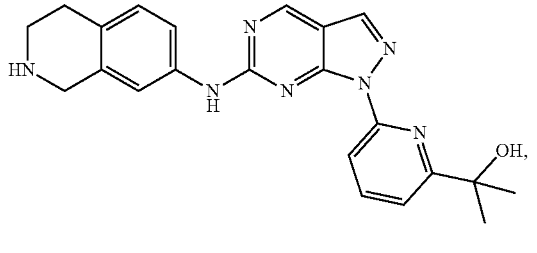
-continued
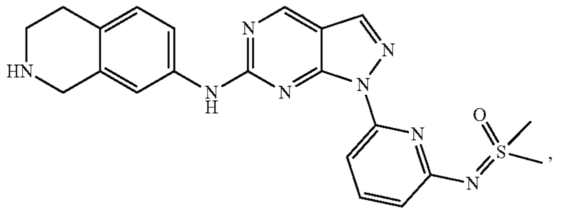
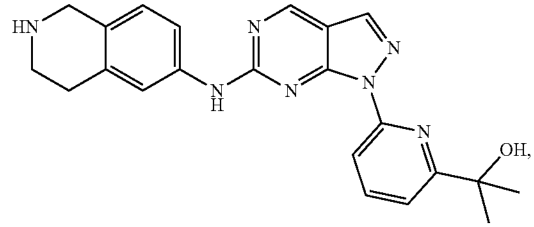
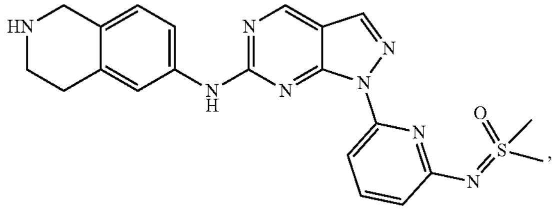
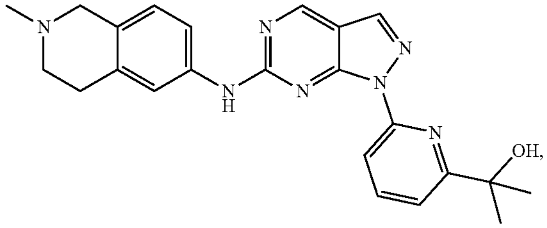
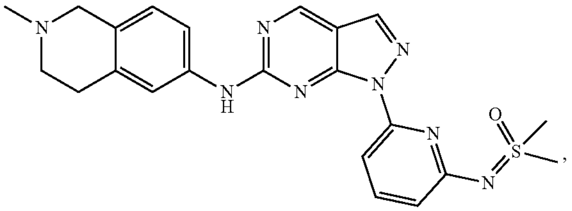
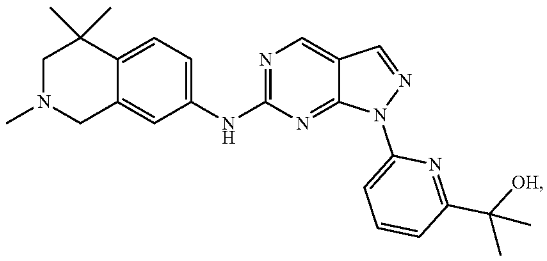
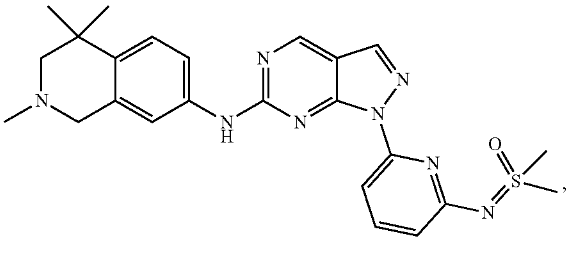

-continued
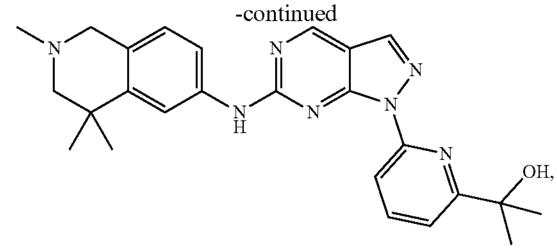
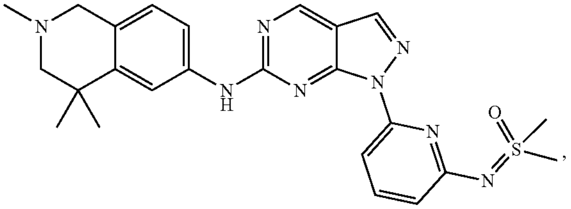
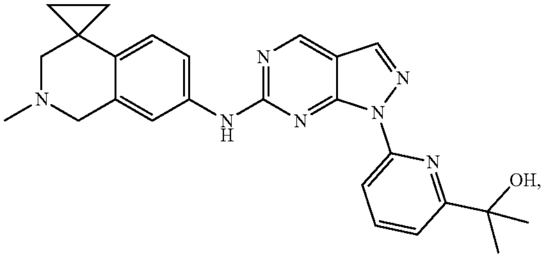
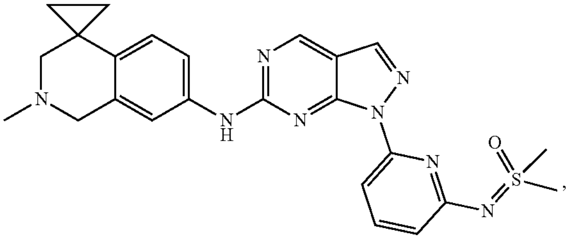
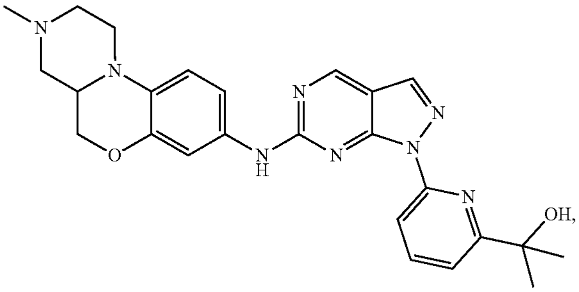
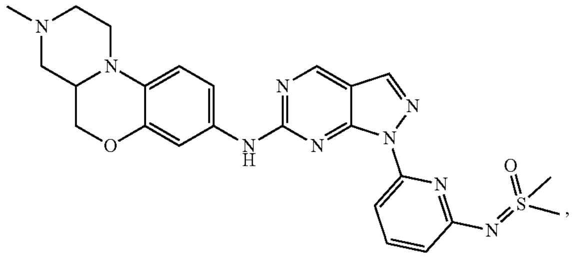
-continued
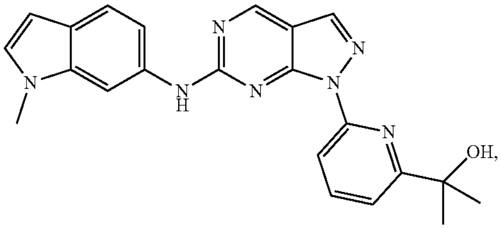
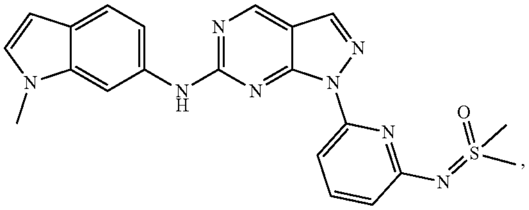
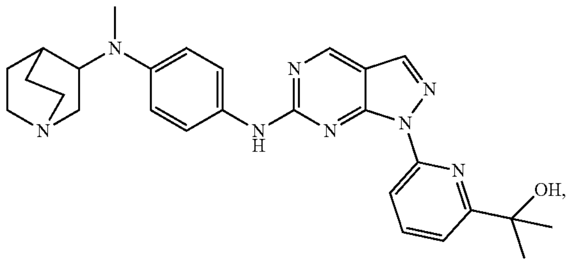
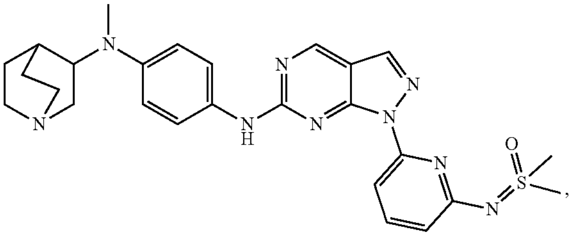
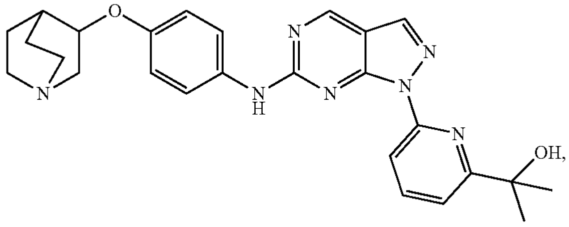
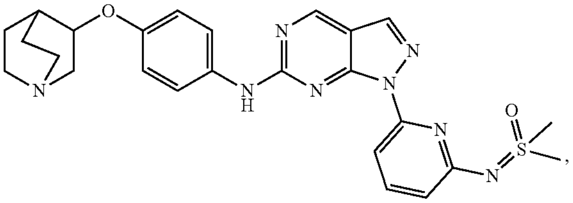
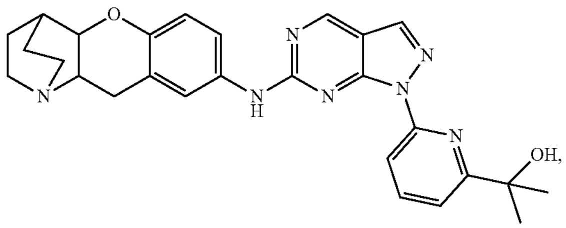

-continued
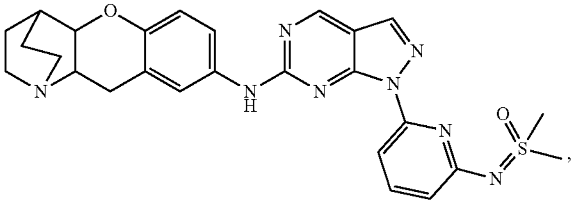
,
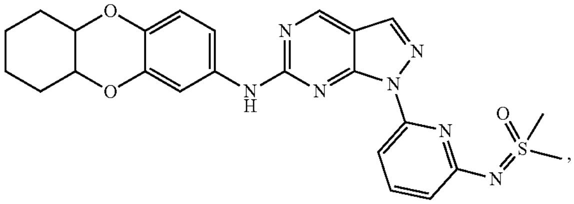
,
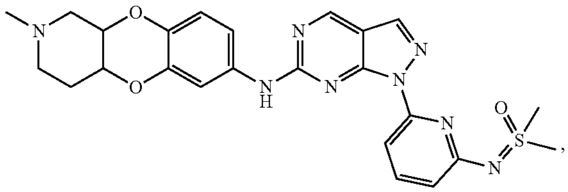
,
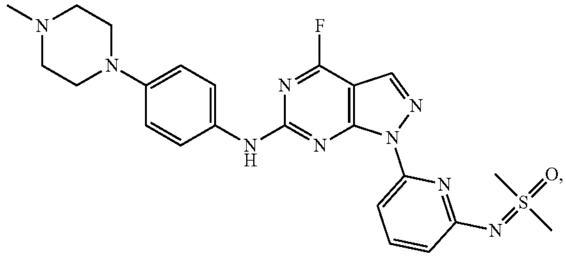
,
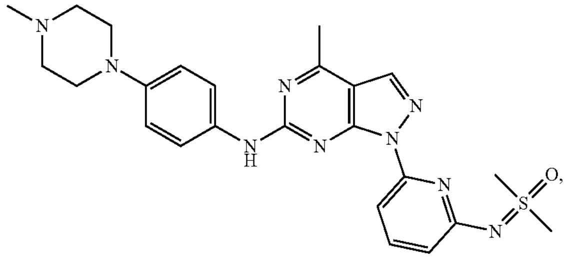
,
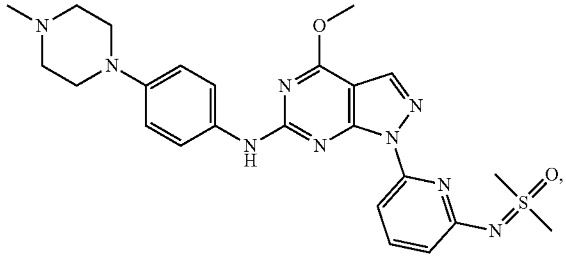
,
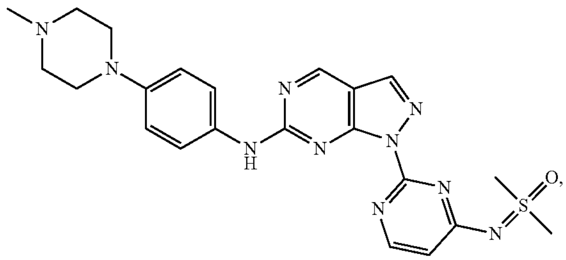
,
-continued
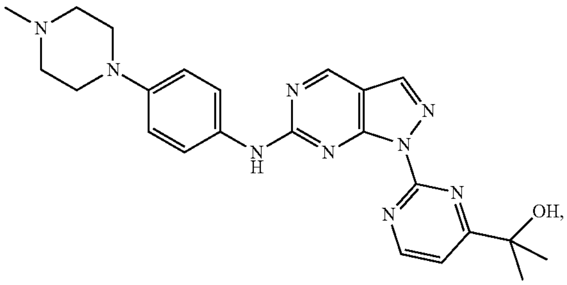
,
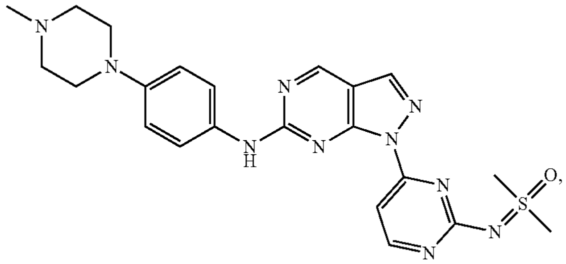
,
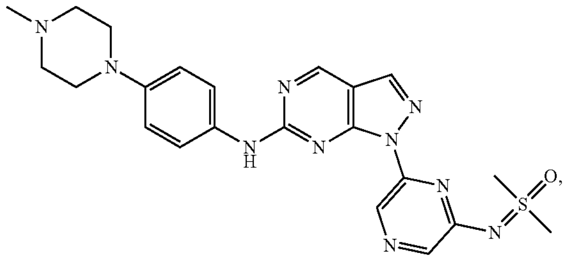
,
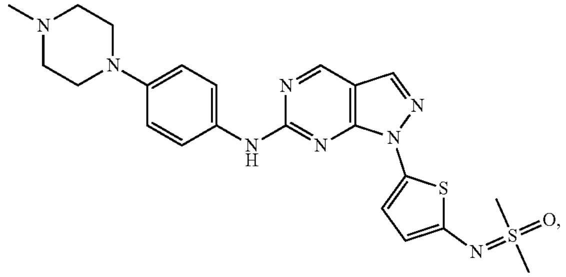
,
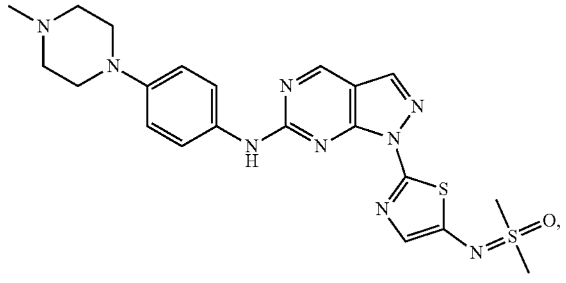
,
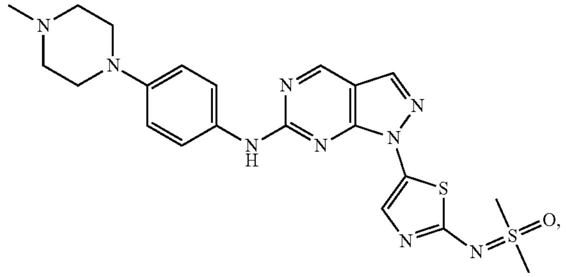
, -continued
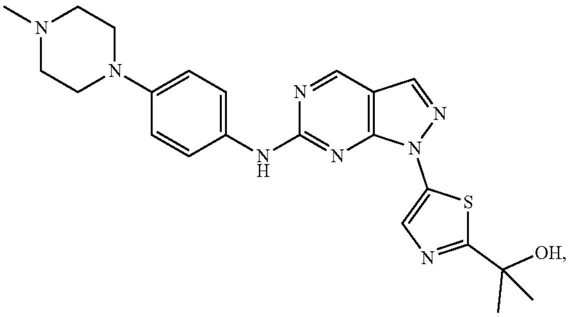
,
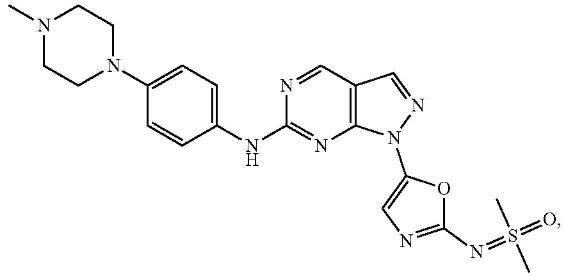
,
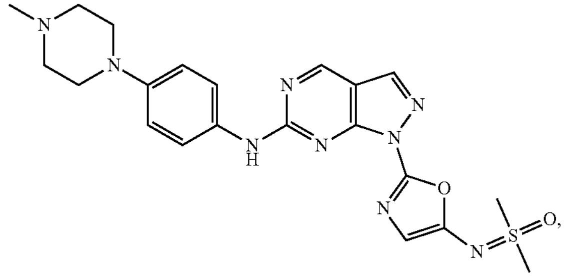
,
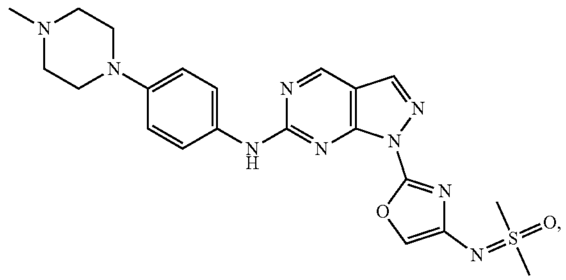
,
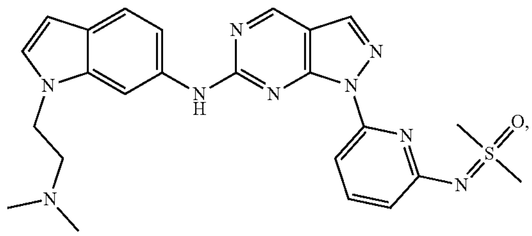
,
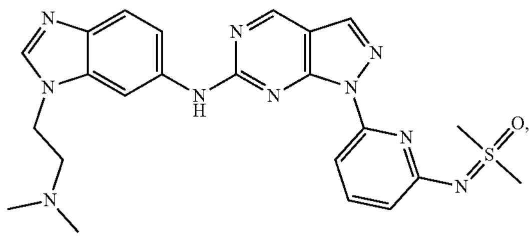
,
-continued
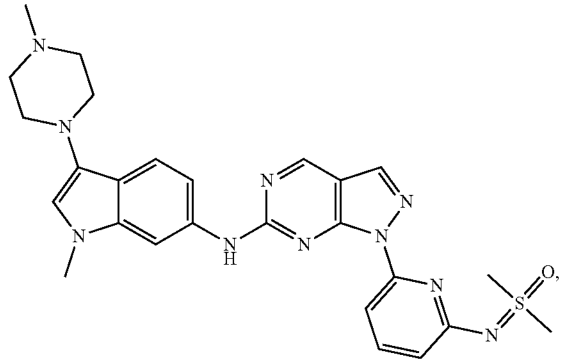
,
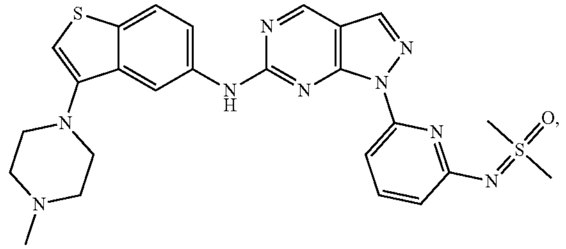
,
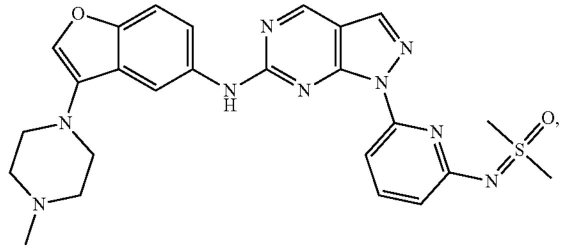
,
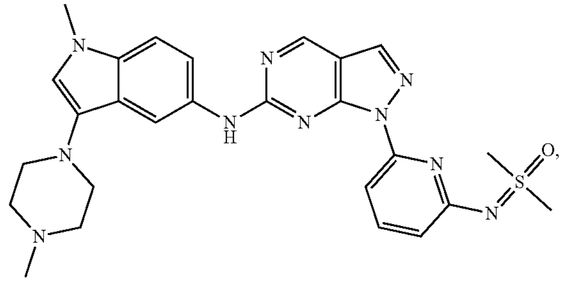
,
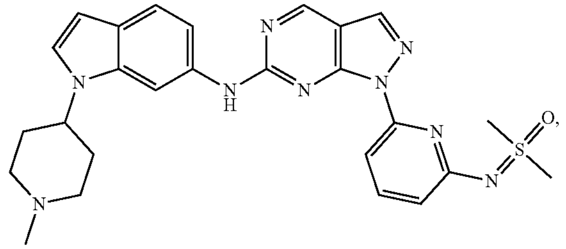
, -continued
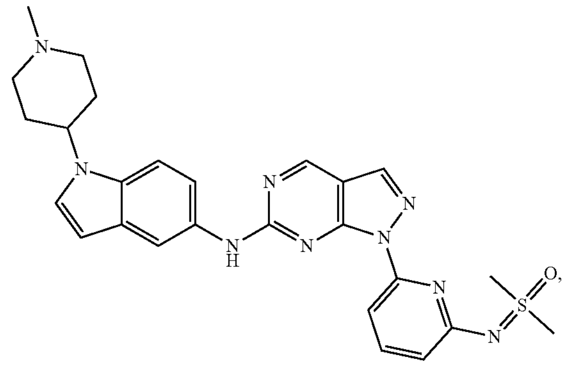
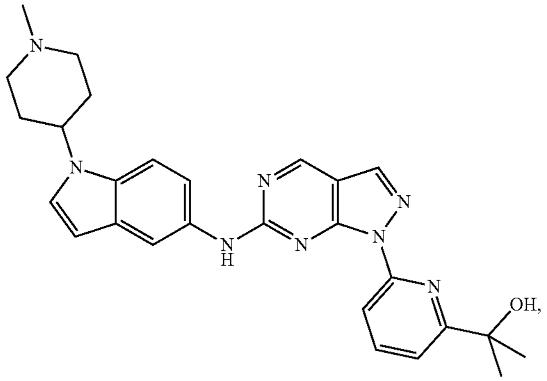
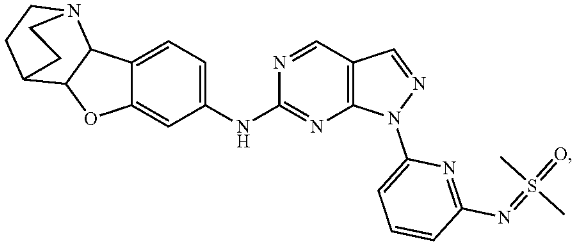
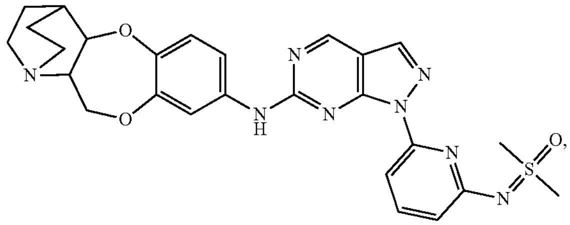
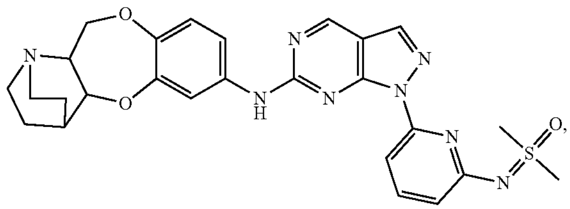
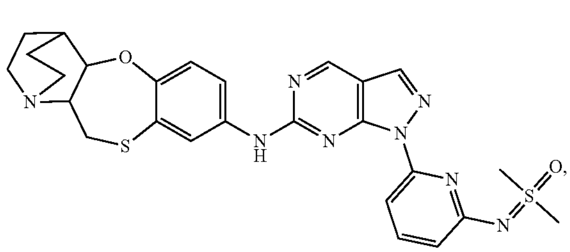
-continued
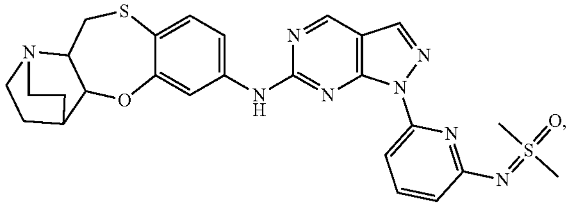
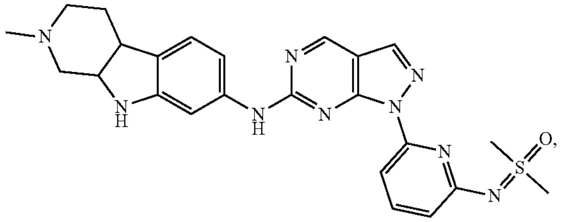
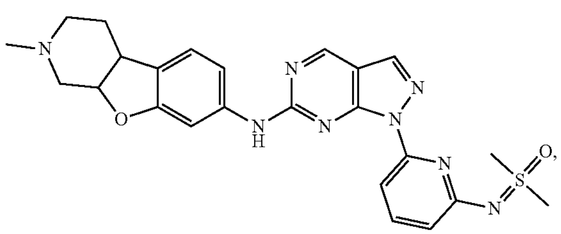
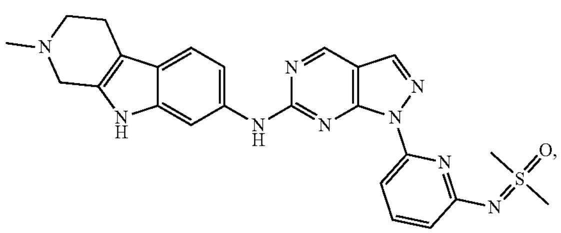
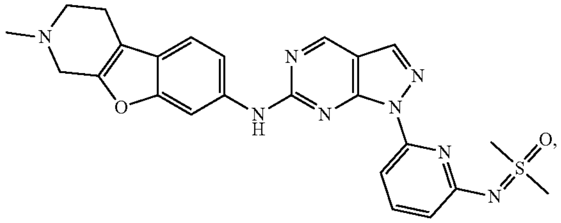
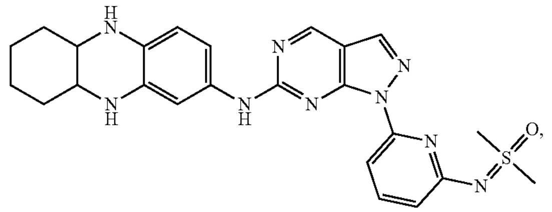
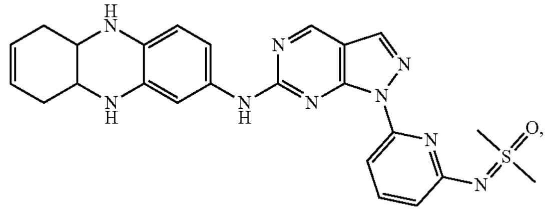

-continued
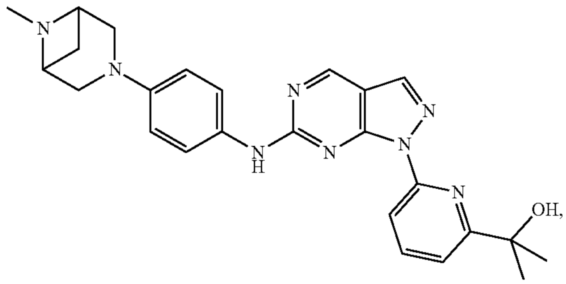
,
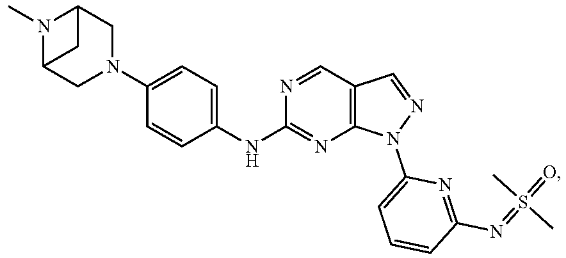
,
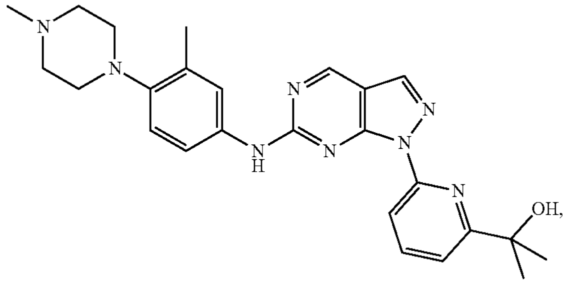
,
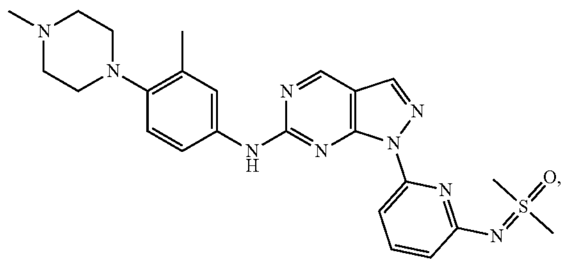
,
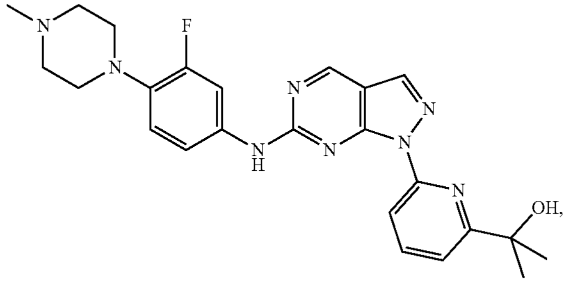
,
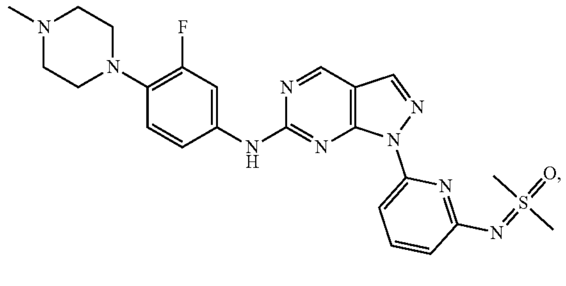
,
-continued
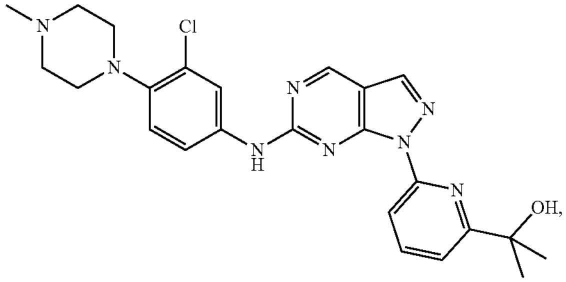
,
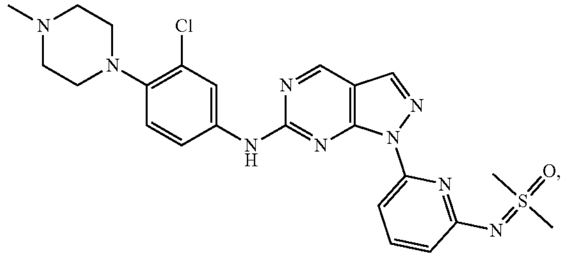
,
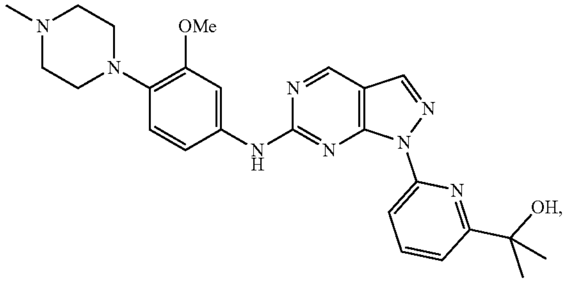
,
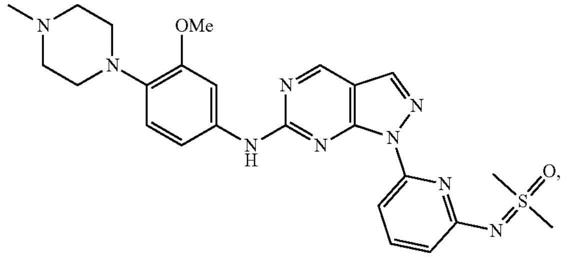
,
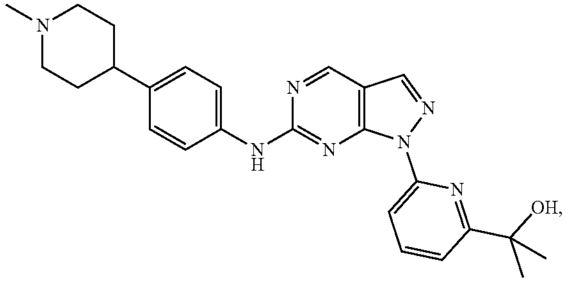
,
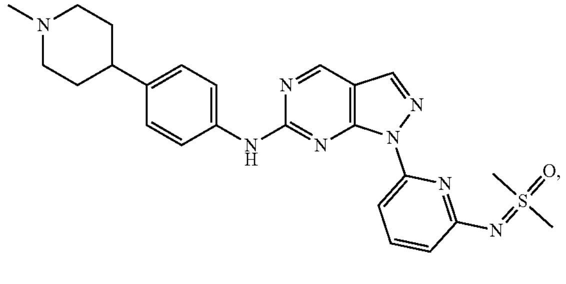
, -continued
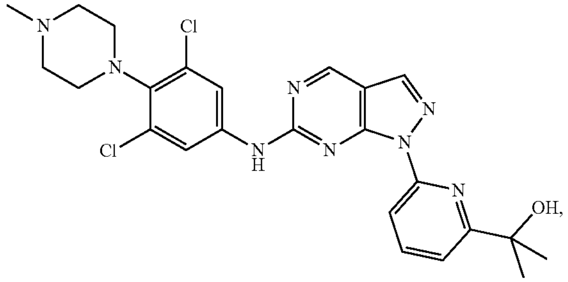
,
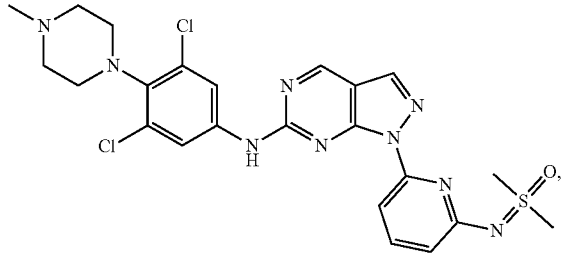
,
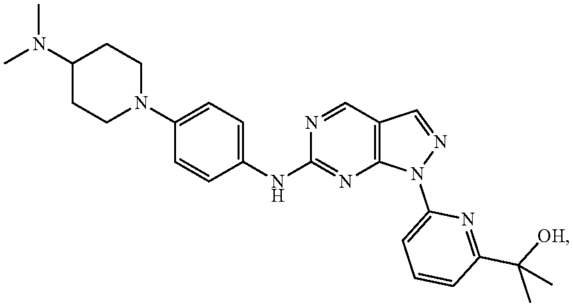
,
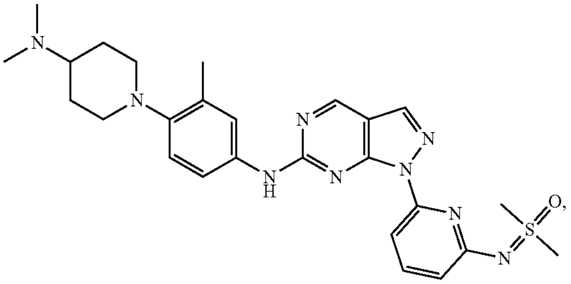
,
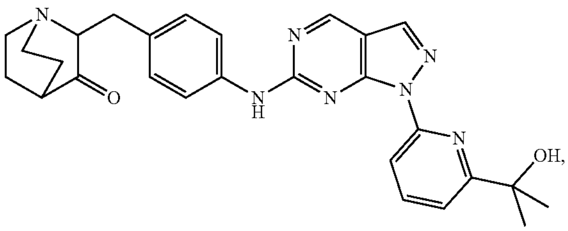
,
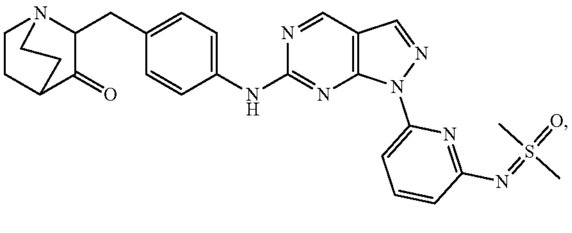
,
-continued
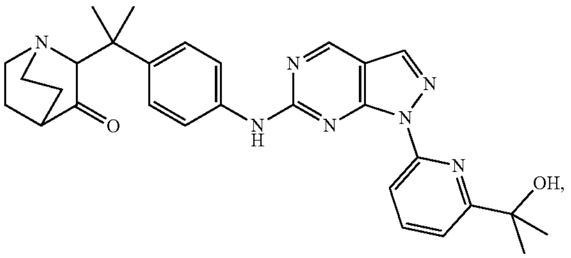
,
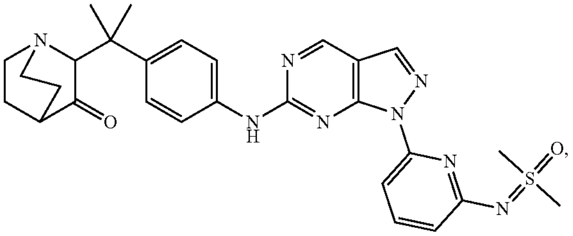
,
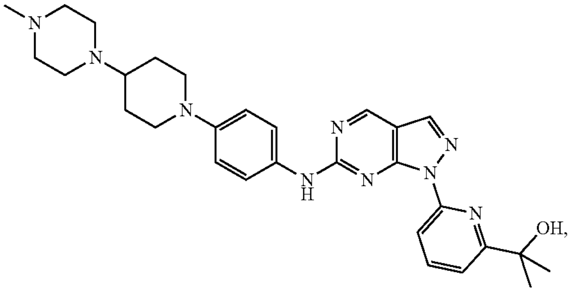
,
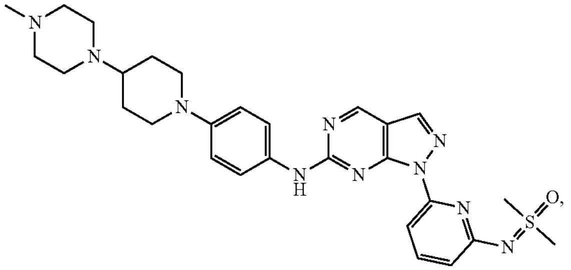
,
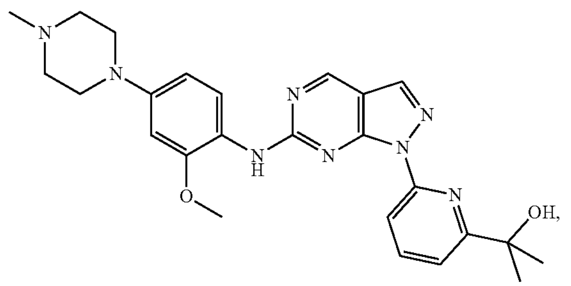
,
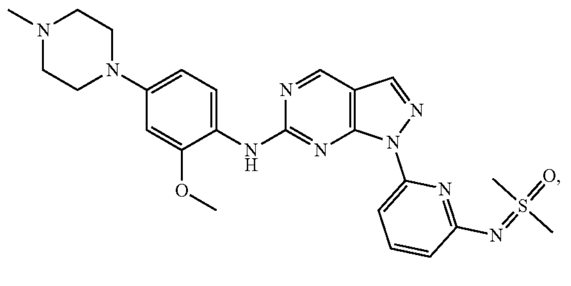
, -continued
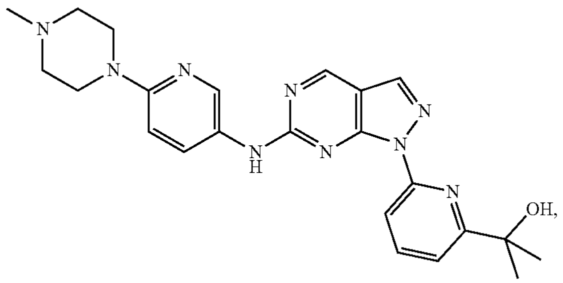
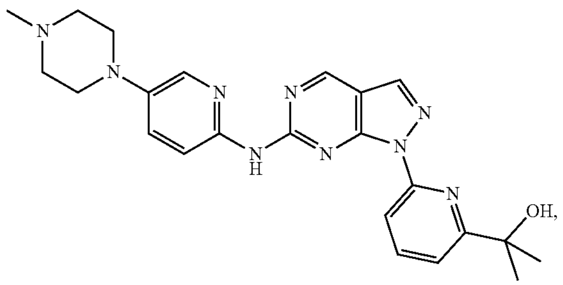
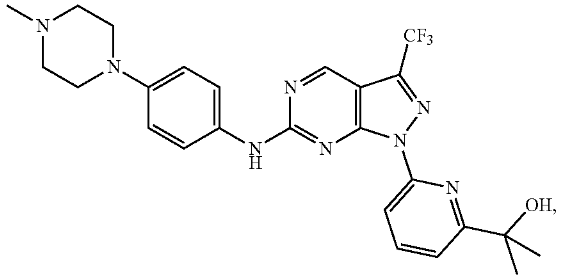
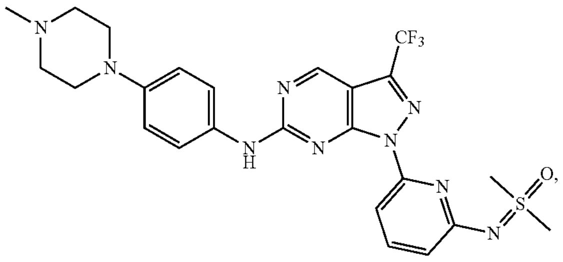
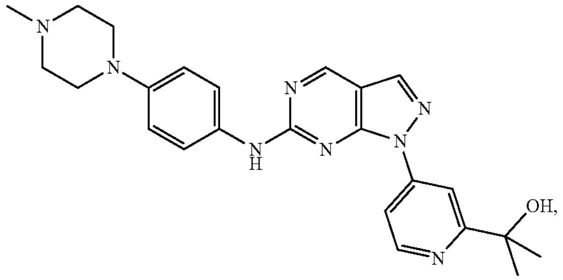
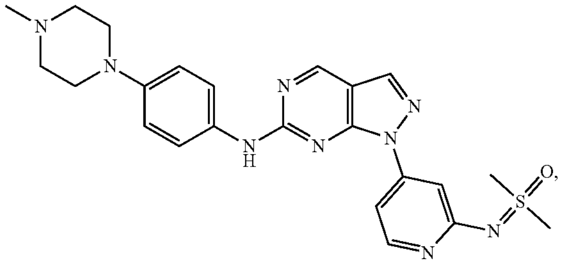
-continued
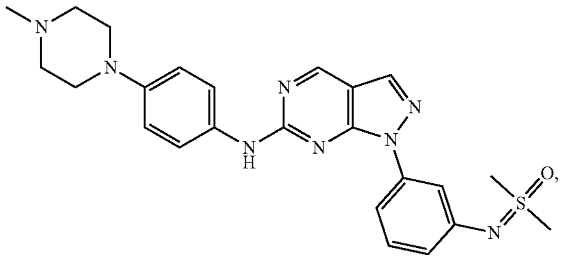
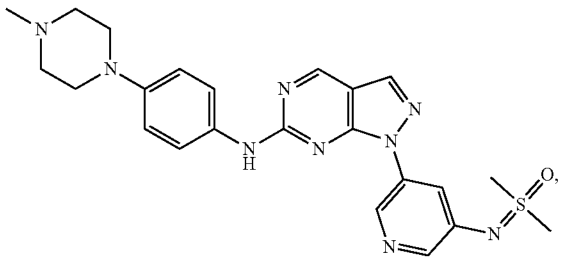
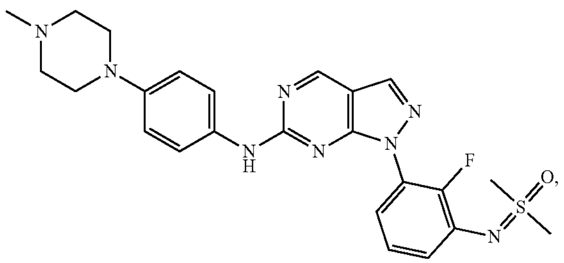
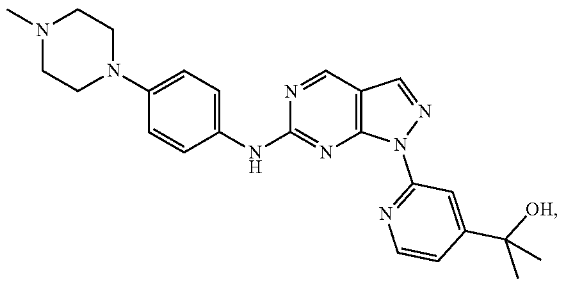
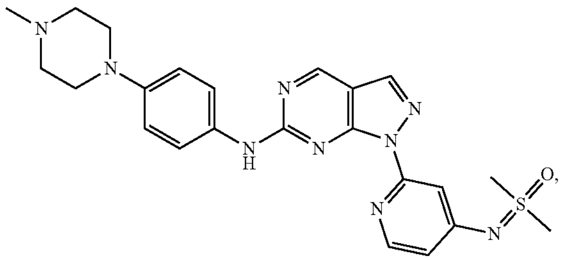
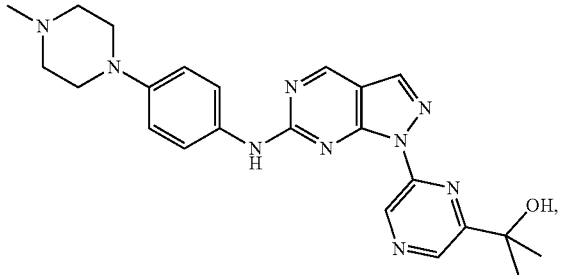

-continued
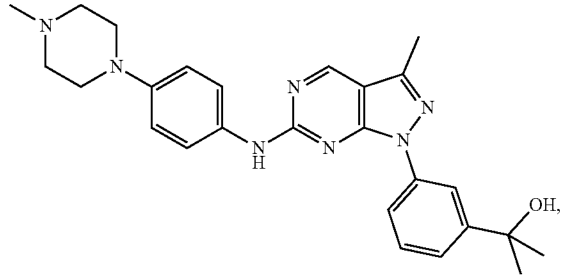
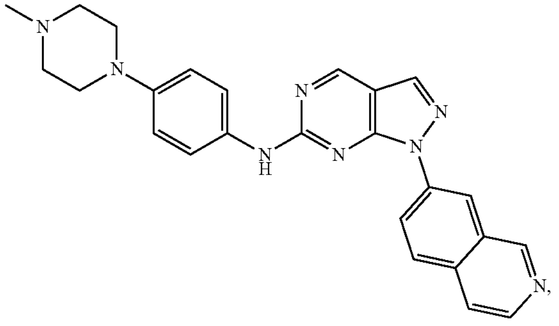
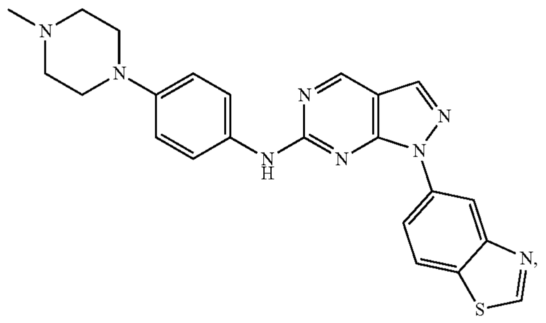
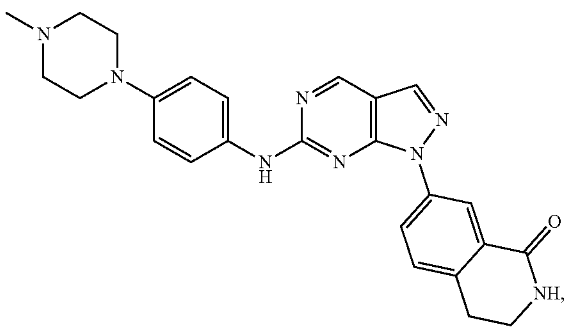
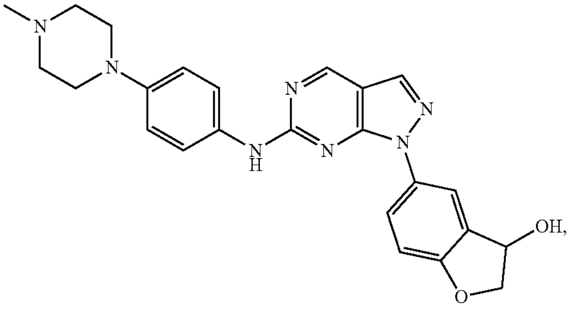
-continued
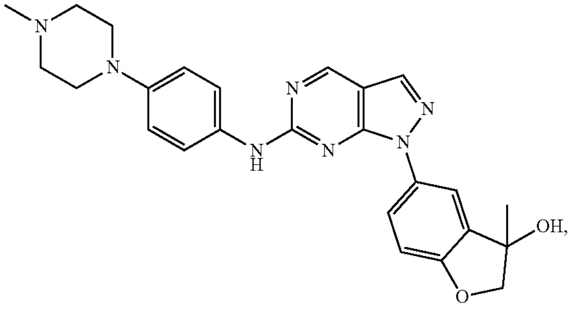
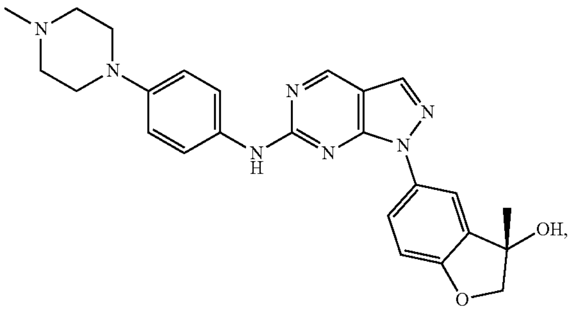
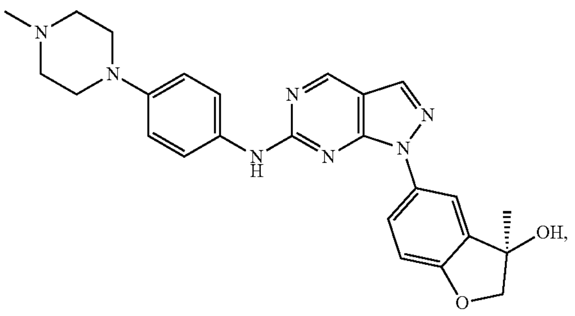
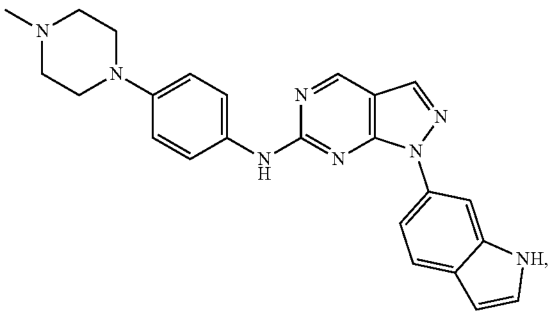
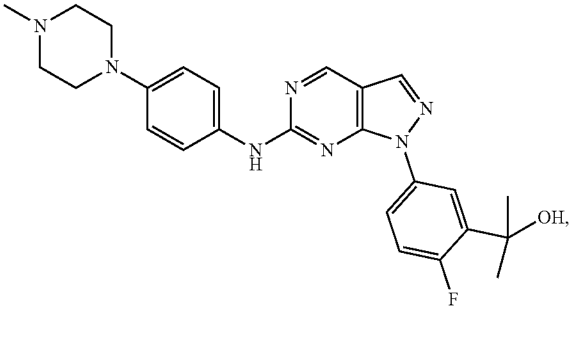

-continued
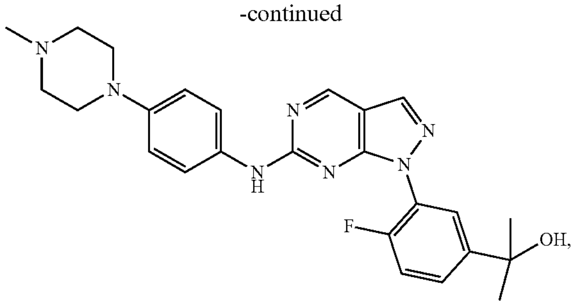
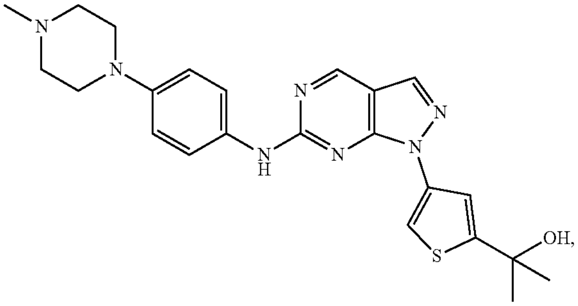
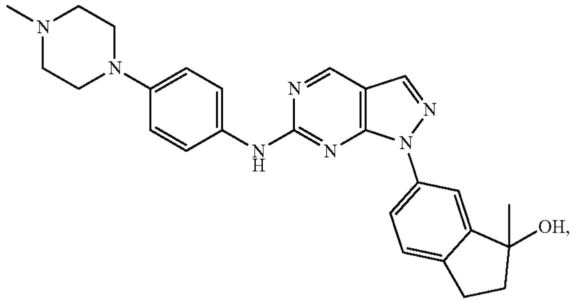
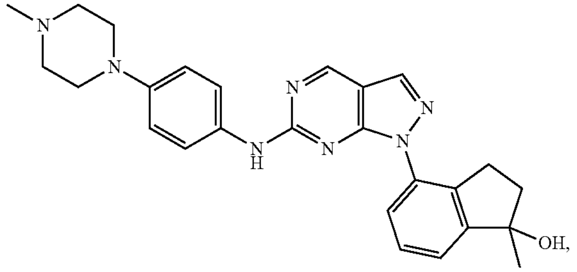
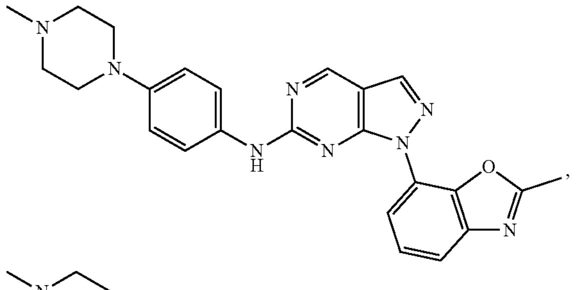
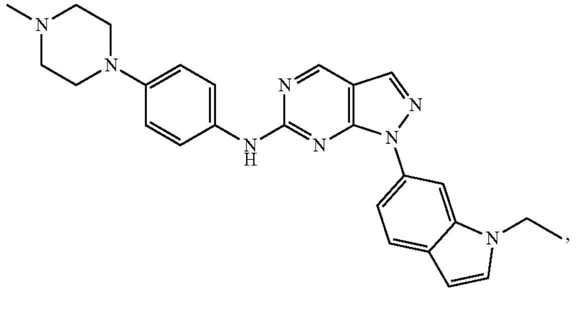
-continued
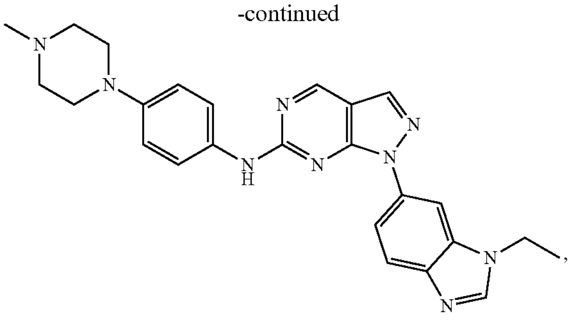
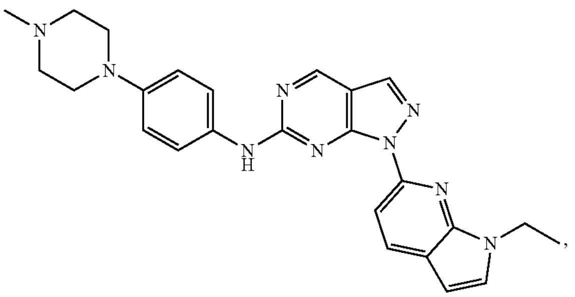
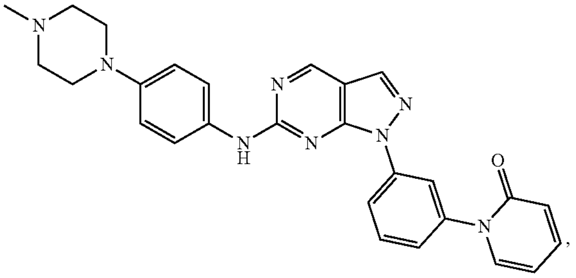
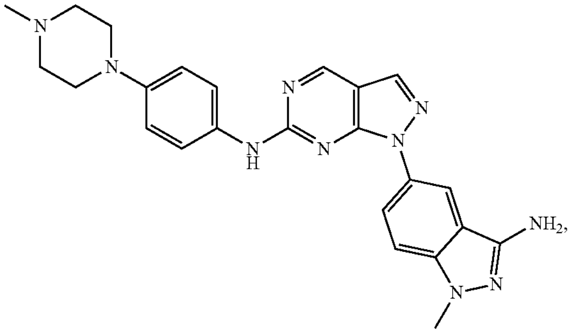
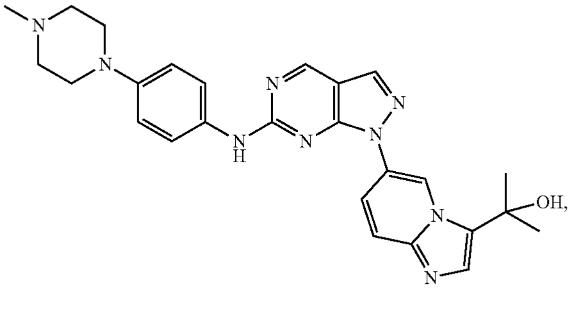

-continued
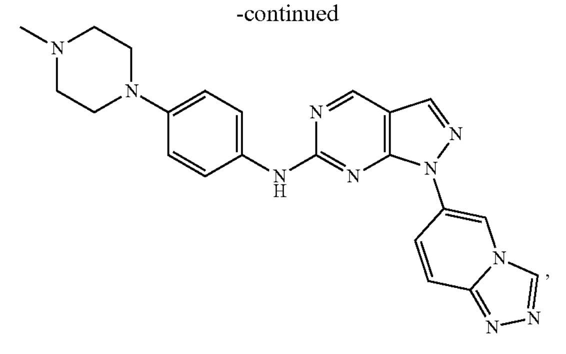
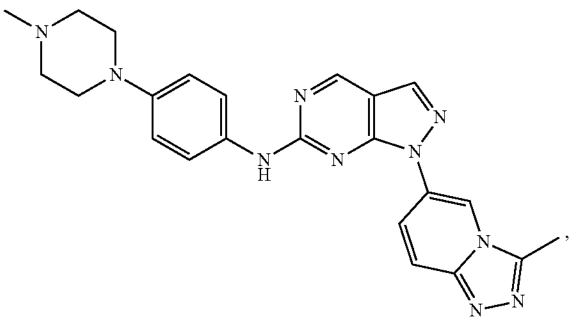
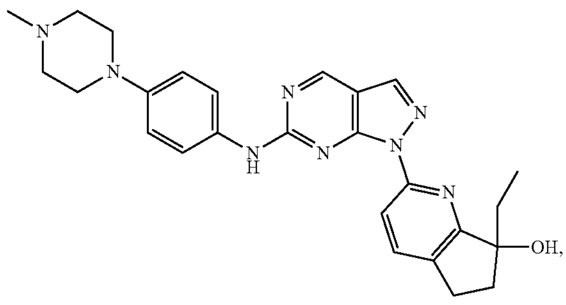
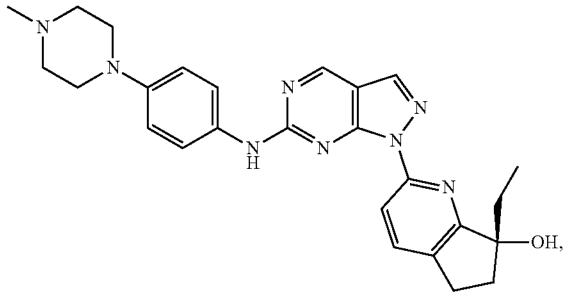
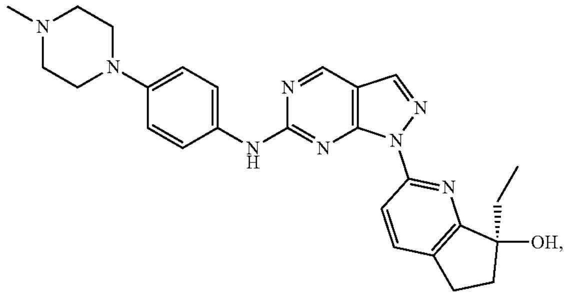
-continued
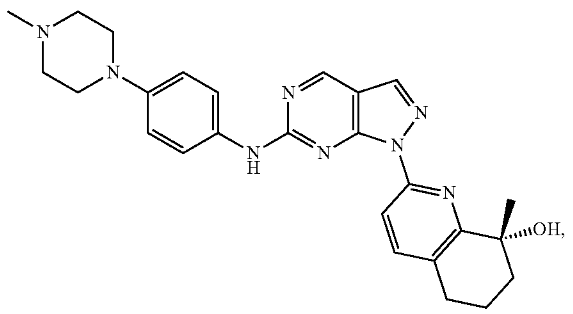
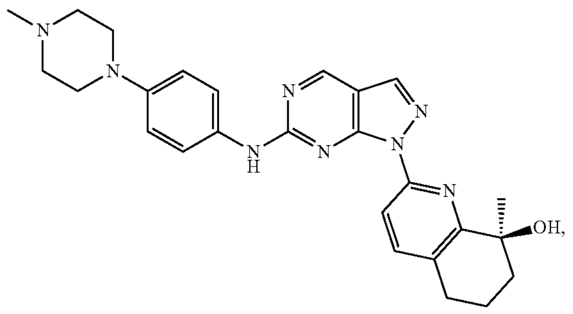
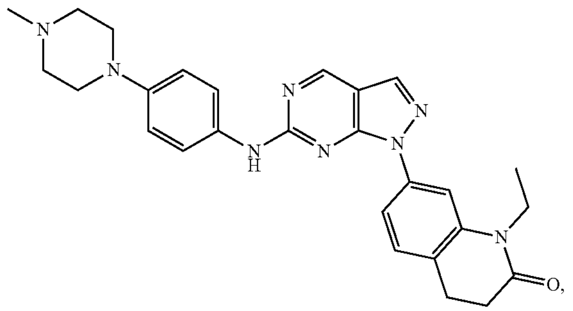
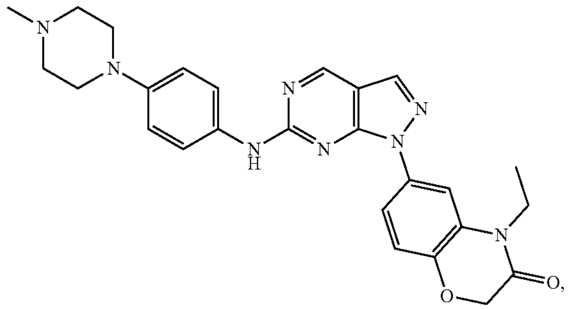
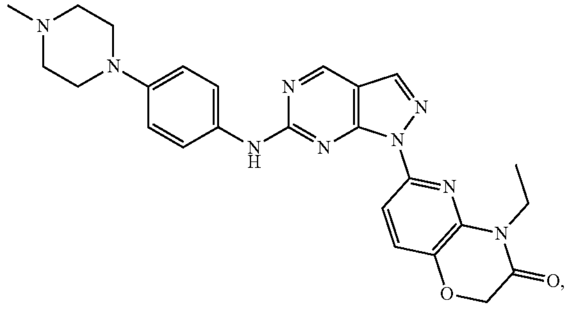

-continued

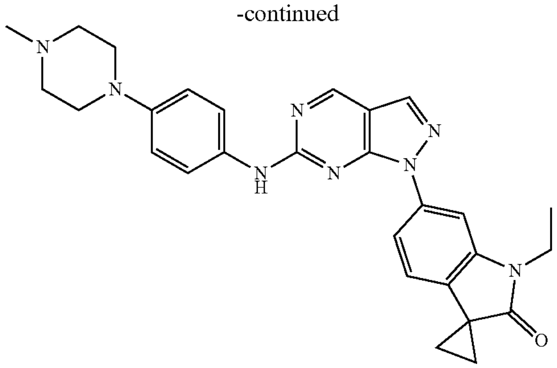

,

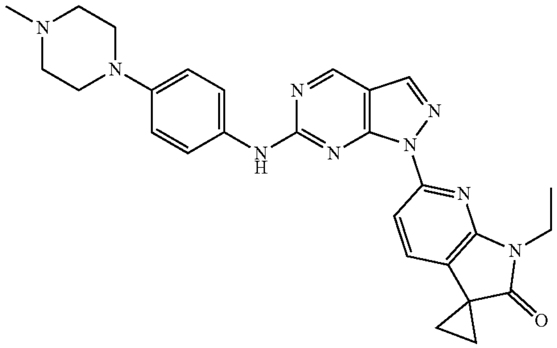

.

The present invention further provides the use of any of the abovementioned compound, or a deuterated compound thereof, or a stereoisomer thereof, or a pharmaceutically acceptable salt thereof in the preparation of a Wee1 inhibitor.

The present invention further provides the use of any of the abovementioned compound, or a deuterated compound thereof, or a stereoisomer thereof, or a pharmaceutically acceptable salt thereof in the preparation of a medicament for preventing and/or treating cancer.

The present invention further provides a pharmaceutical composition, comprising a formulation formed by any of the abovementioned compound, or a deuterated compound thereof, or a stereoisomer thereof, or a pharmaceutically acceptable salt thereof.

The above pharmaceutical composition further comprises a pharmaceutically acceptable carrier, excipient, vehicle.

Compound and derivatives provided in the present invention can be named according to IUPAC (International Union of Pure and Applied Chemistry) or CAS (Chemical Abstracts Service, Columbus, OH) nomenclature system.

Definition of terms used in the present invention: Unless otherwise specified, the initial definition provided by the group or term herein is applicable to the group or term in the whole specification. For terms that are not specifically defined herein, they should be given meanings that can be given by those skilled in the art according to the disclosure and context.

"Substitution" means that the hydrogen atom in the molecule is replaced by other different atoms or groups; or that the lone pair of the atom in the molecule is replaced by other atoms or groups, for example, the lone pair on the S atom can be replaced by the O atom to form

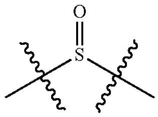

or

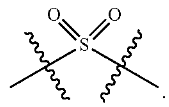

.

"Optionally substituted" means that "substitution" can occur, but does not have to occur, which includes the situations where it occurs or not.

The minimum and maximum values of the carbon atom content in the hydrocarbon group are indicated by prefixes. For example, the prefix $C_{a\sim b}$ alkyl indicates any alkyl group containing "a" to "b" carbon atoms. Therefore, for example, $C_{1\sim 6}$ alkyl refers to alkyl groups containing 1~6 carbon atoms.

"Alkyl" refers to a saturated hydrocarbon chain with a specified number of member atoms. Alkyl groups can be linear or branched. A representative branched alkyl group has one, two or three branches. Alkyl groups can be optionally substituted by one or more substituents as defined herein. Alkyl includes methyl, ethyl, propyl (n-propyl and isopropyl), butyl (n-butyl, isobutyl and tert-butyl), pentyl (n-pentyl, isopentyl and neopentyl) and hexyl. Alkyl group can also be a part of other groups, said other group is for example —O($C_{1\sim 6}$ alkyl).

"Alkylene" refers to a divalent saturated aliphatic hydrocarbonyl group with a specified number of member atoms. $C_{a\sim b}$ alkylene refers to an alkylene group with a to b carbon atoms. Alkylene groups include branched and linear hydrocarbonyl groups. For example, the term "propylene" can be exemplified by the following structure:

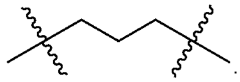 [SMILES: *CCC*]

.

Similarly, the term "dimethylbutylene" can be exemplified by any of the following structures:

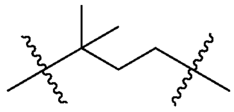

or

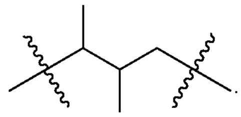

.

—$C_{0\text{-}4}$ alkylene in the present invention can be $C_0$ alkylene, $C_1$ alkylene (for example —$CH_2$—), $C_2$ alkylene (for example —$CH_2CH_2$—, etc.), $C_3$ alkylene or $C_4$ alkylene. $C_0$ alkylene refers to the groups herein connecting by a chemical bond. For example, A-$C_0$ alkylene-B refers to A-B, that is, A group and B group are directly connected by a chemical bond.

"Carbocyclyl" in the present invention refers to a saturated or non-aromatic partially saturated cyclic group having multiple carbon atoms and no cyclic heteroatoms, and having a single ring or multiple rings (fused, bridged, spiro). The term "carbocyclyl" includes cycloalkenyl group, such as, cyclohexenyl. Monocyclic-carbocyclyl group is exemplified by for example cyclopropyl, cyclobutyl, cyclohexyl, cyclopentyl, cyclooctyl, cyclopentenyl and cyclohexenyl. Fused-carbocyclyl system carbocyclyl group is exemplified by bicyclohexyl, bicyclopentyl, bicyclooctyl, etc., with tw kinds of bicycloalkyl polycyclic structures listed and named below:

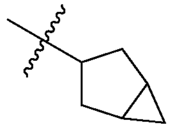 [SMILES: *C1CC2CC2C1]

bicyclohexyl and

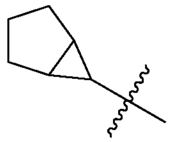 [SMILES: *C1C2CCCC12]

bicyclohexyl. Bridged-carbocyclyl system carbocyclyl group is exemplified by

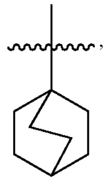,
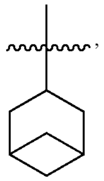, adamantyl, etc. Spiro-carbocyclyl system carbocyclyl group is exemplified by

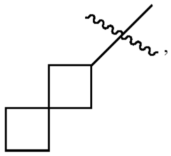,
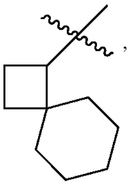, etc. The term "carbocyclyl" further includes the situation of partially saturated cyclic group formed by the fusion of an aromatic ring and a non-aromatic ring, wherein the attachment site can be located at a non-aromatic carbon atom or an aromatic carbon atom, exemplified by 1,2,3,4-tetrahydronaphthylene-5-yl, 5,6,7,8-tetrahydronaphthylene-5-yl.

Unsaturation in the present invention refers to a group or a molecule containing a carbon-carbon double bond, a carbon-carbon triple bond, a carbon-oxygen double bond, a carbon-sulfur double bond, a carbon-nitrogen triple bond, etc.

Furthermore, "heterocylcylalkyl" in the present invention refers to a saturated ring or non-aromatic partially saturated ring comprising at least one heteroatoms and having a single ring or multiple rings (fused, bridged, spiro); wherein the heteroatom refers to nitrogen atom, oxygen atom, sulfur atom, etc. It generally refers to a monovalent saturated or partially unsaturated monocyclic or polycyclic system comprising multiple cyclic atoms, comprising 1, 2 or 3 cyclic heteroatoms selected from a group consisting of N, O and S, with the remaining cyclic atoms being carbon. Monocyclic heterocylcylalkyl system heterocylcylalkyl group is exemplified by oxetanyl, azetidinyl, pyrrolidinyl, 2-oxo-pyrrolidine-3-yl, tetrahydrofuranyl, tetrahydro-thienyl, pyrazolidinyl, imidazolidinyl, thiazolidinyl, piperidinyl, tetrahydropyranyl, tetrahydrothiopyranyl, piperazinyl, morpholinyl, thiomorpholinyl, 1,1-dioxo-thiomorpholine-4-yl, azepanyl, diazepanyl, homopiperazinyl or oxazepanyl, etc. Fused-heterocylcylalkyl system heterocylcylalkyl group is exemplified by 8-aza-bicyclo[3.2.1]octyl, quinuclidinyl, 8-oxa-3-aza-bicyclo[3.2.1]octyl, 9-aza-bicyclo[3.3.1]nonyl, etc. Bridged-heterocylcylalkyl system heterocylcylalkyl group is exemplified by

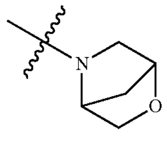,
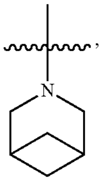,
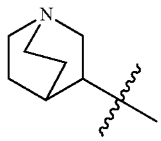, etc. Spiro-heterocylcylalkyl system heterocylcylalkyl group is exemplified by

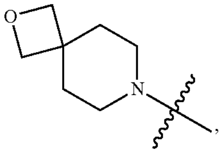,
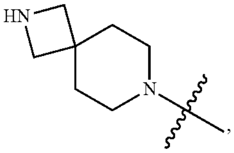, etc. Partially saturated heterocylcylalkyl is exemplified by dihydrofuranyl, imidazolinyl, tetrahydro-pyridinyl or dihydropyranyl, etc. The term "heterocylcylalkyl" further includes the situation of partially saturated cyclic group formed by the fusion of an aromatic ring and a non-aromatic ring, wherein the attachment site can be located at a non-aromatic carbon atom, an aromatic carbon atom or a heteroatom, exemplified by

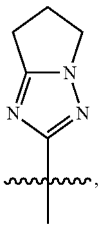,
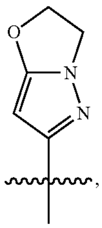,
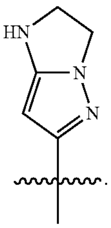.

"Aromatic cyclic group" in the present invention refers to an aromatic hydrocarbonyl group having multiple carbon atoms. Aryl generally refers to a monocyclic, bicyclic or tricyclic aryl group having multiple carbon atoms. Furthermore, the term "aryl" used herein can be a single aromatic ring, or an aromatic substitutent formed by the fusion of multiple aromatic rings. Non-limiting examples include phenyl, naphthylenyl or tetrahydronaphthylenyl.

"Aromatic heterocyclic group" in the present invention refers to an aromatic unsaturated ring comprising at least one heteroatoms, wherein the heteroatom refers to nitrogen atom, oxygen atom, sulfur atom, etc. It generally refers to an aromatic monocyclic or bicyclic hydrocarbon, comprising multiple cyclic atoms, wherein one or more cyclic atoms are heteroatoms selected from a group consisting of O, N, S. Preferable, it has one to three heteroatoms. Aromatic heterocyclic group is exemplified by pyridinyl, indolyl, quinoxalinyl, quinolinyl, isoquinolinyl, benzothienyl, benzofuranyl, benzothienyl, benzopyranyl, benzothiopyranyl, furanyl, pyrrolyl, thiazolyl, oxazolyl, isoxazolyl, triazolyl, tetrazolyl, pyrazolyl, imidazolyl, thienyl, oxadiazolyl, benzimidazolyl, benzothiazolyl, benzoxazolyl.

"Halogen" in the present invention refers to fluorine, chlorine, bromine or iodine.

"Halogen substituted alkyl" in the present invention refers to an alkyl wherein one or more hydrogen atoms are replaced by halogen; for example monofluoromethyl, difluoromethyl, trifluoromethyl.

"Deuterated alkyl" in the present invention refers to an alkyl wherein one or more hydrogen atoms are replaced by deuterium; for example trideuteromethyl.

"—OR", "—NRR" or the like in the present invention refers to an R group and oxygen atom or nitrogen atoms connected by a single bond.

The oxygen atoms in "—C(O)R", "—S(O)$_2$R" or the like in the present invention are connected with the carbon atoms or sulfur atoms by a double bond, wherein the R group and oxygen atom or sulfur atom are connected by a single bond. For example, "—S(O)(NH)R" refers to an oxygen atom and a nitrogen atom connected with a sulfur atom by a double bond, and an R group and a sulfur atom connected by a single bond.

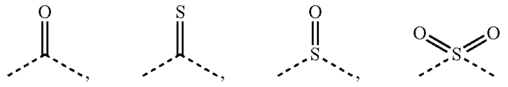

in the present invention refers to an oxygen atom, a sulfur atom connected to the substitution site by a double bond.

"---", "" described in the present invention group is used to described the substitution site of the groups.

"Deuterated compound" in the present invention refers to a molecule wherein one or more hydrogen atoms in the molecule or group are replaced by deuterium atoms, and the proportion of deuterium atoms is greater than the abundance of deuterium in nature.

The term "pharmaceutically acceptable" refers to a medium, carrier, diluent, excipient, and/or a salt formed thereby chemically or physically compatible with other components constituting a pharmaceutical dosage form and physiologically compatible with the receptor.

The term "salt" and "pharmaceutically acceptable salt" refers to an acidic and/or basic salt formed by the abovementioned compound or a stereoisomer thereof, and inorganic and/or organic acid and base, also including zwitterionic salts (internal salts), also including quaternary ammonium salt, for example alkylammonium salt. These salts can be directly obtained in the final separation and purification of the compound. Alternatively, they can be obtained by mixing the abovementioned compound, or a stereoisomer thereof, and a certain amount of acid or base appropriately (for example in same equivalence). These salts may form precipitates in the solution and be collected by filtration, or be recovered after solvent evaporation, or be prepared by freeze-drying after reaction in water medium. Said salt in the present invention can be compound hydrochloride salt, sulfate salt, citrate salt, benzene sulfonate salt, hydrobromide salt, hydrofluoride salt, phosphorate salt, acetate salt, propionate salt, succinate salt, oxalate salt, malate salt, succinate salt, fumarate salt, maleate salt, tartarate salt or trifluoroacetate salt.

In some embodiments, one or more compounds of the present invention can be used in combination with each other. Alternatively, the compound of the present invention can be used in combination with any other active agents. It is used to prepare drugs or pharmaceutical compositions for regulating cell functions or treating diseases. If a group of compounds are used, these compounds can be administered to the subjects simultaneously, separately and orderly.

Obviously, according to the above content of the present invention, according to the common technical knowledge and common means in this field, and without departing from the above basic technical idea of the present invention, other various forms of modification can be made to replace or change.

In the following, the above content of the present invention will be further explained in detail through the concrete implementation in the form of examples. However, it should not be understood that the scope of the above theme of the present invention is limited to the following examples. All technologies realized based on the above content of the present invention belong to the scope of the present invention.

DETAILED DESCRIPTION OF THE PREFERRED EMBODIMENTS

The structure of the compound was determined by nuclear magnetic resonance (NMR) and mass spectrometry (MS). The NMR shift (δ) was given in units of $10^{-6}$ (ppm). The NMR was measured by (Bruker Avance III 400 and Bruker Avance 300) nuclear magnetic apparatus. Deuterated methyl sulfoxide (DMSO-$d_6$), deuterated chloroform ($CDCl_3$) and deuterated methanol ($CD_3OD$) were used as the charaterization solvents, and tetramethylsilane (TMS) was used as the internal standard.

The LC-MS was determined by Shimadzu LC-MS 2020 (ESI). The HPLC was determined by Shimadzu LC-20A. MPLC (medium pressure preparative chromatography) was conducted by Gilson GX-281 reverse phase preparative chromatography. Yantai Huanghai HSGF254 or Qingdao GF254 silica gel plate was used as the silica gel plate for thin-layer chromatography, and the specification of thin-layer chromatography separation and purification products was 0.4 mm~0.5 mm. Column chromatography generally used Yantai Huanghai silica gel 200~300 mesh silica gel as carrier.

The known starting materials of the present invention can be synthesized by or according to the methods known in the field, or can be purchased from Anneiji Chemical, Chengdu Kelon Chemical, Shaoyuan Chemical Technology, Bailingwei Technology and other companies.

Unless otherwise specified in Examples, the reaction was carried out in nitrogen atmosphere. Unless otherwise specified in the examples, the solution refers to an aqueous solution. Unless otherwise specified in Examples, the reaction temperature was room temperature. Unless otherwise specified in Examples, M refers to mole per liter.

Unless otherwise specified in Examples, the HPLC test conditions were as follows:

Method A (Method A)

Column: Boston Green C18 150 mm*4.6 mm 5 μm; Mobile Phase A: 0.05% trifluoroacetic acid aqueous solution, Mobile Phase B: 0.05% trifluoroacetic acid acetonitrile solution; Gradient: 10 mins period Mobile Phase B from 5% to 95%, then kept at 95% for 5 mins; Flow rate: 1.5 mL/min; Column temperature: 40° C.

Method B (Method B)

Column: Boston Green CD18 150 mm*4.6 mm 5 μm; Mobile Phase A: 0.01M sodium bicarbonate aqueous solution, Mobile Phase B: acetonitrile; Gradient: 10 mins period Mobile Phase B from 5% to 95%, then kept at 95% for 5 mins; Flow rate: 1.5 mL/min; Column temperature: 40° C.

Example 1: Synthesis of Compound 1

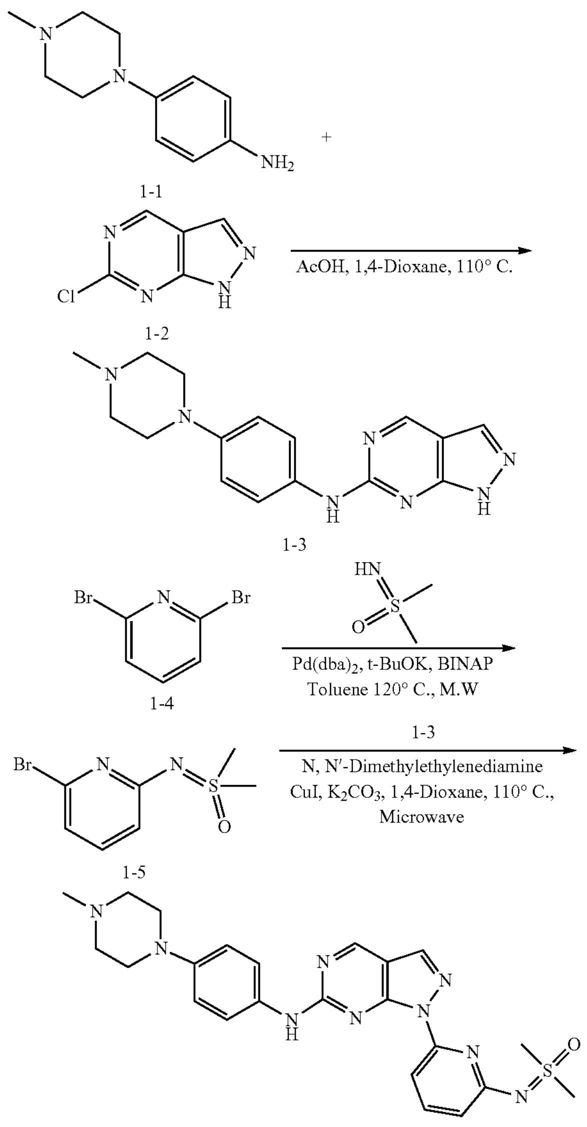

1-1
1-2
1-3
1-4
1-5
1

Step 1: Synthesis of Compound 1-3:

A dry single-necked flask was added with substrate 1-1 (247.51 mg, 1.29 mmol), 1-2 (200 mg, 1.29 mmol), and the mixture was dissolved with acetic acid (2 mL) and 1,4-dioxane (2 mL), and was heated to 110° C. and stirred overnight, monitored by LC-MS. After the reaction was completed, the reaction was extracted three times with water and ethyl acetate, and the organic phase was dried by anhydrous sodium sulfate, and then concentrated under reduced pressure, and the residue was purified by column chromatography to give product 1-3 (400 mg, 1.29 mmol).

Step 2: Synthesis of Compound 1-5:

A dried microwave tube was added with substrate 1-4 (2 g, 8.44 mmol), dimethylsulfoximide (786.42 mg, 8.44 mmol), Pd(dba)$_2$ (48.55 mg, 84.43 μmol), BINAP (52.57 mg, 84.43 μmol), potassium tert-butoxide (1.89 g, 16.89 mmol), and the mixture was added with toluene (10 mL) and dissolved, and the mixture was reacted with the protection of nitrogen under microwave at 120° C. for 30 min, monitored by LC-MS. After the reaction was completed, the reaction was extracted three times with water and ethyl acetate, and the organic phase was dried by anhydrous sodium sulfate, and then concentrated under reduced pressure, and the residue was purified by column chromatography to give product 1-5 (800 mg, 3.21 mmol).

Step 3: Synthesis of Compound 1:

A dried microwave tube was added with substrate 1-5 (109.92 mg, 441.22 μmol), 1-3 (105 mg, 339.40 μmol), N,N'-diethyl ethylenediamine (78.88 mg, 678.80 μmol), CuI (64.64 mg, 339.40 μmol), $K_2CO_3$ (65.57 mg, 475.16 μmol), and the mixture was added with 1,4-dioxane (3 mL) and dissolved, and the mixture was reacted with the protection of nitrogen under microwave at 110° C., monitored by LC-MS. After the reaction was completed, the reaction was extracted three times with water and ethyl acetate, and the organic phase was dried by anhydrous sodium sulfate, and then concentrated under reduced pressure, and the residue was purified by column chromatography to give product 1 (23 mg, 48.16 μmol). $^1H$ NMR (400 MHz, Methanol-$d_4$) δ 8.94 (s, 1H), 8.20 (s, 1H), 7.82 (t, J=8.0 Hz, 1H), 7.71 (d, J=7.6 Hz, 1H), 7.64 (d, J=8.6 Hz, 2H), 7.03 (d, J=8.5 Hz, 2H), 6.81 (d, J=7.7 Hz, 1H), 3.80 (d, J=12.7 Hz, 2H), 3.61 (d, J=12.2 Hz, 2H), 3.47 (d, J=8.6 Hz, 6H), 3.29-3.23 (m, 2H), 3.03 (s, 2H), 2.98 (s, 3H). LCMS ($ESI^+$) m/z: 478.3 $[M+H]^+$, HPLC Method A: $R_T$=4.44 min, purity: 99.9%.

Example 2: Synthesis of Compound 2

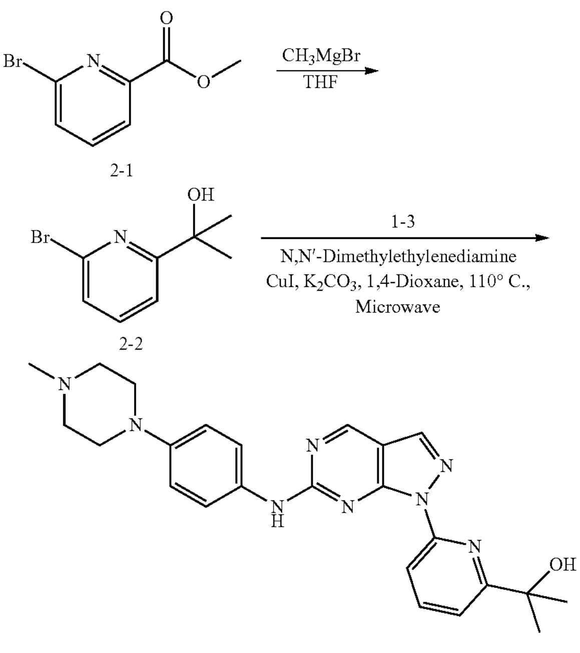

2-1
2-2
2

Step 1: Synthesis of Compound 2-2:

A dry single-necked flask was added with substrate 2-1 (15 g, 69.43 mmol), and the reaction was dissolved in THF (50 mL), and in ice bath, the mixture was added with methylmagnesium bromide (20.70 g, 173.59 mmol), and the reaction was conducted overnight under room temperature, monitored by LC-MS. After the reaction was completed, the reaction was extracted three times with water and ethyl acetate, and the organic phase was dried by anhydrous sodium sulfate, and then concentrated under reduced pressure, and the residue was purified by column chromatography to give product 2-2 (15 g, 69.42 mmol).

Step 2: Synthesis of Compound 2:

Following the synthesis method in the Example 1, Step 3, the synthesis method was conducted similarly by replacing Step 3 1-5 (109.92 mg, 441.22 umol) with 2-1 (45.40 mg, 210.11 umol), to give Compound 2 (10.2 mg, 22.95 μmol). $^{1}$H NMR (400 MHz, Methanol-$d_4$) δ 8.99 (s, 1H), 8.30 (s, 2H), 8.01 (d, J=7.4 Hz, 1H), 7.71 (d, J=8.8 Hz, 2H), 7.56 (d, J=7.6 Hz, 1H), 7.05 (d, J=8.7 Hz, 2H), 3.88-3.73 (m, 2H), 3.69-3.56 (m, 2H), 3.29-3.24 (m, 2H), 3.07 (d, J=12.2 Hz, 2H), 2.99 (s, 3H), 1.62 (s, 6H). LCMS ($ESI^+$) m/z: 445.4 $[M+H]^+$, HPLC Method A: $R_T$=4.83 min, purity: 99.9%.

Example 3: Synthesis of Compound 3

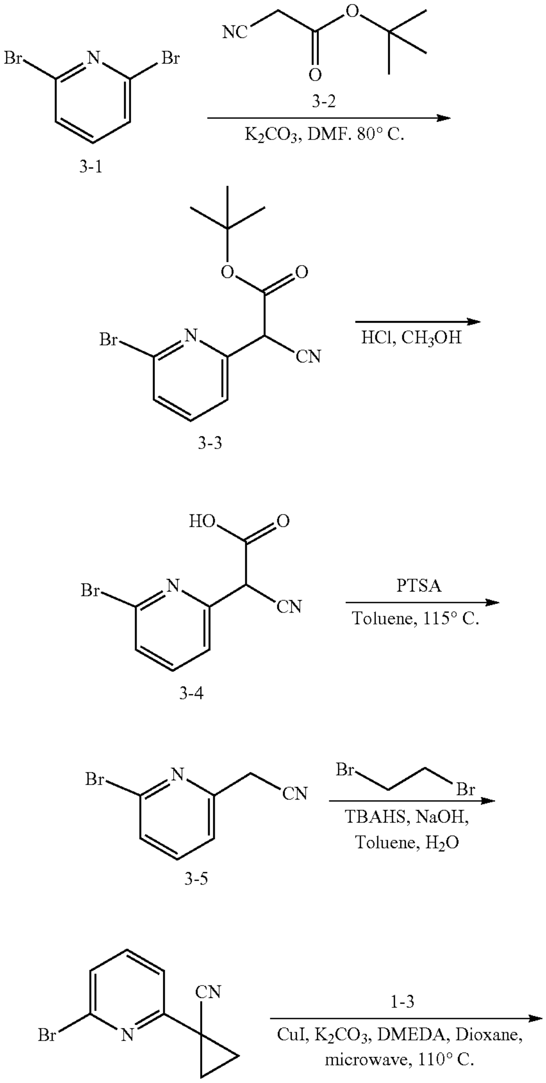

3-1, 3-2, 3-3, 3-4, 3-5, 3-6

-continued

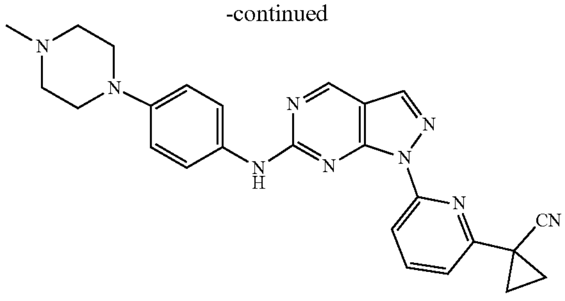

3

Step 1: Synthesis of Compound 3-3:

A dry single-necked flask was added with substrate 3-1 (3 g, 12.66 mmol), 3-2 (1.97 g, 13.93 mmol) and potassium carbonate (3.50 g, 25.33 mmol), and the reaction was dissolved in DMF (10 mL), heated to 80° C. and reacted overnight, monitored by LC-MS. After the reaction was completed, the reaction was extracted three times with water and ethyl acetate, and the organic phase was dried by anhydrous sodium sulfate, and then concentrated under reduced pressure, and the residue was purified by column chromatography to give product 3-3 (3 g, 10.10 mmol).

Step 2: Synthesis of Compound 3-4:

A dry single-necked flask was added with substrate 3-3 (3 g, 10.10 mmol), added with hydrochloric acid (368.11 mg, 10.10 mmol), and the reaction was dissolved in methanol (10 mL), under room temperature and reacted overnight, monitored by LC-MS. After the reaction was completed, the reaction was extracted three times with water and ethyl acetate, and the organic phase was dried by anhydrous sodium sulfate, and then concentrated under reduced pressure, and the residue was purified by column chromatography to give product 3-4 (2.4 g, 9.96 mmol).

Step 3: Synthesis of Compound 3-5:

A dry single-necked flask was added with substrate 3-4 (400 mg, 2.03 mmol), p-toluenesulfonic acid (171.46 mg, 995.68 μmol), and the mixture was added with toluene (10 mL) and dissolved, heated to 115° C. and reacted overnight, monitored by LC-MS. After the reaction was completed, the reaction was extracted three times with water and ethyl acetate, and the organic phase was dried by anhydrous sodium sulfate, and then concentrated under reduced pressure, and the residue was purified by column chromatography to give product 3-5 (400 mg, 2.03 mmol).

Step 4: Synthesis of Compound 3-6:

A dry single-necked flask was added with substrate 3-5 (350 mg, 1.78 mmol), 1,2-dibromoethane (500.56 mg, 2.66 mmol), tetrabutylammonium sulfate (TBAHS, 120.44 mg, 355.27 μmol), NaOH (71.05 mg, 1.78 mmol), and the mixture was added with toluene (5 mL) and dissolved, and the reaction was conducted overnight with the protection of nitrogen and under room temperature, monitored by LC-MS. After the reaction was completed, the reaction was extracted three times with water and ethyl acetate, and the organic phase was dried by anhydrous sodium sulfate, and then concentrated under reduced pressure, and the residue was purified by column chromatography to give product 3-6 (366 mg, 1.64 mmol).

Step 5: Synthesis of Compound 3:

Following the synthesis method in the Example 1, Step 3, the synthesis method was conducted similarly by replacing Step 3 1-5 (109.92 mg, 441.22 μmol) with 3-6 (89.05 mg, 399.20 μmol), to give Compound 3 (30 mg, 66.44 μmol). $^{1}$H NMR (400 MHz, DMSO-$d_6$) δ 9.90 (s, 1H), 9.79 (s, 1H), 9.05 (d, J=0.9 Hz, 1H), 8.34 (d, J=0.9 Hz, 1H), 8.11 (t, J=7.9 Hz, 1H), 8.02 (d, J=8.0 Hz, 1H), 7.71 (d, J=8.7 Hz, 1H), 7.63 (d, J=7.6 Hz, 1H), 7.01 (d, J=8.6 Hz, 2H), 3.78 (d, J=12.7 Hz, 4H), 3.27-3.11 (m, 2H), 3.00-2.91 (m, 2H), 2.88 (s, 3H), 1.81 (d, J=4.2 Hz, 4H). LCMS ($ESI^+$) m/z: 452.4 $[M+H]^+$, HPLC Method A: $R_T$=5.54 min, purity: 99.9%.

Example 4: Synthesis of Compound 4

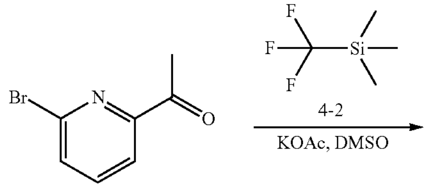

4-1

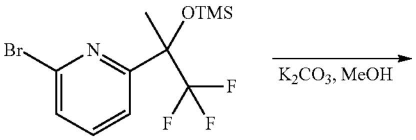

4-3

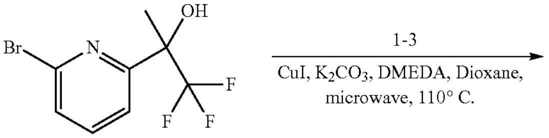

4-4

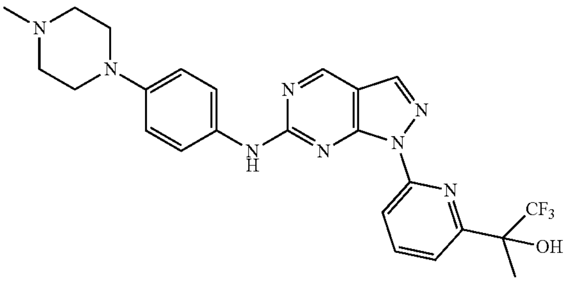

4

Step 1: Synthesis of Compound 4-3:

A dry single-necked flask was added with substrate 4-1 (10 g, 49.99 mmol), 4-2 (15.64 g, 109.98 mmol) and potassium acetate (4.90 g, 49.99 mmol) and the reaction was dissolved in DMSO (80 mL), under room temperature and stirred overnight, monitored by LC-MS. After the reaction was completed, the reaction was extracted three times with water and ethyl acetate, and the organic phase was dried by anhydrous sodium sulfate, and then concentrated under reduced pressure, and the residue was purified by column chromatography to give product 4-3 (17 g, 49.67 mmol).

Step 2: Synthesis of Compound 4-4:

A dry single-necked flask was added with substrate 4-3 (10 g, 49.99 mmol) and potassium carbonate (13.71 g, 99.35 mmol) and the reaction was dissolved in methanol (50 mL), under room temperature and stirred overnight, monitored by LC-MS. After the reaction was completed, the reaction was extracted three times with water and ethyl acetate, and the organic phase was dried by anhydrous sodium sulfate, and then concentrated under reduced pressure, and the residue was purified by column chromatography to give product 4-4 (13 g, 48.14 mmol).

Step 3: Synthesis of Compound 4:

Following the synthesis method in the Example 1, Step 3, the synthesis method was conducted similarly by replacing Step 3 1-5 (109.92 mg, 441.22 μmol) with 4-4 (113.48 mg, 420.21 μmol), to give Compound 4 (60 mg, 120.36 μmol). $^1H$ NMR (400 MHz, Methanol-$d_4$) δ 9.00-8.96 (m, 1H), 8.21 (s, 1H), 7.91-7.76 (m, 2H), 7.75-7.67 (m, 1H), 7.60-7.54 (m, 1H), 7.26-7.18 (m, 1H), 6.85-6.76 (m, 1H), 4.58-4.42 (m, 1H), 4.40-4.26 (m, 1H), 3.76 (s, 2H), 3.50 (s, 6H), 3.20 (s, 1H), 3.16-3.12 (m, 1H), 3.07 (s, 3H). LCMS ($ESI^+$) m/z: 499.5 $[M+H]^+$, HPLC Method A: $R_T$=5.85 min, purity: 99.7%.

Example 5: Synthesis of Compound 5

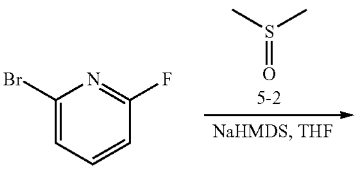

5-1

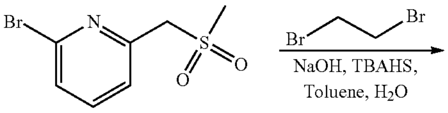

5-3

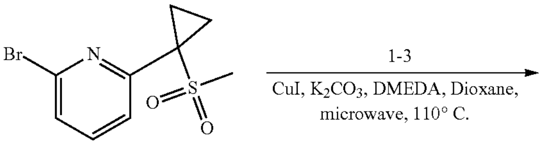

5-4

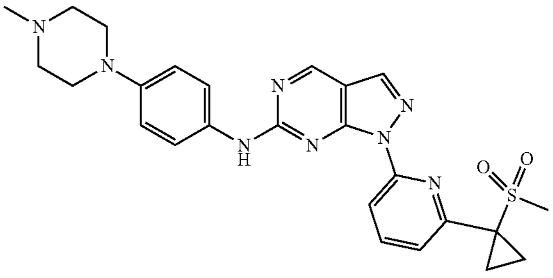

5

Step 1: Synthesis of Compound 5-3:

A dry single-necked flask was added with substrate 5-1 (5 g, 28.41 mmol) and the reaction was dissolved in THF (50 mL), NaHMDS (26.05 g, 142.06 mmol) and 5-2 (5.35 g, 56.82 mmol) added at −17° C. and under nitrogen protection, and the reaction was conducted at −17° C. for 1 h, monitored by LC-MS. After the reaction was completed, diluted by ethyl ether, and was added with water to extract three times, and the organic phase was dried by anhydrous sodium sulfate, and then concentrated under reduced pressure, and the residue was purified by column chromatography to give product 5-3 (6.18 g, 24.71 mmol).

Step 2: Synthesis of Compound 5-4:

A dry single-necked flask was added with substrate 5-3 (3 g, 11.99 mmol) and the reaction was dissolved in toluene (20 mL), was added with 1,2-dibromoethane (3.38 g, 17.99 mmol) and tetrabutylammonium bisulfate (TBAHS, 813.23 mg, 2.40 mmol), under room temperature and stirred overnight, monitored by LC-MS. After the reaction was completed, the reaction was extracted three times with water and ethyl acetate, and the organic phase was dried by anhydrous sodium sulfate, and then concentrated under reduced pressure, and the residue was purified by column chromatography to give product 5-4 (2.4 g, 8.69 mmol).

Step 3: Synthesis of Compound 5:

Following the synthesis method in the Example 1, Step 3, the synthesis method was conducted similarly by replacing Step 3 1-5 (109.92 mg, 441.22 μmol) with 5-4 (116.04 mg, 420.21 μmol), to give Compound 5 (20 mg, 39.63 μmol). $^1H$ NMR (400 MHz, DMSO-$d_6$) δ 9.91 (s, 1H), 9.73 (s, 1H), 9.07 (s, 1H), 8.37 (s, 1H), 8.20 (d, J=8.1 Hz, 1H), 8.16-8.07 (m, 1H), 7.71 (d, J=9.0 Hz, 1H), 7.62 (dd, J=7.5, 0.9 Hz, 1H), 7.02 (d, J=9.1 Hz, 1H), 3.78 (d, J=13.1 Hz, 2H), 3.54 (d, J=12.1 Hz, 2H), 3.20 (s, 3H), 3.24-3.12 (m, 2H), 2.96 (m, 2H), 2.87 (d, J=3.3 Hz, 3H), 1.75-1.67 (m, 2H), 1.63-1.54 (m, 2H). LCMS ($ESI^+$) m/z: 499.5 $[M+H]^+$, HPLC Method A: $R_T$=5.85 min, purity: 99.7%

Example 6: Synthesis of Compound 6

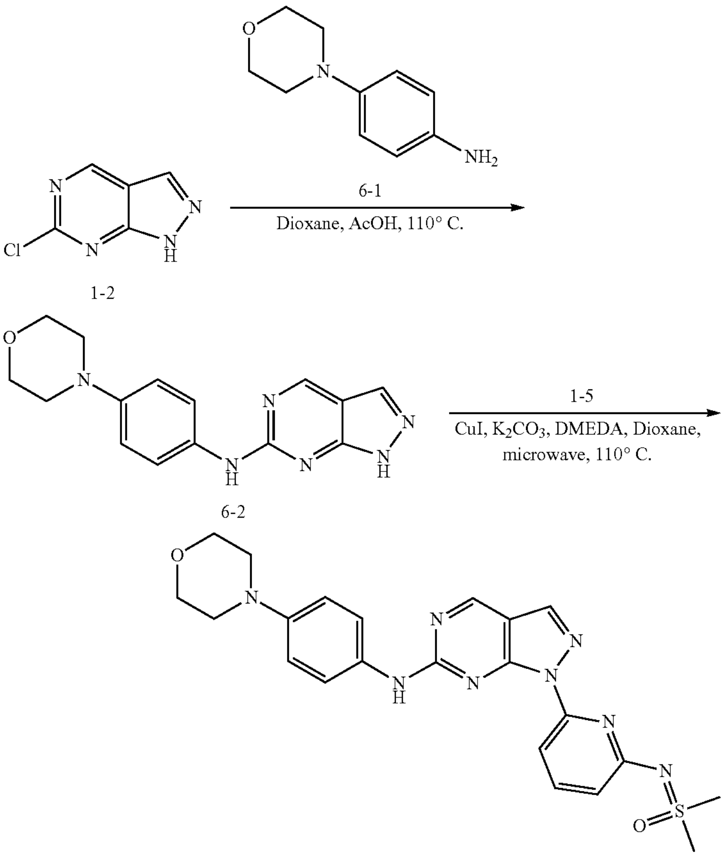

6-1

1-2

6-2

6

Step 1: Synthesis of Compound 6-2;

Following the synthesis method in the Example 1, Step 1, the synthesis method was conducted similarly by replacing Step 1 1-1 (247.51 mg, 1.29 mmol) with 6-1 (115.32 mg, 647.01 μmol), to give Compound 6-2 (122 mg, 262.62 μmol).

Step 2: Synthesis of Compound 6:

Following the synthesis method in the Example 1, Step 3, the synthesis method was conducted similarly by replacing Step 3 1-3 (105 mg, 339.40 μmol) with 6-2 (100 mg, 337.47 μmol), to give Compound 6 (122 mg, 262.62 μmol). $^1H$ NMR (400 MHz, Methanol-$d_4$) δ 7.87 (s, 2H), 7.53 (t, J=7.6 Hz, 2H), 7.19 (d, J=50.6 Hz, 3H), 6.84 (s, 1H), 6.68 (s, 1H), 3.89 (d, J=30.8 Hz, 4H), 3.50-3.34 (m, 10H). LCMS ($ESI^+$) m/z: 465.4 $[M+H]^+$, HPLC Method A: $R_T$=5.07 min, purity: 96.2%.

Example 7: Synthesis of Compound 7

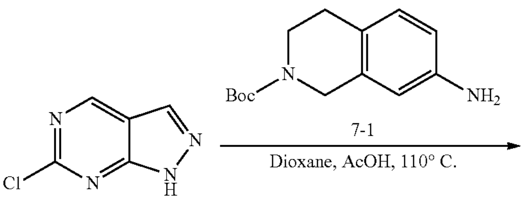

7-1

1-2

-continued

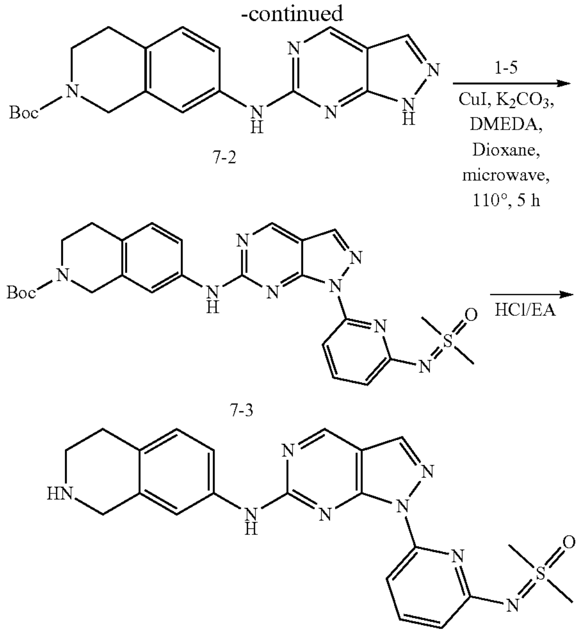

7-2

7-3

7

Step 1: Synthesis of Compound 7-2:

Following the synthesis method in the Example 1, Step 1, the synthesis method was conducted similarly by replacing Step 1 1-1 (247.51 mg, 1.29 mmol) with 7-1 (224.93 mg, 905.81 μmol), to give Compound 7-2 (331 mg, 0.90 mmol).

Step 2: Synthesis of Compound 7-3:

Following the synthesis method in the Example 1, Step 3, the synthesis method was conducted similarly by replacing Step 3 1-3 (105 mg, 339.40 μmol) with 7-2 (224.93 mg, 905.81 μmol), to give Compound 7-3 (100 mg, 187.04 μmol).

Step 3: Synthesis of Compound 7:

A dry single-necked flask was added with substrate 7-3 (350 mg, 93.52 μmol) and the reaction was dissolved in 4M HCl/EA (10 mL), stirred under room temperature for 2 hrs, monitored by LC-MS. After the reaction was completed, the reaction was extracted three times with water and ethyl acetate, and the organic phase was dried by anhydrous sodium sulfate, and then concentrated under reduced pressure, and the residue was purified by column chromatography to give product 7 (32 mg, 73.65 μmol). $^1$H NMR (400 MHz, DMSO-$d_6$) δ 10.09 (s, 1H), 9.11 (s, 1H), 9.09 (s, 1H), 8.38 (s, 1H), 7.91 (s, 1H), 7.88-7.81 (m, 1H), 7.67 (d, J=7.6 Hz, 1H), 7.55 (dd, J=8.4, 2.0 Hz, 1H), 7.19 (d, J=8.4 Hz, 1H), 6.69 (d, J=7.8 Hz, 1H), 4.29 (s, 2H), 3.49 (s, 6H), 3.41 (d, J=5.3 Hz, 2H), 2.96 (t, J=6.1 Hz, 2H). LCMS (ESI$^+$) m/z: 435.4 [M+H]$^+$, HPLC Method A: $R_T$=4.41 min, purity: 99.6%.

Example 8: Synthesis of Compound 8

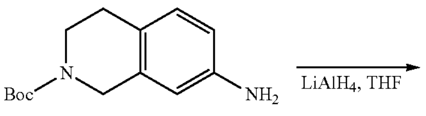

8-1

-continued

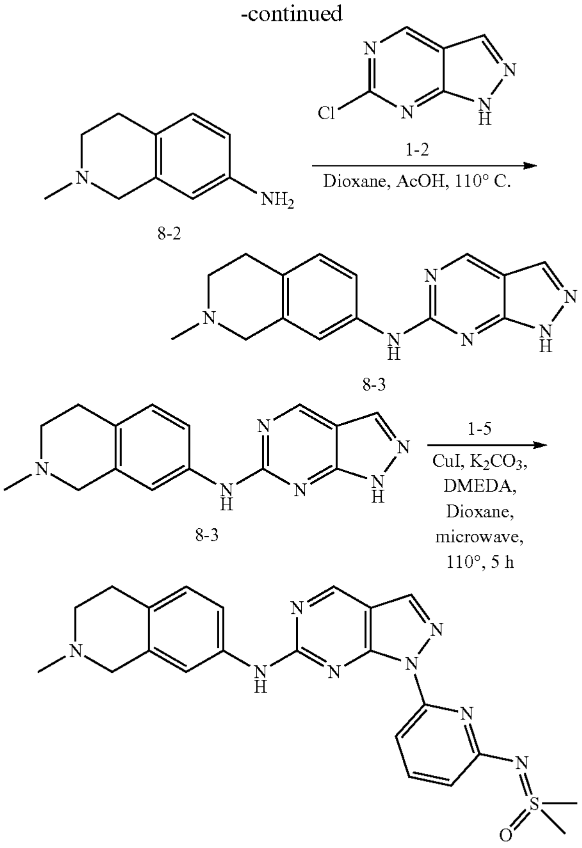

8-2

8-3

8-3

8

Step 1: Synthesis of Compound 8-2:

A dry single-necked flask was added with substrate 8-1 (200 mg, 805.41 μmol) and the reaction was dissolved in dry THF (10 mL), and in ice bath, the mixture was added with lithium aluminum hydride (152.84 mg, 4.03 mmol), and stirred under room temperature for 30 min, monitored by LC-MS. After the reaction was completed, the reaction was extracted three times with water and ethyl acetate, and the organic phase was dried by anhydrous sodium sulfate, and then concentrated under reduced pressure, and the residue was purified by column chromatography to give product 8-2 (130 mg, 801.33 μmol).

Step 2: Synthesis of Compound 8-3:

Following the synthesis method in the Example 1, Step 1, the synthesis method was conducted similarly by replacing Step 1 1-1 (247.51 mg, 1.29 mmol) with 8-2 (130 mg, 801.33 μmol), to give Compound 8-3 (224 mg, 799.07 μmol).

Step 3: Synthesis of Compound 8:

Following the synthesis method in the Example 1, Step 3, the synthesis method was conducted similarly by replacing Step 3 1-3 (105 mg, 339.4 μmol) with 8-3 (100 mg, 356.73 μmol), to give Compound 8 (16 mg, 35.67 μmol). $^1$H NMR (400 MHz, Methanol-$d_4$) δ 9.00-8.96 (m, 1H), 8.21 (s, 1H), 7.91-7.76 (m, 2H), 7.75-7.67 (m, 1H), 7.60-7.54 (m, 1H), 7.26-7.18 (m, 1H), 6.85-6.76 (m, 1H), 4.58-4.42 (m, 1H), 4.40-4.26 (m, 1H), 3.76 (s, 2H), 3.50 (s, 6H), 3.20 (s, 1H), 3.16-3.12 (m, 1H), 3.07 (s, 3H). LCMS (ESI$^+$) m/z: 449.4 [M+H]$^+$, HPLC Method A: $R_T$=4.52 min, purity: 99.5%.

Example 9: Synthesis of Compound 9

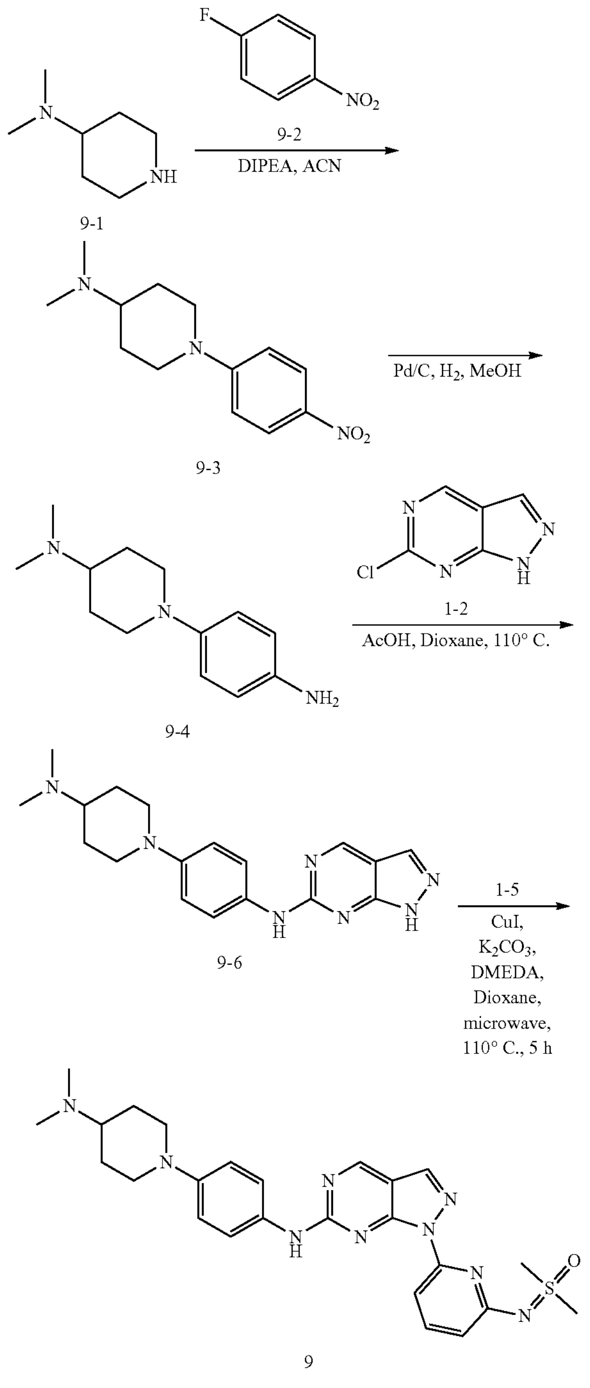

Step 1: Synthesis of Compound 9-3:

A dry single-necked flask was added with substrate p-fluoronitrobenzene (2 g, 14.17 mmol), 9-1 (1.82 g, 14.17 mmol) and DIPEA (2.20 g, 17.01 mmol, 2.96 mL), and the reaction was dissolved in ACN (30 mL), heated to 85° C., stirred for 15 hrs, monitored by LC-MS. After the reaction was completed, the reaction was extracted three times with water and ethyl acetate, and the organic phase was dried by anhydrous sodium sulfate, and then concentrated under reduced pressure, and the residue was purified by column chromatography to give product 9-3 (3.52 g, 14.12 mmol).

Step 2: Synthesis of Compound 9-4:

A dry single-necked flask was added with substrate 9-3 (3.52 g, 14.12 mmol), and the reaction was added with methanol (10 mL) and stirred to dissolve, then was added with Pd/C (170.51 mg, 1.40 mmol), replaced by $H_2$ three times, and then the reaction was conducted under room temperature for 3 hrs, monitored by LC-MS. After the reaction was completed, Pd/C was removed by Celite, and the organic phase was concentrated under reduced pressure, and the residue was purified by column chromatography to give product 9-4 (2.1 g, 9.57 mmol).

Step 3: Synthesis of Compound 9-6:

Following the synthesis method in the Example 1, Step 1, the synthesis method was conducted similarly by replacing Step 1 1-1 (247.51 mg, 1.29 mmol) with 9-4 (123 mg, 560.81 μmol), to give Compound 9-6 (189 mg, 560.13 μmol).

Step 4: Synthesis of Compound 9:

Following the synthesis method in the Example 1, Step 3, the synthesis method was conducted similarly by replacing Step 3 1-3 (105 mg, 339.40 μmol) with 9-6 (189 mg, 560.13 μmol), to give Compound 9 (20 mg, 39.55 μmol). $^1H$ NMR (400 MHz, Chloroform-d) δ 8.94 (s, 1H), 8.20 (s, 1H), 7.80 (t, J=7.9 Hz, 1H), 7.68 (d, J=7.7 Hz, 1H), 7.62 (s, 2H), 7.05 (s, 2H), 6.78 (d, J=8.1 Hz, 1H), 3.89-3.73 (m, 2H), 3.46-3.43 (m, 7H), 3.43-3.34 (m, 2H), 2.92 (s, 6H), 2.19 (s, 2H), 1.91 (s, 2H). LCMS ($ESI^+$) m/z: 506.5 $[M+H]^+$, HPLC Method A: $R_T$=4.31 min, purity: 95.7%.

Example 10: Synthesis of Compound 10

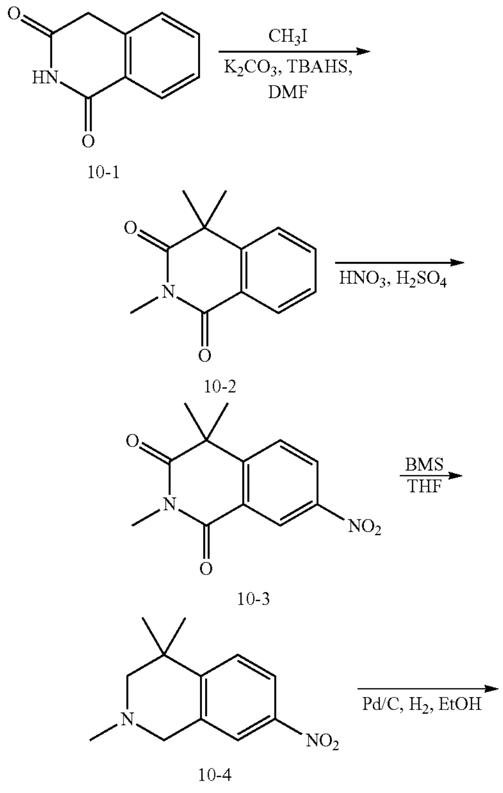

-continued

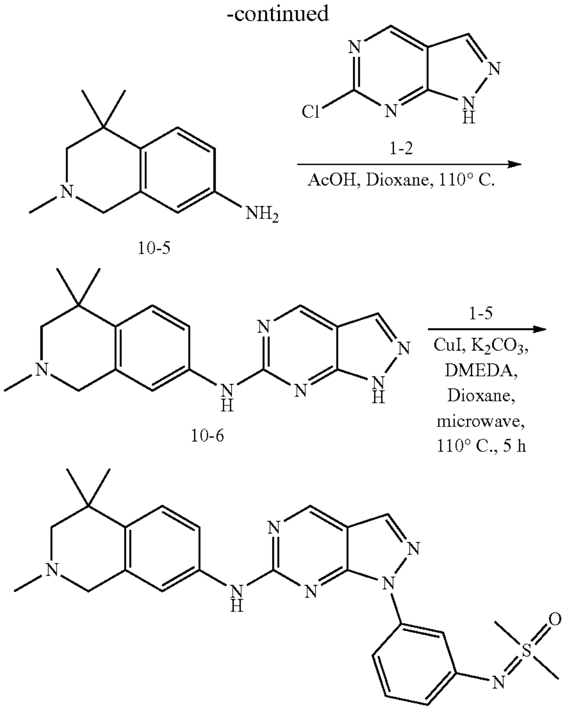

10-5

10-6

10

Step 1: Synthesis of Compound 10-2:

A dry single-necked flask was added with substrate 10-1 (3 g, 18.62 mmol) and iodomethane (8.7 g, 61.43 mmol), and the reaction was dissolved in DMF (20 mL), heated to 70° C., stirred for 15 hrs, monitored by LC-MS. After the reaction was completed, the reaction was quenched with water, was added with ethyl acetate to extract three times, and the organic phase was combined, washed with saturated saline solution, and the organic phase was dried by anhydrous sodium sulfate, and then concentrated under reduced pressure, and the residue was purified by column chromatography to give product 10-2 (3.4 g, 16.73 mmol).

Step 2: Synthesis of Compound 10-3:

A dry single-necked flask was added with substrate 10-2 (3.3 g, 16.24 mmol), and the reaction was dissolved in $H_2SO_4$ (10 mL), $HNO_3$ (1.02 g, 16.24 mmol) was added dropwisely and slowly in ice bath, and was stirred at 0° C. for 6 hrs, monitored by TLC. After the reaction was completed, the reaction was quenched with water, was added with ethyl acetate to extract three times, and the organic phase was combined, washed with saturated saline solution, and the organic phase was dried by anhydrous sodium sulfate, and then concentrated under reduced pressure, and the residue was purified by column chromatography to give product 10-3 (3.9 g, 15.71 mmol).

Step 3: Synthesis of Compound 10-4:

A dry single-necked flask was added with substrate 10-3 (270 mg, 1.09 mmol), and the reaction was dissolved in THF (10 mL), BMS (334.82 mg, 4.35 mmol) was added dropwisely and slowly in ice bath, heated to 70° C. and stirred for 24 hrs, monitored by LC-MS. After the reaction was completed, the reaction was quenched with saturated sodium sulfite, was added with ethyl acetate to extract three times, and the organic phase was combined, washed with saturated saline solution, and the organic phase was dried by anhydrous sodium sulfate, and then concentrated under reduced pressure, and the residue was purified by column chromatography to give product 10-4 (200 mg, 907.99 μmol).

Step 4: Synthesis of Compound 10-5:

A dry single-necked flask was added with substrate 10-4 (200 mg, 907.99 μmol) and the reaction was dissolved in ethanol (10 mL), and was added with Pd/C (110.28 mg, 907.99 μmol), and was replaced by $H_2$ three times, and then stirred under hydrogen for 3 hrs, monitored by LC-MS. After the reaction was completed, the reaction was filtered with Celite, and the organic phase was concentrated under reduced pressure, and the residue was purified by column chromatography to give product 10-5 (170 mg, 893.40 μmol).

Step 5: Synthesis of Compound 10-6:

Following the synthesis method in the Example 1, Step 1, the synthesis method was conducted similarly by replacing Step 1 1-1 (247.51 mg, 1.29 mmol) with 10-5 (132 mg, 693.70 μmol), to give Compound 10-6 (213 mg, 690.71 μmol).

Step 6: Synthesis of Compound 10:

Following the synthesis method in the Example 1, Step 3, the synthesis method was conducted similarly by replacing Step 3 1-3 (105 mg, 339.40 μmol) with 10-6 (100 mg, 324.28 μmol), to give Compound 10 (27 mg, 54.95 μmol). $^1$H NMR (400 MHz, Chloroform-d) δ 8.98 (s, 1H), 8.21 (s, 1H), 7.87-7.78 (m, 2H), 7.68 (d, J=7.3 Hz, 1H), 7.62 (dd, J=8.6, 2.3 Hz, 1H), 7.46 (d, J=8.7 Hz, 1H), 6.83-6.76 (m, 1H), 4.41 (d, J=6.0 Hz, 2H), 3.55-3.45 (m, 7H), 3.40 (s, 1H), 3.11 (s, 3H), 1.46 (s, 6H). LCMS ($ESI^+$) m/z: 477.4 $[M+H]^+$, HPLC Method A: $R_T$=5.02 min, purity: 96.9%.

Example 11: Synthesis of Compound 11

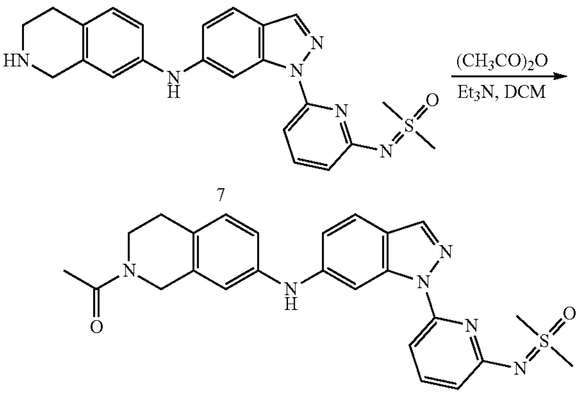

7

11

Step 1: Synthesis of Compound 11:

A dry three-necked flask was added with compound 7 (23 mg, crude), $(CH_3CO)_2O$ (6 mg, 59.0 μmol) and $Et_3N$ (12 mg, 118.0 μmol), and the reaction was dissolved in DCM (1 mL) under room temperature and stirred overnight, monitored by LC-MS. After the reaction was completed, the reaction was extracted three times with water and ethyl acetate, and the organic phase was dried by anhydrous sodium sulfate, and then concentrated under reduced pressure, and the residue was purified by column chromatography to give compound 11 (4 mg, 8.40 μmol). $^1$H NMR (400 MHz, DMSO-$d_6$) δ 9.99 (s, 1H), 9.09 (s, 1H), 8.36 (s, 1H), 7.92-7.83 (m, 2H), 7.73-7.65 (m, 1H), 7.47-7.42 (m, 1H), 7.12 (d, J=8.4 Hz, 1H), 6.69-6.66 (m, 1H), 4.61 (s, 2H), 3.68

(s, 2H), 3.49 (s, 6H), 2.83 (s, 2H), 2.11 (d, J=4 Hz, 3H). LCMS (ESI$^+$) m/z: 477.2 $[M+H]^+$, HPLC Method B: $R_T$=5.77 min, purity: 92.1%.

Example 12: Synthesis of Compound 12

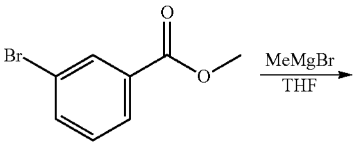

12-1

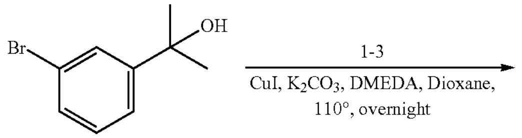

12-2

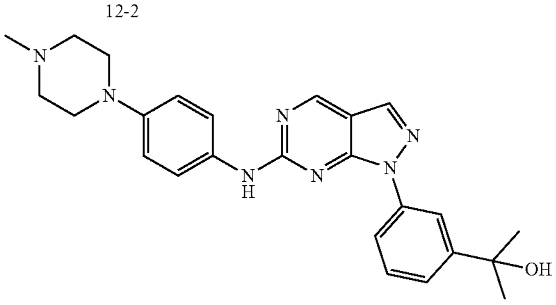

12

Step 1: Synthesis of Compound 12-2:

A dry three-necked flask was added with substrate methylmagnesium bromide (1.0 M in dry THF, 4.4 mL), dissolve substrate 12-1 (8.7 g, 61.43 mmol) in THF (5 mL), and at 0° C. and with the protection of nitrogen, slowly added into a three-necked flask dropwisely, slowly recovered to room temperature and reacted for 16 h, monitored by TLC. After the reaction was completed, the reaction was quenched with water, and the system was adjusted to pH=6-7 with saturated sodium bicarbonate, was added with ethyl acetate to extract three times, and the organic phase was combined, washed with saturated saline solution, and the organic phase was dried by anhydrous sodium sulfate, and then concentrated under reduced pressure, and the residue was purified by column chromatography to give product 12-2 (210 mg, 0.99 mmol). $^1$H NMR (400 MHz, Chloroform-d) δ 7.58 (t, J=1.9 Hz, 1H), 7.32 (t, J=7.9 Hz, 2H), 7.14 (t, J=7.9 Hz, 1H), 2.17 (s, 1H), 1.50 (s, 6H).

Step 2: Synthesis of Compound 12:

Following the synthesis method of Compound 1, Step 3, the synthesis method was conducted similarly by replacing Step 3 1-5 (109.92 mg, 441.22 μmol) with 12-2 (100 mg, 470.0 μmol), to give Compound 12 (11 mg, 25.0 μmol). $^1$H NMR (400 MHz, Chloroform-d) δ 8.77 (s, 1H), 8.30 (t, J=1.8 Hz, 1H), 8.20 (s, 1H), 7.93 (dt, J=7.2, 2.2 Hz, 1H), 7.67 (d, J=8.9 Hz, 2H), 7.53-7.46 (m, 2H), 6.98-6.91 (m, 2H), 3.61 (d, J=39.5 Hz, 4H), 3.35 (s, 2H), 3.04 (s, 2H), 2.88 (s, 3H), 1.62 (s, 6H). LCMS (ESI$^+$) m/z: 444.3 $[M+H]^+$, HPLC Method A: $R_T$=5.32 min, purity: 82.7%.

Example 13: Synthesis of Compound 13

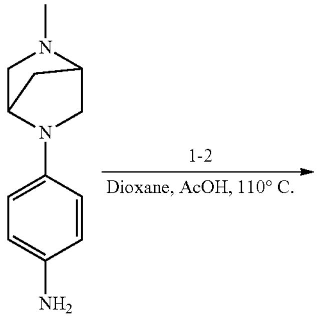

13-1

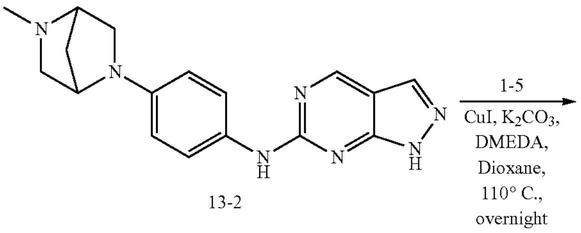

13-2

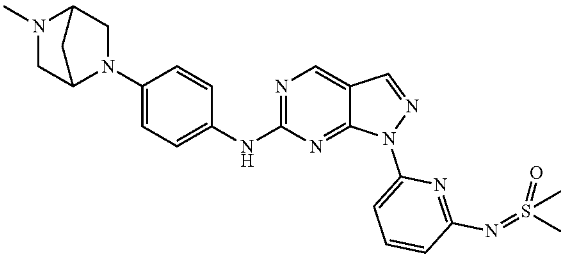

13

Step 1: Synthesis of Compound 13-2:

Following the synthesis method in the Example 1, Step 1, the synthesis method was conducted similarly by replacing Step 1 1-1 (247.51 mg, 1.29 mmol) with 13-1 (120 mg, 0.59 mmol), to give Compound 13-2 (80 mg, 0.25 mmol).

Step 2: Synthesis of Compound 13:

Following the synthesis method in the Example 1, Step 3, the synthesis method was conducted similarly by replacing Step 3 1-5 (109.92 mg, 441.22 μmol) with 13-2 (80 mg, 250.0 μmol), to give Compound 13 (25 mg, 39.91 μmol), which was prepared by acid method, and the product was in the form of trifluoroacetate salt. $^1$H NMR (400 MHz, DMSO-$d_6$) δ 9.66 (s, 1H), 9.02 (s, 1H), 8.31 (s, 1H), 7.80 (dd, J=8.8, 7.0 Hz, 1H), 7.72-7.57 (m, 3H), 6.76-6.62 (m, 3H), 4.62 (s, 1H), 4.34 (d, J=2.3 Hz, 1H), 3.69-3.61 (m, 2H), 3.48 (d, J=1.7 Hz, 6H), 3.28 (d, J=10.9 Hz, 1H), 3.09 (dt, J=11.2, 2.9 Hz, 1H), 2.88 (d, J=5.0 Hz, 3H), 2.44-2.31 (m, 1H), 2.15 (d, J=11.3 Hz, 1H). LCMS (ESI$^+$) m/z: 490.5 $[M+H]^+$, HPLC Method A: $R_T$=4.56 min, purity: 96.4%.

Example 14: Synthesis of Compound 14

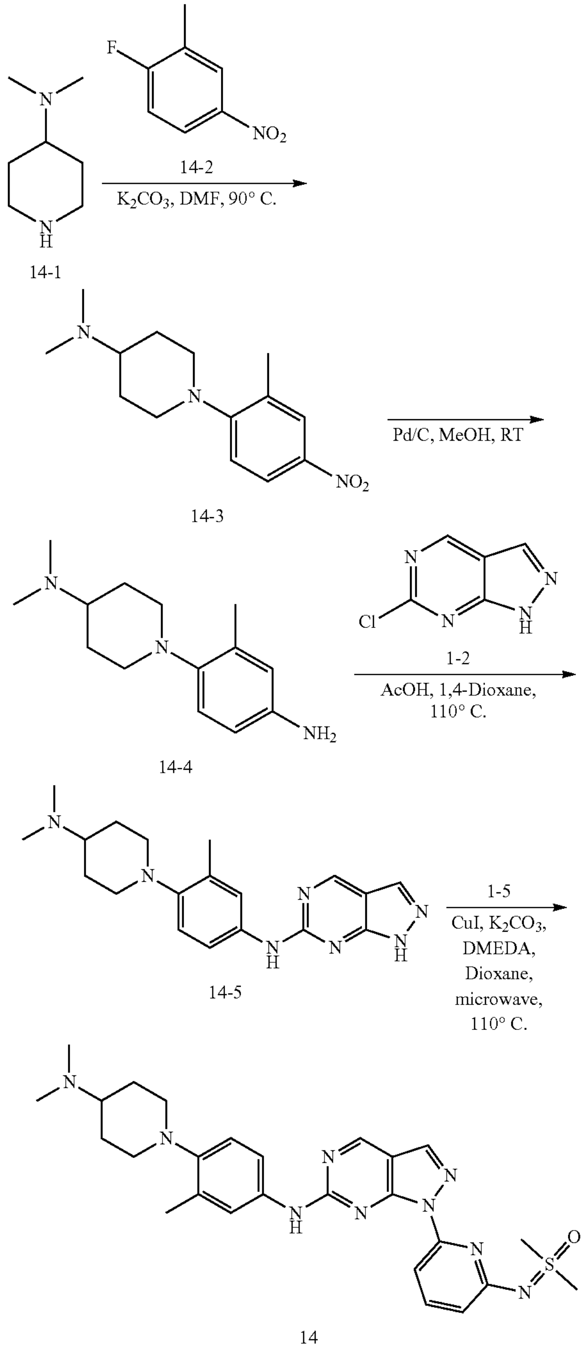

Step 1: Synthesis of Compound 14-3:

A dry three-necked flask was added with substrate 14-1 (182 mg, 1.42 mmol), 14-2 (200 mg, 1.29 mmol) and $K_2CO_3$ (534 mg, 3.87 mmol), and the reaction was dissolved in DMF (10 mL), and with the protection of $N_2$, heated to 90° C. and reacted for 3 h, monitored by LC-MS. After the reaction was completed, the reaction was extracted three times with water and ethyl acetate, and the organic phase was dried by anhydrous sodium sulfate, and then concentrated under reduced pressure, and without purification, the crude product could be used in the reaction in the next step, to give 14-3 (100 mg, crude). LCMS ($ESI^+$) m/z: 264.3 $[M+H]^+$.

Step 2: Synthesis of Compound 14-4:

A dry single-necked flask was added with substrate 14-3 (100 mg, 43.0 μmol), and the reaction was dissolved in MeOH (5 mL), and was added with Pd/C (30 mg), replaced by $H_2$ three times, and then under room temperature stirred for 30 min, monitored by LC-MS. After the reaction was completed, the reaction was filtered with Celite, and the filtrate was concentrated under reduced pressure, to give crude product 14-4 (109 mg, crude), LCMS ($ESI^+$) m/z: 234.2 $[M+H]^+$.

Step 3: Synthesis of Compound 14-5:

Following the synthesis method in the Example 1, Step 1, the synthesis method was conducted similarly by replacing Step 1 1-1 (247.51 mg, 1.29 mmol) with 14-4 (109 mg, 0.468 mmol), to give product 14-5 (53 mg, 0.151 mmol). LCMS ($ESI^+$) m/z: 352.4 $[M+H]^+$.

Step 4: Synthesis of Compound 14:

Following the synthesis method in the Example 1, Step 3, the synthesis method was conducted similarly by replacing Step 3 1-3 (105 mg, 339.40 μmol) with 14-4 (53 mg, 151.0 μmol), to give Compound 14 (11.9 mg, 22.93 μmol). $^1H$ NMR (400 MHz, DMSO-$d_6$) δ 9.79 (s, 1H), 9.03 (d, J=3.6 Hz, 1H), 8.32 (s, 1H), 7.81 (d, J=8 Hz, 1H), 7.77 (d, J=10.4 Hz, 1H), 7.68 (d, J=7.6 Hz, 1H), 7.46-7.44 (m, 1H), 6.98 (d, J=8.4 Hz, 1H), 6.6 (d, J=12.8 Hz, 1H), 3.48 (s, 1H), 3.47 (s, 6H), 3.05 (d, J=10.8 Hz, 4H), 2.24 (d, J=3.6 Hz, 9H), 1.85 (d, J=10.8 Hz, 2H), 1.57-1.53 (m, 2H). LCMS ($ESI^+$) m/z: 520.3 $[M+H]^+$, HPLC Method B: $R_T$=4.75 min, purity: 76.0%.

Example 15: Synthesis of Compound 15

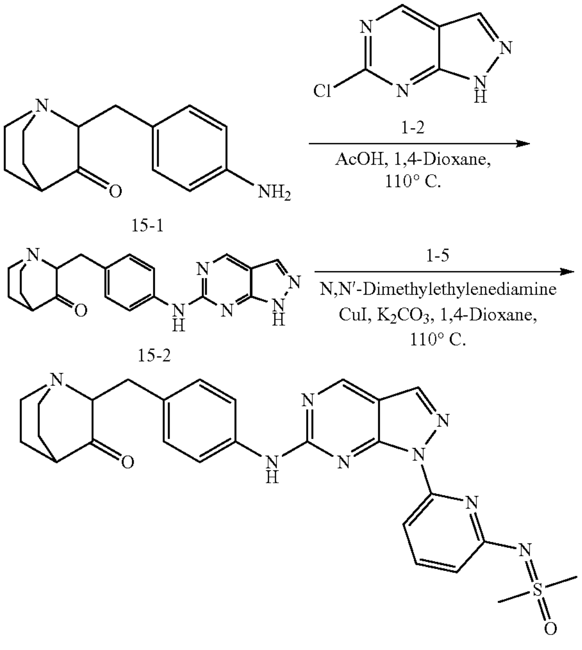

Step 1: Synthesis of Compound 15-2:

Following the synthesis method in the Example 1, Step 1, the synthesis method was conducted similarly by replacing Step 1 1-1 (247.51 mg, 1.29 mmol) with 15-1 (50 mg, 0.217 mmol), to give product 15-2 (35 mg, 0.101 mmol). LCMS ($ESI^+$) m/z: 349.2 $[M+H]^+$.

Step 2: Synthesis of Compound 15:

Following the synthesis method in the Example 1, Step 3, the synthesis method was conducted similarly by replacing Step 3 1-3 (105 mg, 339.40 μmol) with 15-2 (35 mg, 101.0 μmol), to give Compound 15 (11.9 mg, 22.93 μmol). $^1H$ NMR (400 MHz, DMSO-$d_6$) δ 9.86 (s, 1H), 9.07 (s, 1H), 8.34 (s, 1H), 7.79 (t, J=7.6 Hz, 1H), 7.65 (d, J=8.4 Hz, 2H), 7.61 (d, J=7.6 Hz, 1H), 7.19 (d, J=8.4 Hz, 2H), 6.66 (d, J=8.0 Hz, 1H), 3.44 (s, 6H), 3.11 (s, 1H), 3.01-2.87 (m, 2H), 2.77-2.66 (m, 4H), 2.30-2.28 (m, 1H), 1.98-1.88 (m, 4H). LCMS ($ESI^+$) m/z: 517.2 $[M+H]^+$, HPLC Method B: $R_T$=4.84 min, purity: 85.7%.

Example 16: Synthesis of Compound 16

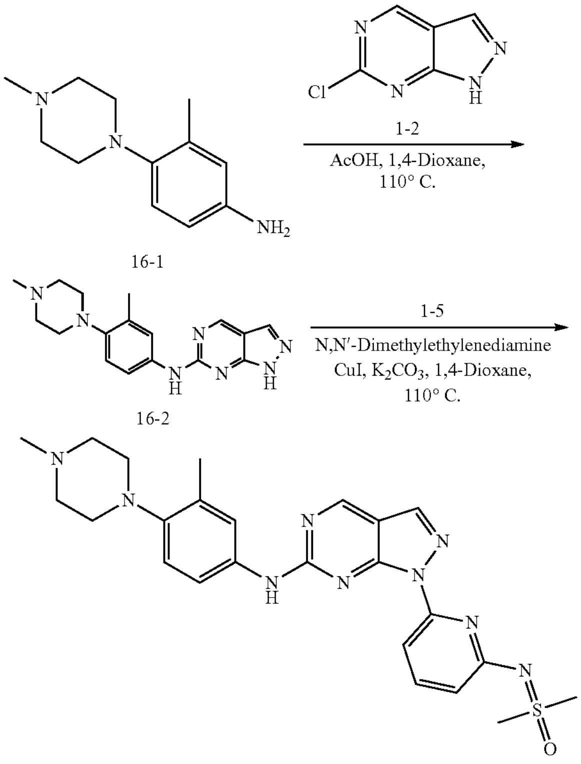

1-2
16-1
1-5
16-2
16

Step 1: Synthesis of Compound 16-2:

Following the synthesis method in the Example 1, Step 1, the synthesis method was conducted similarly by replacing Step 1 1-1 (247.51 mg, 1.29 mmol) with 16-1 (50 mg, 0.217 mmol), to give product 16-2 (98 mg, 0.302 mmol). LCMS ($ESI^+$) m/z: 324.4 $[M+H]^+$.

Step 2: Synthesis of Compound 16:

Following the synthesis method in the Example 1, Step 3, the synthesis method was conducted similarly by replacing Step 3 1-3 (105 mg, 339.40 μmol) with 16-2 (98 mg, 303.0 μmol), to give Compound 16 (22.4 mg, 45.53 μmol). $^1H$ NMR (400 MHz, DMSO-$d_6$) δ 9.82 (s, 1H), 9.05 (d, J=3.6 Hz, 1H), 8.33 (s, 1H), 7.82-7.77 (m, 2H), 7.68 (d, J=7.6 Hz, 1H), 7.47 (dd, J=8.4 Hz, 1H), 7.00 (d, J=8.4 Hz, 1H), 6.66 (d, J=7.6 Hz, 1H), 3.47 (s, 6H), 2.84 (s, 4H), 2.59 (s, 3H), 2.29 (s, 4H), 2.26 (s, 3H). LCMS ($ESI^+$) m/z: 492.2 $[M+H]^+$, HPLC Method B: $R_T$=6.50 min, purity: 92.9%.

Example 17: Synthesis of Compound 17

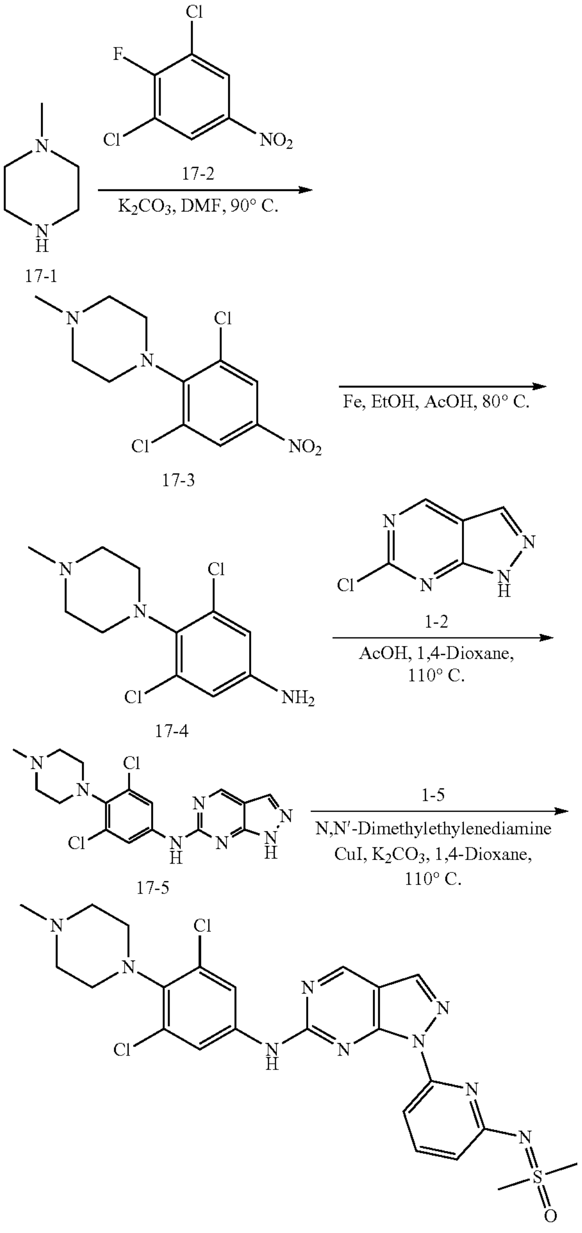

17-2
17-1
17-3
1-2
17-4
1-5
17-5
17

Step 1: Synthesis of Compound 17-3:

Following the synthesis method in the Example 14, Step 1, the synthesis method was conducted similarly by replacing Step 1 14-1 (182 mg, 1.42 mmol) with 17-1 (200 mg, 0.952 mmol), 14-2 (200 mg, 1.29 mmol) with 17-2 (105 mg, 1.05 mmol), to give product 17-3 (400 mg, crude). LCMS ($ESI^+$) m/z: 290.0 $[M+H]^+$.

Step 2: Synthesis of Compound 17-4:

A dry single-necked flask was added with substrate 17-3 (100 mg, 0.346 mmol) and the reaction was dissolved in EtOH (5 mL), added with Fe powder (97 mg, 1.73 mmol)

and AcOH (0.1 mL), heated to 80° C. 搅拌 1 h, monitored by LC-MS. After the reaction was completed, the reaction was filtered with Celite, and the filtrate was concentrated under reduced pressure, to give product 17-4 (66 mg, crude), LCMS ($ESI^+$) m/z: 260.1 $[M+H]^+$.

Step 3: Synthesis of Compound 17-5:

Following the synthesis method in the Example 1, Step 1, the synthesis method was conducted similarly by replacing Step 1 1-1 (247.51 mg, 1.29 mmol) with 17-4 (66 mg, 0.255 mmol), to give product 17-5 (57 mg, 0.151 mmol). LCMS ($ESI^+$) m/z: 378.1 $[M+H]^+$.

Step 4: Synthesis of Compound 17:

Following the synthesis method in the Example 1, Step 3, the synthesis method was conducted similarly by replacing Step 3 1-3 (105 mg, 339.40 μmol) with 17-5 (57 mg, 151.0 μmol), to give Compound 17 (7.5 mg, 13.74 μmol). $^1H$ NMR (400 MHz, DMSO-$d_6$) δ 10.34 (s, 1H), 9.16 (d, J=3.6 Hz, 1H), 8.43 (s, 1H), 8.02 (s, 2H), 7.83-7.79 (m, 2H), 7.64 (d, J=8.0 Hz, 1H), 6.70 (d, J=8.0 Hz, 1H), 3.49 (s, 8H), 3.03 (s, 5H), 2.53 (s, 4H). LCMS ($ESI^+$) m/z: 546.1 $[M+H]^+$, HPLC Method B: $R_T$=7.80 min, purity: 65.4%.

Example 18: Synthesis of Compound 18

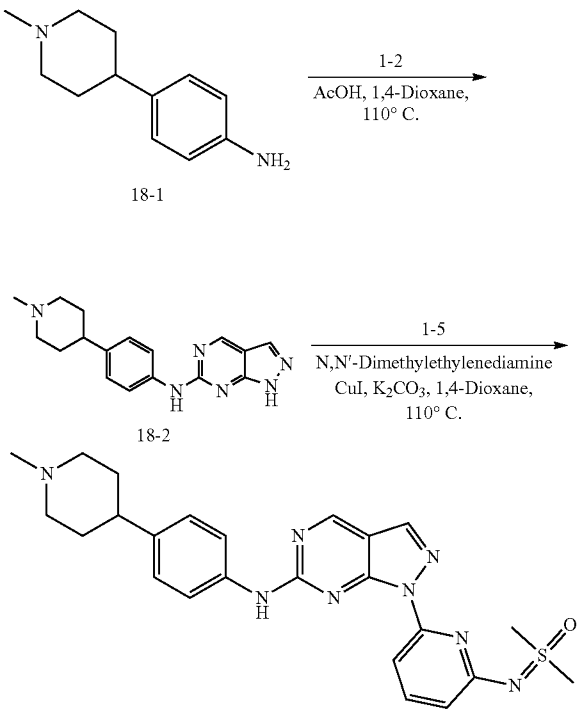

18-1

18-2

18

Step 1: Synthesis of Compound 18-2:

Following the synthesis method in the Example 1, Step 1, the synthesis method was conducted similarly by replacing Step 1 1-1 (247.51 mg, 1.29 mmol) with 18-1 (27 mg, 141.89 μmol), to give product 18-2 (40 mg, 116.74 μmol). LCMS ($ESI^+$) m/z: 309.3 $[M+H]^+$.

Step 2: Synthesis of Compound 18:

Following the synthesis method in the Example 1, Step 3, the synthesis method was conducted similarly by replacing Step 3 1-3 (105 mg, 339.40 μmol) with HGC041-02 (60 mg, 194.57 μmol), to give Compound 18 (23 mg, 47.78 μmol). $^1H$ NMR (400 MHz, DMSO-$d_6$) δ 9.88 (s, 1H), 9.08 (s, 1H), 8.34 (s, 1H), 7.91-7.77 (m, 1H), 7.71 (d, J=8.6 Hz, 2H), 7.62 (d, J=7.5 Hz, 1H), 7.20 (dd, J=8.9, 2.4 Hz, 2H), 6.70-6.61 (m, 1H), 3.46 (s, 6H), 2.90-2.82 (m, 2H), 2.47-2.35 (m, 2H), 2.19 (s, 3H), 2.00-1.90 (m, 2H), 1.75-1.59 (m, 3H). LCMS ($ESI^+$) m/z: 477.3 $[M+H]^+$, HPLC Method B: $R_T$=5.74 min, purity: 99.0%.

Example 19: Synthesis of Compound 19

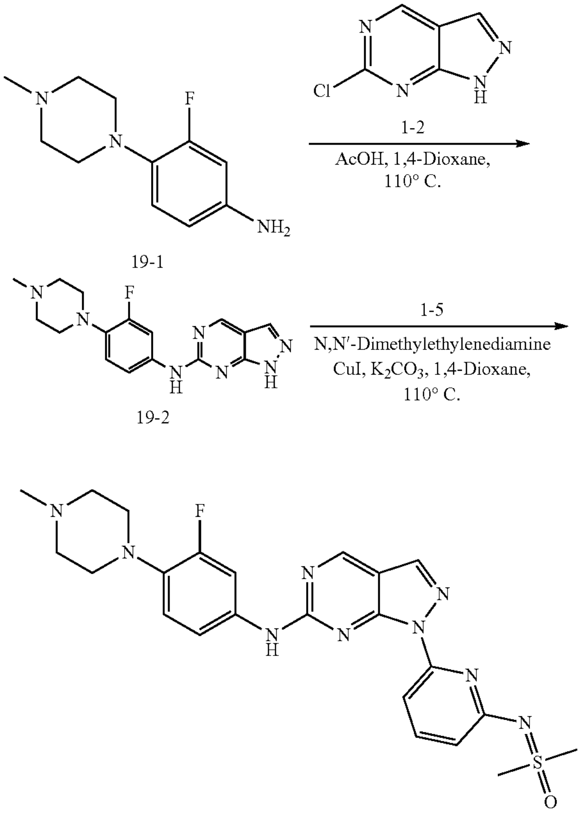

19-1

19-2

19

Step 1: Synthesis of Compound 19-2:

Following the synthesis method in the Example 1, Step 1, the synthesis method was conducted similarly by replacing Step 1 1-1 (247.51 mg, 1.29 mmol) with 19-1 (100 mg, 0.478 mmol), to give product 19-2 (156 mg, 0.477 mmol). LCMS ($ESI^+$) m/z: 328.4 $[M+H]^+$.

Step 2: Synthesis of Compound 19:

Following the synthesis method in the Example 1, Step 3, the synthesis method was conducted similarly by replacing Step 3 1-3 (105 mg, 339.40 μmol) with 19-2 (80 mg, 245.0 μmol), to give Compound 19 (14 mg, 28.27 μmol). $^1H$ NMR (400 MHz, DMSO-$d_6$) δ 10.00 (s, 1H), 9.03 (s, 1H), 8.36 (s, 1H), 7.79 (t, J=8.0 Hz, 2H), 7.61 (d, J=8.0 Hz, 1H), 7.44 (t, J=6.4 Hz, 1H), 7.02 (d, J=9.6 Hz, 1H), 6.68 (d, J=8.0 Hz, 1H), 3.48 (s, 6H), 3.38 (s, 4H), 2.97 (s, 4H), 2.23 (s, 3H). LCMS ($ESI^+$) m/z: 496.1 $[M+H]^+$, HPLC Method B: $R_T$=6.15 min, purity: 88.7%.

Example 20: Synthesis of Compound 20

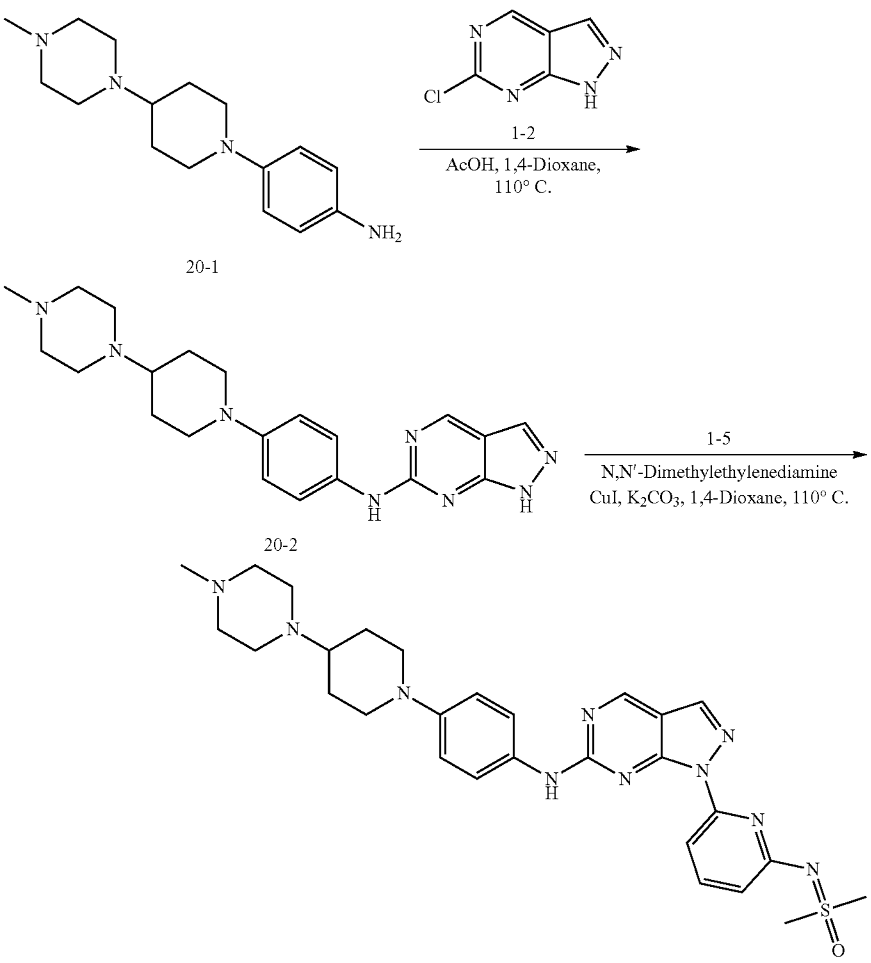

20-1

1-2

20-2

1-5

20

Step 1: Synthesis of Compound 20-2:

Following the synthesis method in the Example 1, Step 1, the synthesis method was conducted similarly by replacing Step 1 1-1 (247.51 mg, 1.29 mmol) with 20-1 (100 mg, 0.365 mmol), to give product 20-2 (168 mg, 0.429 mmol). LCMS ($ESI^+$) m/z: 393.5 $[M+H]^+$.

Step 2: Synthesis of Compound 20:

Following the synthesis method in the Example 1, Step 3, the synthesis method was conducted similarly by replacing Step 3 1-3 (105 mg, 339.40 μmol) with 20-2 (80 mg, 204.0 μmol), to give Compound 20 (20.6 mg, 36.79 μmol). $^1H$ NMR (400 MHz, DMSO-$d_6$) δ 9.71 (s, 1H), 9.02 (s, 1H), 8.31 (s, 1H), 7.81 (t, J=8.0 Hz, 1H), 7.64-7.59 (m, 3H), 6.92 (d, J=8.8 Hz, 2H), 6.65 (d, J=8.0 Hz, 1H), 3.65 (d, J=8.0 Hz, 2H), 3.46 (s, 6H), 2.61 (t, J=11.6 Hz, 2H), 2.51 (d, J=2.0 Hz, 5H), 2.29-2.25 (m, 4H), 2.14 (s, 3H), 1.83 (d, J=12.0 Hz, 2H), 1.54-1.47 (m, 2H). LCMS ($ESI^+$) m/z: 561.3 $[M+H]^+$, HPLC Method B: $R_T$=5.57 min, purity: 87.8%.

Example 21: Synthesis of Compound 21

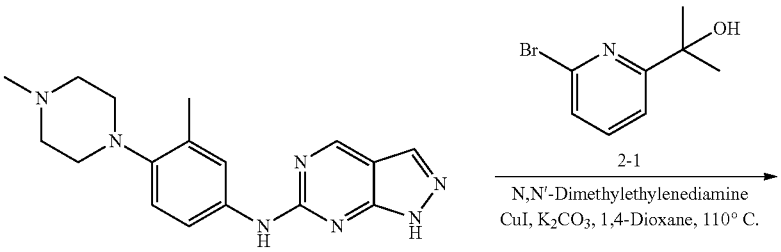

2-1

16-2

-continued

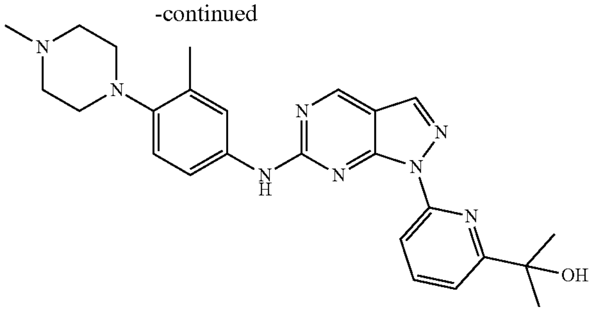

21

Step 1: Synthesis of Compound 21:

Following the synthesis method in the Example 1, Step 3, the synthesis method was conducted similarly by replacing Step 3 1-3 (105 mg, 339.40 μmol) with 16-2 (74 mg, 229.0 μmol), 1-5 (109.92 mg, 441.22 μmol) with 2-1 (41 mg, 191.0 μmol), to give Compound 21 (20.6 mg, 15.72 μmol). $^1$H NMR (400 MHz, DMSO-$d_6$) δ 9.91 (s, 1H), 9.07 (s, 1H), 8.34 (s, 1H), 8.05 (t, J=7.6 Hz, 1H), 7.98 (d, J=8.8 Hz, 1H), 7.75-7.70 (m, 2H), 7.62 (d, J=2.4 Hz, 1H), 6.99 (d, J=8.8 Hz, 1H), 5.34 (s, 1H), 2.95 (s, 7H), 2.61 (s, 4H), 2.56 (s, 3H), 1.51 (s, 6H). LCMS (ESI$^+$) m/z: 459.2 [M+H]$^+$, HPLC Method B: $R_T$=7.24 min, purity: 85.1%.

Example 22: Synthesis of Compound 22

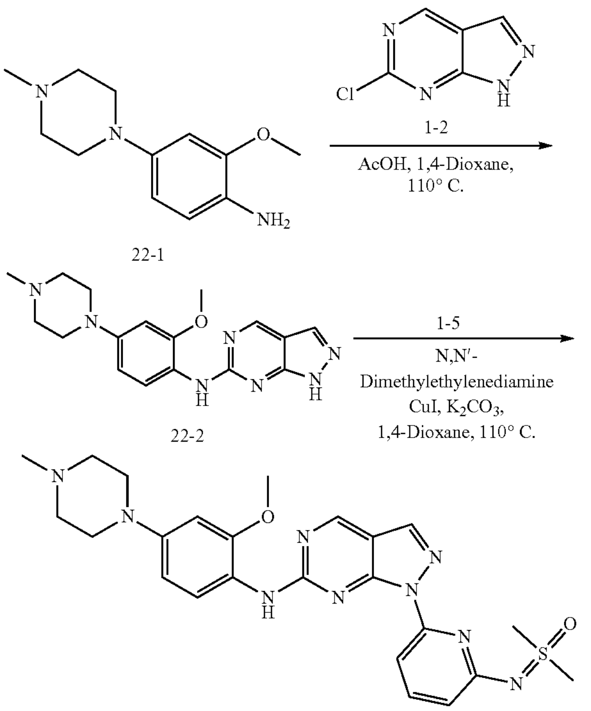

22

Step 1: Synthesis of Compound 22-2:

Following the synthesis method in the Example 1, Step 1, the synthesis method was conducted similarly by replacing Step 1 1-1 (247.51 mg, 1.29 mmol) with 22-1, to give product 22-2 (50 mg, 147.32 μmol). LCMS (ESI$^+$) m/z: 340.4 [M+H]$^+$.

Step 2: Synthesis of Compound 22:

Following the synthesis method in the Example 1, Step 3, the synthesis method was conducted similarly by replacing Step 3 1-3 (105 mg, 339.40 μmol) with 22-2 (50 mg, 147.32 μmol), to give Compound 22 (40 mg, 78.8 μmol). $^1$H NMR (400 MHz, Chloroform-d) δ 8.88 (s, 1H), 8.32 (d, J=9.7 Hz, 1H), 8.07 (s, 1H), 7.76-7.67 (m, 2H), 6.81 (d, J=7.7 Hz, 1H), 6.60-6.55 (m, 2H), 3.91 (s, 3H), 3.50 (s, 6H), 3.30-3.18 (m, 4H), 2.77-2.67 (m, 4H), 2.45 (s, 3H).

Example 23: Synthesis of Compound 23

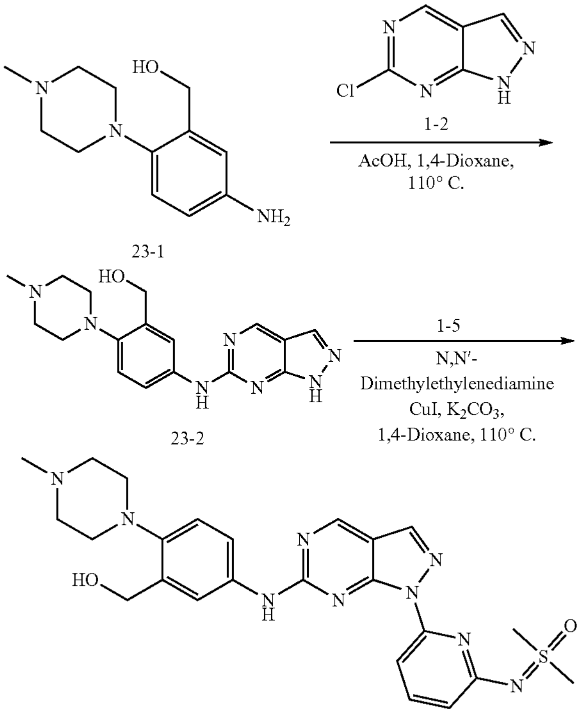

23

Step 1: Synthesis of Compound 23-2:

Following the synthesis method in the Example 1, Step 1, the synthesis method was conducted similarly by replacing Step 1 1-1 (247.51 mg, 1.29 mmol) with 23-1, to give product 23-2 (100 mg, 294.64 μmol). LCMS (ESI$^+$) m/z: 340.4 [M+H]$^+$.

Step 2: Synthesis of Compound 23:

Following the synthesis method in the Example 1, Step 3, the synthesis method was conducted similarly by replacing Step 3 1-3 (105 mg, 339.40 μmol) with 23-2 (100 mg, 294.64 μmol), to give Compound 23 (70 mg, 137.9 μmol). $^1$H NMR (400 MHz, DMSO-$d_6$) δ 9.87 (s, 1H), 9.05 (s, 1H), 8.33 (s, 1H), 7.99 (s, 1H), 7.87-7.72 (m, 2H), 7.55 (d, J=8.7 Hz, 1H), 7.04 (d, J=8.7 Hz, 1H), 6.65 (d, J=8.5 Hz, 1H), 5.76 (s, 1H), 5.14-5.01 (m, 1H), 4.58 (d, J=5.1 Hz, 2H), 3.48 (s, 6H), 2.87-2.81 (m, 4H), 2.53-2.50 (m, 4H), 2.25 (s, 3H); $^1$H NMR (400 MHz, DMSO-$d_6$+$D_2O$) δ 9.05 (s, 1H), 8.33 (s, 1H), 7.95 (s, 1H), 7.83 (t, J=7.9 Hz, 1H), 7.74 (d, J=7.7 Hz, 1H), 7.54 (dd, J=8.6, 2.7 Hz, 1H), 7.07 (d, J=8.7 Hz, 1H), 6.68 (d, J=7.9 Hz, 1H), 5.69 (s, 1H), 4.59 (s, 2H), 3.47 (s, 6H), 2.87-2.81 (m, 4H), 2.53-2.50 (m, 4H), 2.25 (s, 3H).

Example 24: Synthesis of Compound 24

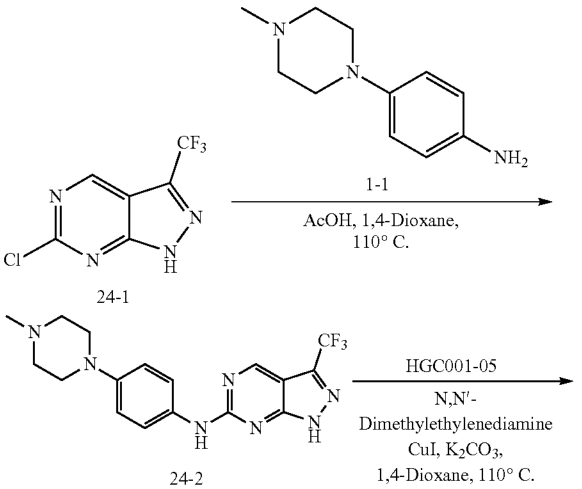

-continued

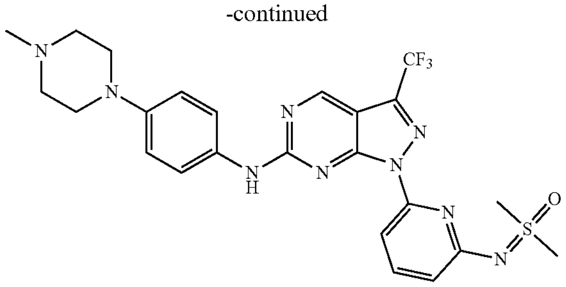

24

Step 1: Synthesis of Compound 24-2:

Following the synthesis method in the Example 1, Step 1, the synthesis method was conducted similarly by replacing Step 1 1-2 (200 mg, 1.29 mmol) with 24-1 (65 mg, 2.57 mmol), to give product 24-2 (65 mg, 0.172 mmol). LCMS (ESI$^+$) m/z: 378.2 [M+H]$^+$.

Step 2: Synthesis of Compound 24:

Following the synthesis method in the Example 1, Step 3, the synthesis method was conducted similarly by replacing Step 3 1-3 (105 mg, 339.40 μmol) with 24-2 (65 mg, 0.172 mmol), to give Compound 24 (31.8 mg, 58.35 μmol). $^1$H NMR (400 MHz, DMSO-$d_6$) δ 10.14 (s, 1H), 9.15 (s, 1H), 7.87 (s, 1H), 7.61 (d, J=5.4 Hz, 3H), 6.94 (d, J=7.2 Hz, 2H), 6.74 (d, J=7.8 Hz, 1H), 3.45 (s, 6H), 3.09 (s, 4H), 2.46 (s, 4H), 2.22 (s, 3H). LCMS (ESI$^+$) m/z: 546.2 [M+H]$^+$, HPLC Method B: $R_T$=7.51 min, purity: 95.3%.

Example 25: Synthesis of Compound 25

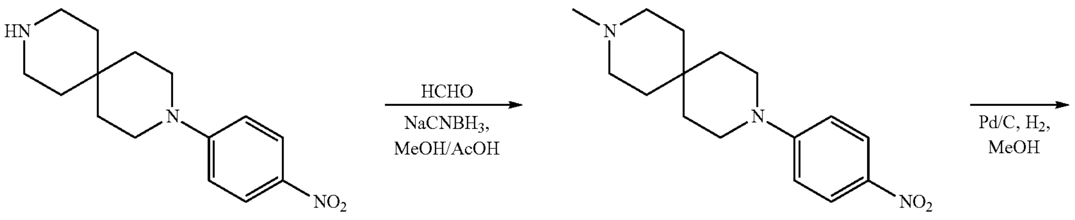

25-1

25-2

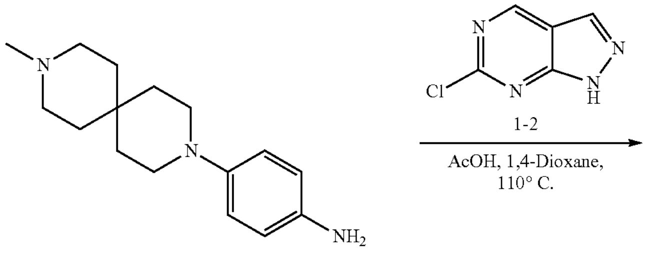

25-3

-continued

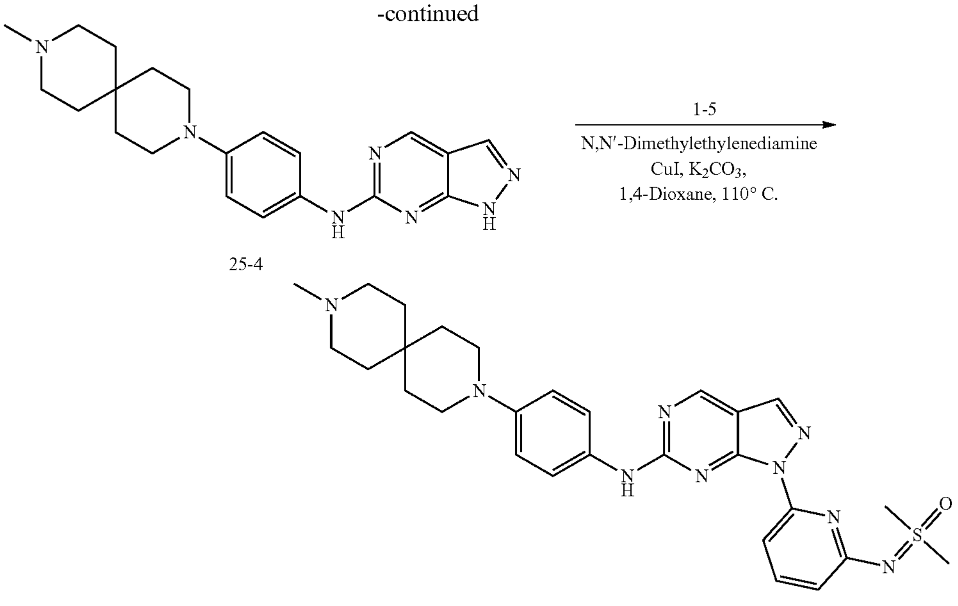

25-4

25

Step 1: Synthesis of Compound 25-2:

A dry single-necked flask was added with substrate 25-1 (261 mg, 947.90 μmol), formaldehyde (85.38 mg, 2.84 mmol) and the reaction was dissolved in methanol (10 mL) and acetic acid (0.1 mL), and under room temperature stirred for 1 h, and then added with $NaCNBH_3$ (148.92 mg, 2.37 mmol), heated to 50° C., stirred for 5 hrs, monitored by LC-MS. After the reaction was completed, and the organic phase was concentrated under reduced pressure, the reaction was extracted three times with water and ethyl acetate, and the organic phase was combined, washed with saturated saline solution, and the organic phase was dried by anhydrous sodium sulfate, and then, to give crude product 25-2 (260 mg, 898.50 μmol). LCMS ($ESI^+$) m/z: 290.3 $[M+H]^+$.

Step 2: Synthesis of Compound 25-3:

A dry single-necked flask was added with substrate 25-2 (260 mg, 898.50 μmol) and the reaction was dissolved in methanol (10 mL), and was added with Pd/C (35.25 mg, 290.28 μmol), replaced by $H_2$ three times, and then the reaction was conducted under room temperature for 3 h, monitored by LC-MS. After the reaction was completed, the reaction was filtered with Celite, and the organic phase was concentrated under reduced pressure, and the residue was purified by column chromatography to give product 25-3 (231 mg, 801.50 μmol). LCMS ($ESI^+$) m/z: 260.4 $[M+H]^+$.

Step 3: Synthesis of Compound 25-4:

Following the synthesis method in the Example 1, Step 1, the synthesis method was conducted similarly by replacing Step 1 1-1 (247.51 mg, 1.29 mmol) with 25-3 (231 mg, 801.50 μmol), to give product 25-4 (60 mg, 158.95 μmol). LCMS ($ESI^+$) m/z: 378.5 $[M+H]^+$.

Step 4: Synthesis of Compound 25:

Following the synthesis method in the Example 1, Step 3, the synthesis method was conducted similarly by replacing Step 3 1-3 (105 mg, 339.40 μmol) with 25-4 (60 mg, 158.95 μmol), to give Compound 25 (35 mg, 51.31 μmol). $^1H$ NMR (400 MHz, DMSO-$d_6$) δ 9.70 (s, 1H), 9.02 (s, 1H), 8.30 (s, 1H), 7.81 (t, J=7.9 Hz, 1H), 7.62 (dd, J=14.0, 8.3 Hz, 3H), 6.92 (d, J=9.0 Hz, 2H), 6.65 (d, J=8.0 Hz, 1H), 3.46 (s, 6H), 3.16-2.92 (m, 4H), 2.33-2.23 (m, 4H), 2.15 (s, 3H), 1.61-1.51 (m, 4H), 1.51-1.40 (m, 4H) LCMS($ESI^+$) m/z: 545.7 $[M+H]^+$, HPLC Method B: $R_T$=6.09 min, purity: 81.9%.

Example 26: Synthesis of Compound 26

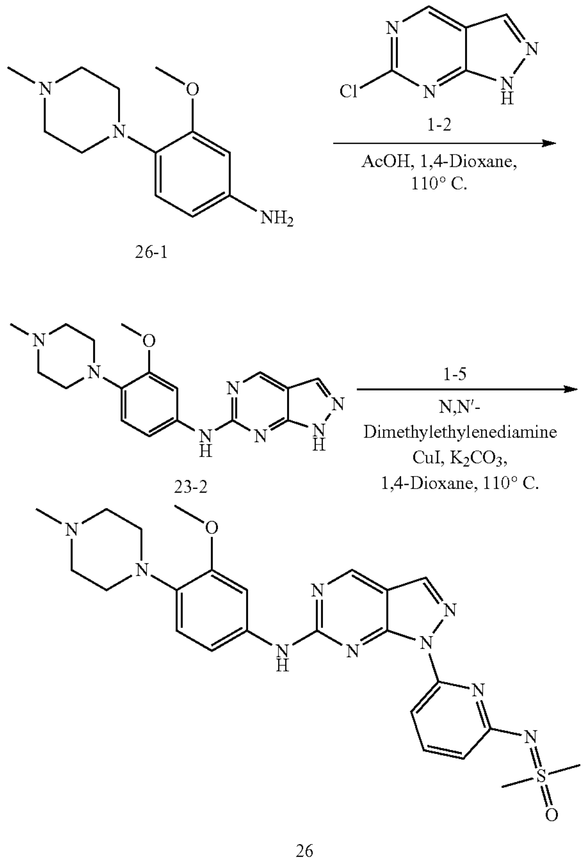

26-1

23-2

26

Step 1: Synthesis of Compound 26-2:

Following the synthesis method in the Example 1, Step 1, the synthesis method was conducted similarly by replacing Step 1 1-1 (247.51 mg, 1.29 mmol) with 26-1, to give product 26-2 (100 mg, 451.88 μmol). LCMS ($ESI^+$) m/z: 340.4 $[M+H]^+$.

Step 2: Synthesis of Compound 26:

Following the synthesis method in the Example 1, Step 3, the synthesis method was conducted similarly by replacing Step 3 1-3 (105 mg, 339.40 μmol) with 26-2 (60 mg, 176.79 μmol), to give Compound 26 (31 mg, 59.85 μmol). $^1H$ NMR (600 MHz, DMSO-$d_6$) δ 9.83 (s, 1H), 9.06 (s, 1H), 8.33 (s, 1H), 7.77 (t, J=7.7 Hz, 1H), 7.62-7.56 (m, 2H), 7.22 (d, J=8.4 Hz, 1H), 6.85 (d, J=8.5 Hz, 1H), 6.67 (d, J=8.0 Hz, 1H), 3.70 (s, 3H), 3.45 (s, 6H), 2.94-2.91 (m, 4H), 2.46-2.43 (m, 4H), 2.21 (s, 3H). LCMS ($ESI^+$) m/z: 508.2 $[M+H]^+$, HPLC Method B: $R_T$=5.64 min, purity: 98.0%.

Example 27: Synthesis of Compound 27

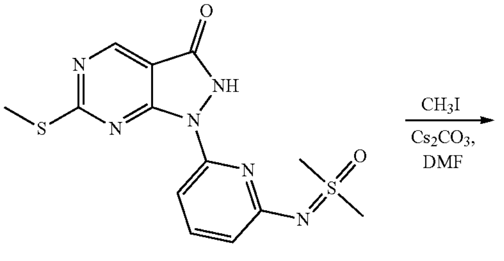

27-1

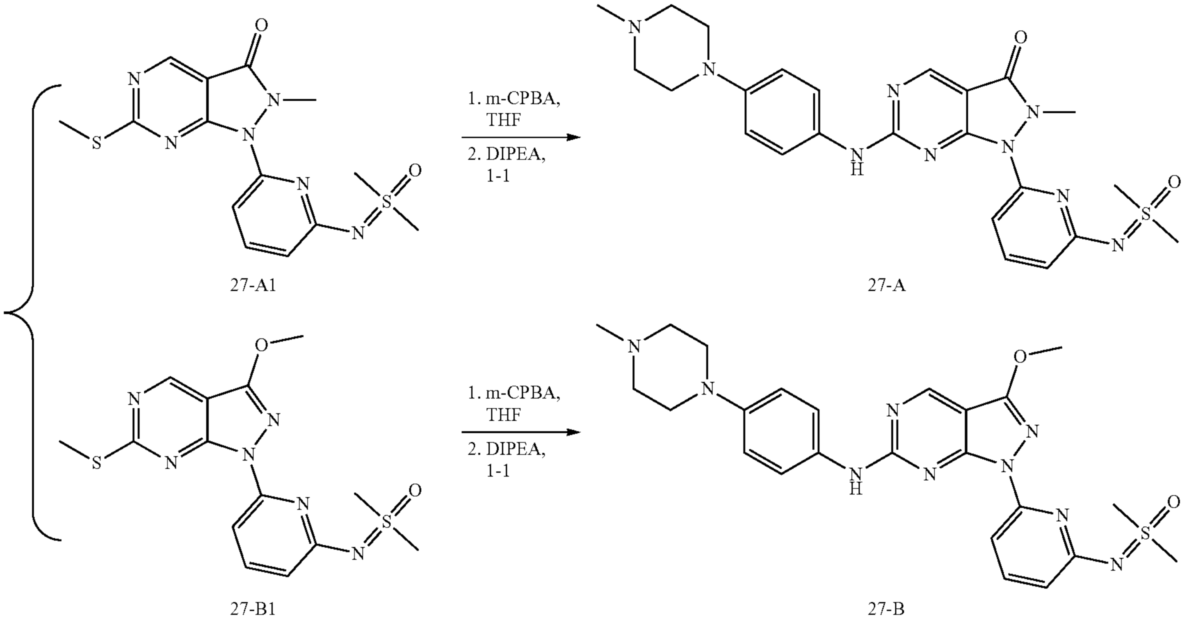

27-A1 27-A

27-B1 27-B

Step 1: Synthesis of Compound 27-A1, 27-B1:

A dry single-necked flask was added with substrate 27-1 (35 mg, 99.88 μmol), $Cs_2CO_3$ (97 mg, 299.64 μmol) and DMF (5 mL), stirred for 5 min, and then added with iodomethane (40.10 mg, 282.52 μmol), heated to 90° C. and reacted, monitored by LC-MS. After the reaction was completed, the reaction was concentrated under reduced pressure, and the residue was purified by medium pressure liquid chromatography (basic method) to give 27-A1 (18 mg, 19.23% yield) or 27-B1 (26 mg, 27.78% yield), LCMS (E+) m/z: 365.3 $[M+H]^+$.

Step 2: Synthesis of Compound 27-A:

A dry single-necked flask was added with substrate 27-A1 (18 mg, 49.39 μmol), tetrahydrofuran (2 mL), stirred and dissolved, and then added with m-CPBA (10.23 mg, 59.27 μmol), under room temperature reacted for 1 h, monitored by LC-MS. After the reaction was completed, the reaction was added with DIPEA (33.39 mg, 258.36 μmol), stirred for 10 min, and then added with 1-1 (20.11 mg, 105.14 μmol), the reaction was conducted under room temperature, monitored by LC-MS. After the reaction was completed, the reaction was concentrated under reduced pressure, and the residue was purified by medium pressure liquid chromatography (basic method) to give 27-A (3 mg, 5.91 mol). $^1H$ NMR (400 MHz, DMSO-$d_6$) δ 8.79 (s, 1H), 7.85 (d, J=6.8 Hz, 1H), 7.58 (s, 2H), 7.33 (d, J=8.0 Hz, 1H), 6.92 (d, J=9.2 Hz, 2H), 6.61 (d, J=8.4 Hz, 1H), 3.43 (s, 3H), 3.36 (s, 6H), 3.10 (s, 4H), 2.53 (s, 4H), 2.24 (s, 3H). $^1H$ NMR (400 MHz, DMSO-$d_6$, $D_2O$) δ 8.79 (s, 1H), 7.85 (s, 1H), 7.57 (s, 2H), 7.33 (d, J=7.8 Hz, 1H), 6.94 (d, J=8.5 Hz, 2H), 6.66 (d, J=7.9 Hz, 1H), 3.44 (s, 3H), 3.35 (s, 6H), 3.11 (s, 4H), 2.49 (s, 4H), 2.24 (s, 3H). LCMS ($ESI^+$) m/z: 508.2 $[M+H]^+$, HPLC Method B: $R_T$=5.36 min, purity: 84.4%.

Step 3: Synthesis of Compound 27-B

A dry single-necked flask was added with substrate 27-B1 (26 mg, 71.34 μmol), and added with tetrahydrofuran (2 mL), stirred and dissolved, and then added with m-CPBA (14.77 mg, 85.61 μmol), under room temperature reacted for 1 h, monitored by LC-MS. After the reaction was completed, the reaction was added with DIPEA (40.81 mg, 315.77 μmol), stirred for 10 min, and then added with 1-1 (30.17 mg, 157.71 μmol), the reaction was conducted under room temperature, monitored by LC-MS. After the reaction was completed, the reaction was concentrated under reduced pressure, and the residue was purified by medium pressure liquid chromatography (basic method) to give 27-B (4 mg, 7.89 μmol). $^1$H NMR (600 MHz, DMSO-$d_6$) δ 9.76 (s, 1H), 8.88 (s, 1H), 7.75 (s, 1H), 7.68 (s, 1H), 7.62-7.61 (m, 2H), 6.95 (d, J=6.0 Hz, 2H), 6.55 (d, J=6.0 Hz, 1H), 4.06 (s, 3H), 3.50 (s, 6H), 3.12 (s, 4H), 2.56 (s, 4H), 2.32 (s, 3H). $^1$H NMR (600 MHz, DMSO-$d_6$, D2O) δ 8.86 (s, 1H), 7.77 (t, J=7.0 Hz, 1H), 7.68 (d, J=7.2 Hz, 1H), 7.60 (d, J=6.6 Hz, 2H), 6.97 (d, J=7.2 Hz, 2H), 6.59 (d, J=7.2 Hz, 1H), 4.07 (s, 3H), 3.50 (s, 6H), 3.14 (s, 4H), 2.65 (s, 4H), 2.31 (s, 3H). LCMS (ESI$^+$) m/z: 508.2 [M+H]$^+$, HPLC Method B: $R_T$=6.54 min, purity: 96.5%.

Example 28: Synthesis of Compound 28

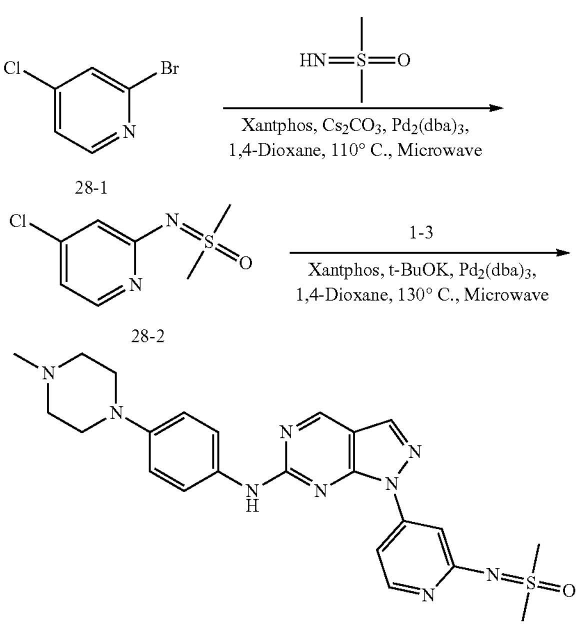

28-1

28-2

28

Step 1: Synthesis of Compound 28-2:

A dried microwave tube was added with substrate 28-1 (500 mg, 2.60 mmol), dimethylsulfoximide (169.41 mg, 1.82 mmol), Xantphos (75.17 mg, 129.91 μmol), Pd2(dba)3 (47.58 mg, 51.96 μmol) and $Cs_2CO_3$ (880.41 mg, 2.70 mmol), and the mixture was added with 1,4-dioxane (30 mL) and dissolved, and the mixture was reacted with the protection of nitrogen under microwave at 110° C. and stirred for 12 hrs, monitored by LC-MS. After the reaction was completed, the reaction was extracted three times with water and ethyl acetate, and the organic phase was dried by anhydrous sodium sulfate, and then concentrated under reduced pressure, and the residue was purified by column chromatography to give product 28-2 (113.4 mg, 217.97 μmol). LCMS (ESI$^+$) m/z: 205.1 [M+H]$^+$.

Step 2: Synthesis of Compound 28:

A dried microwave tube was added with substrate 1-3 (100 mg, 323.24 μmol), 28-2 (55.13 mg, 269.37 μmol), t-BuOK (30.23 mg, 269.37 μmol), $Pd_2(dba)_3$ (8.63 mg, 9.43 μmol) and Xantphos (15.59 mg, 26.94 μmol), and the mixture was added with 1,4-dioxane (3 mL) and dissolved, and the mixture was reacted with the protection of nitrogen under microwave at 130° C. and stirred for 10 hrs, monitored by LC-MS. After the reaction was completed, the reaction was extracted three times with water and ethyl acetate, and the organic phase was dried by anhydrous sodium sulfate, and then concentrated under reduced pressure, and the residue was purified by recrystallization to give product 28 (113.4 mg, 217.97 μmol). $^1$H NMR (400 MHz, DMSO-$d_6$) δ 10.84 (s, 1H), 10.03 (s, 1H), 9.05 (s, 1H), 8.36 (s, 1H), 8.23 (d, J=5.4 Hz, 1H), 7.73 (d, J=6.6 Hz, 3H), 7.05 (d, J=9.0 Hz, 2H), 3.77 (s, 2H), 3.44 (s, 6H), 3.17 (s, 2H), 3.09 (s, 2H), 2.81 (s, 3H), 2.53 (s, 2H). LCMS (ESI$^+$) m/z: 478.2 [M+H]$^+$, HPLC Method B: $R_T$=5.86 min, purity: 91.8%.

Example 29: Synthesis of Compound 29

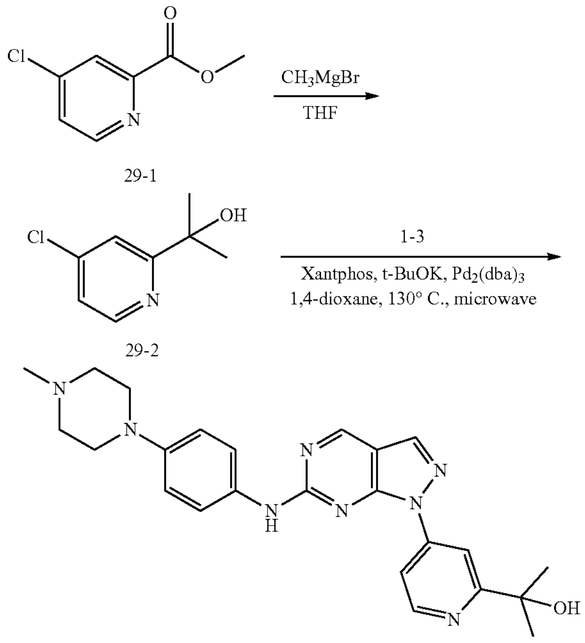

29-1

29-2

29

Step 1: Synthesis of Compound 29-2:

A dry three-necked flask was added with substrate 29-1 (500 mg, 2.91 mmol), and the reaction was dissolved in THF (10 ml) and replaced with $N_2$ three times, and added at 0° C. dropwisely with methylmagnesium bromide (764 mg, 6.41 mmol), and then under room temperature stirred for 1 h, monitored by LC-MS. After the reaction was completed, the reaction was quenched with saturated ammonium chloride solution, and the reaction was extracted three times with water and ethyl acetate, and the organic phase was dried by anhydrous sodium sulfate, and then concentrated under reduced pressure, and the residue was purified by column chromatography to give product 29-2 (165 mg, 0.965 mmol). LCMS (ESI$^+$) m/z: 172.2 [M+H]$^+$.

Step 2: Synthesis of Compound 29:

Following the synthesis method in the Example 28, Step 2, the synthesis method was conducted similarly by replacing Step 2 28-2 (55.13 mg, 269.37 μmol) with 29-2 (38 mg, 0.22 mmol), to give Compound 29 (18 mg, 4.054 μmol). $^1$H NMR (400 MHz, DMSO-$d_6$) δ 10.02 (s, 1H), 9.10 (s, 1H), 8.68 (d, J=5.4 Hz, 1H), 8.61 (s, 1H), 8.44 (s, 1H), 8.20 (S, 1H), 7.76 (d, J=6.6 Hz, 2H), 7.06 (d, J=8.4 Hz, 2H), 5.44 (s, 1H), 3.17 (s, 4H), 2.54 (s, 4H), 2.29 (s, 3H), 1.57 (s, 6H). LCMS ($ESI^+$) m/z: 445.2 $[M+H]^+$, HPLC Method B: $R_T$=6.65 min, purity: 92.9%.

Example 30: Synthesis of Compound 30

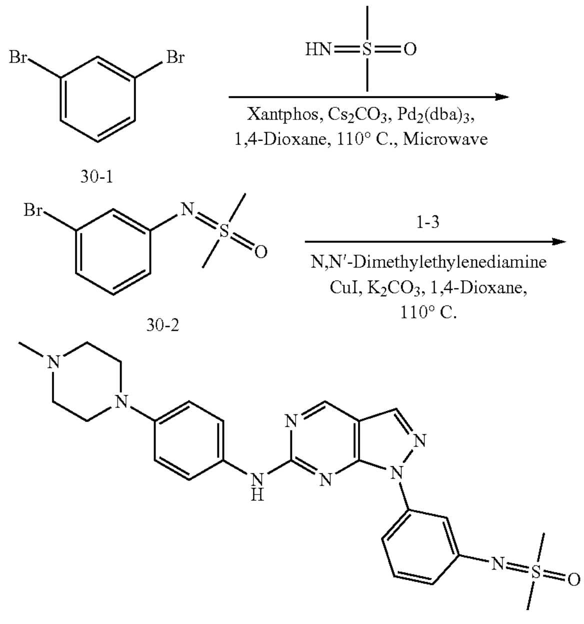

30-1

30-2

30

Step 1: Synthesis of Compound 30-2:

Following the synthesis method in the Example 28, Step 1, the synthesis method was conducted similarly by replacing Step 1 28-1 (500 mg, 2.60 mmol) with 30-1 (500 mg, 2.12 mmol), to give product 30-2 (340 mg, 1.37 mmol). LCMS ($ESI^+$) m/z: 249.0 $[M+H]^+$.

Step 2: Synthesis of Compound 30:

Following the synthesis method in the Example 1, Step 3, the synthesis method was conducted similarly by replacing Step 3 1-5 (109.92 mg, 441.22 μmol) with 30-2 (67 mg, 0.27 mmol), to give Compound 30 (22.8 mg, 44.17 μmol). $^1$H NMR (400 MHz, DMSO-$d_6$) δ 9.81 (s, 1H), 9.02 (s, 1H), 8.27 (s, 1H), 7.82-7.80 (m, 1H), 7.75 (s, 1H), 7.69 (d, J=5.6 Hz, 2H), 7.38 (t, J=5.6 Hz, 1H), 6.95-6.92 (m, 3H), 3.26 (s, 6H), 3.09 (t, J=2.8 Hz, 4H), 2.47 (t, J=2.8 Hz, 4H), 2.23 (s, 3H). LCMS ($ESI^+$) m/z: 477.1 $[M+H]^+$, HPLC Method B: $R_T$=6.11 min, purity: 95.9%.

Example 31: Synthesis of Compound 31

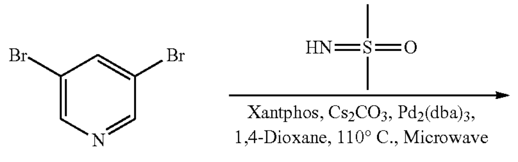

31-1

-continued

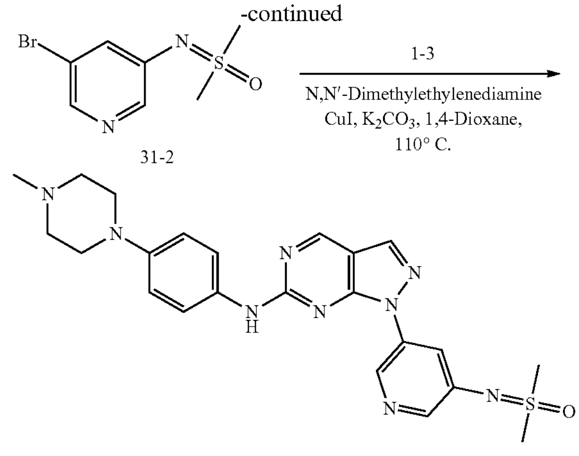

31-2

31

Step 1: Synthesis of Compound 31-2:

Following the synthesis method in the Example 28, Step 1, the synthesis method was conducted similarly by replacing Step 1 28-1 (500 mg, 2.60 mmol) with 31-1 (300 mg, 1.27 mmol), to give product 31-2 (310 mg, 1.24 mmol). LCMS ($ESI^+$) m/z: 249.0 $[M+H]^+$.

Step 2: Synthesis of Compound 31:

Following the synthesis method in the Example 1, Step 3, the synthesis method was conducted similarly by replacing Step 3 1-5 (109.92 mg, 441.22 μmol) with 31-2 (40 mg, 0.16 mmol), to give Compound 31 (25.3 mg, 52.50 μmol). $^1$H NMR (400 MHz, DMSO-$d_6$) δ 9.88 (s, 1H), 9.06 (s, 1H), 9.04 (s, 1H), 8.34 (s, 1H), 8.17 (s, 1H), 8.06 (s, 1H), 7.65 (d, J=6.0 Hz, 2H), 6.93 (d, J=6.0 Hz, 2H), 3.33 (s, 6H), 3.11 (s, 4H), 2.52 (s, 4H), 2.26 (s, 3H). LCMS ($ESI^+$) m/z: 478.1 $[M+H]^+$, HPLC Method B: $R_T$=5.46 min, purity: 98.9%.

Example 32: Synthesis of Compound 32

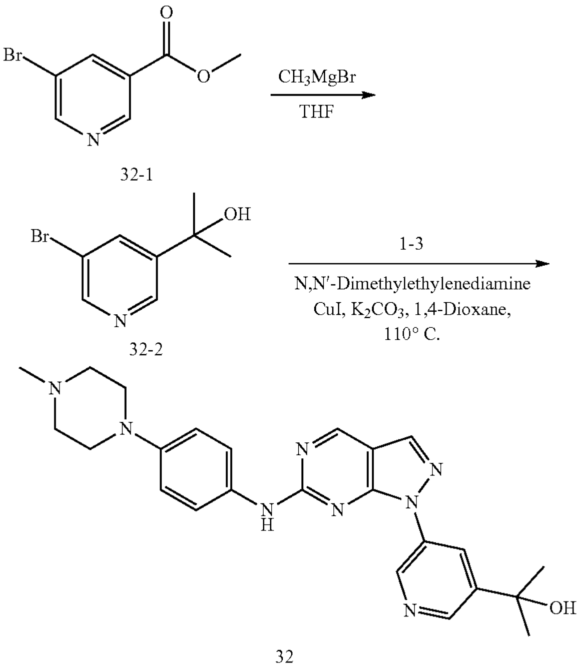

32-1

32-2

32

Step 1: Synthesis of Compound 32-2:

Following the synthesis method in the Example 29, Step 1, the synthesis method was conducted similarly by replacing Step 1 29-1 (500 mg, 2.91 mmol) with 32-1 (300 mg, 1.39 mmol), to give product 32-2 (374 mg, crude). LCMS ($ESI^+$) m/z: 217.0 $[M+H]^+$.

Step 2: Synthesis of Compound 32:

Following the synthesis method in the Example 1, Step 3, the synthesis method was conducted similarly by replacing Step 3 1-5 (109.92 mg, 441.22 μmol) with 32-2 (52 mg, 0.24 mmol), to give Compound 32 (9.8 mg, 21.65 μmol). $^1H$ NMR (400 MHz, DMSO-$d_6$) δ 9.89 (s, 1H), 9.24 (s, 1H), 9.05 (s, 1H), 8.66 (d, J=1.2 Hz, 1H), 8.62 (s, 1H), 8.36 (s, 1H), 7.66 (d, J=6.0 Hz, 2H), 6.93 (d, J=6.0 Hz, 2H), 5.41 (s, 1H), 3.10 (d, J=2.8 Hz, 4H), 2.52 (s, 4H), 2.25 (s, 3H), 1.54 (s, 6H). LCMS ($ESI^+$) m/z: 445.2 $[M+H]^+$, HPLC Method B: $R_T$=5.98 min, purity: 98.2%.

Example 33: Synthesis of Compound 33

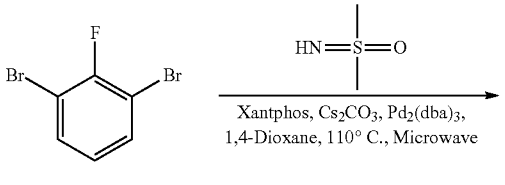

33-1

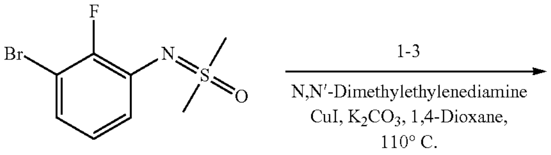

33-2

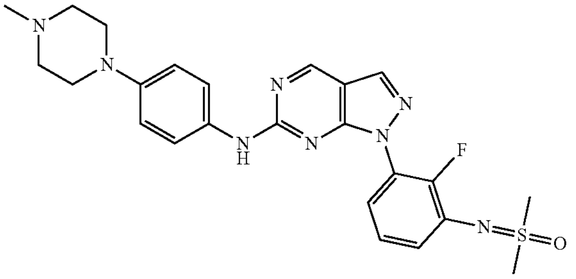

33

Step 1: Synthesis of Compound 33-2:

Following the synthesis method in the Example 28, Step 1, the synthesis method was conducted similarly by replacing Step 1 28-1 (500 mg, 2.60 mmol) with 33-1 (300 mg, 1.18 mmol), to give product 33-2 (230 mg, 0.864 mmol). LCMS ($ESI^+$) m/z: 266.1 $[M+H]^+$.

Step 2: Synthesis of Compound 33:

Following the synthesis method in the Example 1, Step 3, the synthesis method was conducted similarly by replacing Step 3 1-5 (109.92 mg, 441.22 μmol) with 33-2 (60 mg, 0.23 mmol), to give Compound 33 (5.4 mg, 10.59 μmol). $^1H$ NMR (400 MHz, DMSO-$d_6$) δ 9.73 (s, 1H), 9.02 (s, 1H), 8.29 (s, 1H), 7.59 (d, J=8.4 Hz, 2H), 7.32-7.29 (m, 1H), 7.20 (t, J=7.8 Hz, 1H), 7.16 (t, J=6.0 Hz, 1H), 6.83 (d, J=9.0 Hz, 2H), 3.32 (s, 6H), 3.05 (t, J=4.2 Hz, 4H), 2.46 (s, 4H), 2.23 (s, 3H). LCMS ($ESI^+$) m/z: 495.2 $[M+H]^+$, HPLC Method B: RT=5.62 min, purity: 96.1%.

Example 34: Synthesis of Compound 34

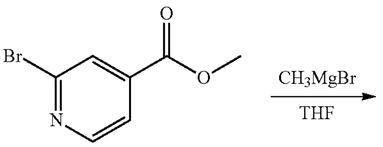

34-1

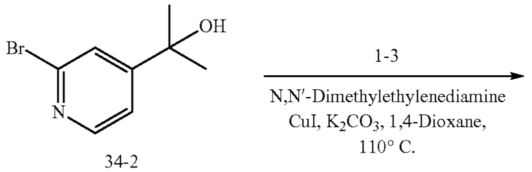

34-2

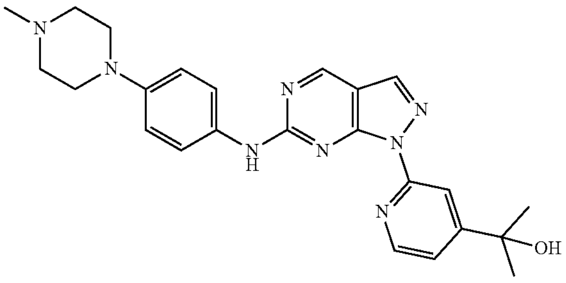

34

Step 1: Synthesis of Compound: 34-2:

Following the synthesis method in the Example 29, Step 1, the synthesis method was conducted similarly by replacing Step 1 29-1 (500 mg, 2.91 mmol) with 34-1 (300 mg, 1.39 mmol), to give product 34-2 (330 mg, crude). LCMS ($ESI^+$) m/z: 216.1 $[M+H]^+$.

Step 2: Synthesis of Compound 34:

Following the synthesis method in the Example 1, Step 3, the synthesis method was conducted similarly by replacing Step 3 1-5 (109.92 mg, 441.22 μmol) with 34-2 (59 mg, 0.272 mmol), to give Compound 34 (30.7 mg, 66.91 μmol). $^1H$ NMR (400 MHz, DMSO-$d_6$) δ 9.84 (s, 1H), 9.03 (s, 1H), 8.57 (s, 1H), 8.31 (s, 1H), 8.15 (s, 1H), 7.78 (d, J=7.2 Hz, 2H), 7.51 (s, 1H), 6.91 (d, J=9.0 Hz, 2H), 5.43 (s, 1H), 3.07 (t, J=4.2 Hz, 4H), 2.46 (t, J=4.2 Hz, 4H), 2.22 (s, 3H), 1.49 (s, 6H). LCMS ($ESI^+$) m/z: 445.3 $[M+H]^+$, HPLC Method B: $R_T$=5.60 min, purity: 96.7%.

Example 35: Synthesis of Compound 35

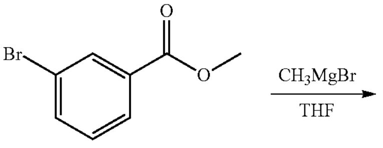

35-1

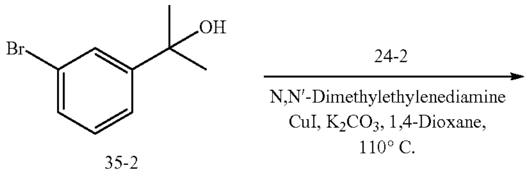

35-2

-continued

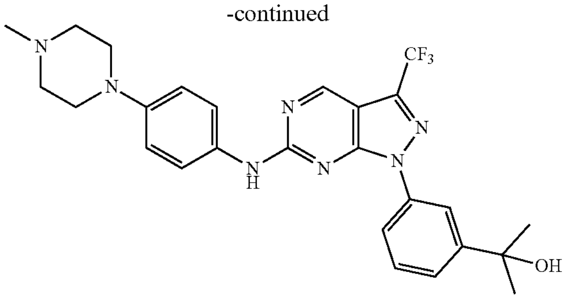

35

Step 1: Synthesis of Compound 35-2:

Following the synthesis method in the Example 29, Step 1, the synthesis method was conducted similarly by replacing Step 1 29-1 (500 mg, 2.91 mmol) with 35-1 (400 mg, 1.86 mmol), to give product 35-2 (360 mg, crude). TLC (PE/EA=3/1) showed that the raw materials were completely reacted, and new points were obtained.

Step 2: Synthesis of Compound 35:

Following the synthesis method in the Example 1, Step 3, the synthesis method was conducted similarly by replacing Step 3 1-5 (109.92 mg, 441.22 μmol) with 35-2 (52 mg, 0.242 mmol), 1-3 (105 mg, 339.40 umol) with 24-2 (97 mg, 0.259 mmol), to give Compound 35 (4.6 mg, 7.81 μmol). $^1$H NMR (400 MHz, DMSO-$d_6$) δ 10.19 (s, 1H), 9.16 (s, 1H), 8.57 (s, 1H), 8.21 (s, 1H), 7.91 (s, 1H), 7.68 (d, J=3.6 Hz, 2H), 7.57-7.53 (m, 2H), 6.94 (d, J=9.0 Hz, 2H), 5.25 (s, 1H), 3.09 (t, J=4.2 Hz, 4H), 2.46 (t, J=4.8 Hz, 4H), 2.23 (s, 3H), 1.50 (s, 6H). LCMS (ESI$^+$) m/z: 512.2 [M+H]$^+$, HPLC Method B: $R_T$=8.86 min, purity: 87.4%.

Example 36: Synthesis of Compound 36

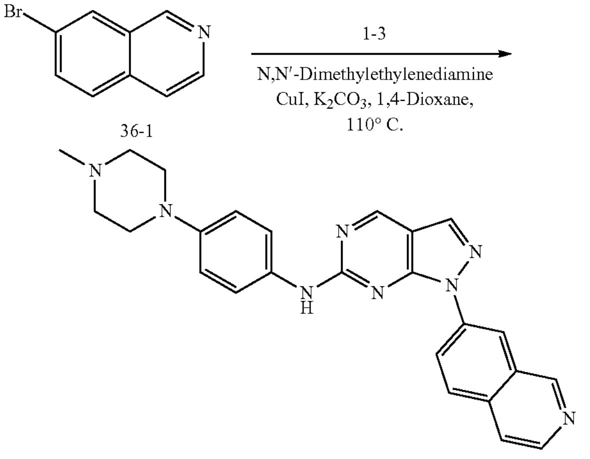

36-1

36

Step 1: Synthesis of Compound 36:

Following the synthesis method in the Example 1, Step 3, the synthesis method was conducted similarly by replacing Step 3 1-5 (109.92 mg, 441.22 μmol) with 36-1 (37 mg, 0.162 mmol), to give Compound 36 (32.5 mg, 64.85 μmol). $^1$H NMR (600 MHz, DMSO-$d_6$) δ 9.92 (s, 1H), 9.36 (s, 1H), 9.08 (s, 1H), 9.02 (s, 1H), 8.69 (d, J=8.4 Hz, 1H), 8.54 (d, J=5.4 Hz, 1H), 8.39 (s, 1H), 8.20 (d, J=9.0 Hz, 1H), 7.91 (d, J=6.0 Hz, 1H), 7.70 (d, J=7.8 Hz, 2H), 7.01 (d, J=9.0 Hz, 2H), 3.14 (d, J=4.8 Hz, 4H), 2.52 (s, 4H), 2.24 (s, 3H). LCMS (ESI$^+$) m/z: 437.2 [M+H]$^+$, HPLC Method B: $R_T$=7.63 min, purity: 87.1%.

Example 37: Synthesis of Compound 37

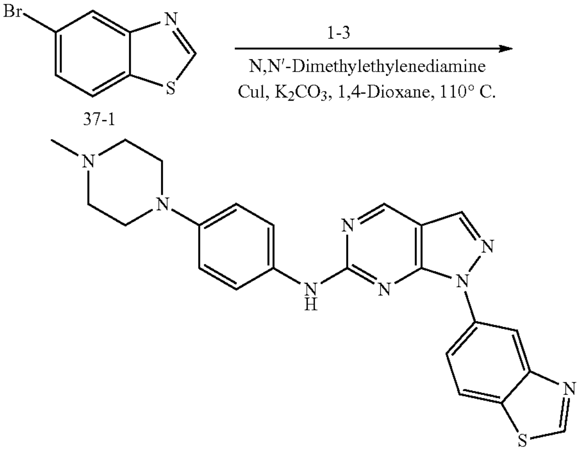

37-1

37

Step 1: Synthesis of Compound 37:

Following the synthesis method in the Example 1, Step 3, the synthesis method was conducted similarly by replacing Step 3 1-5 (109.92 mg, 441.22 μmol) with 37-1 (55 mg, 0.259 mmol), to give Compound 37 (5.9 mg, 13.11 μmol). $^1$H NMR (600 MHz, DMSO-$d_6$) δ 9.93 (s, 1H), 9.52 (s, 1H), 9.07 (s, 1H), 8.96 (s, 1H), 8.41 (dd, J=9.0 Hz, 1H), 8.38 (d, J=7.2 Hz, 2H), 7.73 (d, J=7.8 Hz, 2H), 6.98 (d, J=9.0 Hz, 2H), 3.19 (s, 4H), 2.79 (s, 3H), 2.52 (s, 4H). LCMS (ESI$^+$) m/z: 443.1 [M+H]$^+$, HPLC Method B: $R_T$=7.47 min, purity: 98.3%.

Example 38: Synthesis of Compound 38

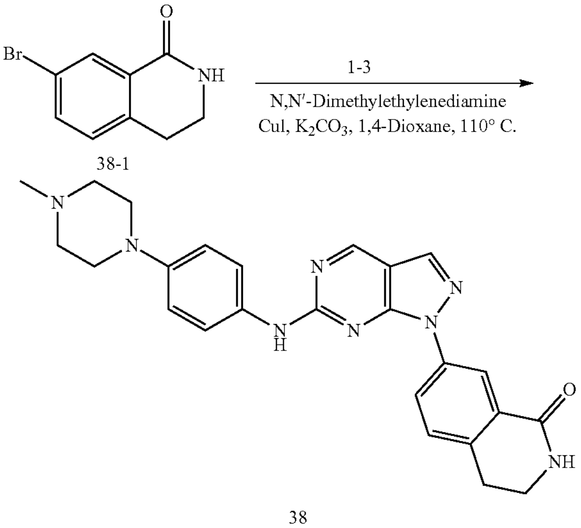

38-1

38

Step 1: Synthesis of Compound 38:

Following the synthesis method in the Example 1, Step 3, the synthesis method was conducted similarly by replacing Step 3 1-5 (109.92 mg, 441.22 μmol) with 38-1 (37 mg, 0.162 mmol), to give Compound 38 (28.7 mg, 53.80 μmol). $^1$H NMR (600 MHz, DMSO-$d_6$) δ 9.88 (s, 1H), 9.04 (s, 1H), 8.72 (s, 1H), 8.31 (d, J=9.0 Hz, 2H), 8.10 (s, 1H), 7.75 (d, J=7.8 Hz, 2H), 7.53 (d, J=8.4 Hz, 1H), 7.00 (d, J=8.6 Hz, 2H), 3.45-3.43 (m, 2H), 3.10 (s, 4H), 2.99 (t, J=6.0 Hz, 2H), 2.52 (s, 4H), 2.27 (s, 3H). LCMS ($ESI^+$) m/z: 455.2 $[M+H]^+$, HPLC Method B: $R_T$=6.25 min, purity: 85.2%.

Example 39: Synthesis of Compound 39

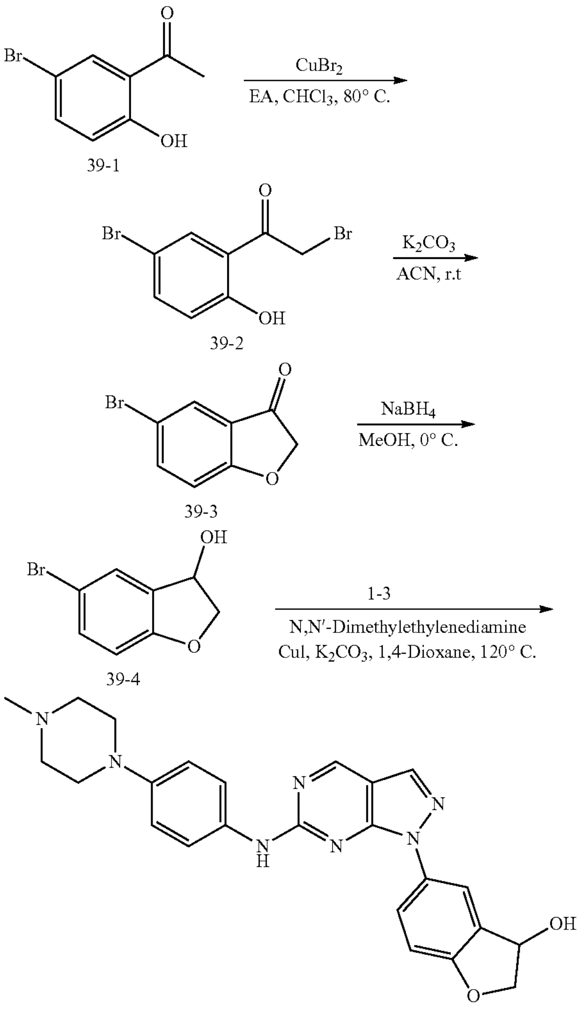

39-1

39-2

39-3

39-4

39

Step 1: Synthesis of Compound 39-2:

A dry single-necked flask was added with $CuBr_2$ (16.70 g, 72.00 mmol) solution in ethyl acetate (30 mL), and under room temperature, the reaction was slowly added drop-wisely with substrate 39-1 (5.20 g, 24.00 mmol) solution in trichloromethane (30 mL), stirred for 30 min, and then moved to 80° C. oil bath to continue the reaction, monitored by TLC. After the reaction was completed, the reaction was filtered, and the stock solution was extracted three times with water and ethyl acetate, and the organic phase was dried by anhydrous sodium sulfate, and then concentrated under reduced pressure to give product 39-2 (7.00 g, 23.90 mmol).

Step 2: Synthesis of Compound 39-3:

A dry single-necked flask was added with substrate 39-2 (7.00 g, 23.90 mmol), $K_2CO_3$ (3.96 g, 28.68 mmol), and the reaction was dissolved in ACN (50 ml), and was stirred under room temperature for 1 h, monitored by LC-MS. After the reaction was completed, the reaction was extracted three times with water and ethyl acetate, and the organic phase was dried by anhydrous sodium sulfate, and then concentrated under reduced pressure, and the residue was purified by column chromatography to give product 39-3 (1.41 g, 6.59 mmol), LCMS ($ESI^+$) m/z: 215.1 $[M+H]^+$.

Step 3: Synthesis of Compound 39-4:

A dry single-necked flask was added with substrate 39-3 (427.9 mg, 2.00 mmol), and the reaction was dissolved in ACN (4 ml), and in ice bath, slowly added with $NaBH_4$ (151.8 mg, 4.00 mmol), and reacted in ice water bath for 1 h, monitored by TLC. After the reaction was completed, the reaction was extracted three times with water and ethyl acetate, and the organic phase was dried by anhydrous sodium sulfate, and then concentrated under reduced pressure to give product 39-4 (210.00 mg, 0.98 mmol).

Step 4: Synthesis of Compound 39

Following the synthesis method in the Example 1, Step 3, the synthesis method was conducted similarly by replacing Step 3 1-5 (109.92 mg, 441.22 μmol) with 39-4 (42.79 mg, 0.20 mmol), to give Compound 39 (10.0 mg, 22.56 μmol). $^1$H NMR (600 MHz, Methanol-$d_6$) δ 9.82 (s, 1H), 9.02 (s, 1H), 8.25 (s, 1H), 8.17 (s, 1H), 7.95 (d, J=8.4 Hz, 1H), 7.72 (d, J=8.4 Hz, 2H), 7.05 (d, J=8.4 Hz, 1H), 6.95 (d, J=9.0 Hz, 2H), 5.80 (d, J=6.0 Hz, 1H), 5.39 (q, J=3.2 Hz, 1H), 4.66-4.63 (m, 1H), 4.35-4.33 (m, 1H), 3.08 (s, 4H), 2.46 (s, 4H), 2.23 (s, 3H). LCMS ($ESI^+$) m/z: 444.2 $[M+H]^+$, HPLC Method B: $R_T$=6.24 min, purity: 88.2%.

Example 40: Synthesis of Compound 40

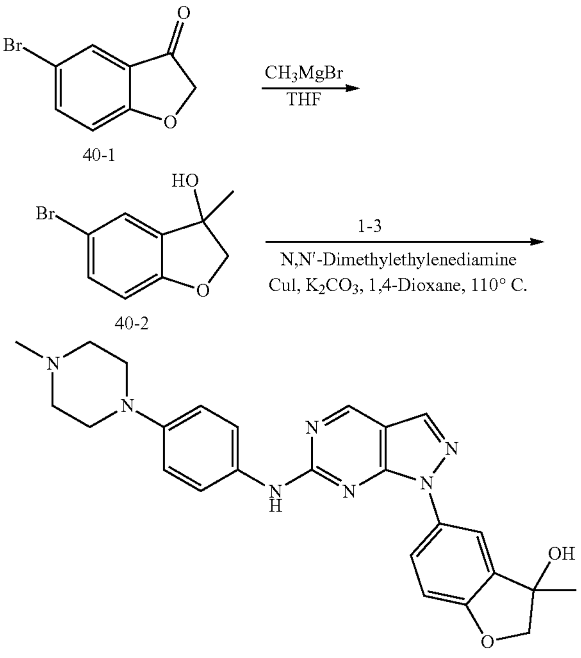

40-1

40-2

40

40

SFC

-continued

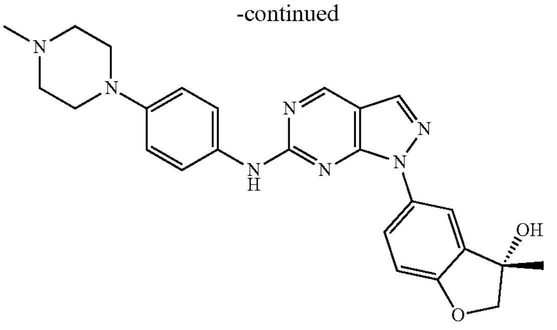

40-A

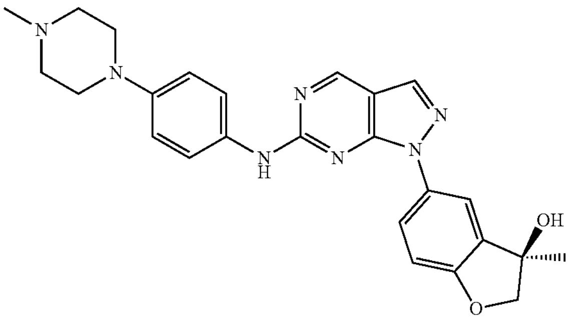

40-B

Step 1: Synthesis of Compound 40-2:

Following the synthesis method in the Example 29, Step 1, the synthesis method was conducted similarly by replacing Step 1 29-1 (500 mg, 2.91 mmol) with 40-1 (423.90 mg, 2.00 mmol), to give Compound 40-2 (210.00 mg, 0.98 mmol), LCMS ($ESI^+$) m/z: 211.2 $[M+H—H_2O]^+$.

Step 2: Synthesis of Compound 40:

Following the synthesis method in the Example 1, Step 3, the synthesis method was conducted similarly by replacing Step 3 1-5 (109.92 mg, 441.22 μmol) with 40-2 (45.59 mg, 0.20 mmol), to give Compound 40 (20.00 mg, 43.74 μmol). $^1H$ NMR (600 MHz, Methanol-$d_4$) δ 9.83 (s, 1H), 9.02 (s, 1H), 8.25 (s, 1H), 8.15 (s, 1H), 7.93 (d, J=9.6 Hz, 1H), 7.72 (d, J=8.4 Hz, 2H), 7.03 (d, J=9.0 Hz, 1H), 6.95 (d, J=8.4 Hz, 2H), 5.68 (s, 1H), 4.42 (d, J=9.6 Hz, 1H), 4.38 (d, J=9.6 Hz, 1H), 3.08 (s, 4H), 2.46 (s, 4H), 2.22 (s, 3H), 1.61 (s, 3H). LCMS ($ESI^+$) m/z: 458.1 $[M+H]^+$, HPLC Method B: $R_T$=6.53 min, purity: 87.3%. Compound 40 was chirally separated, to give Compound 40-A and Compound 40-B.

40-A: $^1H$ NMR (600 MHz, DMSO-$d_6$) δ 9.83 (s, 1H), 9.02 (s, 1H), 8.25 (s, 1H), 8.16 (s, 1H), 7.93 (d, J=8.4 Hz, 1H), 7.72 (d, J=8.4 Hz, 2H), 7.03 (d, J=8.4 Hz, 1H), 6.95 (d, J=9.6 Hz, 2H), 5.69 (s, 1H), 4.42 (d, J=9.6 Hz, 1H), 4.38 (d, J=9.6 Hz, 1H), 3.07 (s, 4H), 2.46 (s, 4H), 2.22 (s, 3H), 1.62 (s, 3H). LCMS ($ESI^+$) m/z: 458.1 $[M+H]^+$. HPLC: Method B: $R_T$:6.40 min, purity: 95.5%.

40-B: $^1H$ NMR (600 MHz, DMSO-$d_6$) δ 9.83 (s, 1H), 9.02 (s, 1H), 8.25 (s, 1H), 8.15 (s, 1H), 7.93 (d, J=8.4 Hz, 1H), 7.72 (d, J=8.4 Hz, 2H), 7.03 (d, J=8.4 Hz, 1H), 6.95 (d, J=9.6 Hz, 2H), 5.69 (s, 1H), 4.43 (d, J=9.6 Hz, 1H), 4.38 (d, J=9.6 Hz, 1H), 3.08 (s, 4H), 2.50-2.46 (m, 4H), 2.22 (s, 3H), 1.61 (s, 3H). LCMS ($ESI^+$) m/z: 458.1 $[M+H]^+$. HPLC: Method B, $R_T$: 6.53 min, purity: 100%.

Example 41: Synthesis of Compound 41

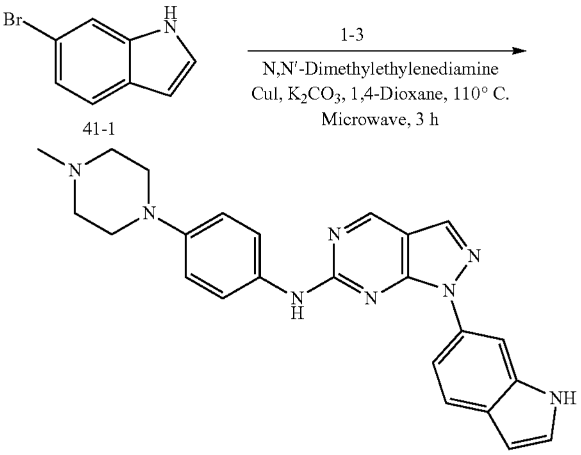

41-1

41

Step 1: Synthesis of Compound 41:

Following the synthesis method in the Example 1, Step 3, the synthesis method was conducted similarly by replacing Step 3 1-5 (109.92 mg, 441.22 μmol) with 41-1 (38 mg, 0.194 mmol), to give Compound 41 (2.0 mg, 4.50 μmol). $^1H$ NMR (600 MHz, DMSO-$d_6$) δ 11.34 (s, 1H), 9.79 (s, 1H), 9.03 (s, 1H), 8.28 (d, J=4.8 Hz, 1H), 8.08 (s, 1H), 7.85 (dd, J=8.4 Hz, 1H), 7.75-7.71 (m, 3H), 7.46 (t, J=2.4 Hz, 1H), 6.95 (d, J=9.0 Hz, 2H), 6.52 (s, 1H), 3.09 (s, 4H), 2.48 (s, 4H), 2.24 (s, 3H). LCMS ($ESI^+$) m/z: 425.1 $[M+H]^{30}$, HPLC Method B: $R_T$=7.54 min, purity: 95.5%.

Example 42: Synthesis of Compound 42

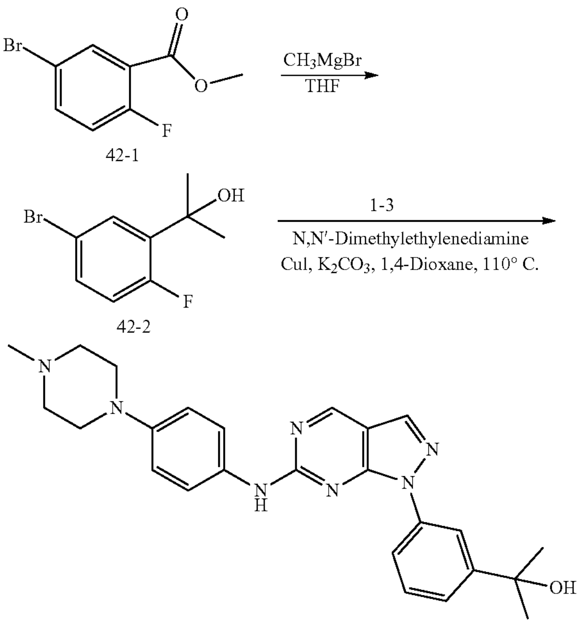

42-1

42-2

42

Step 1: Synthesis of Compound 42-2:

Following the synthesis method in the Example 29, Step 1, the synthesis method was conducted similarly by replacing Step 1 29-1 (500 mg, 2.91 mmol) with 42-1 (1 g, 4.29 mmol), to give Compound 42-2 (850 mg, crude). TLC (PE/EA=3/1) showed that the raw materials were completely reacted, and new points were obtained.

Step 2: Synthesis of Compound 42:

Following the synthesis method in the Example 1, Step 3, the synthesis method was conducted similarly by replacing Step 3 1-5 (109.92 mg, 441.22 μmol) with 42-2 (63 mg, 0.269 mmol), to give Compound 42 (12 mg, 23.56 μmol). $^1H$ NMR (600 MHz, DMSO-$d_6$) δ 9.85 (s, 1H), 9.03 (s, 1H), 8.40 (d, J=4.8 Hz, 1H), 8.29 (s, 1H), 8.06 (s, 1H), 7.73 (d, J=7.8 Hz, 2H), 7.37 (q, J=11.4 Hz, 1H), 6.96 (d, J=9.0 Hz, 2H), 5.47 (s, 1H), 3.09 (s, 4H), 2.47 (s, 3H), 2.23 (s, 4H), 1.58 (s, 6H). LCMS (ESI$^+$) m/z: 462.1 $[M+H]^+$, HPLC Method B: $R_T$=7.56 min, purity: 93.9%.

Example 43: Synthesis of Compound 43

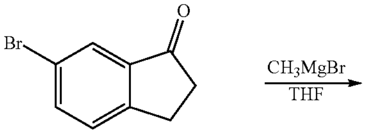

43-1

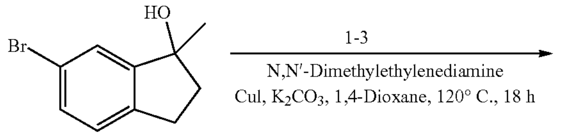

43-2

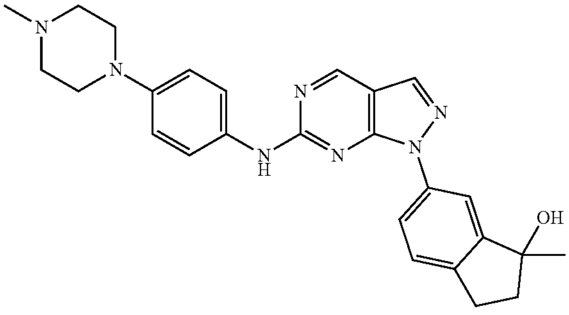

43

Step 1: Synthesis of Compound 43-2:

Following the synthesis method in the Example 29, Step 1, the synthesis method was conducted similarly by replacing Step 1 29-1 (500 mg, 2.91 mmol) with 43-1 (452.00 mg, 2.00 mmol), to give Compound 43-2 (200 mg, 0.88 mmol), LCMS (ESI$^+$) m/z: 209.2 $[M+H—H_2O]^+$.

Step 2: Synthesis of Compound 43:

Following the synthesis method in the Example 1, Step 3, the synthesis method was conducted similarly by replacing Step 3 1-5 (109.92 mg, 441.22 μmol) with 43-2 (45.20 mg, 0.20 mmol), to give Compound 43 (10.00 mg, 21.96 μmol). $^1H$ NMR (600 MHz, Methanol-$d_6$) δ 9.85 (s, 1H), 9.02 (s, 1H), 8.27 (s, 1H), 8.17 (s, 1H), 7.74 (d, J=8.4 Hz, 2H), 7.39 (d, J=8.4 Hz, 1H), 7.16 (d, J=8.4 Hz, 1H), 6.84 (d, J=8.4 Hz, 2H), 5.13 (s, 1H), 3.09 (s, 4H), 2.87-2.79 (m, 2H), 2.49 (s, 4H), 2.26 (s, 3H), 2.04 (t, J=7.2 Hz, 2H), 1.47 (s, 3H). LCMS (ESI$^+$) m/z: 456.1 $[M+H]^+$, HPLC Method B: $R_T$=7.17 min, purity: 93.5%.

Example 44: Synthesis of Compound 44

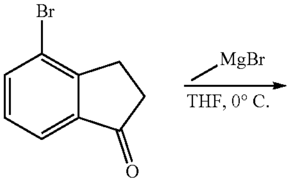

44-1

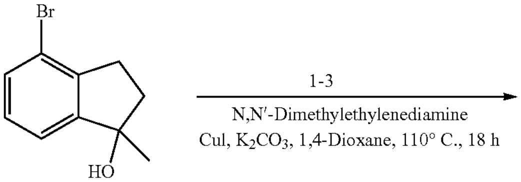

44-2

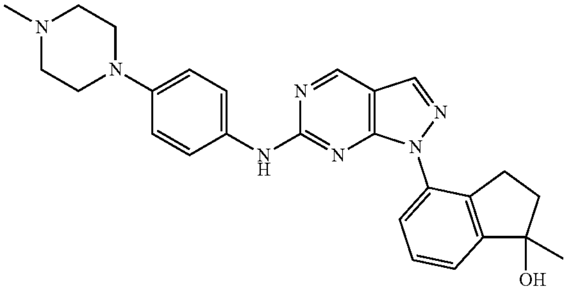

44

Step 1: Synthesis of Compound 44-2:

在 Following the synthesis method in the Example 29, Step 1, the synthesis method was conducted similarly by replacing Step 1 29-1 (500 mg, 2.91 mmol) with 44-1 (452.00 mg, 2.00 mmol) to give Compound 44-2 (200.00 mg, 0.88 mmol), LCMS (ESI$^+$) m/z: 209.2 $[M+H—H_2O]^+$.

Step 2: Synthesis of Compound 44:

Following the synthesis method in the Example 1, Step 3, the synthesis method was conducted similarly by replacing Step 3 1-5 (109.92 mg, 441.22 μmol) with 44-2 (45.20 mg, 0.20 mmol), to give Compound 44 (10.0 mg, 21.96 μmol). $^1H$ NMR (600 MHz, DMSO-$d_6$) δ 9.75 (s, 1H), 9.02 (s, 1H), 8.27 (s, 1H), 7.62 (d, J=8.4 Hz, 2H), 7.57 (d, J=8.4 Hz, 1H), 7.45-7.40 (m, 2H), 6.84 (d, J=8.4 Hz, 2H), 5.19 (s, 1H), 3.05 (s, 4H), 2.95-2.84 (m, 2H), 2.47 (s, 4H), 2.23 (s, 3H), 2.06 (t, J=7.2 Hz, 2H), 1.46 (s, 3H). LCMS (ESI$^+$) m/z: 456.1 $[M+H]^+$, HPLC Method B: $R_T$=6.50 min, purity: 94.0%.

Example 45: Synthesis of Compound 45

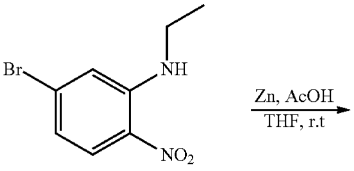

45-1

-continued

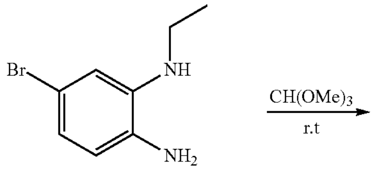

42-2

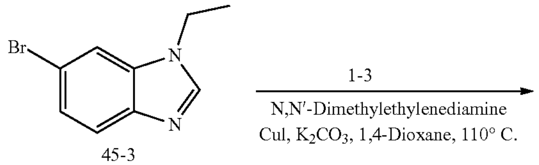

45-3

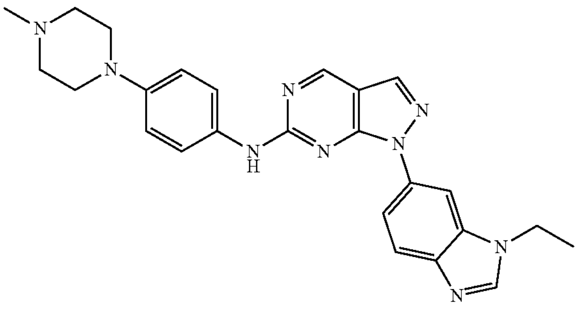

45

Step 1: Synthesis of Compound 45-2:

A dry single-necked flask was added with substrate 45-1 (1.23 g, 5.00 mmol), AcOH (1 mL) solution in THF (4 ml), and under room temperature slowly added with Zn powder (3.30 g, 50.00 mmol), under room temperature stirred for 0.5 h, monitored by TLC. After the reaction was completed, the reaction was filtered with Celite, and the stock solution was extracted three times with water and ethyl acetate, and the organic phase was dried by anhydrous sodium sulfate, and then concentrated under reduced pressure to give product 45-2 (0.86 g, 4.0 mmol).

Step 2: Synthesis of Compound 45-3:

A dry single-necked flask was added with substrate 45-2 (214.0 mg, 1.0 mmol) and $CH(OMe)_3$ (3 mL), under room temperature stirred for 1 h, monitored by LC-MS. After the reaction was completed, the reaction was concentrated under reduced pressure to give product 45-3 (210.00 mg, 0.95 mmol), LCMS ($ESI^+$) m/z: 225.2 $[M+H]^+$.

Step 3: Synthesis of Compound 45

Following the synthesis method in the Example 1, Step 3, the synthesis method was conducted similarly by replacing Step 3 1-5 (109.92 mg, 441.22 μmol) with 45-3 (44.79 mg, 0.20 mmol), to give Compound 45 (10.00 mg, 22.06 μmol). $^1$H NMR (600 MHz, DMSO-$d_6$) δ 9.82 (s, 1H), 9.04 (s, 1H), 8.40 (s, 2H), 8.31 (s, 1H), 8.05 (d, J=7.8 Hz, 1H), 7.86 (s, 1H), 7.68 (d, J=8.4 Hz, 2H), 6.94 (d, J=9.0 Hz, 2H), 4.31 (q, J=7.2 Hz, 2H), 3.10 (s, 4H), 2.47 (s, 4H), 2.23 (s, 3H), 1.42 (t, J=7.2 Hz, 3H). LCMS ($ESI^+$) m/z: 454.1 $[M+H]^+$, HPLC Method B: $R_T$=6.44 min, purity: 96.5%.

Example 46: Synthesis of Compound 46

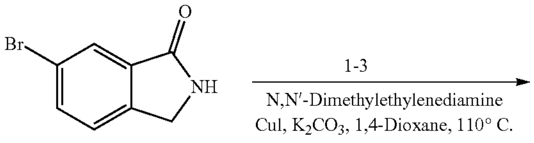

46-1

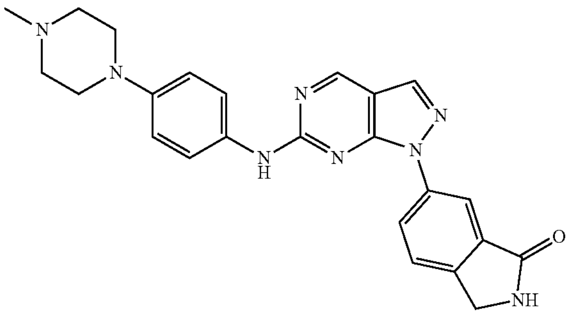

46

Step 1: Synthesis of Compound 46:

Following the synthesis method in the Example 1, Step 3, the synthesis method was conducted similarly by replacing Step 3 1-5 (109.92 mg, 441.22 μmol) with 46-1 (57 mg, 0.269 mmol), to give Compound 46 (8.8 mg, 19.26 μmol). $^1$H NMR (600 MHz, DMSO-$d_6$) δ 9.83 (s, 1H), 9.05 (s, 1H), 8.78 (s, 1H), 8.68 (s, 1H), 8.42 (d, J=8.4 Hz, 1H), 8.34 (s, 1H), 7.79-7.74 (m, 3H), 7.02 (d, J=8.4 Hz, 2H), 4.46 (s, 2H), 3.10 (s, 4H), 2.47 (s, 4H), 2.23 (s, 3H). LCMS ($ESI^+$) m/z: 441.1 $[M+H]^+$, HPLC Method B: $R_T$=7.56 min, purity: 96.5%.

Example 47: Synthesis of Compound 47

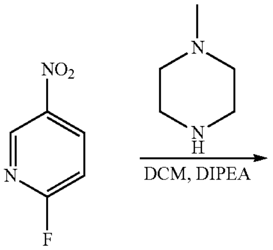

47-1

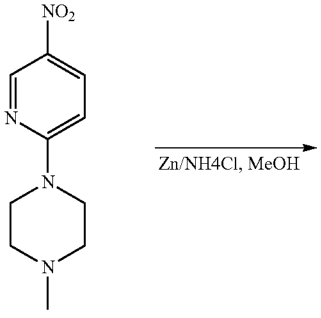

47-2

-continued

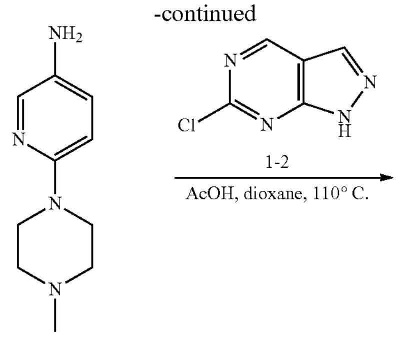

47-3

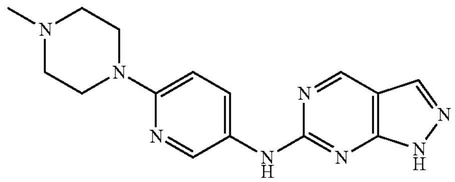

47-4

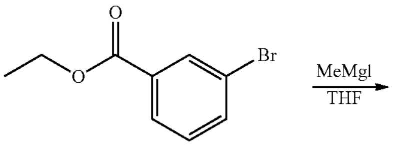

47-5

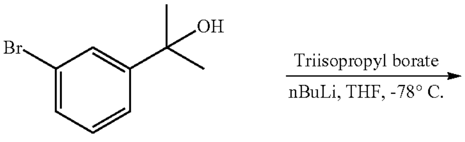

47-6

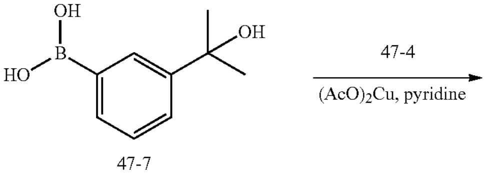

47-7

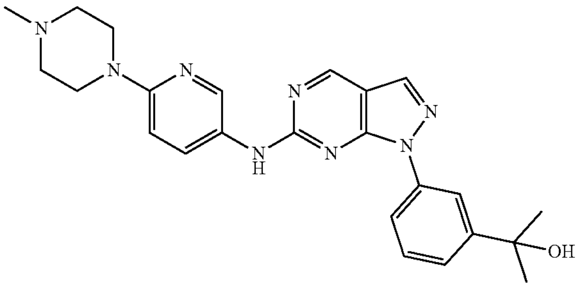

47

Step 1: Synthesis of Compound 47-2:

A dry single-necked flask was added with 47-1 (3 g, 21 mmol), added with DCM (60 mL) and dissolved, and further in sequence added with DIPEA (3.27 g, 25 mmol) and N-methylpiperazine (2.1 g, 21 mmol), stirred under room temperature for 1 hr. The reaction was added with water (50 mL), and after fully stirring, the liquid was separated, and the organic phase was dried by anhydrous sodium sulfate, and then filtered, and the filtrate was concentrated, and without purification, crude product could be used in the reaction in the next step, to give crude product 47-2 (4.2 g, crude) as yellow solid.

Step 2: Synthesis of Compound 47-3:

A dry single-necked flask was added with 47-2 (2.2 g, 10 mmol), and the reaction was added with methanol (100 mL) and dissolved, added with ammonium chloride (2.6 g, 50 mmol), and under stirring condition, slowly added with zinc powder (3.3 g, 50 mmol), with exothermic phenomenon occurred, and stirred under room temperature for 2 hrs. The reaction was filtered, and the filtrate was concentrated, and the residue was purified by column chromatography with silica gel column (DCM:MeOH=8:1) to give product 47-3 (1.2 g) as brown solid.

Step 3: Synthesis of Compound 47-4:

A dry single-necked flask was added with 47-3 (400 mg, 2.1 mmol) and 1-2 (323 mg, 2.1 mmol), and the mixture was added with 1,4-dioxane/acetic acid (20 mL/2 mL) mixture solvent to dissolve, and heated to 110° C., reacted for 4 hrs, After the reaction was completed, the reaction was cooled, and the solvent was concentrated, and the residue impurity was purified by column chromatography with silica gel column (DCM:MeOH=10:1) to give 47-4 (260 mg) as yellow solid.

Step 4: Synthesis of Compound 47-6:

A dry two-necked flask was added with methylmagnesium iodide (2 M in THF, 21.5 mL), and in ice bath and with the protection of nitrogen, added with 47-5 (2 g, 8.7 mmol) solution in THF (dry, 20 mL), slowly heated to room temperature and stirred overnight. The reaction was quenched with saturated ammonium chloride solution (50 mL), and then extracted with ethyl acetate three times, and the organic phase was combined, and was dried with anhydrous sodium sulfate and filtered, and the filtrate was concentrated under reduced pressure, and the residue was purified by column chromatography with silica gel column (PE/EA=5/1) to give product 47-6 (1.8 g) as clear oil.

Step 5: Synthesis of Compound 47-7:

A dry three-necked flask was added with 47-6 (430 mg, 2 mmol), added with anhydrous THF (20 mL) and dissolved, and with the protection of nitrogen cooled to −78° C., and then slowly added dropwisely with n-butyl lithium (2.5 M, 1.2 mL), stirred for 0.5 hrs, and then added with isopropyl borate (560 mg, 3 mmol), and continued to stir for 2 hrs, and the reaction was quenched with water (30 mL), and then extracted with ethyl acetate three times, and the organic phase was combined and dried with anhydrous sodium sulfate and then filtered, and the filtrate was concentrated under reduced pressure, to give crude product 47-7 (380 mg, crude) as white solid, and the crude product was used directly in the next step reaction.

Step 6: Synthesis of Compound 47:

A dry single-necked flask was added with 47-4 (31 mg, 0.1 mmol), 47-7 (27 mg, 0.15 mmol) and pyridine (16 mg, 0.2 mmol), and the reaction was dissolved in DCM, added with copper acetate (36 mg, 0.2 mmol), and stirred under room temperature for 16 hrs. The reaction was filtered, and the filtrate was concentrated under reduced pressure, and the residue was purified by Prep-TLC and then further purified by Prep-HPLC to give Compound 47 (3 mg, 6.15 μmol). $^{1}$H NMR (600 MHz, Methanol-$d_4$) δ 8.94 (s, 1H), 8.59 (d, J=2.7 Hz, 1H), 8.32 (d, J=1.7 Hz, 1H), 8.17 (s, 1H), 8.04 (dd, J=9.1, 2.7 Hz, 1H), 7.95 (d, J=5.6 Hz, 1H), 7.54-7.45 (m, 2H), 6.92 (d, J=9.1 Hz, 1H), 3.61 (s, 4H), 2.87 (s, 4H), 2.57 (s, 3H), 1.58 (s, 6H). LCMS ($ESI^+$) m/z: 445.2 $[M+H]^+$, HPLC Method B: $R_T$=5.12 min, purity: 91.1%.

Example 48: Synthesis of Compound 48

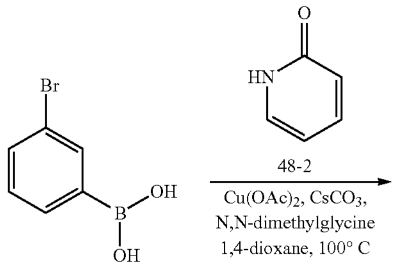

48-1

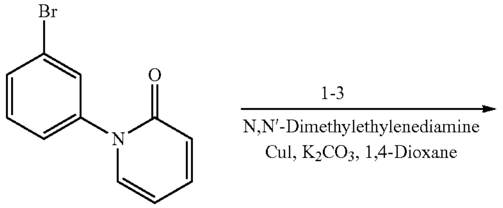

48-3

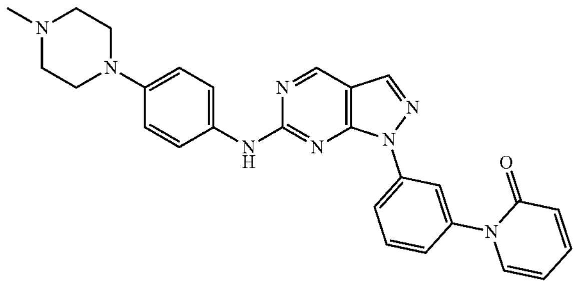

48

Step 1: Synthesis of Compound 48-3:

A dry single-necked flask was added with substrate 48-1 (399.9 mg, 2.0 mmol), substrate 48-2 (190.08 mg, 2.0 mmol), $Cu(OAc)_2$ (39.93 mg, 0.2 mmol), cesium carbonate (325.82 mg, 1.0 mmol) and N,N-dimethylglycine (206.22 mg, 2.00 mmol) solution in 1,4-dioxane (4 mL), and at 100° C. stirred for 18 h, monitored by LC-MS. After the reaction was completed, the reaction was filtered with Celite, and the stock solution was extracted three times with water and ethyl acetate, and the organic phase was dried by anhydrous sodium sulfate, and then concentrated under reduced pressure, and the residue was purified by column chromatography to give product 48-3 (250.00 mg, 1.03 mmol), LCMS ($ESI^+$) m/z: 250.1 $[M+H]^+$.

Step 2: Synthesis of Compound 48:

Following the synthesis method in the Example 1, Step 3, the synthesis method was conducted similarly by replacing Step 3 1-5 (109.92 mg, 441.22 μmol) with 48-3 (49.79 mg, 0.20 mmol), to give Compound 48 (12.00 mg, 25.09 μmol). $^1$H NMR (600 MHz, DMSO-$d_6$) δ 9.93 (s, 1H), 9.05 (s, 1H), 8.53 (s, 1H), 8.35 (s, 1H), 8.19 (s, 1H), 7.81 (d, J=6.6 Hz, 1H), 7.73-7.71 (m, 1H), 7.62 (d, J=8.4 Hz, 2H), 7.60-7.57 (m, 1H), 7.37 (d, J=8.4 Hz, 1H), 6.73 (d, J=8.4 Hz, 2H), 6.57 (d, J=9.3 Hz, 1H), 6.40-6.37 (m, 1H), 3.02 (s, 4H), 2.48 (s, 4H), 2.24 (s, 3H). LCMS ($ESI^+$) m/z: 479.3 $[M+H]^+$, HPLC Method B: $R_T$=6.35 min, purity: 96.9%.

Example 49: Synthesis of Compound 49

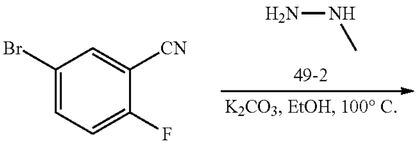

49-1

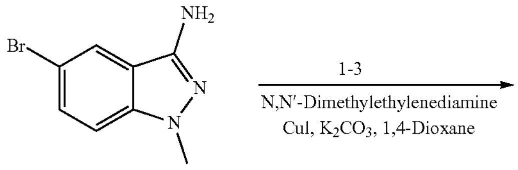

49-3

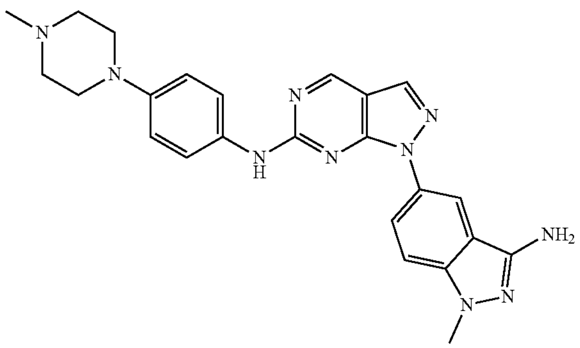

49

Step 1: Synthesis of Compound 49-3:

A dry single-necked flask was added with substrate 49-2 (2.3 g, 50.0 mmol) and $K_2CO_3$ (11.06 g, 80.0 mmol) solution in ethanol (60 mL), and with the protection of nitrogen cooled to 5° C., and then added with 49-1 (2.0 g, 10 mmol), and at 80° C. stirred for 18 h, monitored by LC-MS. After the reaction was completed, the reaction was cooled to room temperature, and the reaction was concentrated under reduced pressure, and the reaction was extracted three times with water and ethyl acetate, and the organic phase was dried by anhydrous sodium sulfate, and then concentrated under reduced pressure, and the residue was purified by column chromatography (PE/EA=2/3) to give product 49-3 (1.8 g, 7.96 mmol), LCMS ($ESI^+$) m/z: 226.1 $[M+H]^+$.

Step 2: Synthesis of Compound 49:

Following the synthesis method in the Example 1, Step 3, the synthesis method was conducted similarly by replacing Step 3 1-5 (109.92 mg, 441.22 μmol) with 49-3 (40.69 mg, 0.18 mmol), to give Compound 49 (1.50 mg, 2.84 μmol). $^1$H NMR (600 MHz, DMSO-$d_6$) δ 9.77 (s, 1H), 9.03 (s, 1H), 8.39-8.33 (m, 1H), 8.27 (s, 1H), 8.02 (dd, J=9.0, 2.1 Hz, 1H), 7.73 (d, J=8.1 Hz, 2H), 7.53 (d, J=9.0 Hz, 1H), 6.94 (d, J=8.5 Hz, 2H), 5.55 (s, 2H), 3.80 (s, 3H), 3.07 (d, J=5.0 Hz, 4H), 2.46 (s, 4H), 2.23 (s, 3H). LCMS($ESI^+$) m/z: 455.2 $[M+H]^+$, HPLC Method B: $R_T$=8.92 min, purity=86.2%.

Example 50: Synthesis of Compound 50

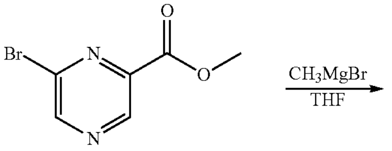

50-1

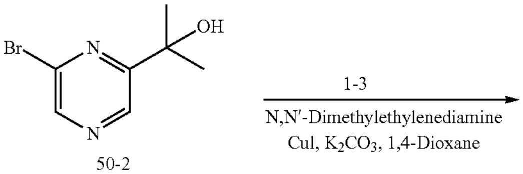

50-2

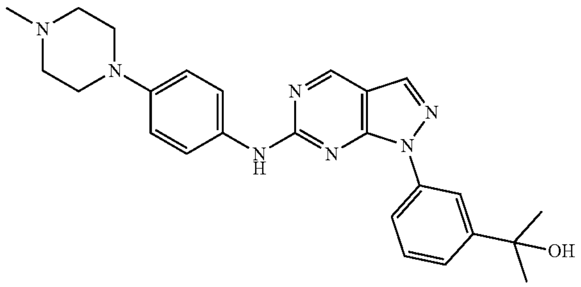

50

Step 1: Synthesis of Compound 50-2:

在 Following the synthesis method in the Example 29, Step 1, the synthesis method was conducted similarly by replacing Step 1 29-1 (500 mg, 2.91 mmol) with 50-1 (434.04 mg, 2 mmol), to give Compound 50-2 (200 mg, 878.09 μmol) as white solid.

Step 2: Synthesis of Compound 50:

Following the synthesis method in the Example 1, Step 3, the synthesis method was conducted similarly by replacing Step 3 1-5 (109.92 mg, 441.22 μmol) with 50-2 (37.89 mg, 174.55 μmol), to give Compound 50 (17 mg, 38.16 μmol). $^{1}$H NMR (600 MHz, Chloroform-d) δ 9.44 (s, 1H), 8.89 (s, 1H), 8.70 (s, 1H), 8.17 (s, 1H), 7.57 (d, J=8.4 Hz, 2H), 7.43 (d, J=7.9 Hz, 1H), 6.99 (d, J=8.9 Hz, 2H), 3.25 (t, J=4.9 Hz, 4H), 2.69 (t, J=4.8 Hz, 4H), 2.42 (s, 3H), 1.69 (s, 6H). LCMS(ESI$^{+}$) m/z: 445.2[M+H]$^{+}$, HPLC Method B: $R_T$=7.98 min, purity>87.1%.

Example 51: Synthesis of Compound 51

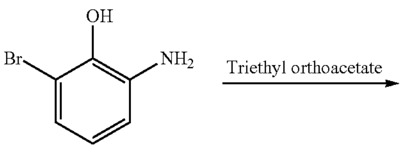

51-1

-continued

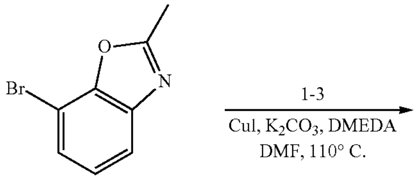

51-2

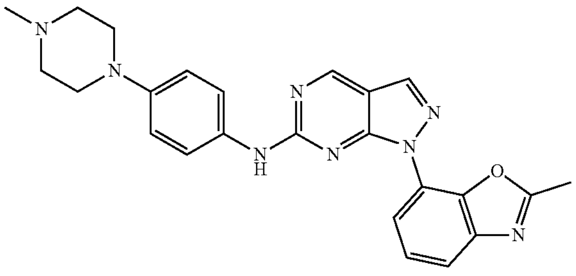

51

Step 1: Synthesis of Compound 51-2:

A dry single-necked flask was added with substrate 51-1 (600 mg, 3.19 mmol) and triethyl orthoacetate (1.5 mL), heated to 100° C. and reacted for 12 h, with reaction monitored by LC-MS. After the reaction was completed, the reaction was concentrated under reduced pressure, the reaction was extracted three times with water and ethyl acetate, and the organic phase was dried by anhydrous sodium sulfate, and then concentrated under reduced pressure, to give crude product 51-2 (650 mg, crude), directly used in the next step reaction.

Step 2: Synthesis of Compound 51:

Following the synthesis method in the Example 1, Step 3, the synthesis method was conducted similarly by replacing Step 3 1-5 (109.92 mg, 441.22 μmol) with 51-2 (65.80 mg, 310.31 μmol), 1,4-dioxane (3 mL) with DMF (2 mL), to give Compound 51 (18.1 mg, 36.78 μmol). $^{1}$H NMR (600 MHz, DMSO-$d_6$) δ 9.86 (s, 1H), 9.07 (s, 1H), 8.39 (s, 1H), 7.87 (d, J=7.8 Hz, 1H), 7.76 (d, J=7.8 Hz, 1H), 7.59 (d, J=8.4 Hz, 2H), 7.76 (t, J=7.8 Hz, 1H), 6.81 (d, J=9.0 Hz, 2H), 3.05 (s, 4H), 2.59 (s, 3H), 2.45 (s, 4H), 2.22 (s, 3H). LCMS (ESI$^{+}$) m/z: 441.2 [M+H]$^{+}$, HPLC Method B: $R_T$=6.48 min, purity: 89.5%.

Example 52: Synthesis of Compound 52

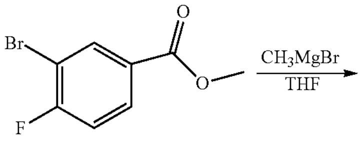

52-1

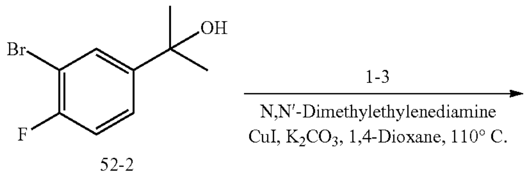

52-2

-continued

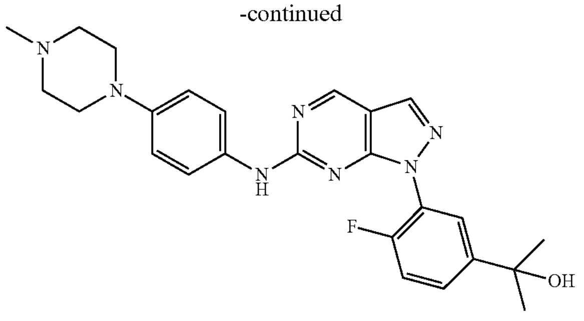

52

Step 1: Synthesis of Compound 52-2:

Following the synthesis method in the Example 29, Step 1, the synthesis method was conducted similarly by replacing Step 1 29-1 (500 mg, 2.91 mmol) with 52-1 (500.00 mg, 2.15 mmol), to give Compound 52-2 (300 mg, 1.29 mmol).

Step 2: Synthesis of Compound 52:

Following the synthesis method in the Example 1, Step 3, the synthesis method was conducted similarly by replacing Step 3 1-5 (109.92 mg, 441.22 μmol) with 52-2 (67.81 mg, 290.92 μmol), to give Compound 52 (4.5 mg, 9.23 μmol). $^1$H NMR (600 MHz, DMSO-$d_6$) δ 8.79 (s, 1H), 8.04 (s, 1H), 7.73 (dd, J=6.6 Hz, 1H), 7.46 (d, J=8.4 Hz, 3H), 7.27 (s, 1H), 7.21 (d, J=9.0 Hz, 1H), 6.81 (d, J=9.0 Hz, 2H), 3.09 (s, 4H), 2.53 (s, 4H), 2.29 (s, 3H), 1.55 (s, 6H). LCMS (ESI$^+$) m/z: 462.2 [M+H]$^+$, HPLC Method B: $R_T$=6.42 min, purity: 94.7%.

Example 53: Synthesis of Compound 53

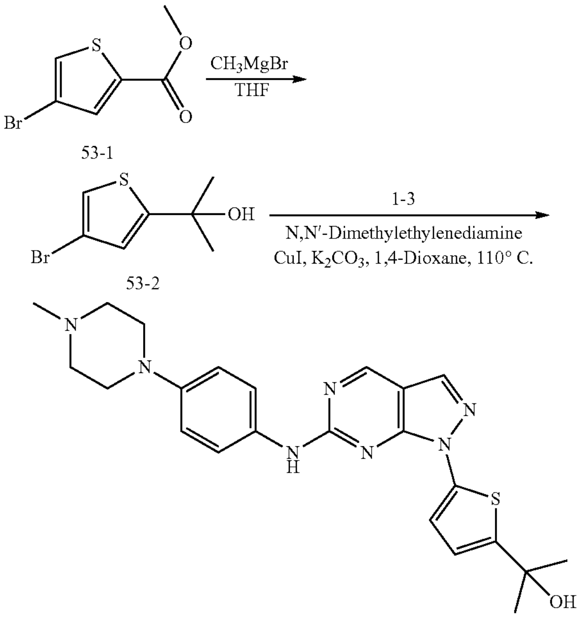

53

Step 1: Synthesis of Compound 53-2:

Following the synthesis method in the Example 29, Step 1, the synthesis method was conducted similarly by replacing Step 129-1 (500 mg, 2.91 mmol) with 53-1 (1.11 g, 5 mmol), to give Compound 53-2 (1.0 g, 4.49 mmol).

Step 2: Synthesis of Compound 53:

Following the synthesis method in the Example 1, Step 3, the synthesis method was conducted similarly by replacing Step 3 1-5 (109.92 mg, 441.22 μmol) with 53-2 (39.80 mg, 180.00 μmol), to give Compound 53 (7.1 mg, 12.10 μmol). $^1$H NMR (600 MHz, Chloroform-d) δ 8.82 (s, 1H), 8.00 (s, 1H), 7.79 (d, J=1.7 Hz, 1H), 7.75 (d, J=1.6 Hz, 1H), 7.61-7.56 (m, 2H), 7.31 (s, 1H), 7.01-6.95 (m, 2H), 3.22 (t, J=4.9 Hz, 4H), 2.65 (t, J=4.8 Hz, 4H), 2.40 (s, 3H), 1.73 (s, 6H). LCMS (ESI$^+$) m/z: 450.2[M+H]$^+$, HPLC Method B: $R_T$=8.55 min, purity>76.6%.

Example 54: Synthesis of Compound 54

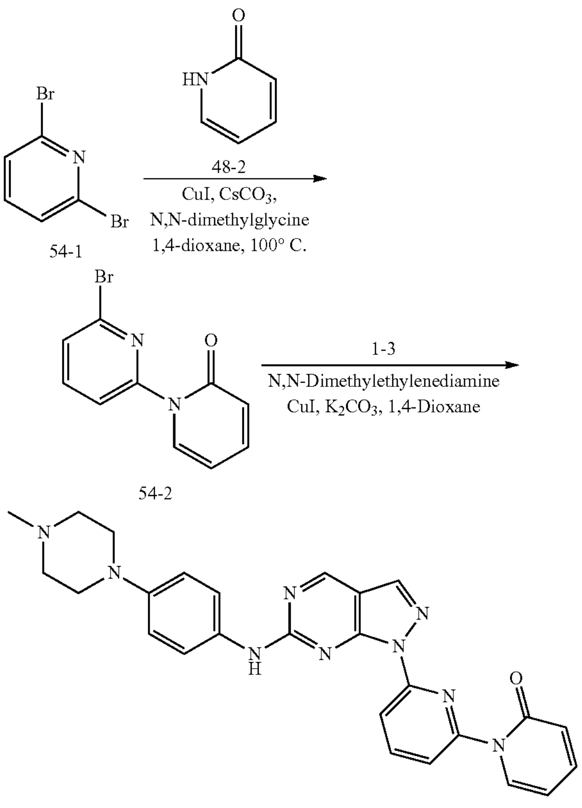

54

Step 1: Synthesis of Compound 54-2:

A dry single-necked flask was added with substrate 54-1 (472 mg, 1.99 mmol), substrate 48-2 (94.74 mg, 996.23 μmol), CuI (37.95 mg, 0.2 mmol), cesium carbonate (323.78 mg, 1.0 mmol) and N,N-dimethylglycine (102.73 mg, 1.0 mmol) solution in 1,4-dioxane (4 mL), and at 100° C. stirred for 18 h, monitored by LC-MS. After the reaction was completed, the reaction was filtered with Celite, and the stock solution was extracted three times with water and ethyl acetate, and the organic phase was dried by anhydrous sodium sulfate, and then concentrated under reduced pressure, and the residue was purified by column chromatography to give product 54-2 (100 mg, 398.28 μmol).

Step 2: Synthesis of Compound 54:

Following the synthesis method in the Example 1, Step 3, the synthesis method was conducted similarly by replacing Step 3 1-5 (109.92 mg, 441.22 μmol) with 54-2 (49.51 mg, 197.18 μmol), to give Compound 54 (20 mg, 38.12 μmol).

$^1$H NMR (600 MHz, DMSO-$d_6$) δ 9.91 (s, 1H), 9.05 (s, 1H), 8.37 (s, 1H), 8.26-8.23 (m, 1H), 8.11 (d, J=8.4 Hz, 1H), 8.02-8.01 (m, 1H), 7.79 (d, J=7.8 Hz, 1H), 7.74 (d, J=8.4 Hz, 2H), 7.61-7.58 (m, 1H), 6.68 (d, J=8.4 Hz, 2H), 6.61 (d, J=9.0 Hz, 1H), 6.35 (t, J=6.6 Hz, 1H), 3.01 (t, J=4.8 Hz, 4H), 2.47 (d, J=5.0 Hz, 4H), 2.24 (s, 3H). LCMS (ESI$^+$) m/z: 480.1[M+H]$^+$, HPLC Method B: $R_T$=8.16 min, purity>91.4%.

Example 55: Synthesis of Compound 55

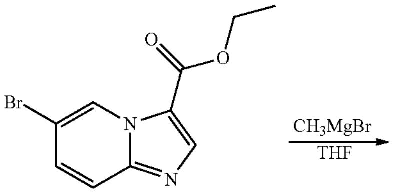

55-1

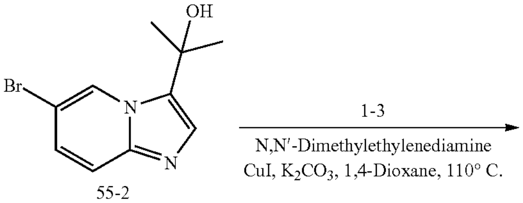

55-2

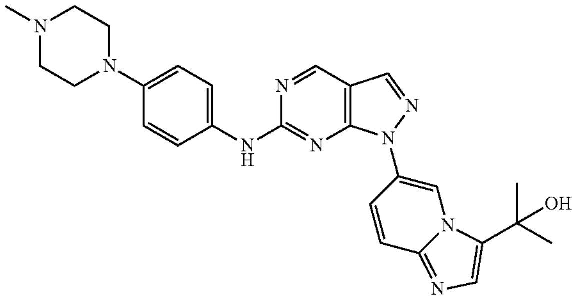

55

Step 1: Synthesis of Compound 55-2:

Following the synthesis method in the Example 29, Step 1, the synthesis method was conducted similarly by replacing Step 1 29-1 (500 mg, 2.91 mmol) with 55-1, to give Compound 55-2.

Step 2: Synthesis of Compound 55:

Following the synthesis method in the Example 1, Step 3, the synthesis method was conducted similarly by replacing Step 3 1-5 (109.92 mg, 441.22 μmol) with 55-2 (50 mg, 195.99 μmol), to give Compound 55 (17 mg, 35.16 μmol). $^1$H NMR (600 MHz, Methanol-$d_4$) δ 9.56 (s, 1H), 8.93 (s, 1H), 8.27 (d, J=8.7 Hz, 1H), 8.20 (s, 1H), 7.70 (d, J=9.7 Hz, 1H), 7.64-7.39 (m, 3H), 6.97 (d, J=9.0 Hz, 2H), 3.17 (t, J=5.1 Hz, 4H), 2.64 (t, J=5.0 Hz, 4H), 2.36 (s, 3H), 1.73 (s, 6H). LCMS (ESI$^+$) m/z: 484.2[M+H]$^+$, HPLC Method B: $R_T$=5.21 min, purity 90.0%.

Example 56: Synthesis of Compound 56

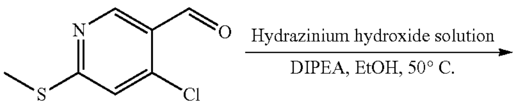

56-1

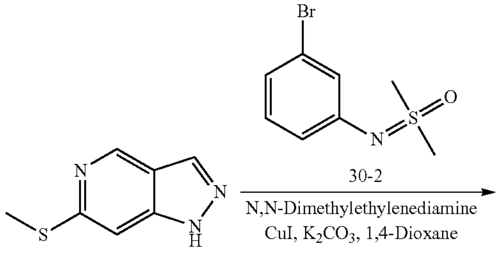

56-2

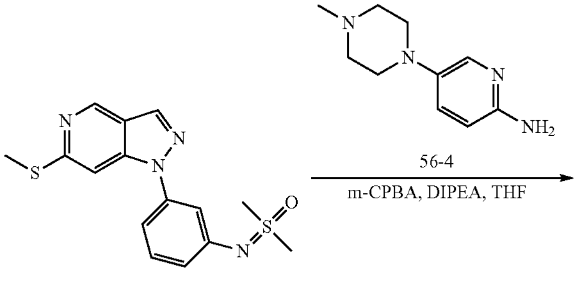

56-3

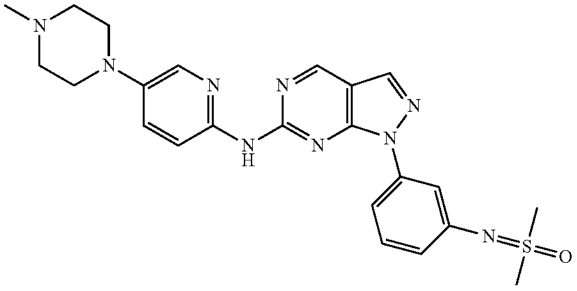

56

Step 1: Synthesis of Compound 56-2:

A dry single-necked flask was added with substrate 56-1 (943.17 mg, 5 mmol) and EtOH (10 mL) and stirred to dissolve, then was added with DIPEA (969.30 mg, 7.50 mmol, 1.31 mL), and at 0° C. slowly added dropwisely with hydrazine hydrate (272.38 mg, 8.50 mmol), heated to 50° C. reacted for 1 h. After the reaction was completed, the reaction was concentrated under reduced pressure, to give crude product 56-2 (790 mg, 4.75 mmol).

Step 2: Synthesis of Compound 56-3:

Following the synthesis method in the Example 1, Step 3, the synthesis method was conducted similarly by replacing Step 3 1-5 (109.92 mg, 441.22 μmol) with 30-2 (332.41 mg, 2 mmol), 1-3 (105 mg, 339.40 μmol) with 56-2 (330.85 mg, 1.33 mmol), to give Compound 56-3 (252 mg, 755.78 μmol).

Step 3: Synthesis of Compound 56:

A dry single-necked flask was added with substrate 56-3 (66.69 mg, 0.2 mmol), m-CPBA (26.45 mg, 300.00 μmol) and THF (0.8 mL), under room temperature stirred for 10 min, and then added with DIPEA (129.24 mg, 1.00 mmol), under room temperature stirred for 5 min, and then added with substrate 56-4 (57.68 mg, 300.00 μmol), and at 100° C.

reacted for 6 h, monitored by LCMS. After the reaction was completed, the reaction was concentrated under reduced pressure, the reaction was extracted three times with water and ethyl acetate, and the organic phase was dried by anhydrous sodium sulfate, and then concentrated under reduced pressure, and the residue was purified by column chromatography to give compound 56 (6.5 mg). $^1H$ NMR (600 MHz, DMSO-$d_6$) δ 9.96 (s, 1H), 9.09 (s, 1H), 8.33 (s, 1H), 8.18 (d, J=9.1 Hz, 1H), 8.05 (d, J=3.1 Hz, 1H), 7.79 (dd, J=8.0, 2.1 Hz, 1H), 7.76-7.75 (m, 1H), 7.47 (dd, J=9.1, 3.1 Hz, 1H), 7.41-7.39 (m, 1H), 6.94 (dd, J=8.0, 2.1 Hz, 1H), 3.27 (s, 6H), 3.17-3.14 (m, 4H), 2.48 (t, J=4.9 Hz, 4H), 2.23 (s, 3H). LCMS($ESI^+$) m/z: 478.2$[M+H]^+$, HPLC Method B: $R_T$=5.69 min, purity 89.9%.

Example 57: Synthesis of Compound 57

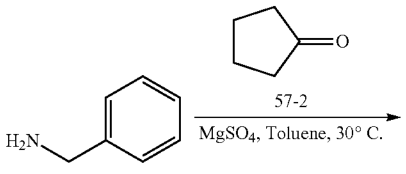

57-1

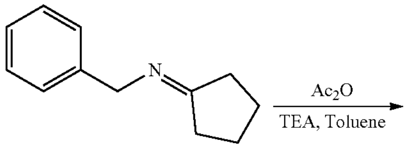

57-3

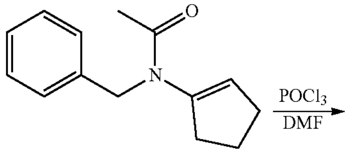

57-4

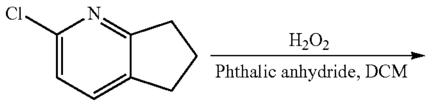

57-5

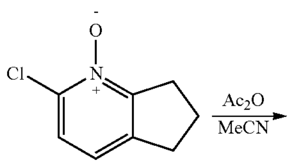

57-6

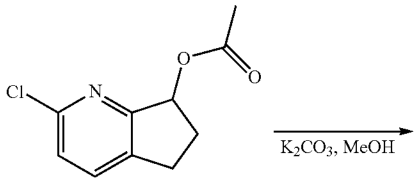

57-7

-continued

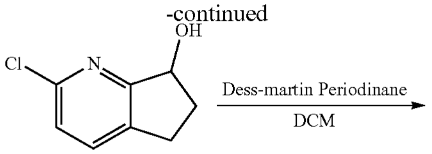

57-8

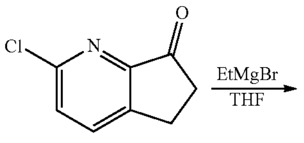

57-9

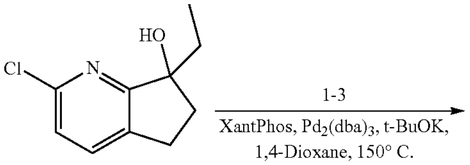

57-10

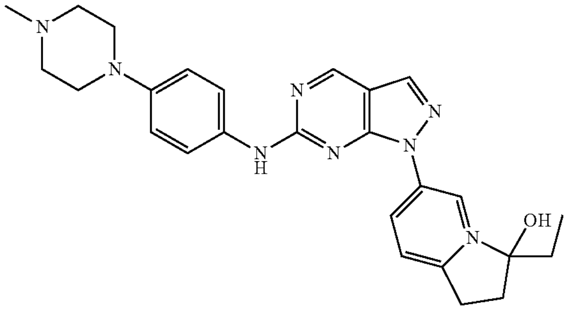

57

Step 1: Synthesis of Compound 57-3:

A dry single-necked flask was added with substrate 57-1 (20 g, 186.65 mmol) and toluene (120 mL) solution, added with substrate 57-2 (15.70 g, 186.65 mmol) and $MgSO_4$ (22.40 g, 186.08 mmol), and at 30° C. stirred for 18 h, monitored by LC-MS. After the reaction was completed, the reaction was filtered, washed with toluene (40 mL) solution, and filtered to give product 57-3 (32.34 g, crude).

Step 2: Synthesis of Compound 57-4:

A dry single-necked flask was added with substrate 57-3 (32.34 g, 186.66 mmol) and toluene (160 mL) solution, and at 0° C., added with TEA (19.27 g, 190.40 mmol), slowly added dropwisely with $Ac_2O$ (19.44 g, 190.40 mmol), and under room temperature stirred for 18 h, monitored by LC-MS. After the reaction was completed, the reaction was washed with water twice, dried with anhydrous sodium sulfate and then concentrated under reduced pressure, and the residue was purified by column chromatography to give product 57-4 (22.3 g, 103.58 mmol) as yellow oil, LCMS ($ESI^+$) m/z. 216.2 $[M+H]^+$.

Step 3: Synthesis of Compound 57-5:

A dry three-necked flask was added with substrate 57-4 (22.3 g, 103.58 mmol), and the reaction was dissolved in DMF (75.46 mL), and at −10° C. and with the protection of nitrogen, added dropwisely with $POCl_3$ (39.71 g, 258.95 mmol) and $MgSO_4$ (22.40 g, 186.08 mmol), and under room temperature stirred for 1 h, and then heated to 105° C. and reacted for 16 h, monitored by LC-MS. After the reaction was completed, the reaction was quenched with ice water, adjusted to pH=9-10 with 30% sodium hydroxide aqueous solution. The reaction was extracted three times with water and ethyl acetate, dried with anhydrous sodium sulfate, and filtered, and then concentrated under reduced pressure, and the residue was purified by column chromatography to give product 57-5 (10.6 g, 69.01 mmol) as yellow solid, LCMS ($ESI^+$) m/z: 154.1 $[M+H]^+$.

Step 4: Synthesis of Compound 57-6:

A dry single-necked flask was added with substrate 57-5 (3 g, 19.53 mmol) and phthalic anhydride (5.79 g, 39.06 mmol), and the reaction was dissolved in DCM (13.5 mL), added with $H_2O_2$ (6.64 g, 58.59 mmol), and at 40° C. stirred for 18 h, monitored by LC-MS. After the reaction was completed, the reaction was concentrated under reduced pressure, and the residue was purified by column chromatography to give product 57-6 (3 g, 17.69 mmol) as white solid, LCMS ($ESI^+$) m/z: 170.0$[M+H]^+$.

Step 5: Synthesis of Compound 57-7:

A dry single-necked flask was added with $Ac_2O$ (9.03 g, 88.44 mmol), and at 85° C. added dropwisely with 57-6 (3 g, 17.69 mmol) solution in MeCN (20 mL), and at 85° C. stirred for 3 h, monitored by LCMS. After the reaction was completed, the reaction was concentrated under reduced pressure, and the residue was adjusted to pH=8-9 with saturated sodium bicarbonate solution, extracted with DCM three times, dried with anhydrous sodium sulfate, and filtered, and then concentrated under reduced pressure to give product 57-7 (3.8 g, crude) as bright yellow oil, LCMS ($ESI^+$) m/z: 212.2 $[M+H]^+$.

Step 6: Synthesis of Compound 57-8:

A dry single-necked flask was added with substrate 57-7 (3.74 g, 17.67 mmol), $K_2CO_3$ (7.32 g, 53.01 mmol) and MeOH solution (40 mL), and at 15° C. stirred for 2 h, monitored by LCMS. After the reaction was completed, the reaction was filtered and concentrated under reduced pressure, and the residue was purified by column chromatography to give product 57-8 (1.94 g, 11.44 mmol) as bright yellow oil, LCMS ($ESI^+$) m/z: 170.1 $[M+H]^+$.

Step 7: Synthesis of Compound 57-9:

A dry single-necked flask was added with substrate 57-8 (3.74 g, 17.67 mmol), and the reaction was dissolved in DCM (40 mL), added with Dess-martin Periodinane (7.36 g, 17.36 mmol), and at 15° C. stirred for 2 h, monitored by LCMS. After the reaction was completed, the reaction was adjusted to pH=8-9 with saturated sodium bicarbonate solution, extracted with DCM three times, dried with anhydrous sodium sulfate, and filtered, and then concentrated under reduced pressure to give product 57-9 (2 g, crude) as white solid, LCMS ($ESI^+$) m/z: 168.0 $[M+H]^+$.

Step 8: Synthesis of Compound 57-10:

A dry three-necked flask was added with substrate 57-9 (0.5 g, 2.98 mmol), and the reaction was dissolved in anhydrous THF (15 mL), and in ice bath and with the protection of nitrogen, slowly added dropwisely with methylmagnesium bromide (1 M in THF, 11.93 mL), and slowly heated to room temperature and stirred for 1 h. The reaction was quenched with saturated ammonium chloride solution, and then extracted with EA three times, and the organic phase was combined, and dried with anhydrous sodium sulfate, filtered, and the filtrate was concentrated, and the residue was purified by column chromatography to give product 57-10 (0.29 g, 1.47 mmol) as yellow oil, LCMS ($ESI^+$) m/z: 198.0 [M+H]+.

Step 9: Synthesis of Compound 57:

A dry single-necked flask was added with substrate 57-10 (16 mg, 80.95 μmol), 1-3 (25 mg, 80.81 μmol), XantPhos (4.67 mg, 8.09 μmol), $Pd_2(dba)_3$ (2.59 mg, 2.83 μmol), t-BuOK (9.08 mg, 80.95 μmol), and the mixture was added with 1,4-dioxane (1 mL) and dissolved, and with the protection of nitrogen and at 150° C. stirred for 1 h, monitored by LC-MS. After the reaction was completed, the reaction was extracted three times with water and ethyl acetate, and the organic phase was dried by anhydrous sodium sulfate, and then concentrated under reduced pressure, and the residue was purified by column chromatography to give product 57 (8.33 mg, 17.70 μmol). $^1H$ NMR (600 MHz, DMSO-$d_6$) δ 9.79 (s, 1H), 8.05 (s, 1H), 8.01 (d, J=9.6 Hz, 1H), 7.66 (d, J=7.6 Hz, 1H), 7.55 (d, J=8.4 Hz, 2H), 7.34 (s, 1H), 6.89 (d, J=9.0 Hz, 2H), 3.23 (s, 4H), 3.00-2.96 (m, 1H), 2.95-2.78 (s, 1H), 2.71 (s, 4H), 2.42 (s, 3H), 2.36-2.31 (m, 1H), 2.22-2.17 (m, 1H), 2.06-2.02 (m, 1H), 1.83-1.79 (m, 1H), 0.94 (t, J=7.2 Hz, 3H). LCMS ($ESI^+$) m/z: 471.1 $[M+H]^+$, HPLC Method B: $R_T$=4.90 min, purity 99.9%.

Example 58: Synthesis of Compound 58

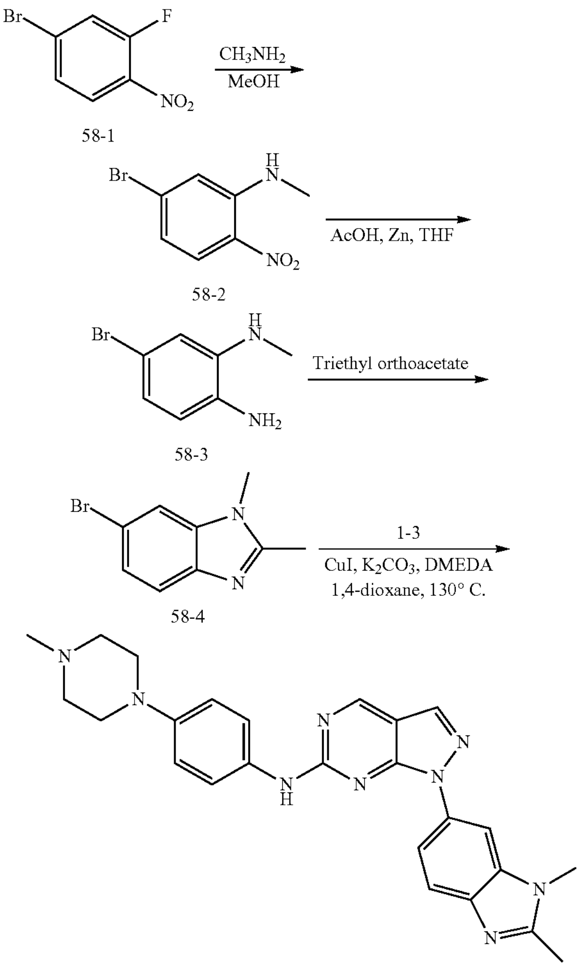

58-1

58-2

58-3

58-4

58

Step 1: Synthesis of Compound 58-2:

A dry single-necked flask was added with substrate 58-1 (87 mg, 395.46 μmol) and methylamine (120.00 mg, 3.86 mmol, 1M tetrahydrofuran solution), and under room temperature reacted for 2 h, monitored by LC-MS. After the reaction was completed, the reaction was concentrated under reduced pressure to give crude product 58-2, directly used in the next step reaction.

Step 2: Synthesis of Compound 58-3:

A dry single-necked flask was added with substrate 58-2 and THF (1 mL) and stirred to dissolve, added with $CH_3COOH$ (1 mL) and zinc powder (500 mg), and under room temperature reacted for 2 h, monitored by LC-MS. After the reaction was completed, the zinc powder and insoluble substance was filtered and removed with Celite, and the filtrate was concentrated under reduced pressure, to give crude product 58-3 (25 mg, crude).

Step 3: Synthesis of Compound 58-4:

A dry single-necked flask was added with substrate 58-3 (25 mg, crude) and triethyl orthoacetate (1 mL), and under room temperature reacted for 2 h, monitored by LC-MS. After the reaction was completed, the reaction was concentrated under reduced pressure, and the residue was purified by column chromatography to give product 58-4 (7 mg, 31.10 μmol).

Step 4: Synthesis of Compound 58:

Following the synthesis method in the Example 1, Step 3, the synthesis method was conducted similarly by replacing Step 3 1-5 (109.92 mg, 441.22 μmol) with 58-4 (34.7 mg, 154.16 μmol), to give Compound 58 (2.0 mg, 4.41 μmol). $^1H$ NMR (600 MHz, DMSO-$d_6$) δ 9.82 (s, 1H), 9.04 (s, 1H), 8.30 (d, J=4.1 Hz, 2H), 7.96 (dd, J=8.7, 2.1 Hz, 1H), 7.72 (d, J=8.4 Hz, 2H), 7.69 (d, J=8.6 Hz, 1H), 6.98-6.92 (m, 2H), 3.78 (s, 3H), 3.10 (t, J=4.9 Hz, 4H), 2.58 (s, 3H), 2.47 (t, J=4.9 Hz, 4H), 2.23 (s, 3H). LCMS ($ESI^+$) m/z: 454.1 $[M+H]^+$, HPLC Method B: $R_T$=6.50 min, purity 92.2%.

Example 59: Synthesis of Compound 59

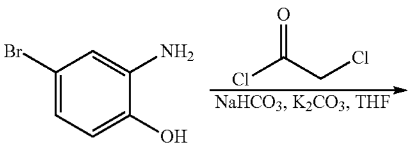

59-1

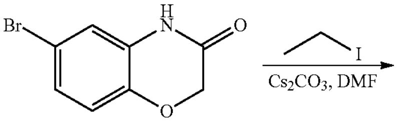

59-2

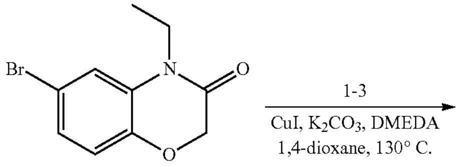

59-3

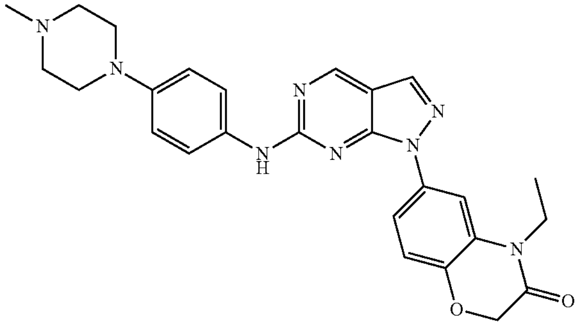

59

Step 1: Synthesis of Compound 59-2:

A dry two-necked flask was added with substrate 59-1 (1 g, 5.32 mmol) and sodium bicarbonate (893.62 mg, 10.64 mmol), added with THF (8 mL) and dissolved, and at 0° C. and with the protection of nitrogen, added with chloroacetyl chloride (600.69 mg, 5.32 mmol), stirred for 30 min and then added with $K_2CO_3$ (1.47 g, 10.64 mmol), heated to 80° C. and reacted for 3 h. After the reaction was completed, the reaction was extracted three times with water and ethyl acetate, the organic phase was dried with anhydrous sodium sulfate, concentrated under reduced pressure to give crude product 59-2 (1.4 g, crude).

Step 2: Synthesis of Compound 59-3:

A dry two-necked flask was added with substrate 59-2 (500 mg, 2.19 mmol) and cesium carbonate (785.82 mg, 2.41 mmol), added with DMF (2.5 mL) and stirred to dissolve, and at 0° C. and with the protection of nitrogen was added with iodoethane (341.96 mg, 2.19 mmol), recovered to room temperature and reacted for 2 h. After the reaction was completed, the reaction was extracted three times with water and ethyl acetate, the organic phase was dried with anhydrous sodium sulfate, concentrated under reduced pressure, and the residue was purified by medium pressure column chromatography to give product 59-3 (190 mg, 741.91 μmol).

Step 3: Synthesis of Compound 59:

Following the synthesis method in the Example 1, Step 3, the synthesis method was conducted similarly by replacing Step 3 1-5 (109.92 mg, 441.22 μmol) with 59-3 (34.60 mg, 135.11 μmol), to give Compound 59 (3.49 mg, 7.07 μmol). $^1H$ NMR (600 MHz, DMSO-$d_6$) δ 9.78 (s, 1H), 9.03 (s, 1H), 8.29 (s, 1H), 7.88 (d, J=2.4 Hz, 1H), 7.82 (dd, J=8.4 Hz, 1H), 7.60 (d, J=9.0 Hz, 2H), 7.23 (d, J=3.0 Hz, 1H), 6.93 (d, J=9.0 Hz, 2H), 4.70 (s, 2H), 3.90 (d, J=7.2 Hz, 2H), 3.09 (t, J=4.8 Hz, 4H), 2.47 (s, 4H), 2.23 (s, 3H), 1.08 (t, J=7.2 Hz, 3H). LCMS ($ESI^+$) m/z: 485.2 $[M+H]^+$, HPLC Method B: $R_T$=5.67 min, purity: 95.1%.

Example 60: Synthesis of Compound 60

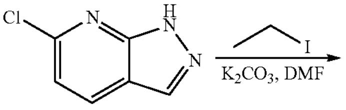

60-1

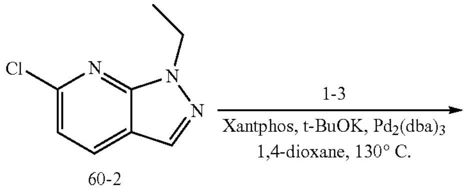

60-2

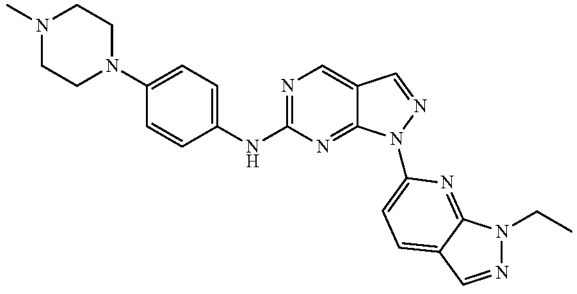

60

Step 1: Synthesis of Compound 60-2:

A dry two-necked flask was added with substrate 60-1 (200 mg, 1.30 mmol) and potassium carbonate (540 mg, 3.91 mmol), added with DMF (2.5 mL) and stirred to dissolve, and at 0° C. and with the protection of nitrogen was added with iodoethane (406.24 mg, 2.60 mmol), heated to 75° C. reacted for 1 h. After the reaction was completed, the reaction was extracted three times with water and ethyl acetate, the organic phase was dried with anhydrous sodium sulfate, concentrated under reduced pressure, and the residue was purified by medium pressure column chromatography to give product 60-2 (140 mg, 770.83 μmol).

Step 2: Synthesis of Compound 60:

Following the synthesis method in the Example 28, Step 2, the synthesis method was conducted similarly by replacing Step 2 28-2 (55.13 mg, 269.37 μmol) with 60-2 (35.22 mg, 193.94 μmol), to give Compound 60 (4.13 mg, 8.20 μmol). $^1$H NMR (400 MHz, DMSO-$d_6$) δ 9.91 (s, 1H), 9.05 (s, 1H), 8.55 (s, 1H), 8.44 (d, J=8.8 Hz, 1H), 8.36 (s, 1H), 7.97 (s, 2H), 7.90 (d, J=8.8 Hz, 1H), 6.98 (d, J=8.8 Hz, 2H), 4.54 (q, J=16.8 Hz, 2H), 3.09 (t, J=4.4 Hz, 4H), 2.47 (t, J=4.8 Hz, 4H), 2.23 (s, 3H), 1.59 (t, J=3.2 Hz, 3H). LCMS (ESI$^+$) m/z: 455.1 [M+H]$^+$, HPLC Method A: $R_T$=5.86 min, purity: 90.3%.

Example 61: Synthesis of Compound 61

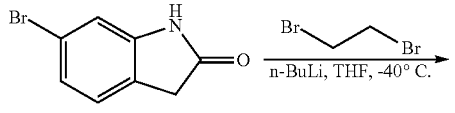

61-1

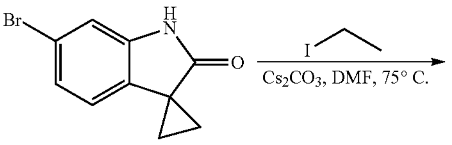

61-2

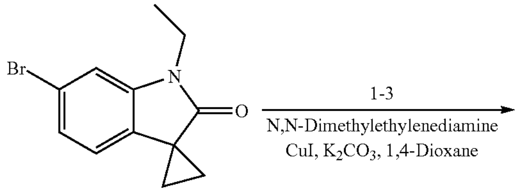

61-3

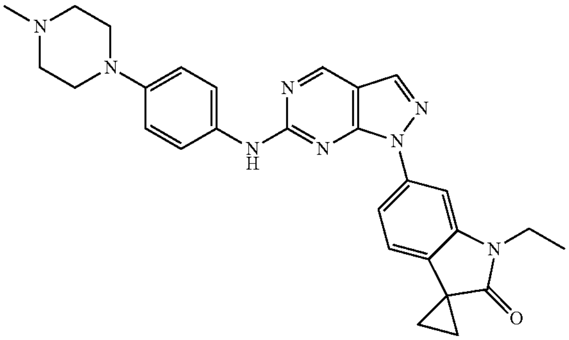

61

Step 1: Synthesis of Compound 61-2:

A dry three-necked flask was added with substrate 61-1 (1 g, 4.72 mmol) and THF (10 mL) solution, and with the protection of nitrogen cooled to −40° C., slowly added dropwisely with n-BuLi (2.5 M in THF, 4.15 mL), and at −40° C. stirred for 1 h, and then slowly added dropwisely with 1,2-dibromoethane (2.66 g, 14.15 mmol), slowly recovered to room temperature and stirred for 12 h, monitored by LC-MS. After the reaction was completed, the reaction was quenched with 4 N HCl (5 mL), and the reaction was extracted three times with water and ethyl acetate, and the organic phase was dried by anhydrous sodium sulfate, and then concentrated under reduced pressure, and the residue was purified by column chromatography to give product 61-2 (1.2 g, crude), LCMS (ESI$^+$) m/z: 238.1 [M+H]$^+$.

Step 2: Synthesis of Compound 61-3:

A single-necked flask was added with substrate 61-2 (700 mg, 2.94 mmol), iodoethane (458.57 mg, 2.94 mmol), $Cs_2CO_3$ (1.05 g, 3.23 mmol), added with DMF (3 mL) and stirred to dissolve, reacted under 75° C. for 8 h, monitored by LCMS. After the reaction was completed, the reaction was quenched with 4 N HCl (5 mL), the reaction was extracted three times with water and ethyl acetate, the organic phase was dried with anhydrous sodium sulfate, concentrated under reduced pressure, and the residue was purified by column chromatography to give product 61-3 (285 mg, 1.07 mmol), LCMS (ESI$^+$) m/z: 266.1 [M+H]$^+$.

Step 3: Synthesis of Compound 61:

Following the synthesis method in the Example 1, Step 3, the synthesis method was conducted similarly by replacing Step 3 1-5 (109.92 mg, 441.22 μmol) with 61-3 (30 mg, 112.73 μmol), to give Compound 61 (8.85 mg, 17.89 μmol). $^1$H NMR (400 MHz, DMSO-$d_6$) δ 9.82 (s, 1H), 9.03 (s, 1H), 8.30 (s, 1H), 7.89-7.85 (m, 2H), 7.64 (d, J=8.8 Hz, 2H), 7.21 (d, J=8.4 Hz, 1H), 6.93 (d, J=9.2 Hz, 2H), 3.80 (q, J=14.0 Hz, 2H), 3.09 (t, J=4.8 Hz, 4H), 2.46 (t, J=4.8 Hz, 4H), 2.23 (s, 3H), 1.71-1.68 (m, 2H), 1.58-1.57 (m, 2H), 1.13 (t, J=7.2 Hz, 3H). LCMS (ESI$^+$) m/z: 495.3 [M+H]$^+$, HPLC Method A: $R_T$=6.17 min, purity 99.9%.

Example 62: Synthesis of Compound 62

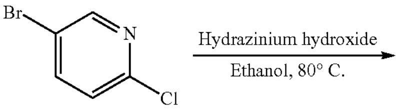

62-1

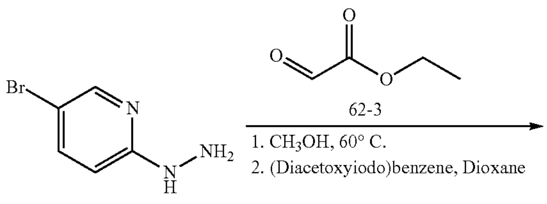

62-2

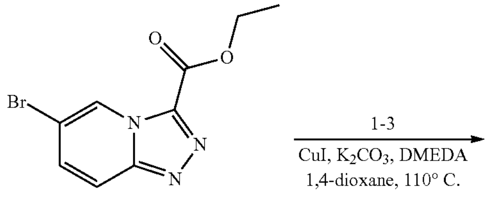

62-4

-continued

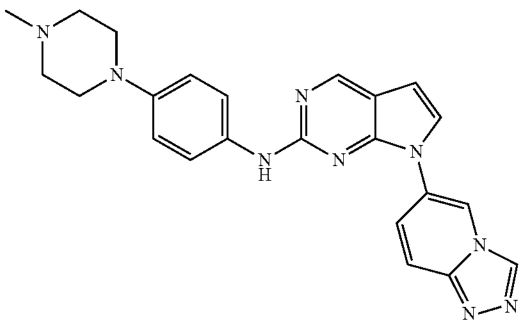

62

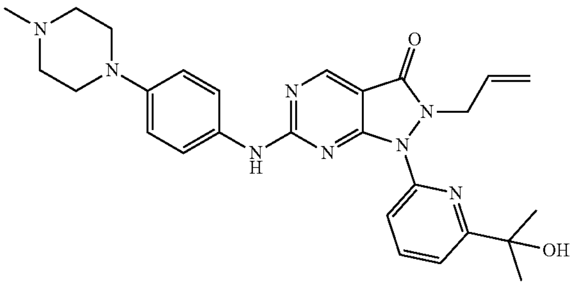

Chemical Formula: $C_{27}H_{32}N_8O_2$
Molecular Weight: 500.61

Step 1: Synthesis of Compound 62-2:

A dry single-necked flask was added with substrate 62-1 (192 mg, 997.71 μmol) and hydrazine hydrate solution (160 mg, 4.99 mmol), added with ethanol (3 mL) and stirred to dissolve, heated to 80° C. and reacted for 16 h, monitored by LC-MS. After the reaction was completed, the reaction was concentrated under reduced pressure, and the residue was purified by medium pressure column chromatography to give product 62-2 (180 mg, 957.32 μmol).

Step 2: Synthesis of Compound 62-4:

A dried microwave tube was added with substrate 62-2 (142 mg, 755.2 μmol), 62-3 (77.1 mg, 755.2 μmol) and methanol (2 mL), and with the protection of nitrogen and in 60° C. oil bath reacted for 1 h. After the reaction was completed, the reaction was concentrated under reduced pressure, and then the mixture was added with 1,4-dioxane (2 mL) and iodobenzene acetate (267.2 mg, 830.7 μmol), and with the protection of nitrogen and under room temperature reacted overnight, monitored by LC-MS. After the reaction was completed, the reaction was concentrated under reduced pressure, extracted with ethyl acetate and water three times, the organic phase was washed with saturated saline solution three times, dried with anhydrous sodium sulfate, concentrated under reduced pressure to give crude product 62-4 (116 mg, 429.5 μmol) as orange solid.

Step 3: Synthesis of Compound 62:

Following the synthesis method in the Example 1, Step 3, the synthesis method was conducted similarly by replacing Step 3 1-5 (109.92 mg, 441.22 μmol) with 62-4 (134 mg, 496.14 μmol), and during the reaction, decarboxylation reaction occurred, and thus gives Compound 62 (10 mg, 19.06 μmol). $^1$H NMR (600 MHz, DMSO-$d_6$) δ 9.94 (s, 1H), 9.36 (d, J=18.3 Hz, 2H), 9.06 (s, 1H), 8.38 (s, 1H), 8.32 (dd, J=9.8, 2.0 Hz, 1H), 8.07 (d, J=9.9 Hz, 1H), 7.66 (d, J=8.6 Hz, 2H), 7.00 (d, J=8.7 Hz, 2H), 3.17 (d, J=5.3 Hz, 1H), 3.12 (t, J=5.0 Hz, 4H), 2.49-2.47 (m, 4H), 2.23 (s, 3H). LCMS (ESI$^+$) m/z: 427.2 [M+H]$^+$, HPLC Method B: $R_T$=5.48 min, purity: 97%.

Biological Activity Evaluation Assay:

Unless otherwise specified, some biological evaluation experiments in this part of Example were compared with compound AZD-1775 as control. The structural information of AZD-1775 (CAS No.: 955365-80-7) is as follows:

Test Example 1: The Binding of Compound to Weel Protein and Tracer 178 was Evaluated by TR-Fret Method First, solutions of the compounds in different concentration gradients were prepared. The compounds were dissolved in DMSO and the compounds were diluted 4 folds with a total of 10 dose points and 2 parallel replicates for each concentration. DMSO was added as a positive control (maximal signal control) and a negative control (minimal signal control) and a final level of 0.25% DMSO was ensured in each reaction well.

WEE1 (Thermo Fisher, Cat #PR7373A) protein in buffer (50 mM Hepes pH 7.5, 10 mM $MgCl_2$, 1 mM EGTA, 0.01% Brij-35) at 15 nM) in different concentrations of compound, and Tracer 178 (Invitrogen, PV5593) and MAb Anti-GST-Eu crypate (Cisbio, 61GSTKLA) were added to 384-well plates (Corning, cat #3574), centrifuged at 1000 rpm for 1 min and the 384-well plates were incubated in a constant temperature shaker for 60 min at 25° C. and 300 rpm. Tracer 178 and MAb Anti-GST-Eu crypate were prepared in buffer (50 mM HEPES pH 7.5, 10 mM $MgCl_2$, 1 mM EGTA, 0.01% Brij-35) with a final reaction concentration of 50 nM for Tracer 178 and a final concentration of 2 nM for MAb Anti-GST-Eu crypate, where the negative control (minimal signal control) used an equal amount of buffer in place of the protein solution.

After incubation, readings were performed using BMG PHERAStar (excitation light at 337 nm and emission light at wavelength values of 620 nm and 665 nm to read the fluorescence signal values). The ratio of the fluorescence signal was calculated: 665/620*1000 was the final signal value of the enzyme activity, and the TR-FRET signal of the reads obtained from the positive control (maximum signal control) and the negative control (minimum signal control) was normalized to give the inhibition rate for different concentrations of the compound. The $IC_{50}$ for inhibition of enzyme activity by the compounds was then calculated using GraphPad Prism 6 and fitted with a log (inhibitor) vs. response-Variable slope mode. The fitting equation was: Y=Bottom+(Top-Bottom)/(1+10^((Log IC50-X)*Hill-Slope)), where Y represents the percentage of residual enzyme activity known and X represents the known concentration of compound after the logarithm.

The Weel inhibitory activity of the compounds in the Examples was tested according to the method described above and the results are shown in Table 1, where the $IC_{50}$ of each compound is categorized as follows:

"–" represents $IC_{50}$ measured value of more than 10 μM;

"+" represents $IC_{50}$ measured value of less than or equal to 10 μM and more than 1 μM;

"++" represents $IC_{50}$ measured value of less than or equal to 1 μM and more than 100 nM;

"+++" represents $IC_{50}$ measured value of less than or equal to 100 nM and more than 10 nM;

"++++" represents $IC_{50}$ measured value of less than or equal to 10 nM and more than 1 nM;

"+++++" represents $IC_{50}$ measured value of less than or equal to 1 nM.

TABLE 1

The inhibitory activity against Weel kinase of the compounds of the present invention

| Compound No. | $IC_{50}$ measured value |
|---|---|
| 1 | ++++ |
| 2 | +++ |
| 3 | +++ |
| 4 | +++ |
| 5 | +++ |
| 6 | +++ |
| 7 | ++++ |
| 8 | ++++ |
| 9 | ++++ |
| 10 | ++++ |
| 11 | +++ |
| 12 | +++ |
| 13 | ++++ |
| 14 | ++++ |
| 15 | +++ |
| 16 | ++++ |
| 17 | +++ |
| 18 | ++++ |
| 19 | +++ |
| 20 | ++++ |
| 21 | +++ |
| 22 | ++ |
| 23 | ++++ |
| 24 | +++ |
| 25 | ++++ |
| 26 | ++++ |
| 27A | ++++ |
| 27B | +++ |
| 28 | ++ |
| 29 | ++ |
| 30 | +++ |
| 31 | +++ |
| 32 | ++ |
| 33 | ++ |
| 34 | ++ |
| 35 | ++ |
| 36 | +++ |
| 37 | +++ |
| 38 | +++ |
| 39 | +++ |
| 40 | +++ |
| 41 | +++ |
| 42 | +++ |
| 43A | +++ |
| 43B | +++ |
| 44 | ++ |
| 45 | +++ |
| 46 | +++ |
| 47 | ++ |
| 48 | +++ |
| 49 | ++ |
| 50 | ++ |
| 51 | +++ |
| 52 | ++ |
| 53 | +++ |
| 54 | +++ |
| 55 | +++ |
| 56 | ++ |
| 57 | ++ |

TABLE 1-continued

The inhibitory activity against Weel kinase of the compounds of the present invention

| Compound No. | $IC_{50}$ measured value |
|---|---|
| 58 | +++ |
| 59 | +++ |
| 60 | +++ |
| 61 | ++ |
| 62 | ++ |
| AZD-1775 | ++++ |

The above experiments showed that the disclosed compounds of the present invention have significant inhibitory activity against Wee1 kinase.

Test Example 2: Evaluation of the Anti-Proliferative Effect of Compounds on H1299 and MIA Paca-2 Cells by the Cell Titer-Glo Method Compound solutions of different concentration gradients were prepared. DMSO was dissolved to a concentration of 10 mM test compound and 10 mM reference compound AZD1775, and the compounds were serially diluted in culture medium for a total of 9 dose points, with 2 parallel replicates set at each concentration. The cell growth group without compound was used as a positive control (maximum signal control) and the medium was used as a negative control (minimum signal control), while ensuring that the final level of DMSO in each reaction well was 0.2%. After removing the medium from the 384-well plate, 25 ul of the configured compound at different concentrations was transferred into the well plate and the compound and cells were incubated in the cell incubator at 37° C. with 5% $CO_2$ for 3 days.

The 384-well plates were removed from the cell incubator and allowed to equilibrate for 1 h to room temperature. 25 ul of Cell Titer-Glo assay was added to each well, lysed on a shaker for 2 min and then read out (Luminescence) using a BMG PHERAStar after 10 min incubation. Calculate the inhibition rate from the luminescence signal: first calculate the average of the positive control (maximum signal control) and the negative control (minimum signal control).

$$\text{Inhibition }\% = 1 - \left(\frac{S(\text{Compound signal value}) - S(\text{Negative Control signal value})}{S(\text{Positive Control signal value}) - S(\text{Negative Control signal value})}\right) \times 100\%$$

to calculate the rate of inhibition of the cells by different concentrations of the compounds. The IC50 of the compound on cell activity inhibition was calculated by fitting a log(inhibitor) vs. response-Variable slope model to GraphPad Prism 6. The fitted equation was: Y=Bottom+(Top−Bottom)/(1+10^((Log IC50−X)*HillSlope)), where Y represents the rate of inhibition and X represents the concentration of the known compound after Log.

The results of the in vitro anti-cell proliferation assays of H1299 and MIA Paca-2 for the example compounds according to the method described above are shown in Table 2, where the IC50 of each compound was determined and classified according to the description as follows:

"−" represents $IC_{50}$ measured value of more than 50 μM;

"+" represents $IC_{50}$ measured value of less than or equal to 50 μM and more than 20 μM;

"++" represents $IC_{50}$ measured value of less than or equal to 20 μM and more than 5 μM;

"+++" represents $IC_{50}$ measured value of less than or equal to 5 μM and more than 1 μM;

"++++" represents $IC_{50}$ measured value of less than or equal to 1 μM and more than 0.1 μM;

"+++++" represents $IC_{50}$ measured value of less than or equal to 0.1 μM.

TABLE 2

Inhibitory activity of compounds of the present invention on the proliferation of H1299 and MIA Paca-2 cells in vitro

| Compound No. | $IC_{50}$ measured value H1299 | MIA Paca-2 |
|---|---|---|
| 1 | +++ | ++++ |
| 2 | +++ | ND |
| 3 | +++ | ND |
| 4 | +++ | ND |
| 5 | +++ | ND |
| 6 | ++++ | ND |
| 7 | +++ | ND |
| 8 | +++ | ND |
| 9 | +++ | ND |
| 10 | +++ | ++++ |
| 11 | +++ | ND |
| 12 | ++++ | ND |
| 13 | ++ | ND |
| 14 | ++++ | +++++ |
| 15 | +++ | ++++ |
| 16 | ++++ | ++++ |
| 17 | ++ | ++++ |
| 18 | +++ | ++++ |
| 19 | +++ | ++++ |
| 20 | +++ | ++++ |
| 21 | +++ | ++++ |
| 22 | ++ | ++ |
| 23 | ++++ | ++++ |
| 24 | +++ | +++ |
| 25 | ++++ | ++++ |
| 26 | +++ | ++++ |
| 27A | ++++ | ++++ |
| 27B | +++ | ++++ |
| 28 | ++ | +++ |
| 29 | ++++ | ++++ |
| 30 | +++ | ++++ |
| 31 | +++ | ++++ |
| 32 | ++++ | ++++ |
| 33 | +++ | +++ |
| 34 | ++++ | ++++ |
| 35 | ++ | ++ |
| 36 | +++ | +++ |
| 37 | ++++ | ++++ |
| 38 | ++++ | ++++ |
| 39 | +++ | ++++ |
| 40 | ++++ | ++++ |
| 41 | +++ | +++ |
| 42 | ++++ | ++++ |
| 43A | ++++ | ++++ |
| 43B | +++ | ++++ |
| 44 | ++++ | ++++ |
| 45 | ++++ | ++++ |
| 46 | +++ | ++++ |
| 47 | ++++ | ++++ |
| 48 | +++ | +++ |
| 49 | +++ | +++ |
| 50 | ++++ | ++++ |
| 51 | ++++ | ++++ |
| 52 | ++++ | ++++ |
| 53 | ++++ | ++++ |
| 54 | ++ | +++ |
| 55 | +++ | +++ |

TABLE 2-continued

Inhibitory activity of compounds of the present invention on the proliferation of H1299 and MIA Paca-2 cells in vitro

| Compound No. | $IC_{50}$ measured value H1299 | MIA Paca-2 |
|---|---|---|
| 56 | ++ | ++ |
| 57 | +++ | ++++ |
| 58 | +++++ | ++++ |
| 59 | ++++ | ++++ |
| 60 | +++ | ++++ |
| 61 | ++ | +++ |
| 62 | ++ | +++ |
| AZD-1775 | ++++ | ++++ |

Conclusion: The compounds of the present invention exhibit strong cell proliferation inhibitory activity against H1299 and MIA Paca-2

Test Example 3: Evaluation of the Metabolic Stability of Liver Microsomes (Mouse and Human) In Vitro 1. Preparation of Working Solution:

Microsomes were taken out from the −80° C. refrigerator, rapidly melted in a 37° C. water bath and placed on ice until ready to use. The test article was diluted with DMSO to prepare a 10 mM stock solution, and then diluted with acetonitrile to a 0.5 mM secondary stock solution. The microsomes were diluted to 0.75 mg/ml using Buffer C; the secondary stock solution was then added to a final concentration of 1.5 μM of compound as working solution, based on n=2, 5 time points, 350 μL of each compound was prepared and placed on ice prior to use. NADPH was diluted with Buffer C to a working solution of 6 mM for the starter solution. An acetonitrile solution containing an internal standard was prepared as the precipitant, and Verapamil-HCl was chosen as the internal standard at a concentration of 4 ng/ml.

2. Experimental Procedure:

A round-bottom well plate was taken, noted as the reaction plate, and the prepared working solution for each compound was dispensed into the well plate according to the number of replicates and time points (0 h samples are also added to the reaction plate), 30 μL/well; the plate was incubated at 37° C. for 10 min. A separate plate with pointed bottom wells, noted as a precipitation plate, was added with 135 μL precipitant per well; 0 h samples were transferred to the plate after 10 min incubation and 15 μL of starter solution was added; the plate was placed on ice before centrifugation.

The diluted starter solution was added in sufficient quantity to the dispensing plate to facilitate the multichannel pipette aspiration operation.

The reaction was carried out on a warm incubation shaker and 15 μL of starter solution/sample is added to the plate using a multichannel pipette. The reaction was mixed with a slight shake to initiate the reaction, which was accurately timed and recorded using a timer;

After the reaction time had elapsed, all the solution in the plate was aspirated using the multichannel pipette and added to the precipitation plate to terminate the reaction at that point in time. After all reactions had been terminated, the plates were shaken for ten minutes on a plate shaker at 600 rpm to precipitate the protein. The plate was centrifuged at 4° C. for 15 minutes at maximum rpm. 80 μL of supernatant was taken, 320 μL of pure water was added and mixed for LC-MS analysis.

3 Test Results.

| Compound No. | Mouse $T_{1/2}$/min | Human $T_{1/2}$/min | Compound No. | Mouse $T_{1/2}$/min | Human $T_{1/2}$/min |
|---|---|---|---|---|---|
| compound 1 | 60.3 | >120 | compound 2 | 15.6 | >120 |
| compound 14 | 67.3 | >120 | compound 16 | 8.9 | >120 |
| compound 18 | >120 | >120 | compound 40 | 20.4 | ND |
| compound 45 | 10.3 | ND | AZD-1775 | 30.1 | >120 |

Conclusion: The compounds of the present invention have good in vitro hepatic microsomal (mouse and human) metabolic stability.

Test Example 4: Evaluation of Plasma Protein Binding (PPB)

1. Experimental Procedure

Sample preparation: The compound was dissolved in DMSO to a stock solution of 10 mM, then the compound was diluted with PBS to a secondary stock solution of 0.02 mM, and then the above 0.02 mM was diluted to 1 μM using blank plasma, which was the sample to be incubated.

Dialysis set-up preparation: 400 μL of blank PBS was first added to the white wells of the equilibrated dialysis plate and 200 μL of the configured plasma sample was added to the red wells, and the dialysis plate was sealed with a sealing film.

Recovery plate preparation: Two 96-well deep-well plates, labelled T0 and T5, were prepared and all plasma samples were added at n=2. 300 μL of acetonitrile (Verapamil-HCl, 4 ng/mL) was added directly to the TO plate, followed by 50 μL of blank PBS mix well for 5 min and left to stand in a 4° C. refrigerator until the end of the incubation.

Experimental Operation: The dialysis device and the T5 plate were incubated together for 5 h in a microplate thermostatic shaker (37° C., using 300 rpm or minimum speed). At the end of the incubation, 300 μL of acetonitrile (Verapamil-HCl, 4 ng/mL) was added and 50 μL of PBS solution was added. At the end of the dialysis incubation, a new 96-well deep well plate was taken. Add 50 μL of plasma well sample to the corresponding position of the 96-well plate, 300 μL of acetonitrile and 50 μL of blank PBS; take 50 μL of buffer well sample to the corresponding position of the 96-well plate, then add 300 μL of acetonitrile and 50 μL of blank plasma. Add 300 μL of acetonitrile (Verapamil-HCl, 4 ng/mL) to the plasma-containing wells of the T5 plate, and then 50 μL of PBS solution was added. Shake for 5 min to fully precipitate the proteins and centrifuge at 20,000 g for 10 min at 4° C. Add 200 μL of supernatant to 200 μL of pure water, mix well and perform LC-MS/MS analysis.

2. Data Processing and Parameter Calculation $$\text{Plasma protein binding rate}=[(Rpe-Rb)/Rpe]\times 100\%$$

$$\text{Recovery}=[(Rpe+Rb)/R5h]\times 100\%$$

$$\text{Stability}=(R5/R0)\times 100\%$$

where $R_{pe}$=ratio of plasma-side testing sample peak area to internal standard $R_b$=ratio of buffer side testing sample peak area to internal standard $R_5$=ratio of incubator stability sample peak area to internal standard $R_0$=ratio of refrigerator stability sample peak area to internal standard 3. Test Results:

| Compound | Plasma protein binding rate (%) | | | Compound | Plasma protein binding rate (%) | | |
|---|---|---|---|---|---|---|---|
| No. | Mouse | Rat | Human | No. | Mouse | Rat | Human |
| AZD-1775 | 91.3 | 62.6 | 64.0 | Compound 1 | 77.4 | 59.6 | 85.6 |
| Compound 14 | 86.2 | 75.4 | / | Compound 16 | 90.8 | 82.1 | / |

Conclusion: The compounds of the present invention have a good plasma protein binding to free drug ratio. Compared to AZD-1775, the compounds of the present invention have similar plasma protein binding and less interspecies fluctuation differences.

Test Example 5: Membrane Permeability Study (Caco-2)

Caco-2 cells were purchased from the American Model Tissue Cell Collection (Rockville, MD). The cell culture medium was modified Eagle's medium (MEM) containing 10% inactivated fetal bovine serum and 1% non-essential amino acids. Cells were inoculated on polycarbonate filter membranes (Cat no. 3396) and incubated at 37° C. in a 5% CO2 incubator.

The cells were incubated for 21-28 days after inoculation for transport experiments and the apparent permeability (Papp) of Lucifer Yellow was used to characterize and verify the compactness of the cell monolayer. A stock solution of 10 mM was prepared by dissolving the compound in DMSO and diluted using Hanks Balanced Salt Solution (HBSS, Invitrogen, Cat #14025-092) containing 25 mM HEPES (pH 7.4) to obtain the working solution. A 10 μM working solution of the compound to be tested was added to the apical side and basolateral side of Caco-2 and incubated at 37° C. for 90 min. After the incubation, dilute the samples on the apical side and basolateral side, and the concentrations of compounds on the apical and basolateral sides were detected by LC-MS/MS, and the concentrations of the compounds were quantified by standard curve.

Test Results:

| | Papp ($10^{-6}$ cm/s) | | Efflux |
|---|---|---|---|
| Compound No. | A to B | B to A | Ration |
| AZD-1775 | 14.53 | 35.28 | 2.43 |
| Compound 1 | 8.93 | 41.74 | 4.67 |
| Compound 14 | 5.86 | 20.76 | 3.54 |
| Compound 16 | 8.07 | 20.28 | 2.51 |

-continued

| | Papp ($10^{-6}$ cm/s) | | Efflux |
|---|---|---|---|
| Compound No. | A to B | B to A | Ration |
| Compound 40 | 18.61 | 16.62 | 0.89 |
| Compound 45 | 4.09 | 7.34 | 1.79 |

Conclusion: The compounds of the present invention have good membrane permeability properties.

Test Example 6: Evaluation of Compound Pharmacokinetics

To investigate the pharmacokinetic properties of the compound in mice, six male ICR mice were given the compound by oral gavage (10 mg/kg) at the corresponding dose, and each route of administration was divided into two groups: group A mice had anticoagulated whole blood collected at 5 min, 30 min, 2 h and 8 h after administration, while group B mice had anticoagulated whole blood collected at 15 min, 1 h, 4 h and 24 h after administration, isolated plasma;

The plasma concentrations of the compounds were determined by LC-MS using a standard curve calibration method. Plasma concentration-time data were fitted to pharmacokinetic parameters using Winnolin 5.2 software.

Test Results:

| PK Parameters | AZD-1775 | Compound 1 | Compound 28 | Compound 40 |
|---|---|---|---|---|
| T½, hr | 0.77 | 1.71 | 1.78 | 0.70 |
| $C_{max}$ (ng/mL) | 445 | 169 | 337 | 377 |
| $AUC_{inf\_Pred}$ (hr*ng/mL) | 500 | 260 | 743 | 493 |
| Cl_pred (L/hr/kg) | 20.8 | 39.5 | 13.8 | 24.3 |

Conclusion: The compounds of the present invention have good in vivo pharmacokinetic properties and are capable of significantly increasing the half-life and reducing the clearance of the compounds.

Test Example 7: Solubility Test

The compound was placed in a buffer solution and shaken at constant temperature for 24 h. The supernatant was prepared into a solution of about 100 μg/ml of the test article, and the solubility was calculated by reversed-phase high performance liquid chromatography with gradient elution and external standard method. Chromatographic conditions: C18 column, mobile phase A: 0.02 M potassium dihydrogen phosphate:acetonitrile=90:10, mobile phase B: acetonitrile; V: 1.0 ml/min, T: 35° C., λ: 210 nm.

Test Results

| Compound No. | Solubility (mg/mL) |
|---|---|
| AZD-1775 | 0.03 |
| Compound 1 | 0.12 |
| Compound 3 | 0.06 |
| Compound 16 | 0.35 |

Conclusion: The solubility of the compounds of the invention was significantly better than that of AZD-1775.

Test Example 8: Evaluation of Compound Inhibition of Cytochrome P450

Enzymatic experiments were performed to quantify the inhibition of CYP450 enzyme activity of each isoform of CYP450 by small molecule inhibitors through fluorescence generated by the oxidation of the substrate by cytochrome P450. The experiments were performed in 384-well plates (Corning, Cat #3575) using a reaction buffer of 142.86 mM Potassium Phosphate, pH 7.4. The Solution A components used in the experiments were: 26.13 mM NADP+ (Sigma-aldrich, Cat #N0505) 65.77 mM G6P (J&K, Cat #968161) and 65.42 mM MgCl2 (Sigma-aldrich, Cat #M2670). The Solution B composition used for the experiment was: 40 U/mL G6PDH (Sigma-aldrich, Cat #G6378). The substrate mix was 0.05× Solution A, 0.01× Solution B, 50 mM Potassium Phosphate, 0.01 mM BOMCC/0.01 mM EOMCC/0.001 mM DBOMF. For CYP3A4 and CYP2C9, the reaction system was 50 μL or 20 μL, respectively, including 3 nM CYP3A4 or 120 nM CYP2C9, BOMCC substrate mixed solution and different concentrations of compounds to be tested. For CYP2C19, CYP2D6 and CYP1A2, the reaction system was 20 μL and included 12.5 nM CYP2C19, 80 nM CYP2D6 or 1 nM CYP1A2, EOMCC substrate mix and various concentrations of the compounds to be tested. For CYP2C8, the reaction system is 50 μL and includes 1.5 nM CYP2C8, DBOMF substrate mix and various concentrations of compound to be tested. After preincubation with the enzyme for 10 minutes, the substrate was added and the fluorescence signal was read at different wavelengths (BOMCC/EOMCC Ex430 nm/Em480 nm, DBOMF Ex490 nm/Em520 nm) using BMG PHERAStar depending on the substrate, with reaction intervals of 30 seconds or more (depending on the actual number of wells) and reaction times of 30 minutes. The data were analyzed and processed using GraphPad Prism 6 software to obtain IC50 values.

Test Results:

| Compound | Compound | CYP inhibition/% | | | | | | |
|---|---|---|---|---|---|---|---|---|
| No. | concentration | 1A2 | 2C8 | 2C9 | 2C19 | 2D6 | 3A4 | 2B6 |
| AZD-1775 | 1 μM | 20.2 | 7.1 | 15.4 | 25.4 | 3.4 | −14.0 | ND |
| | 10 μM | 17.5 | 17.3 | 6.4 | 71.9 | 1.5 | −32.9 | 17.39 |
| Compound 1 | 1 μM | 18.4 | −5.3 | 7.5 | 3.3 | 2.8 | 8.1 | ND |
| | 10 μM | 16.3 | 3.2 | 18.6 | 10.7 | 2.0 | 10.9 | 4.38 |
| Compound 2 | 1 μM | 13.5 | −11.0 | −10.6 | 3.8 | 0.3 | 0.0 | ND |
| | 10 μM | 14.2 | 0.24 | −16.0 | 9.8 | 3.1 | −10.6 | ND |
| Compound 6 | 1 μM | 15.5 | −14.3 | 15.3 | −16.5 | −7.6 | −26.1 | ND |
| | 10 μM | 23.3 | 20.9 | 13.1 | −8.3 | −19.4 | −25.7 | ND |

Conclusion: None of the compounds of the invention had a significant CYP inhibitory effect.

Test Example 9: hERG Potassium Channel Inhibition Assay

Experimental Procedure:

(1) Experimental Materials:

A. CHO (Chinese Hamster Ovary Cells) Stably Transfected Cell Line Culture

The cell line used for the patch clamp assay was a 10th generation CHO cell overexpressing hERG potassium channel cDNA.

CHO hERG cells were cultured in Petri dishes or flasks at 37° C. in a 5% CO2 incubator. Cells were dropped onto circular slides 24-48 hours prior to electrophysiological experiments and cultured in cell culture medium and used for experiments after the cells had been adhered.

Cell Culture Medium (Purchased from Invitrogen) Composition:

Ham's F12 medium

10% (v/v) heat inactivated FBS

100 μg/ml Hygromycin B (thaumatin)

100 μg/ml Geneticin (Genomycin, G418)

B. Compound Preparation

Compound powders are dissolved in the extracellular solution and are subjected to a routine 5 to 10 minute sonication and shaking to ensure complete dissolution of the compound.

The final concentrations of compounds used for electrophysiological assays were 5, 20 μM and the final concentration of DMSO was 0.1%.

(II) Experimental Protocol:

A. Experimental Procedure for Electrophysiological Recordings

Cell membrane currents were recorded using a HEKA EPC-10 USB patch-clamp amplifier (HEKA Elektronik, Germany).

1) A coverslip with a large number of uniformly growing individual CHO hERG cells on its surface was taken. Place in a continuous recording cell on an inverted microscope, perfused with extracellular fluid (approximately 1 ml per minute) and recorded continuously, waiting for the current to stabilize.

2) Record HERG channel currents for individual cells using standard whole cell recording mode. The membrane voltage is first clamped at −80 mV and the cell is given a +20 mV stimulus for 5 s to activate the hERG potassium channel, then repolarized to −50 mV for 5 s to generate an outward tail current, which is continuously perfused until the current is stable, at which point the peak tail current is the control current value.

3) The extracellular solution containing the drug to be tested was then perfused and recorded until the inhibitory effect of the drug on the hERG current reached a steady state, at which point the peak tail current was the post-drug current value.

4) The cells are again perfused with the extracellular solution until the hERG current returns to or approaches the level prior to the addition of the drug, then the perfusion can be continued to test other concentrations or drugs. One or more compound or drug concentrations may be tested on each cell.

5) Cisapride (C4740-10 mg, Sigma) is used as a positive control in the experiment to ensure that the cells used respond properly.

(III) Quality Control

The following criteria need to be met for the reported experimental data:

Electrophysiological Recording Parameters a) Sealing resistance>500MΩ b) contact resistance (Ra)<10MΩ c) Initial tail current amplitude>200 pA d) Current rundown (spontaneous reduction)<2%/min e) Leakage current<200 pA or 10% of peak hERG current (within 90% of recording time)

Test Results:

| Compound No. | hERG inhibition/% 5 μM | 20 μM |
|---|---|---|
| AZD-1775 | 21.45 | 49.98 |
| Compound 1 | 5.07 | 15.08 |

Conclusion: The hERG inhibitory activity of the compounds of the present invention was significantly lower than that of AZD-1775.

The invention claimed is:

1. A compound represented by formula I, or a deuterated compound thereof, or a stereoisomer thereof, or a pharmaceutically acceptable salt thereof:

I

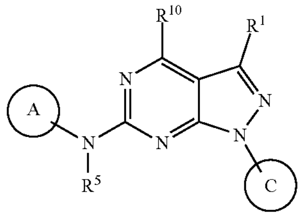

wherein,

R1 is H;

C-ring is selected from a group consisting of

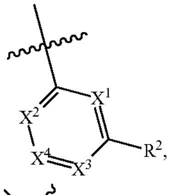

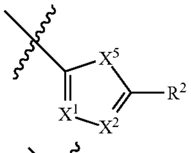

,

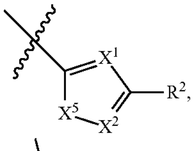

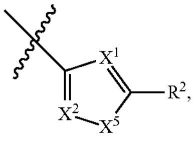

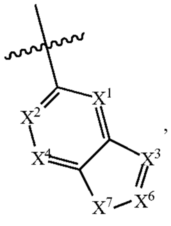

,

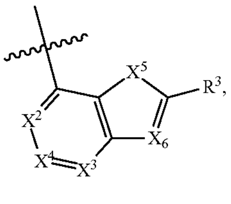

-continued

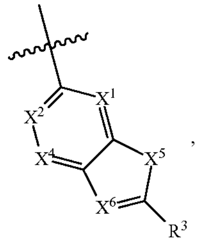
,
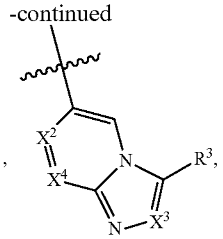

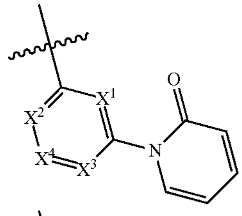
,
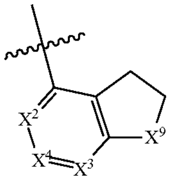
,

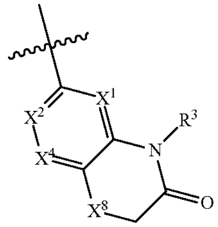
or
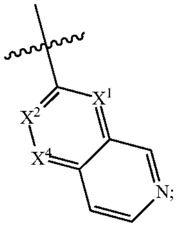

X1, X2, X4 is independently selected from a group consisting of N or CR4;
X3 is selected from a group consisting of N or CR3;
X5 is selected from a group consisting of O, S or NR4;
X6 is selected from a group consisting of CR4 or N;
X8 is selected from a group consisting of CR4R4, O;
X7 is selected from a group consisting of S, NR4;
X9 is selected from a group consisting of CR4R4;
R2 is selected from a group consisting of

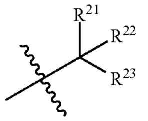
or
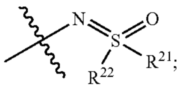

R21, R22 is independently selected from a group consisting of H, halogen, cyano, —C1~6 alkyl, —C2~6 alkenyl, —C2~6 alkynyl, halogen substituted —C1~6 alkyl, halogen substituted —C2~6 alkenyl, halogen substituted —C2~6 alkynyl, —C0~4 alkylene-OR24, —C0~4 alkylene-NR24R24;

each R24 is independently selected from a group consisting of H, —C1~6 alkyl, —C2~6 alkenyl, —C2~6 alkynyl, halogen substituted —C1~6 alkyl, halogen substituted —C2~6 alkenyl, halogen substituted —C2~6 alkynyl;

or, R21, R22 together with the atom adjacent therewith form 3~8-membered carbocyclyl, 4~8-membered heterocylcylalkyl,

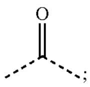

R23 is selected from a group consisting of H, halogen, cyano, —C1~6 alkyl, —C2~6 alkenyl, —C2~6 alkynyl, halogen substituted —C1~6 alkyl, halogen substituted —C2~6 alkenyl, halogen substituted —C2~6 alkynyl, —C0~4 alkylene-C(O)R25, —C0~4 alkylene-C(O)NR25R25, —C0~4 alkylene-C(O)OR25, —C0~4 alkylene-S(O)2R25, —C0~4 alkylene-S(O)R25, —C0~4 alkylene-S(O)(NH)R25, —C0~4 alkylene-S(NH)2R25, —C0~4 alkylene-S(O)2NR25R25, —C0~4 alkylene-S(O)NR25R25, —C0~4 alkylene-S(O)(NH)NR25R25, —C0~4 alkylene-S(NH)2NR25R25, —C0~4 alkylene-OR25, —C0~4 alkylene-OC(O)R25, —C0~4 alkylene-OS(O)2R25, —C0~4 alkylene-OS(O)R25, —C0~4 alkylene-NR25R25, —C0~4 alkylene-NR25C(O)R25, —C0~4 alkylene-NR25S(O)2R25, —C0~4 alkylene-NR25S(O)R25, —C0~4 alkylene-NR25S(O)(NH)R25, —C0~4 alkylene-NR25S(NH)2R25;

each R25 is independently selected from a group consisting of H, —C1~6 alkyl, —C2~6 alkenyl, —C2~6 alkynyl, halogen substituted —C1~6 alkyl, halogen substituted —C2~6 alkenyl, halogen substituted —C2~6 alkynyl;

or, R23, R3 together with the atom adjacent therewith form 4~8-membered carbocyclyl, 4~8-membered heterocylcylalkyl;

R3 is selected from a group consisting of H, halogen, cyano, —C1~6 alkyl, —C2~6 alkenyl, —C2~6 alkynyl, hydroxy substituted —C1~6 alkyl, halogen substituted —C1~6 alkyl, halogen substituted —C2~6 alkenyl, halogen substituted —C2~6 alkynyl, —C0~4 alkylene-OH, —C0~4 alkylene-O(C1~6 alkyl), —C0~4 alkylene-NH2, —C0~4 alkylene-NH(C1~6 alkyl), —C0~4 alkylene-N(C1~6 alkyl)(C1~6 alkyl);

each R4 is independently selected from a group consisting of H, halogen, cyano, —C1~6 alkyl, —C2~6 alkenyl, —C2~6 alkynyl, halogen substituted —C1~6 alkyl, halogen substituted —C2~6 alkenyl, halogen substituted —C2~6 alkynyl, —C0~4 alkylene-OH, —C0~4 alkylene-O(C1~6 alkyl), —C0~4 alkylene-NH2, —C0~4 alkylene-NH(C1~6 alkyl), —C0~4 alkylene-N(C1~6 alkyl) (C1~6 alkyl);

R5 is selected from a group consisting of H, —C1~6 alkyl;

A-ring is selected from a group consisting of

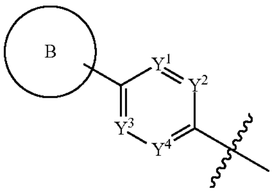
,
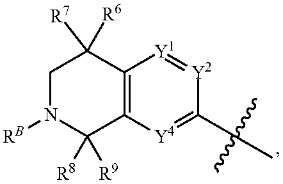
,
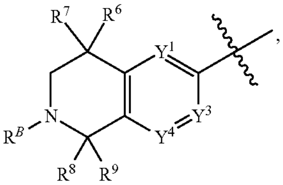
,

-continued

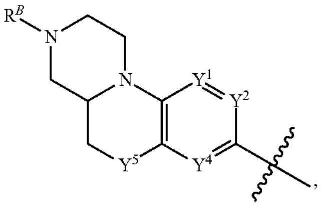

,

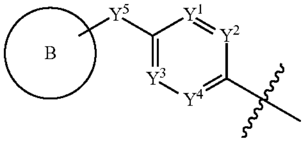

,

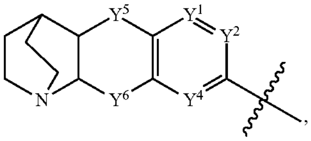

,

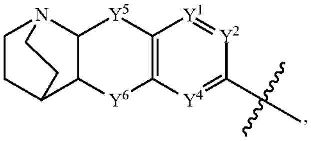

,

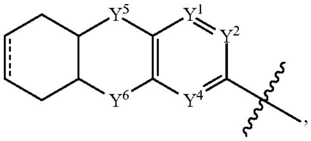

,

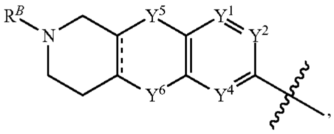

,

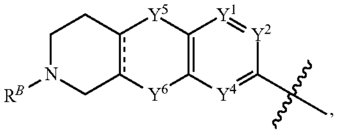

,

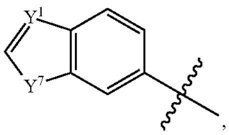

,

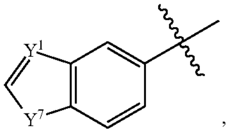

,

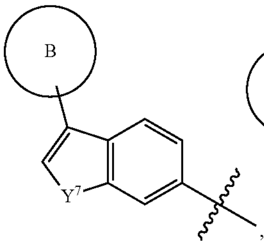

,

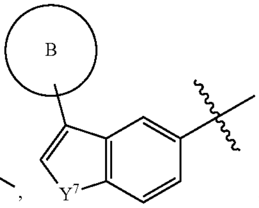

,

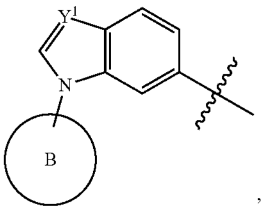

,

-continued

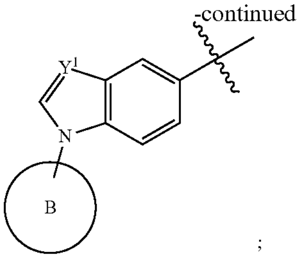

;

⎓ represents a single bond or double bond;

Y1, Y2, Y3, Y4 is independently selected from a group consisting of N or CRY;

each RY is independently selected from a group consisting of H, halogen, cyano, —C1~6 alkyl, —C2~6 alkenyl, —C2~6 alkynyl, halogen substituted —C1~6 alkyl, halogen substituted —C2~6 alkenyl, halogen substituted —C2~6 alkynyl, —C0~4 alkylene-OH, —C0~4 alkylene-O(C1~6 alkyl), —C0~4 alkylene-NH2, —C0~4 alkylene-NH(C1~6 alkyl), —C0~4 alkylene-N(C1~6 alkyl) (C1~6 alkyl);

B-ring is selected from a group consisting of 3~12-membered carbocyclyl, 4~12-membered heterocylcylalkyl; said carbocyclyl, heterocylcylalkyl is optionally substituted by one, two, three, four or five RB;

each RB is independently selected from a group consisting of H, halogen, cyano, —C1~6 alkyl, —C2~6 alkenyl, —C2~6 alkynyl, halogen substituted —C1~6 alkyl, halogen substituted —C2~6 alkenyl, halogen substituted —C2~6 alkynyl, —C0~4 alkylene-ORB1, —C0~4 alkylene-OC(O)RB1, —C0~4 alkylene-SRB1, —C0~4 alkylene-S(O)2RB1, —C0~4 alkylene-S(O) RB1, —C0~4 alkylene-S(O)2NRB1RB1, —C0~4 alkylene-S(O)NRB1RB1, —C0~4 alkylene-C(O)RB1, —C0~4 alkylene-C(O)ORB1, —C0~4 alkylene-C(O) NRB1RB1, —C0~4 alkylene-NRB1RB1, —C0~4 alkylene-NRB1C(O)RB1, 3~12-membered carbocyclyl, 4~12-membered heterocylcylalkyl; said carbocyclyl, heterocylcylalkyl is optionally substituted by one, two, three, four or five RB1; or, two independent RB together with the atom adjacent therewith form

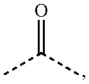

,

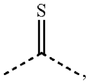

,

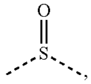

,

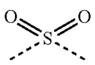

;

each RB1 is independently selected from a group consisting of H, —C1~6 alkyl, —C2~6 alkenyl, —C2~6 alkynyl, halogen substituted —C1~6 alkyl, halogen substituted —C2~6 alkenyl, halogen substituted —C2~6 alkynyl;

R6, R7, R8, R9 is independently selected from a group consisting of H, halogen, cyano, —C1~6 alkyl, —C2~6 alkenyl, —C2~6 alkynyl, halogen substituted —C1~6 alkyl, halogen substituted-C2~6 alkenyl, halogen substituted —C2~6 alkynyl, —C0~4 alkylene-OH, —C0~4 alkylene-O(C1~6 alkyl), —C0~4 alkylene-NH2, —C0~4 alkylene-NH(C1~6 alkyl), —C0~4 alkylene-N(C1~6 alkyl) (C1~6 alkyl);

or, R6, R7 together with the atom adjacent therewith form 3~8-membered carbocyclyl, 4~8-membered heterocylcylalkyl; or, R8, R9 together with the atom adjacent therewith form 3~8-membered carbocyclyl, 4~8-membered heterocylcylalkyl;

Y5, Y6 is independently selected from a group consisting of chemical bond, —C0~4 alkylene-O—, —C0~4 alkylene-S—, —C0~4 alkylene-NRY51-, CRY51RY51;

each RY51 is independently selected from a group consisting of H, —C1~6 alkyl, —C2~6 alkenyl, —C2~6 alkynyl, halogen substituted —C1~6 alkyl, halogen substituted —C2~6 alkenyl, halogen substituted —C2~6 alkynyl, —C0~4 alkylene-OH, —C0~4 alkylene-O(C1~6 alkyl), —C0~4 alkylene-NH2, —C0~4 alkylene-NH(C1~6 alkyl), —C0~4 alkylene-N(C1~6 alkyl) (C1~6 alkyl);

Y7 is selected from a group consisting of O, S or NRY71;

RY71 is selected from a group consisting of H, —C1~6 alkyl, —C2~6 alkenyl, —C2~6 alkynyl, halogen substituted —C1~6 alkyl, halogen substituted —C2~6 alkenyl, halogen substituted-C2~6 alkynyl, —C0~4 alkylene-OH, —C0~4 alkylene-O(C1~6 alkyl), —C0~4 alkylene-NH2, —C0~4 alkylene-NH(C1~6 alkyl), —C0~4 alkylene-N(C1~6 alkyl) (C1~6 alkyl);

R10 is selected from a group consisting of H, halogen, cyano, —C1~6 alkyl, —C2~6 alkenyl, —C2~6 alkynyl, halogen substituted —C1~6 alkyl, halogen substituted —C2~6 alkenyl, halogen substituted —C2~6 alkynyl, —C0~4 alkylene-OH, —C0~4 alkylene-O (C1~6 alkyl), —C0~4 alkylene-NH2, —C0~4 alkylene-NH(C1~6 alkyl), —C0~4 alkylene-N(C1~6 alkyl) (C1~6 alkyl).

2. The compound according to claim 1, wherein:

R10 is selected from a group consisting of H, halogen, cyano, —C1~6 alkyl, halogen substituted —C1~6 alkyl, —OH, —O(C1~6 alkyl), —NH2, —NH(C1~6 alkyl), —N(C1~6 alkyl) (C1~6 alkyl).

3. The compound according to claim 2, wherein:

R10 is selected from a group consisting of H, halogen, —C1~6 alkyl, —O(C1~6 alkyl).

4. The compound according to claim 1, wherein:

C-ring is selected from a group consisting of

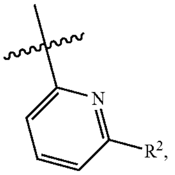
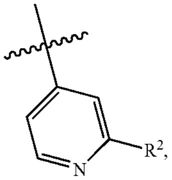
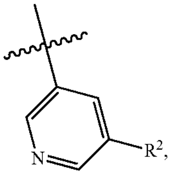
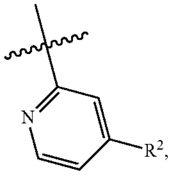
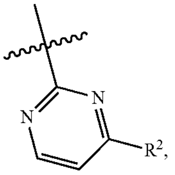
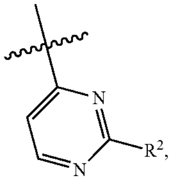
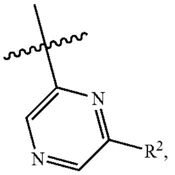
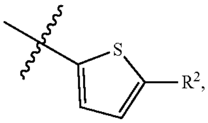

-continued

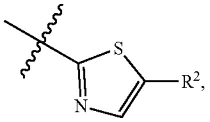
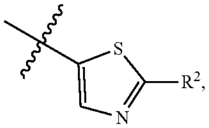
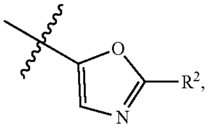
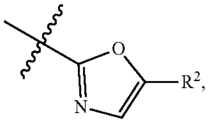
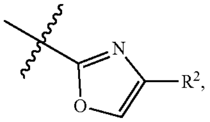
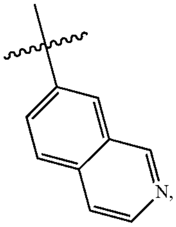
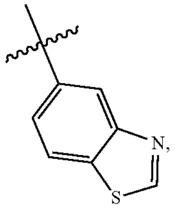
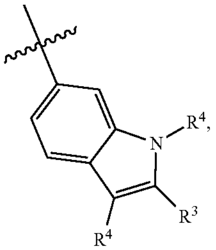
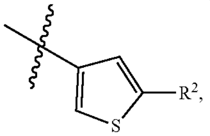
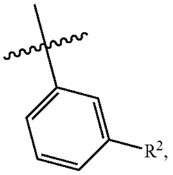
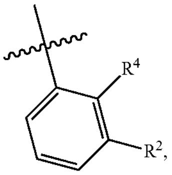
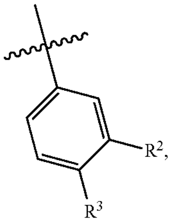
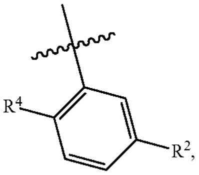
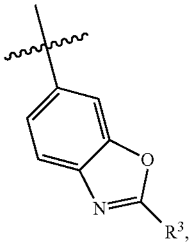
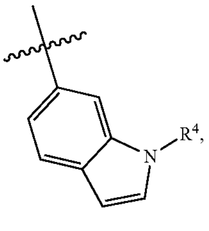
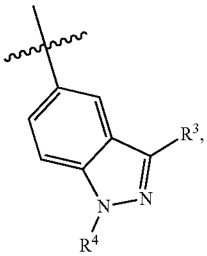

-continued

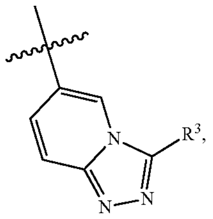

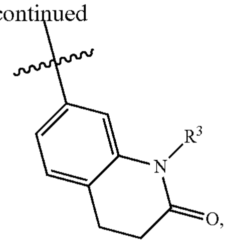

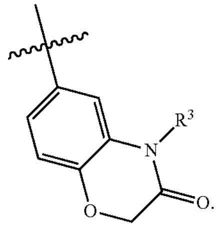

5. The compound according to claim 4, wherein:

R2 is selected from a group consisting of

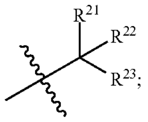

R21, R22 is independently selected from a group consisting of H, halogen, cyano, —C1~6 alkyl, halogen substituted —C1~6 alkyl, —OR24;

each R24 is independently selected from a group consisting of H, —C1~6 alkyl;

or, R21, R22 together with the atom adjacent therewith form carbonyl, 3-membered carbocyclyl, 4-membered carbocyclyl, 5-membered carbocyclyl, 6-membered carbocyclyl, 4-membered heterocylcylalkyl, 5-membered heterocylcylalkyl, 6-membered heterocylcylalkyl; said heteroatom in the heterocylcylalkyl is selected from a group consisting of N, O, S;

R23 is selected from a group consisting of H, halogen, cyano, —C1~6 alkyl, halogen substituted —C1~6 alkyl, —S(O)2R25, —S(O)R25, —S(O) (NH) R25, —S(NH)2R25;

each R25 is independently selected from a group consisting of H, —C1~6 alkyl.

6. The compound according to claim 5, wherein:

R2 is selected from a group consisting of

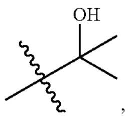 , 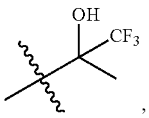 , 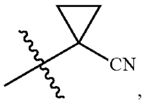 ,

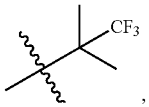 , 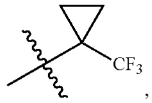 , 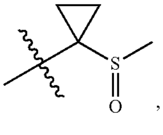 ,

-continued

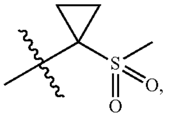

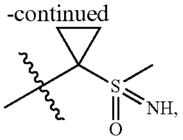

7. The compound according to claim 1, wherein:

C-ring is selected from a group consisting of

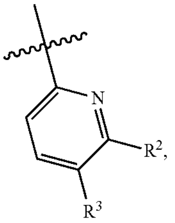

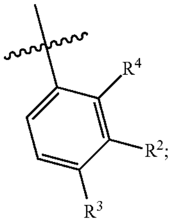

R2 is selected from a group consisting of

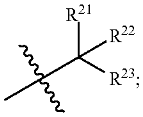

R21, R22 is independently selected from a group consisting of H, halogen, cyano, —C1~6 alkyl, halogen substituted —C1~6 alkyl, —OR24;

each R24 is independently selected from a group consisting of H, —C1~6 alkyl;

R23, R3 together with the atom adjacent therewith form 4-membered carbocyclyl, 5-membered carbocyclyl, 6-membered carbocyclyl, 7-membered carbocyclyl, 5-membered heterocylcylalkyl, 6-membered heterocylcylalkyl.

8. The compound according to claim 7, wherein:

C-ring is selected from a group consisting of

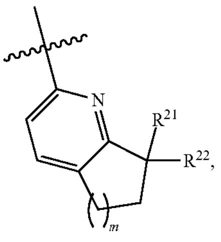

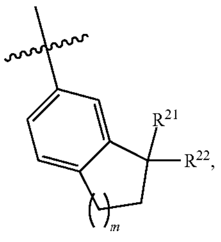

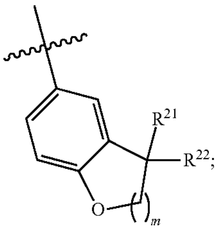

wherein, m is selected from a group consisting of 0, 1, 2, 3.

9. The compound according to claim 4, wherein:

R2 is selected from a group consisting of

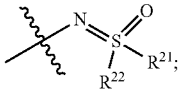

R21, R22 is independently selected from a group consisting of H, —C1~6 alkyl.

10. The compound according to claim 1, wherein:

A-ring is selected from a group consisting of

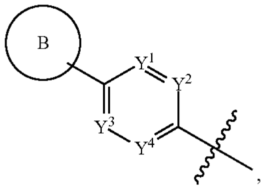
,
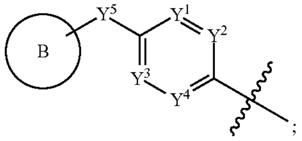
;

Y1, Y2, Y3, Y4 is independently selected from a group consisting of N or CRY;

each RY is independently selected from a group consisting of H, halogen, cyano, —C1~6 alkyl, halogen substituted —C1~6 alkyl, —C0~4 alkylene-OH, —C0~4 alkylene-O(C1~6 alkyl), —C0~4 alkylene-NH2, —C0~4 alkylene-NH(C1~6 alkyl), —C0~4 alkylene-N(C1~6 alkyl) (C1~6 alkyl);

B-ring is selected from a group consisting of 3~8-membered monocyclic-carbocyclyl, 4~8-membered monocyclic heterocylcylalkyl, 5~10-membered bridged-carbocyclyl, 5~10-membered bridged-heterocylcylalkyl, 5~10-membered spiro-carbocyclyl, 5~10-membered spiro-heterocylcylalkyl, 8~12-membered fused-carbocyclyl, 8~12-membered fused-heterocylcylalkyl; said monocyclic-carbocyclyl, monocyclic heterocylcylalkyl, bridged-carbocyclyl, bridged-heterocylcylalkyl, spiro-carbocyclyl, spiro-heterocylcylalkyl, fused-carbocyclyl, fused-heterocylcylalkyl is optionally substituted by one, two, three, four or five RB;

each RB is independently selected from a group consisting of H, halogen, cyano, —C1~6 alkyl, halogen substituted —C1~6 alkyl, —ORB1, —SRB1, —S(O) 2RB1, —S(O)RB1, —C(O)RB1, —C(O)ORB1, —NRB1RB1, 3~12-membered carbocyclyl, 4~12-membered heterocylcylalkyl; said carbocyclyl, heterocylcylalkyl is optionally substituted by one, two, three, four or five RB1; or, two independent RB together with the atom adjacent therewith form

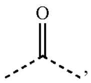
,
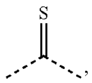
,
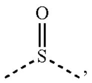
,
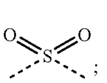
;

each RB1 is independently selected from a group consisting of H, —C1~6 alkyl, halogen substituted —C1~6 alkyl;

Y5 is selected from a group consisting of O, S, NRY51, CRY51RY51;

each RY51 is independently selected from a group consisting of H, —C1~6 alkyl.

11. The compound according to claim 10, wherein:

B-ring is selected from a group consisting of

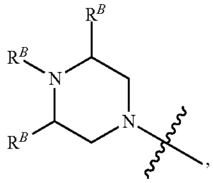
,
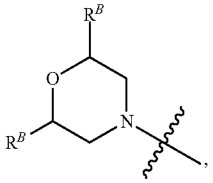
,
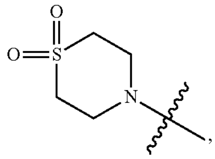
,
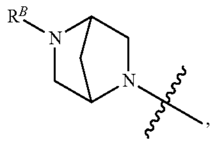
,
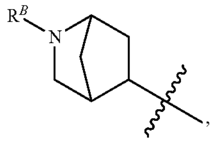
,
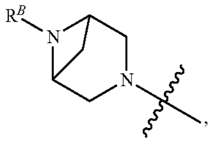
,
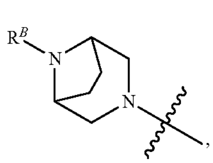
,
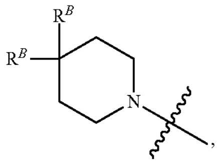
,
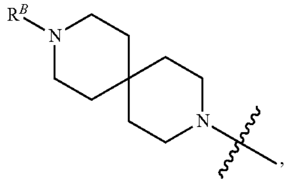
,
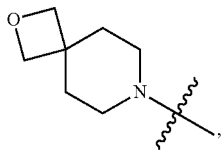
,
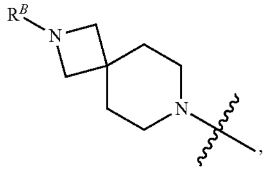
,
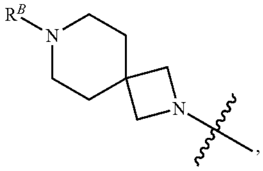
,
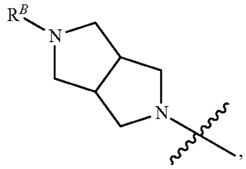
,
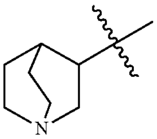
,
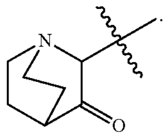
.

12. The compound according to claim 11, wherein:

B-ring is selected from a group consisting of

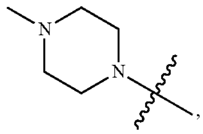
,
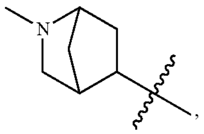
,

-continued

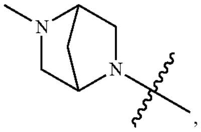,
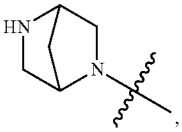,
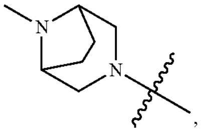,
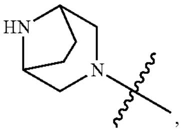,
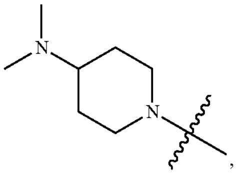,
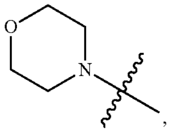,
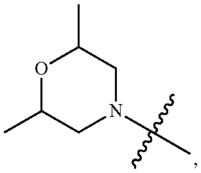,
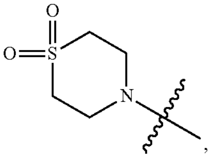,
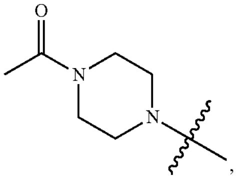,
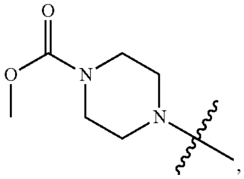,
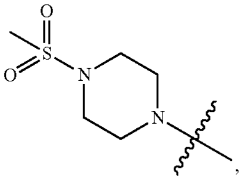,
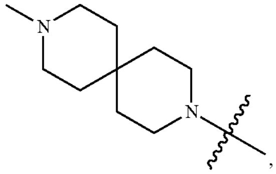,
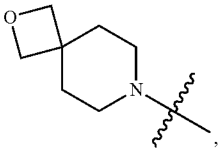,
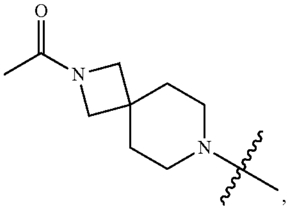,
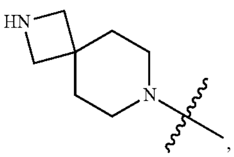,
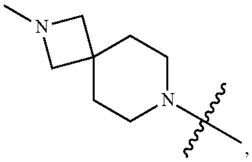,
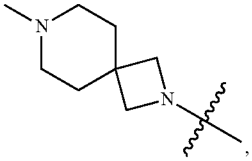,
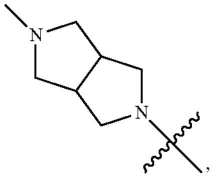,
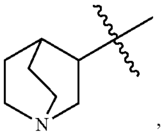,
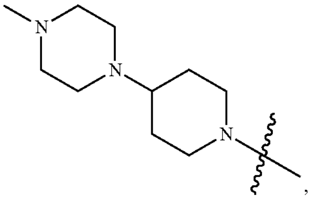, -continued

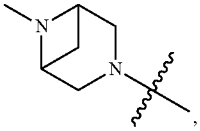,
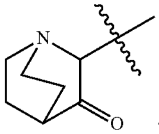.

13. The compound according to claim 1, wherein:

A-ring is selected from a group consisting of

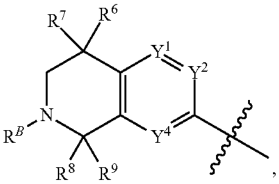,
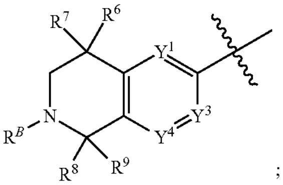;

Y1, Y2, Y3, Y4 is independently selected from a group consisting of N or CRY;

each RY is independently selected from a group consisting of H, halogen, cyano, —C1~6 alkyl, halogen substituted —C1~6 alkyl, —C0~4 alkylene-OH, —C0~4 alkylene-O(C1~6 alkyl), —C0~4 alkylene-NH2, —C0~4 alkylene-NH(C1~6 alkyl), —C0~4 alkylene-N(C1~6 alkyl) (C1~6 alkyl);

R6, R7, R8, R9 is independently selected from a group consisting of H, —C1~6 alkyl;

or, R6, R7 together with the atom adjacent therewith form 3-membered carbocyclyl, 4-membered carbocyclyl, 5-membered carbocyclyl, 6-membered carbocyclyl, 4-membered heterocylcylalkyl, 5-membered heterocylcylalkyl, 6-membered heterocylcylalkyl; or, R8, R9 together with the atom adjacent therewith form 3-membered carbocyclyl, 4-membered carbocyclyl, 5-membered carbocyclyl, 6-membered carbocyclyl, 4-membered heterocylcylalkyl, 5-membered heterocylcylalkyl, 6-membered heterocylcylalkyl;

RB is selected from a group consisting of H, —C1~6 alkyl, halogen substituted —C1~6 alkyl, —S(O)2RB1, —S(O)RB1, —C(O)RB1, —C(O)ORB1;

each RB1 is independently selected from a group consisting of H, —C1~6 alkyl, halogen substituted —C1~6 alkyl.

14. The compound according to claim 13, wherein:

A-ring is selected from a group consisting of

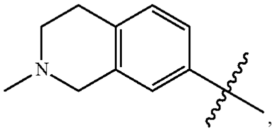,
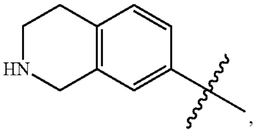,

-continued

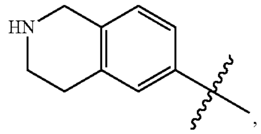

,

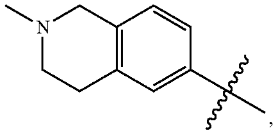

,

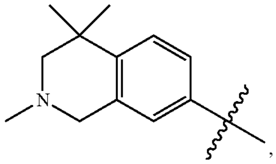

,

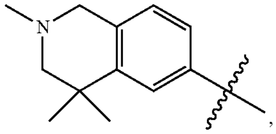

,

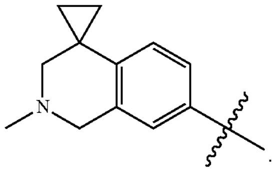

.

15. The compound according to claim 1, wherein: A-ring is selected from a group consisting of

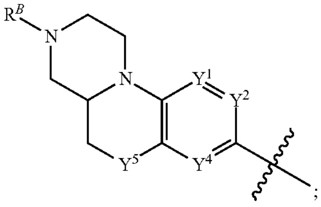

;

Y1, Y2, Y4 is independently selected from a group consisting of N or CRY;

each RY is independently selected from a group consisting of H, halogen, cyano, —C1~6 alkyl, halogen substituted —C1~6 alkyl, —C0~4 alkylene-OH, —C0~4 alkylene-O(C1~6 alkyl), —C0~4 alkylene-NH2, —C0~4 alkylene-NH(C1~6 alkyl), —C0~4 alkylene-N(C1~6 alkyl) (C1~6 alkyl);

RB is selected from a group consisting of H, —C1~6 alkyl, halogen substituted —C1~6 alkyl, —S(O)2RB1, —S(O)RB1, —C(O)RB1, —C(O)ORB1;

each RB1 is independently selected from a group consisting of H, —C1~6 alkyl, halogen substituted —C1~6 alkyl;

Y5 is selected from a group consisting of chemical bond, O, S, NRY51, CRY51RY51;

each RY51 is independently selected from a group consisting of H, —C1~6 alkyl.

16. The compound according to claim 15, wherein: A-ring is selected from a group consisting of

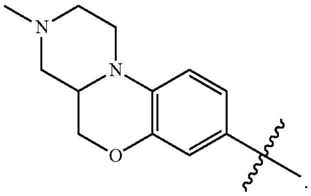 [SMILES: *c1ccc2c(c1)OCC1CN(C)CCN21]

.

17. The compound according to claim 1, wherein: A-ring is selected from a group consisting of,

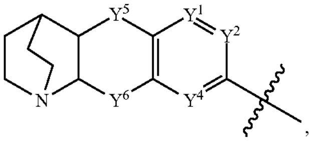

,

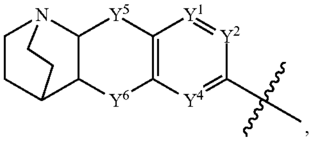

,

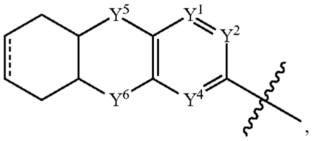

,

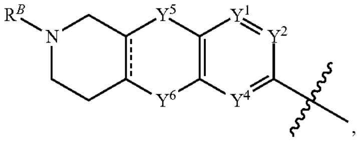

,

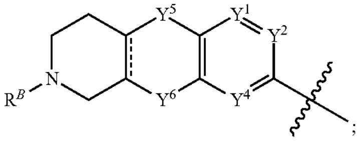

;

⎓ represents a single bond or double bond;

Y1, Y2, Y4 is independently selected from a group consisting of N or CRY;

each RY is independently selected from a group consisting of H, halogen, cyano, —C1~6 alkyl, halogen substituted —C1~6 alkyl, —C0~4 alkylene-OH, —C0~4 alkylene-O(C1~6 alkyl), —C0~4 alkylene-NH2, —C0~4 alkylene-NH(C1~6 alkyl), —C0~4 alkylene-N(C1~6 alkyl) (C1~6 alkyl);

RB is selected from a group consisting of H, —C1~6 alkyl, halogen substituted —C1~6 alkyl, —S(O)2RB1, —S(O)RB1, —C(O)RB1, —C(O)ORB1;

each RB1 is independently selected from a group consisting of H, —C1~6 alkyl, halogen substituted —C1~6 alkyl;

Y5, Y6 is independently selected from a group consisting of chemical bond, —C0~1 alkylene-O—, —C0~1 alkylene-S—, —C0~1 alkylene-NRY51-, CRY51RY51;

each RY51 is independently selected from a group consisting of H, —C1~6 alkyl.

18. The compound according to claim 17, wherein:

A-ring is selected from a group consisting of

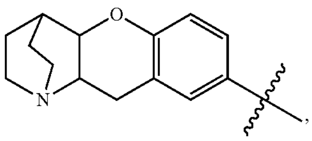,

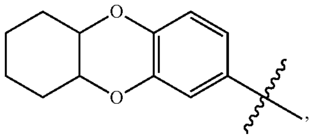,

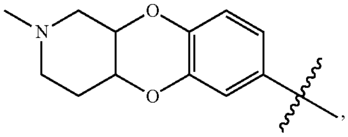,

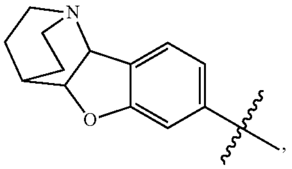,

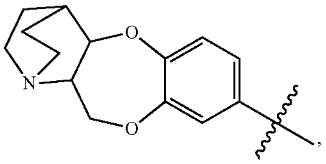,

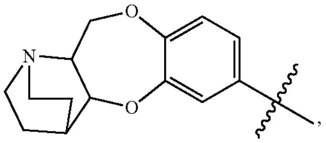,

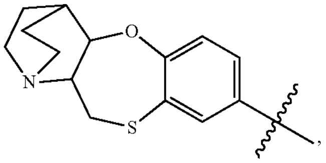,

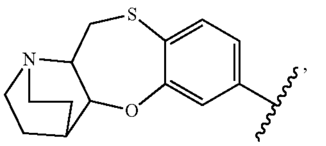,

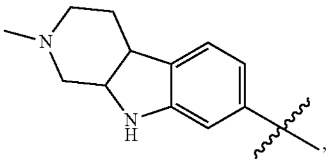,

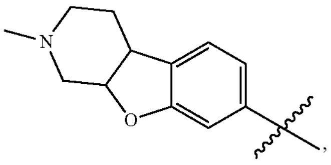,

-continued

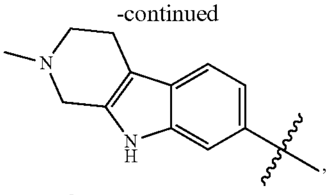,

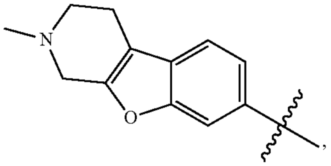,

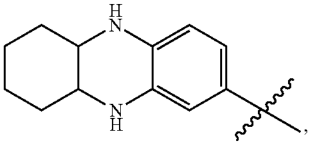,

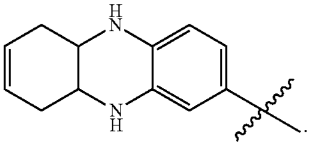.

19. The compound according to claim 1, wherein: A-ring is selected from a group consisting of

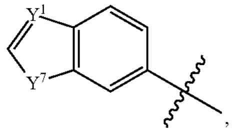, 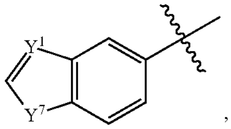, 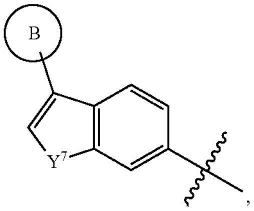, 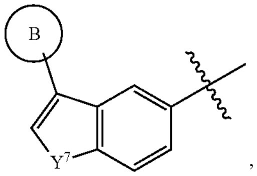, 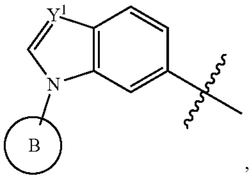, 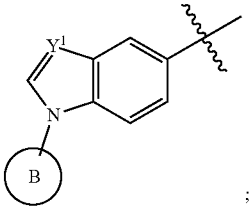;

Y1 is selected from a group consisting of N or CRY;

RY is selected from a group consisting of H, halogen, cyano, —C1~6 alkyl, halogen substituted —C1~6 alkyl, —C0~4 alkylene-OH, —C0~4 alkylene-O(C1~6 alkyl), —C0~4 alkylene-NH2, —C0~4 alkylene-NH (C1~6 alkyl), —C0~4 alkylene-N(C1~6 alkyl) (C1~6 alkyl);

B-ring is selected from a group consisting of 3~8-membered monocyclic-carbocyclyl, 4~8-membered monocyclic heterocylcylalkyl; said monocyclic-carbocyclyl, monocyclic heterocylcylalkyl is optionally substituted by one, two, three, four or five RB;

each RB is independently selected from a group consisting of H, halogen, cyano, —C1~6 alkyl, halogen substituted —C1~6 alkyl, —ORB1, —SRB1, —S(O)2RB1, —S(O)RB1, —C(O)RB1, —C(O)ORB1, —NRB1RB1; or, two independent RB together with the atom adjacent therewith form

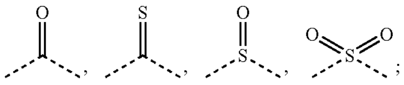

each RB1 is independently selected from a group consisting of H, —C1~6 alkyl, halogen substituted —C1~6 alkyl;

Y7 is selected from a group consisting of O, S or NRY71;

RY71 is selected from a group consisting of H, —C1~6 alkyl, halogen substituted —C1~6 alkyl, —C1~4 alkylene-OH, —C1~4 alkylene-O(C1~6 alkyl), —C1~4 alkylene-NH2, —C1~4 alkylene-NH(C1~6 alkyl), —C1~4 alkylene-N(C1~6 alkyl) (C1~6 alkyl).

20. The compound according to claim 19, wherein:

A-ring is selected from a group consisting of

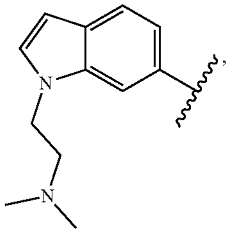

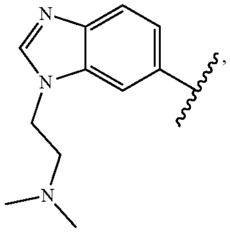

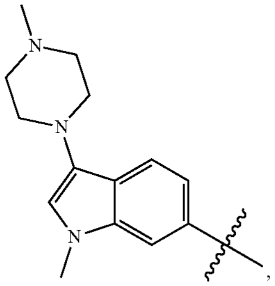

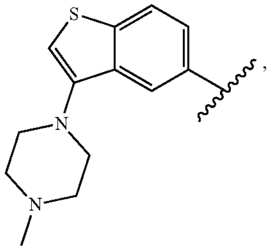

-continued

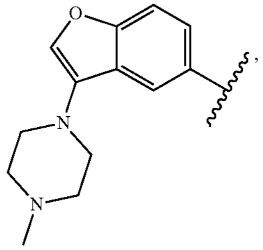

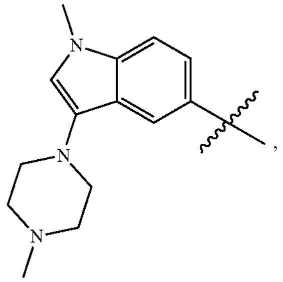

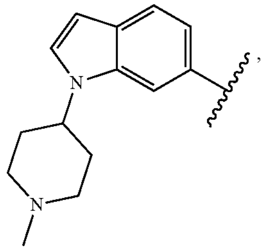

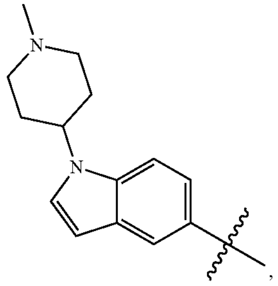

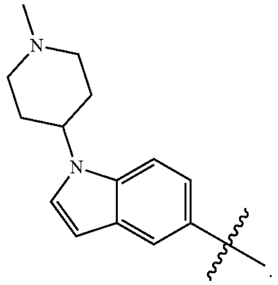

21. The compound according to claim 1, wherein:

C-ring is selected from a group consisting of

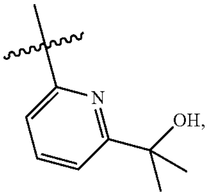

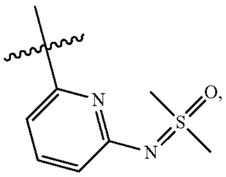

-continued
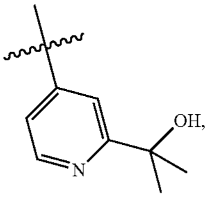
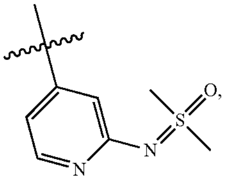
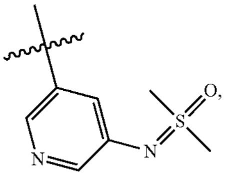
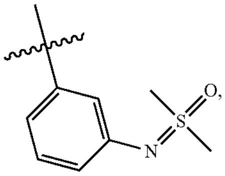
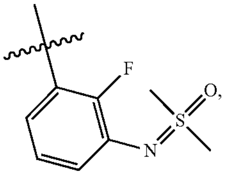
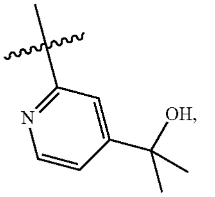
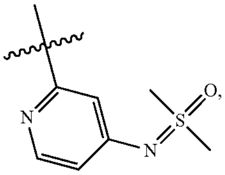
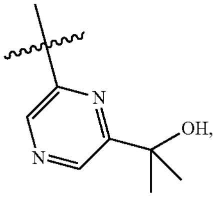
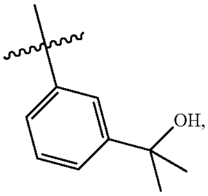
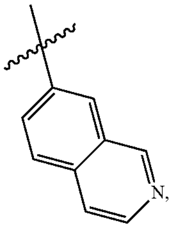
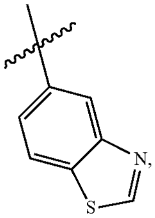
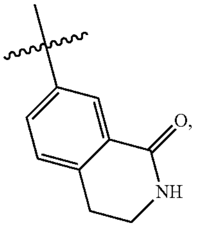
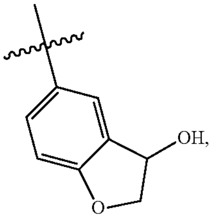
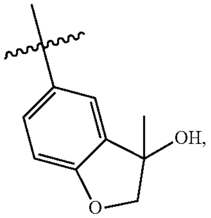
-continued
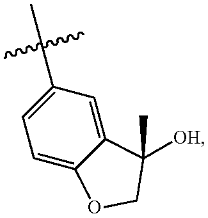
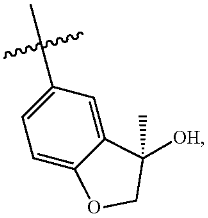
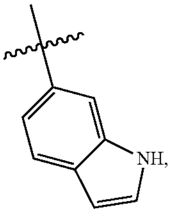
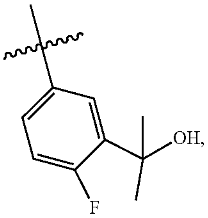
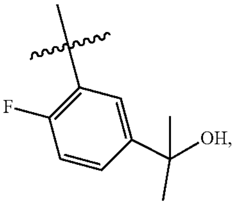
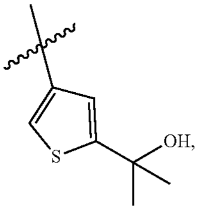
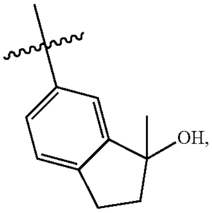
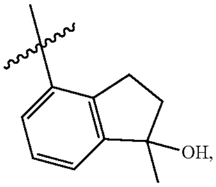
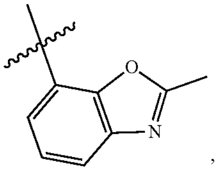
,
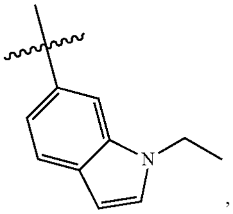
,
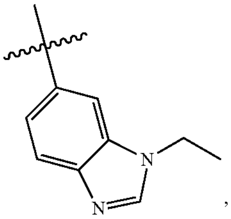
,
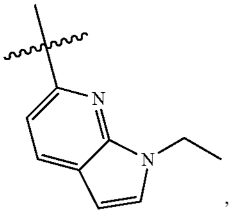
,
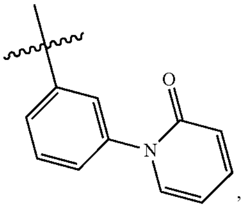
,
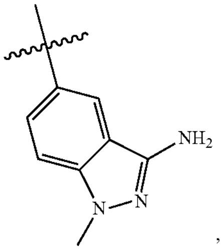
, -continued
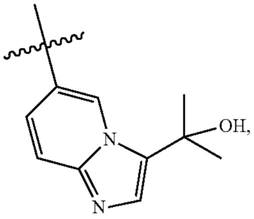
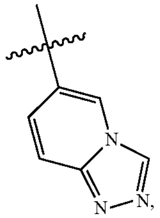
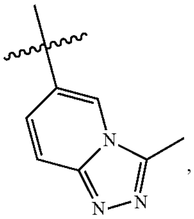
,
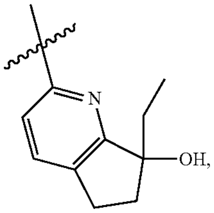
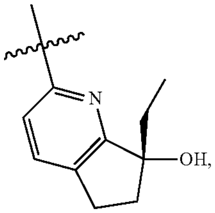
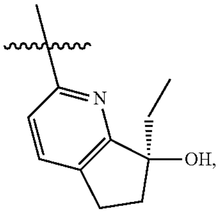
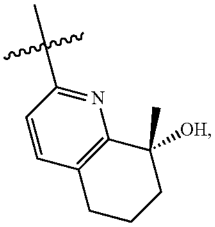
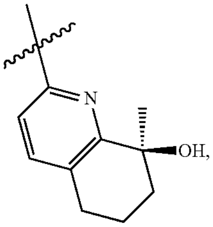
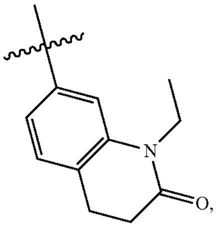
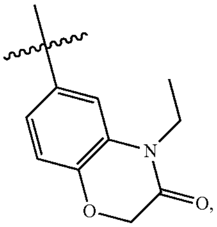
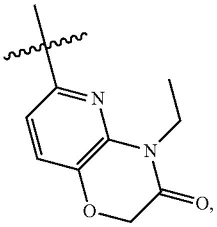
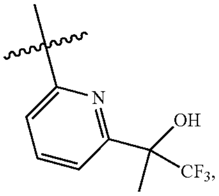
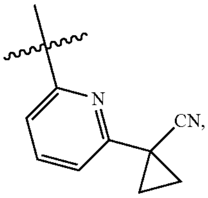
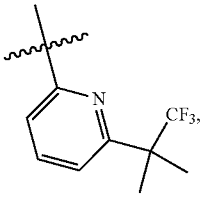
-continued
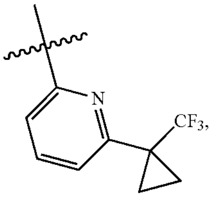
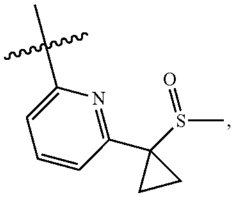
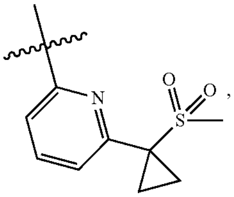
,
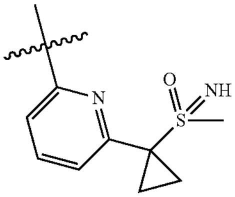
or
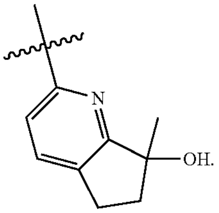
22. The compound according to claim 10, wherein: A-ring is selected from a group consisting of
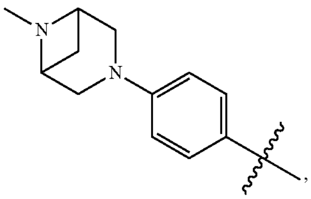
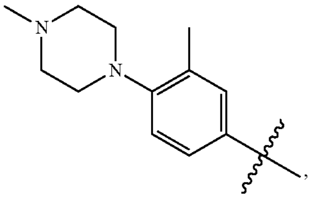
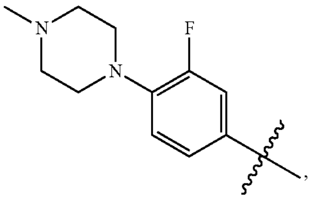
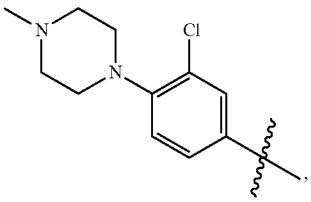

-continued
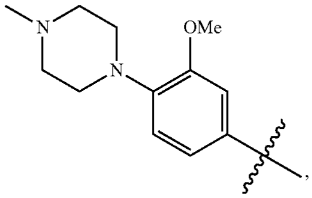
,
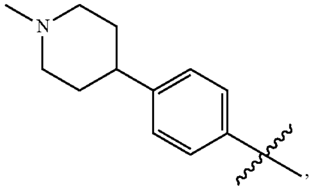
,
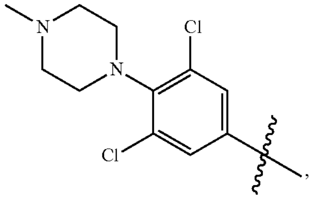
,
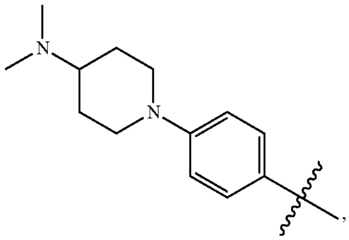
,
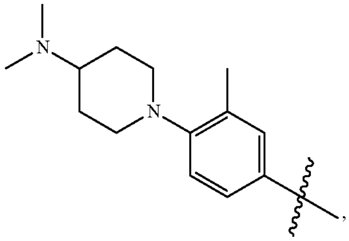
,
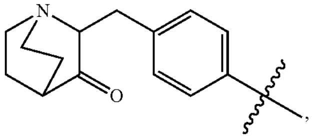
,
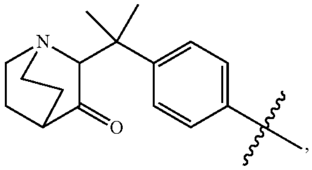
,
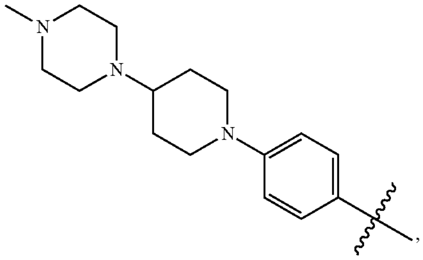
,
-continued
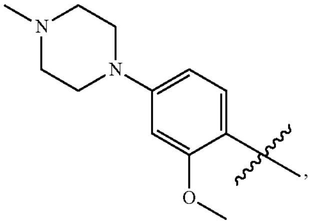
,
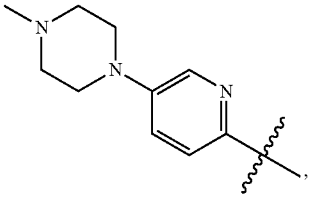
,
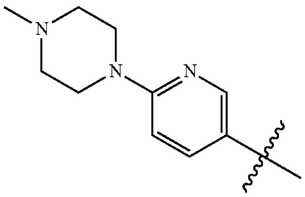
or
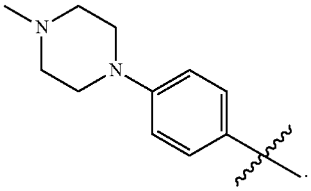
.
23. A compound, or a deuterated compound thereof, or a stereoisomer thereof, or a pharmaceutically acceptable salt thereof, selected from the group comprising:
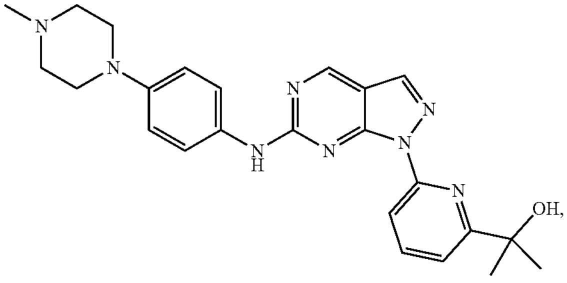
,
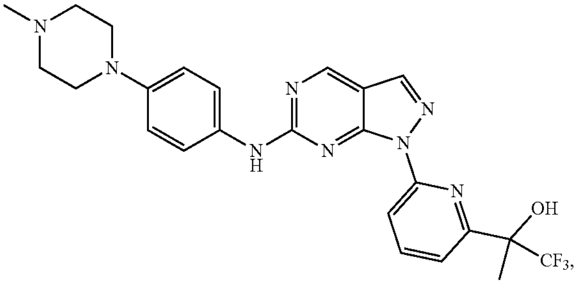
, -continued
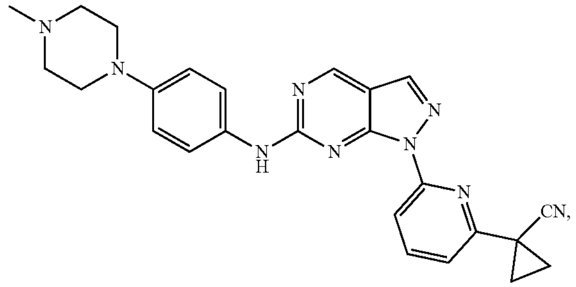
,
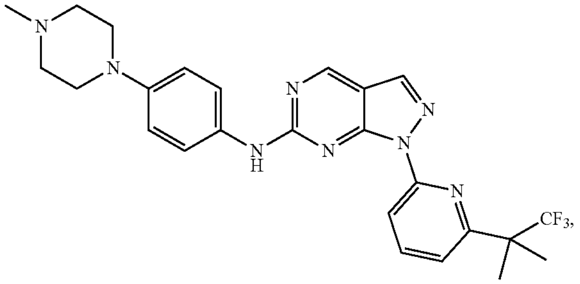
,
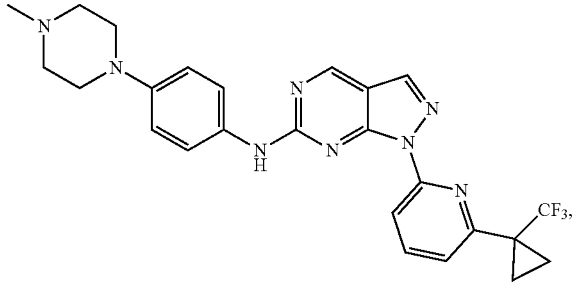
,
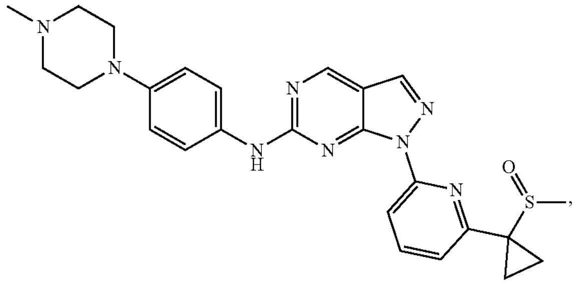
,
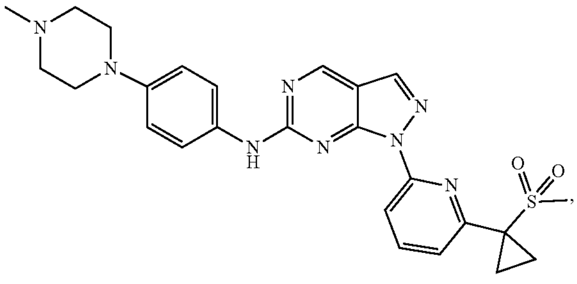
,
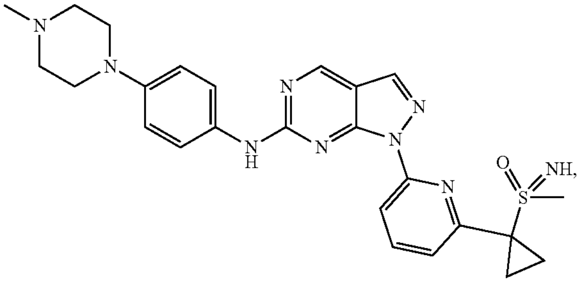
,
-continued
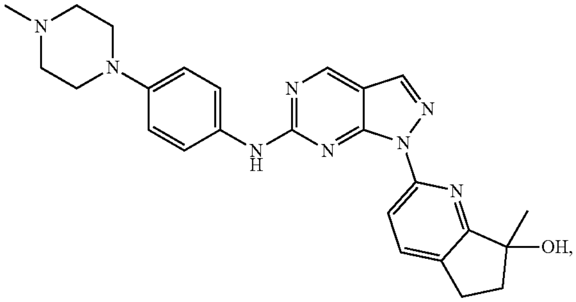
,
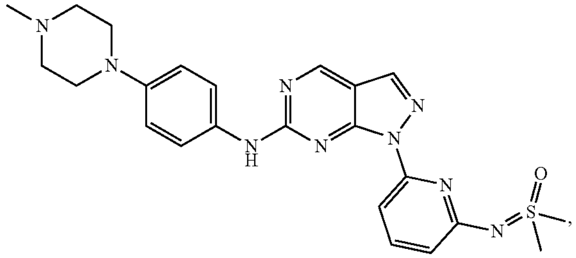
,
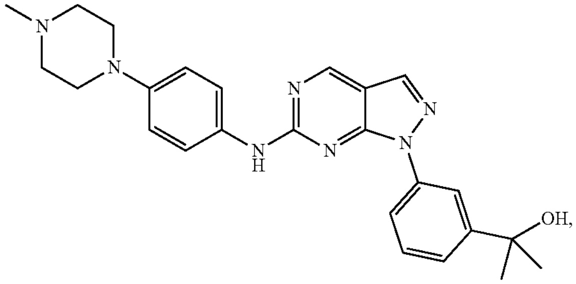
,
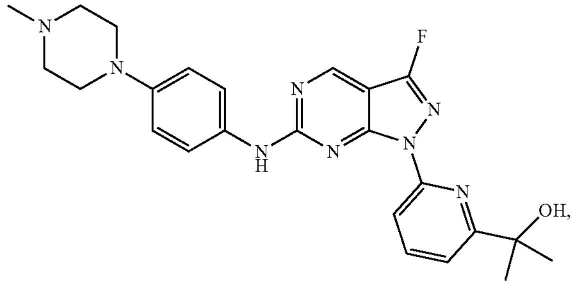
,
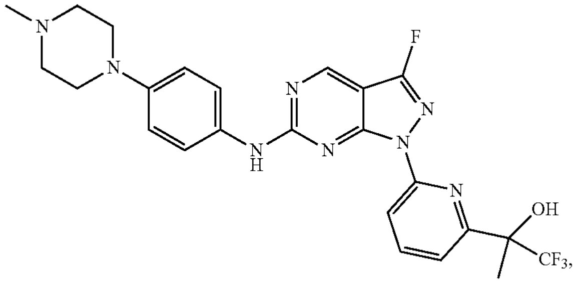
,
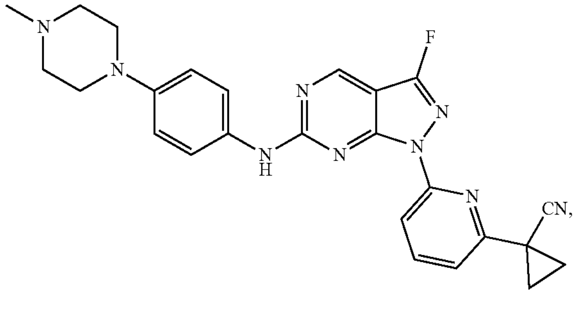
,

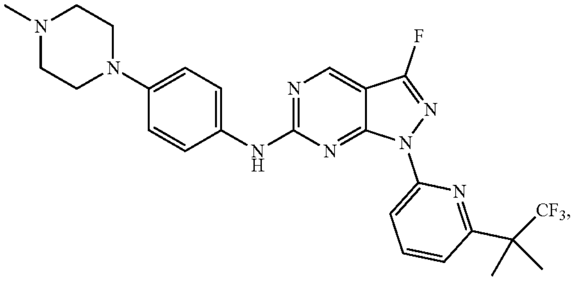
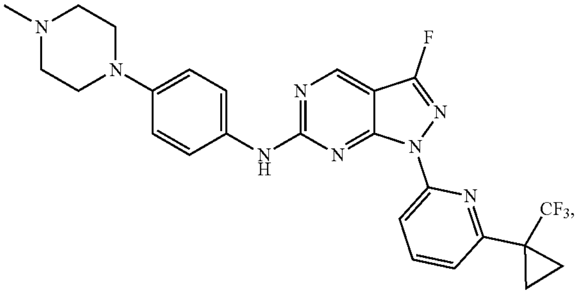
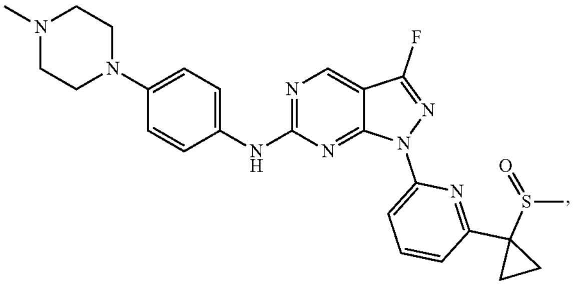
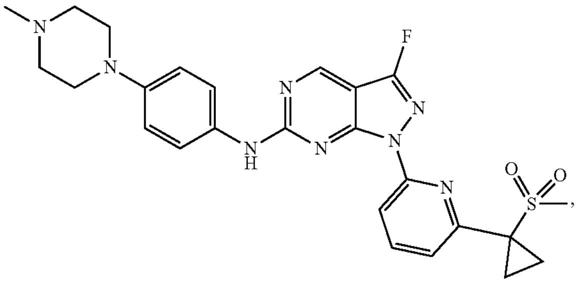
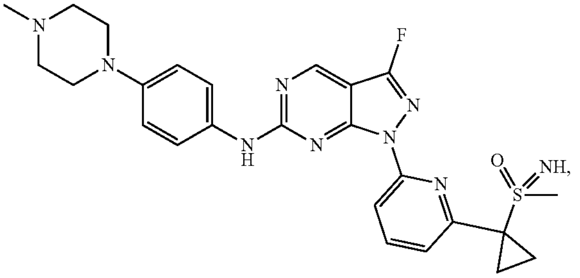
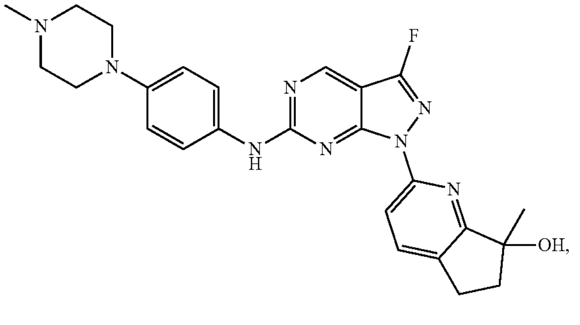
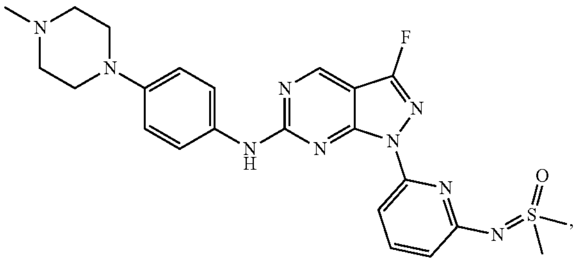
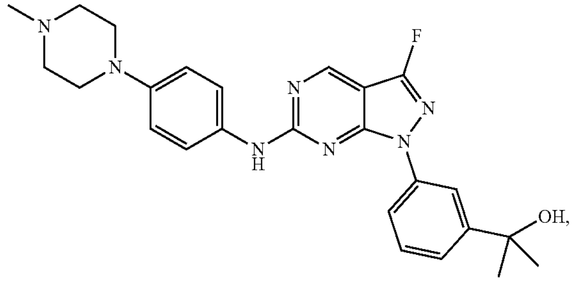
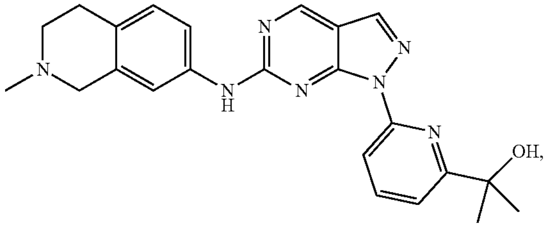
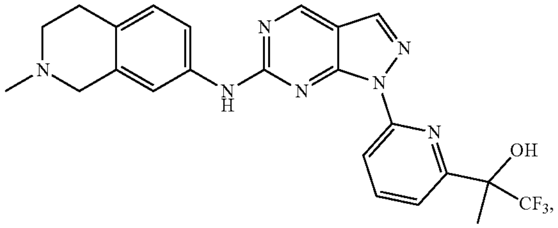
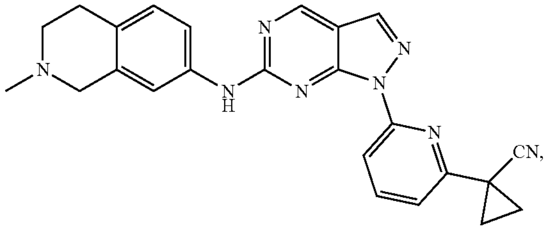
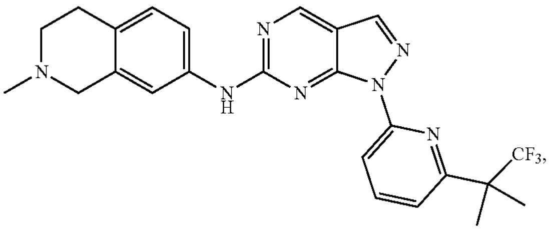
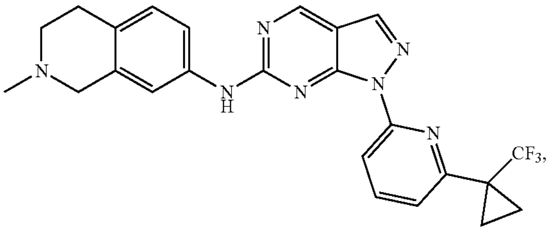

-continued
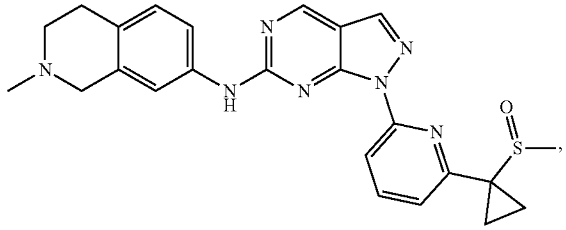
,
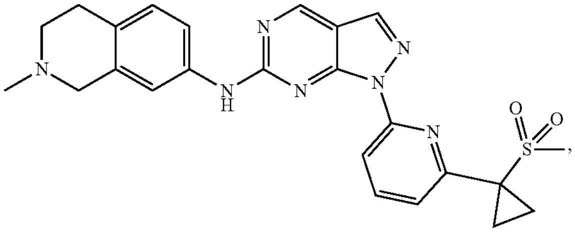
,
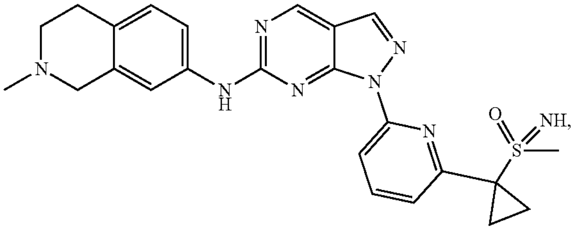
,
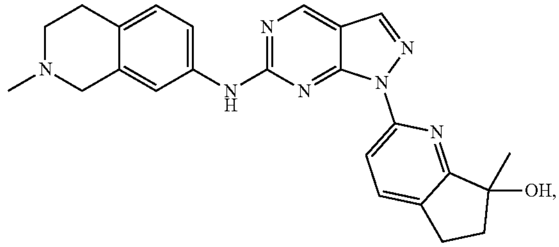
,
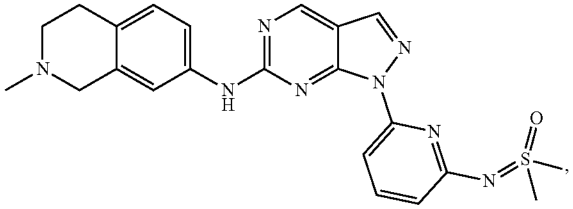
,
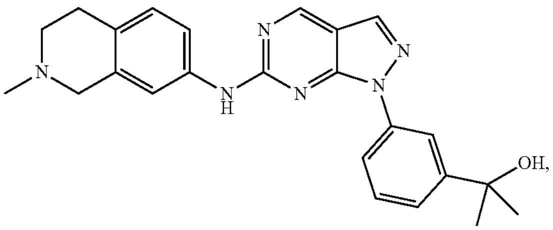
,
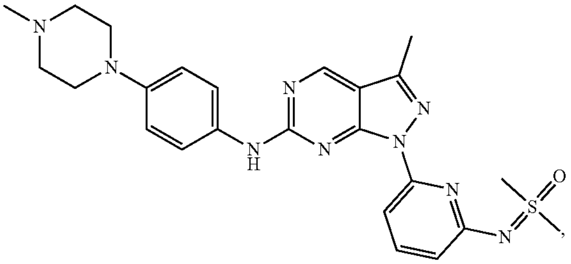
,
-continued
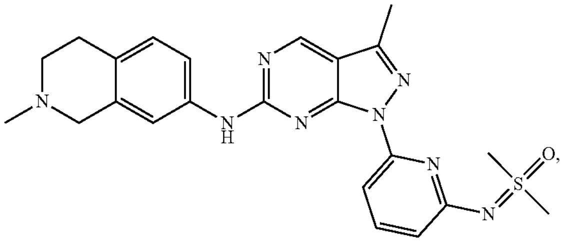
,
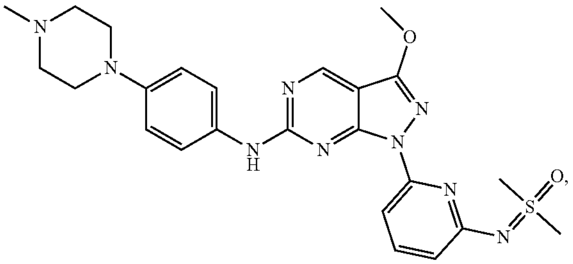
,
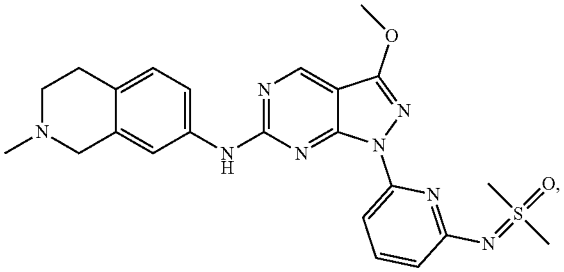
,
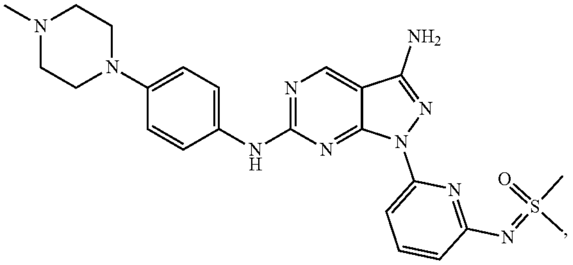
,
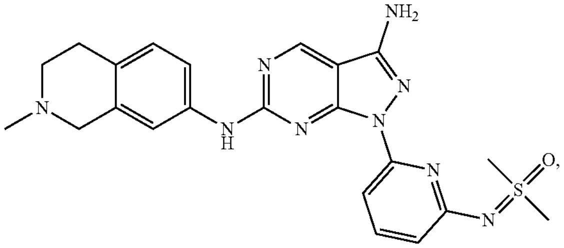
,
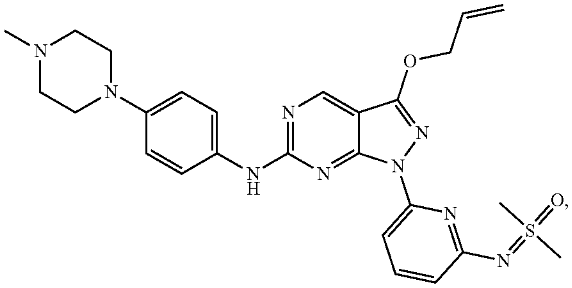
, -continued
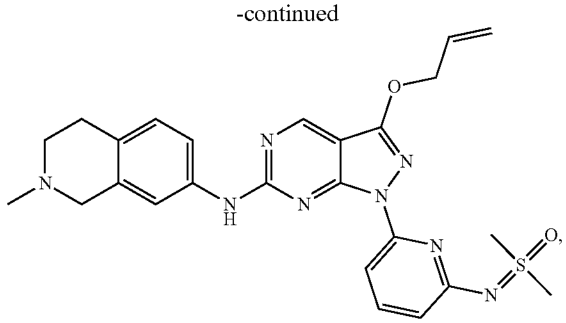
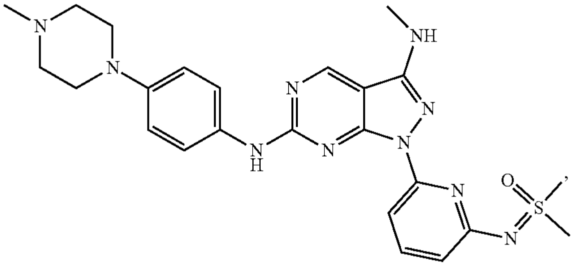
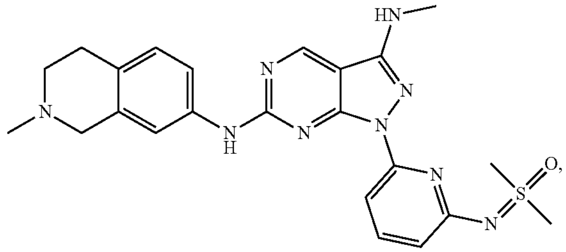
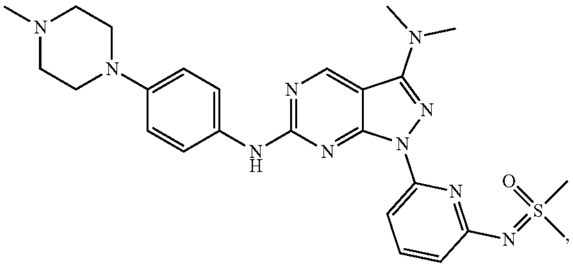
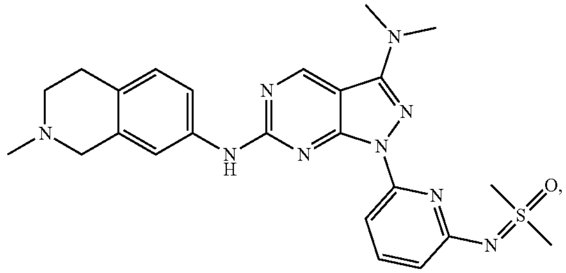
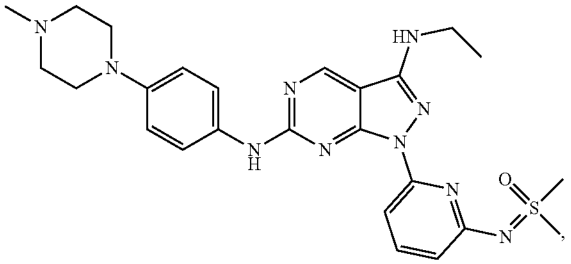
-continued
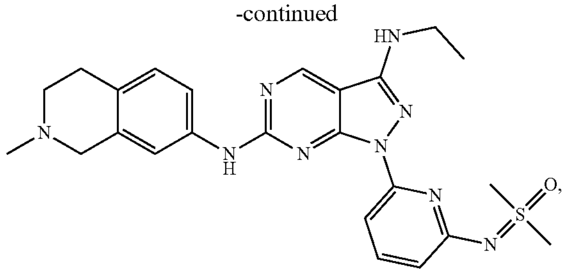
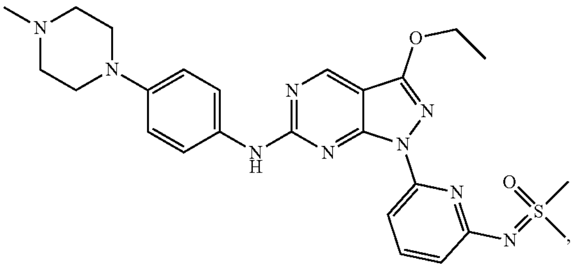
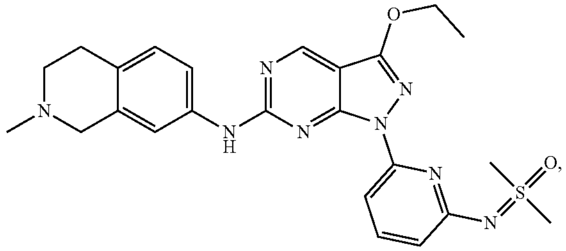
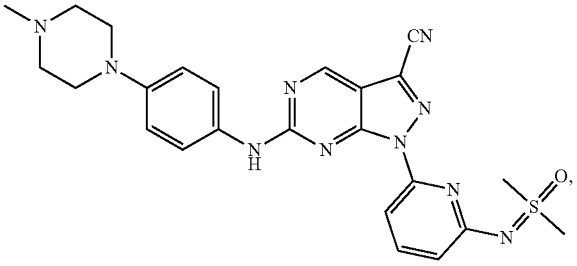
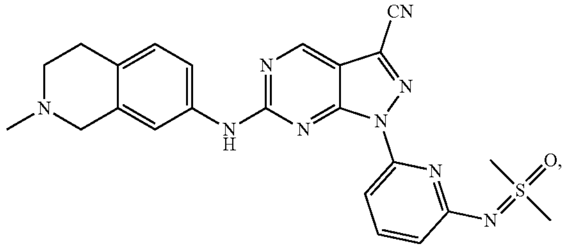
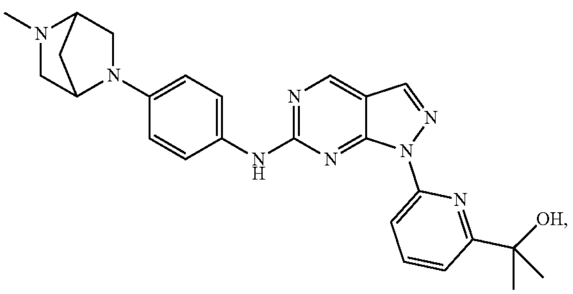

-continued
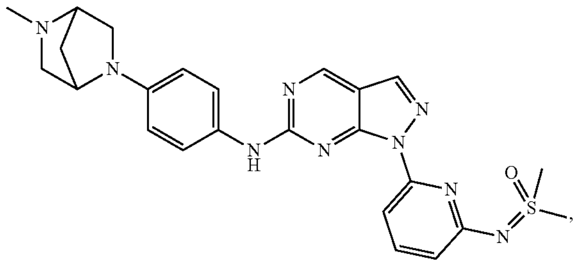
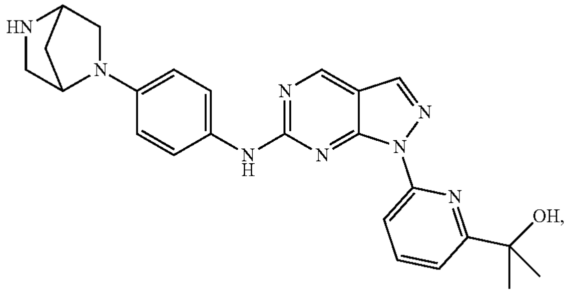
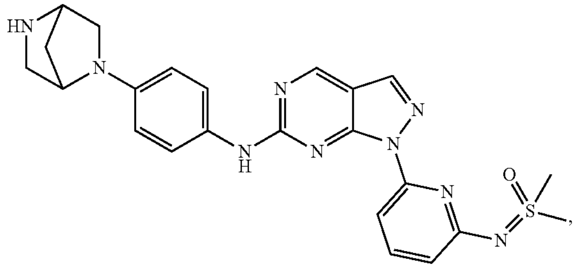
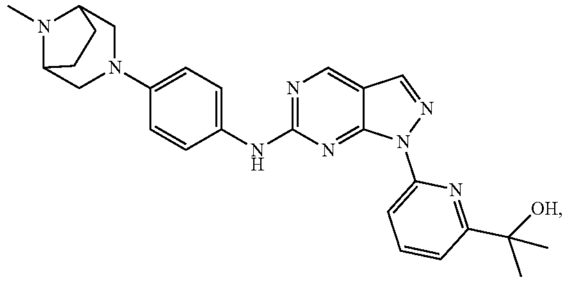
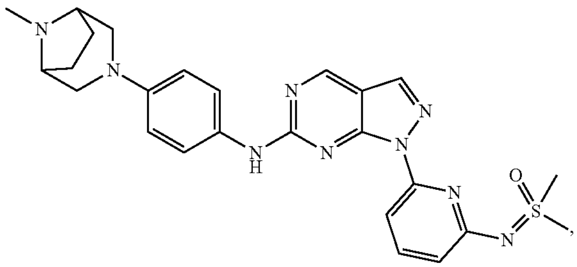
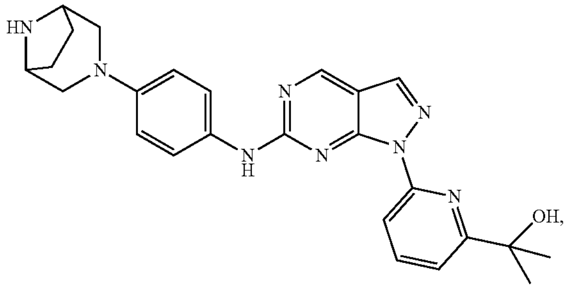
-continued
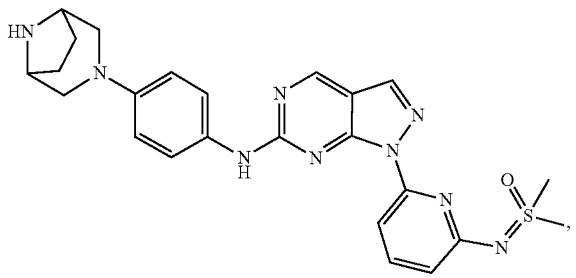
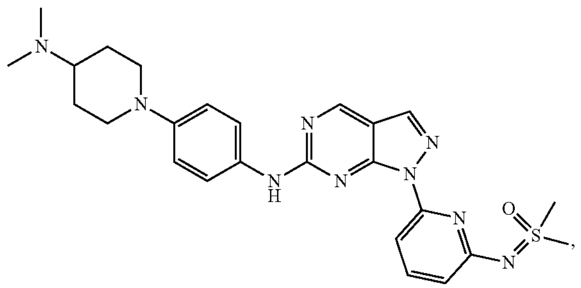
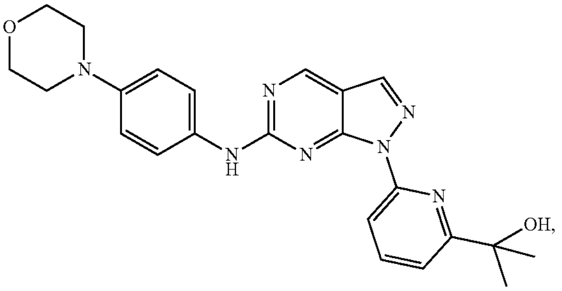
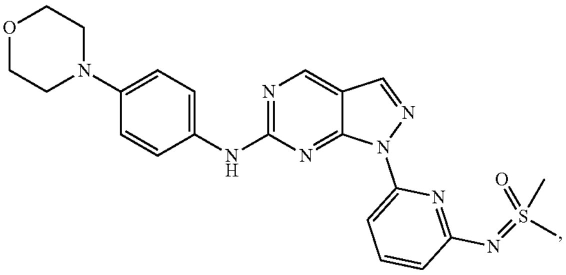
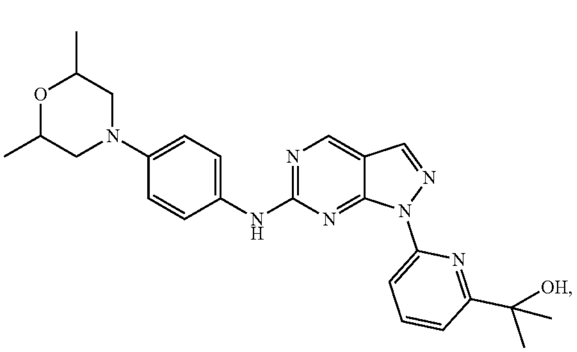

-continued
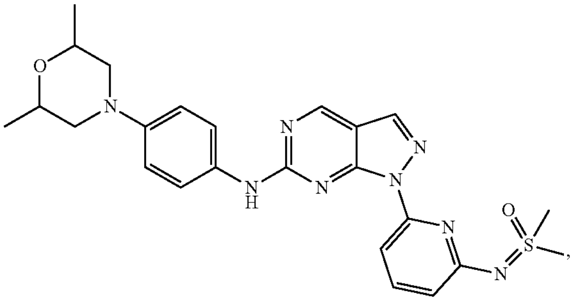
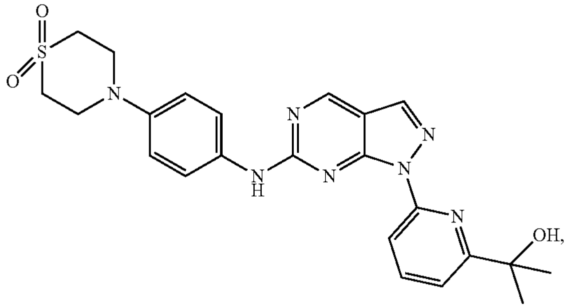
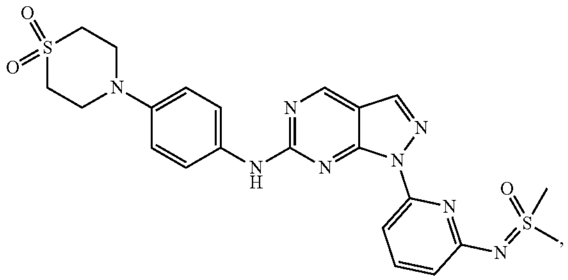
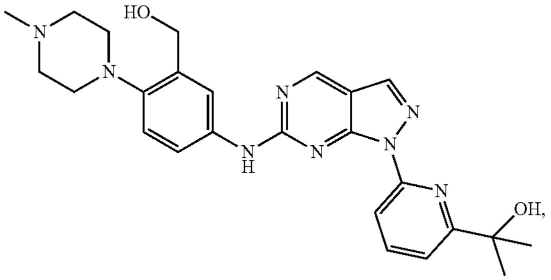
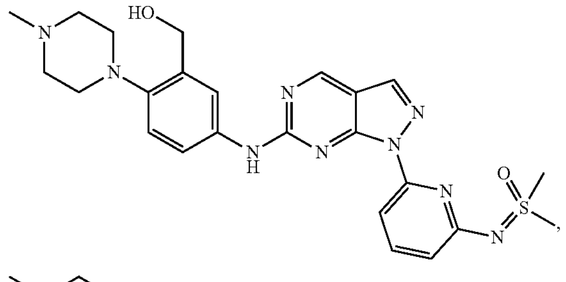
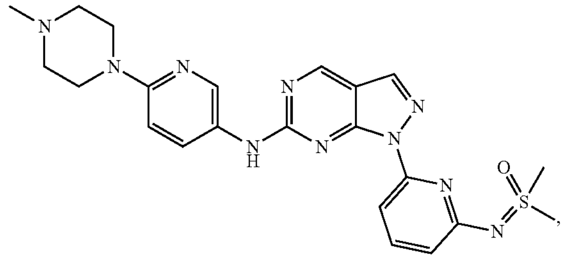
-continued
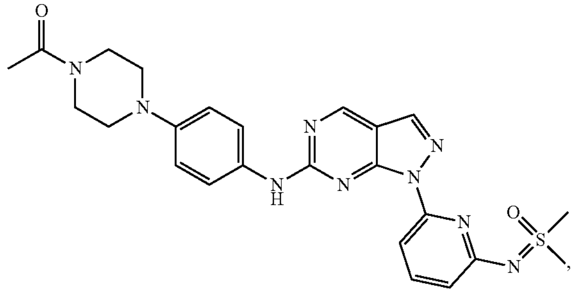
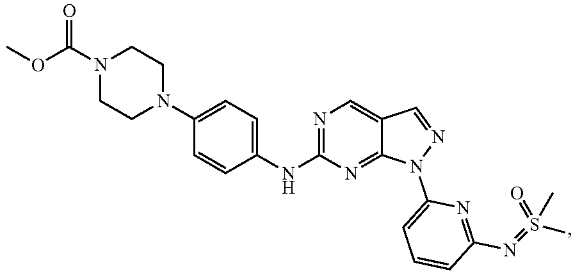
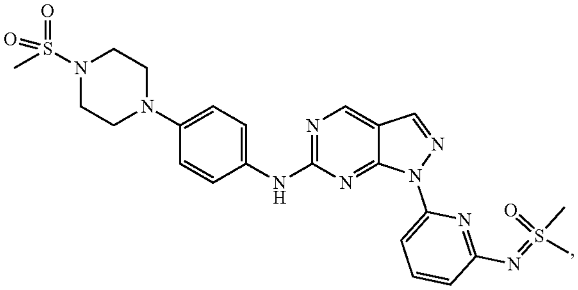
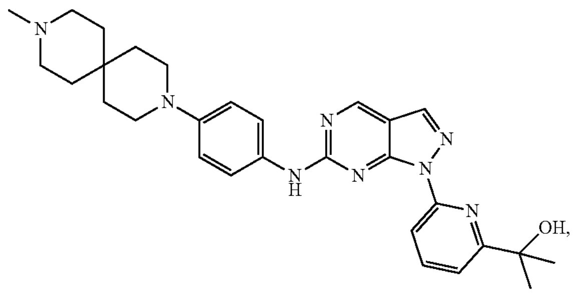
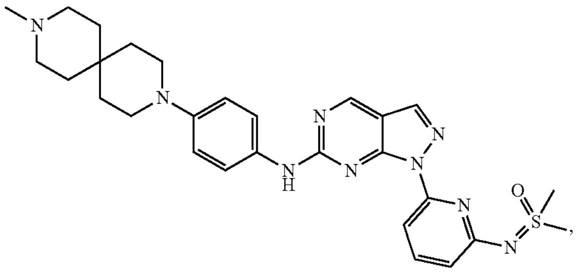
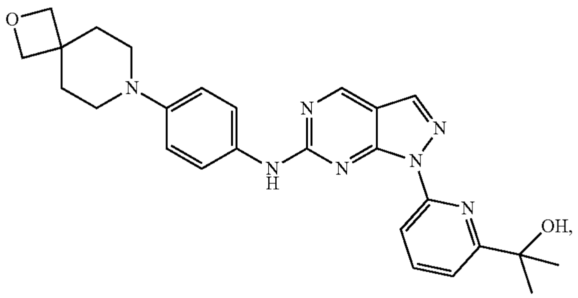

-continued
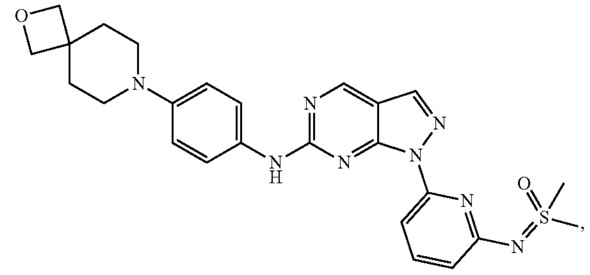,
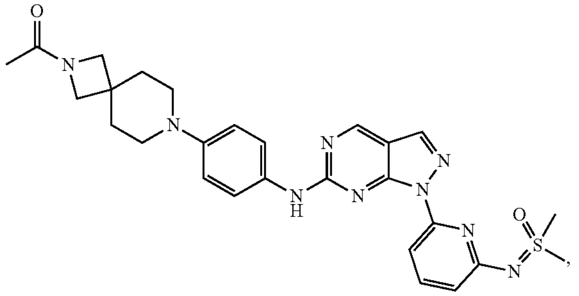,
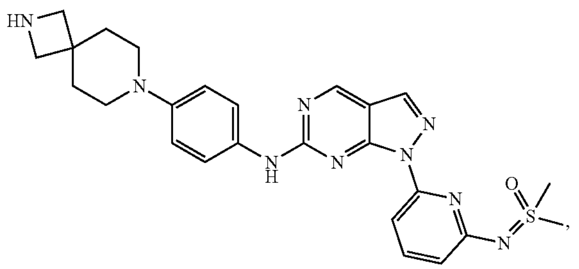,
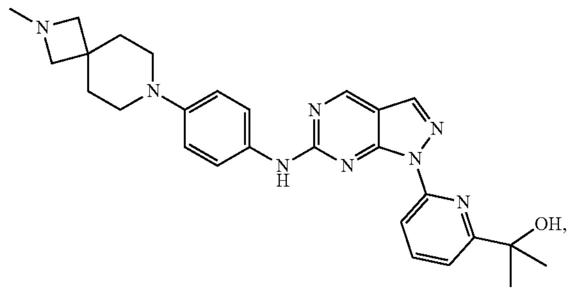,
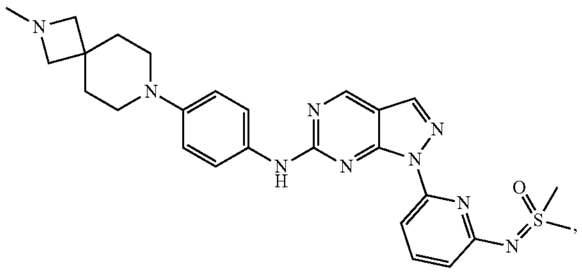,
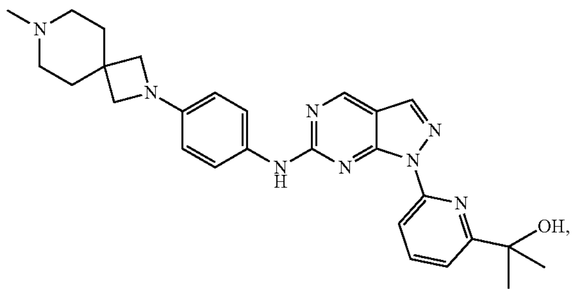,
-continued
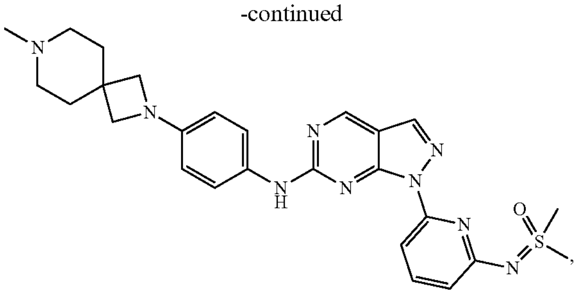,
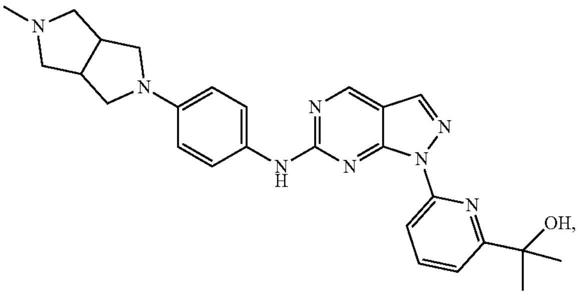,
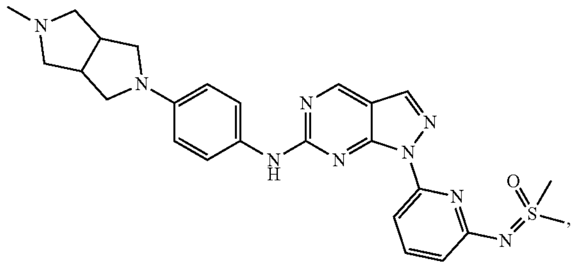,
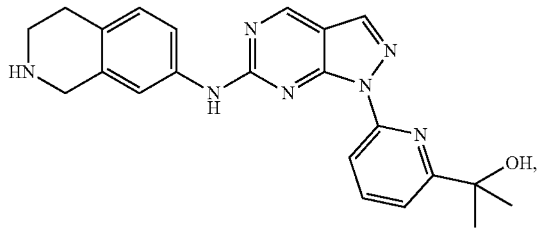,
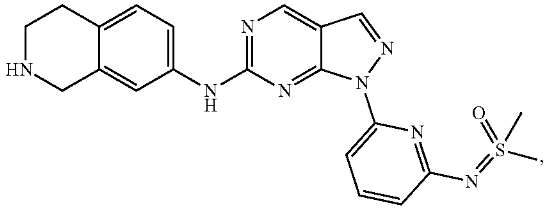,
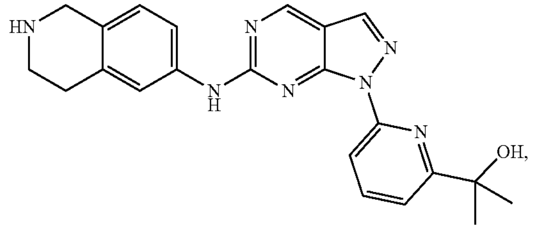,
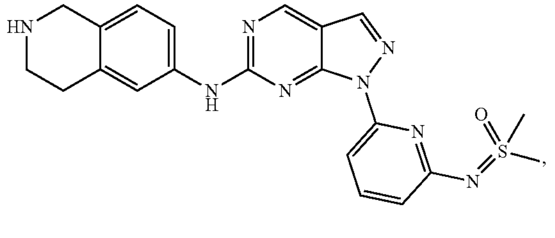, -continued
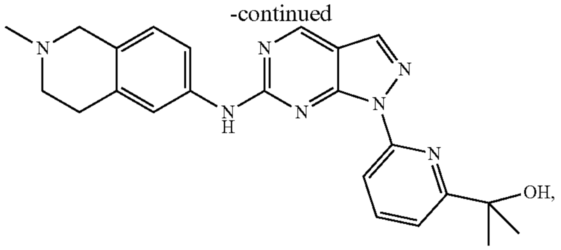
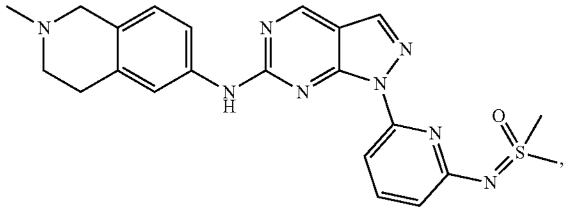
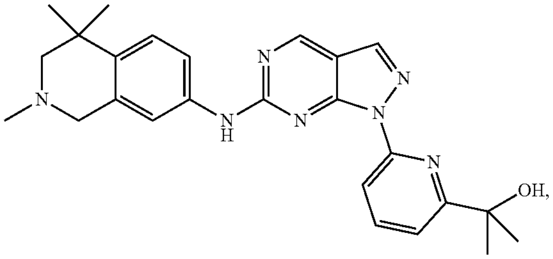
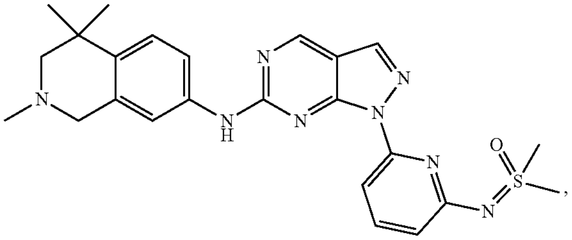
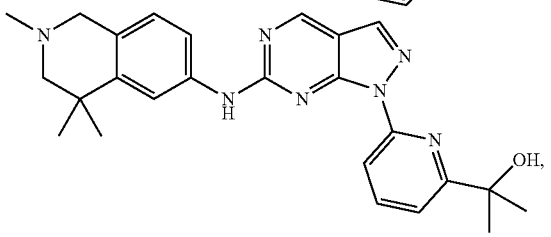
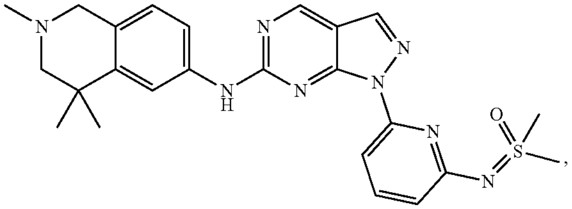
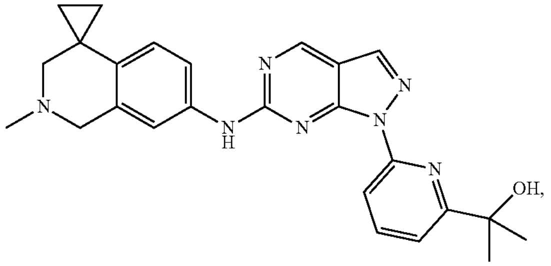
-continued
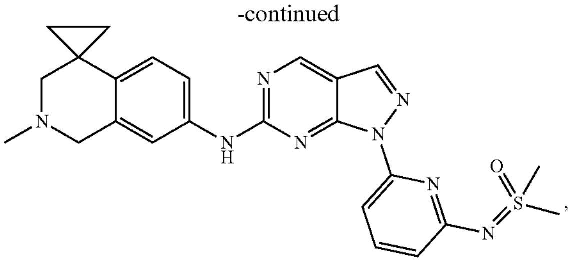
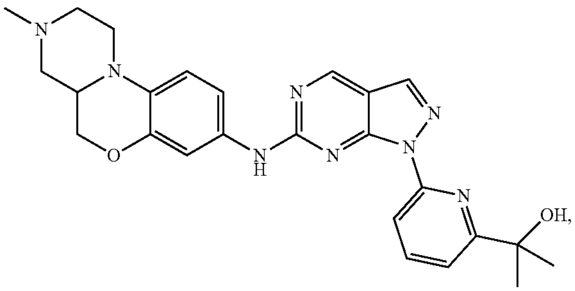
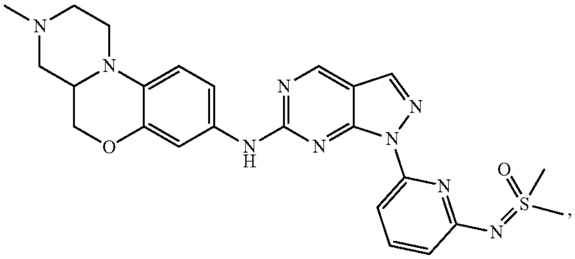
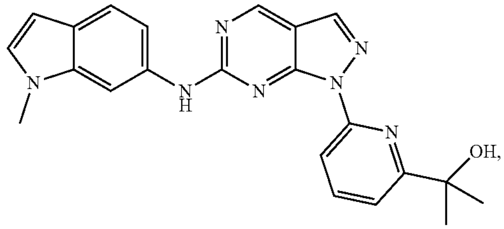
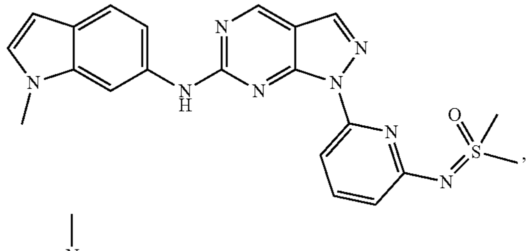
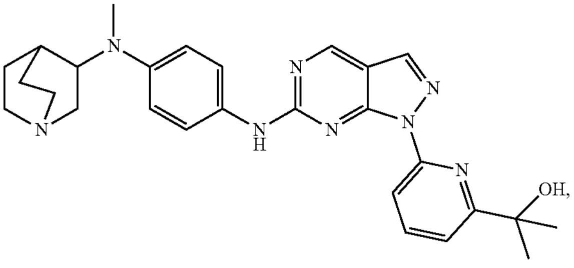
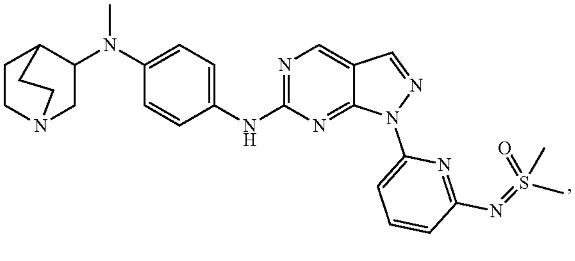

-continued
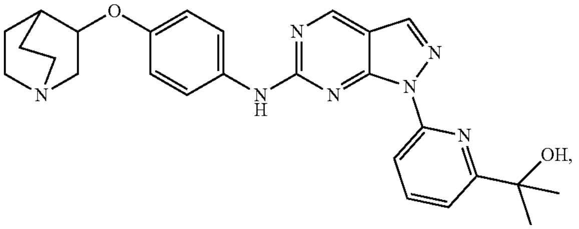
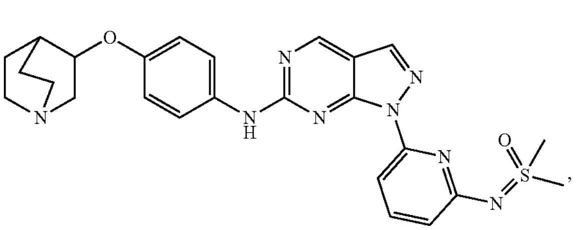
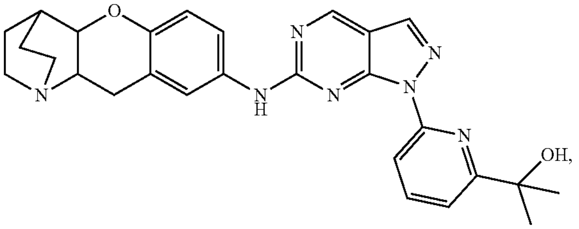
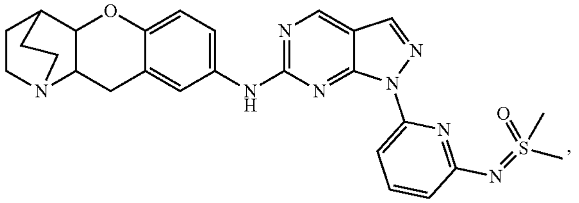
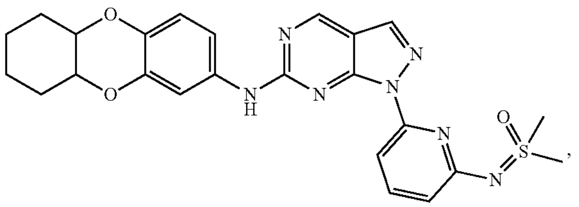
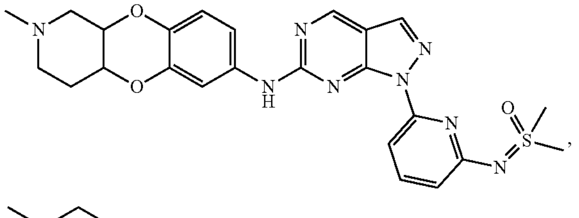
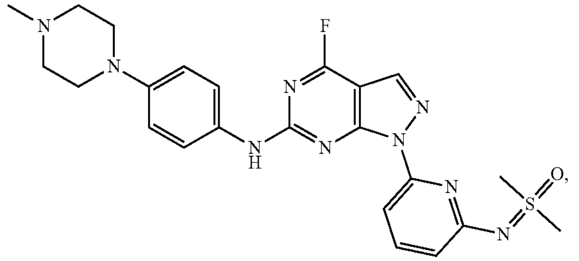
-continued
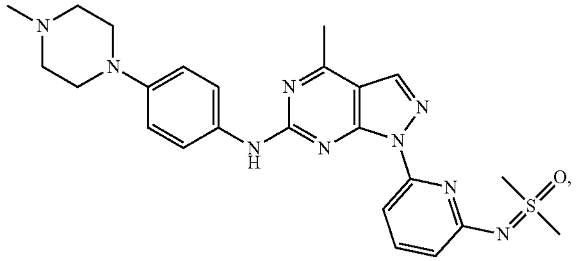
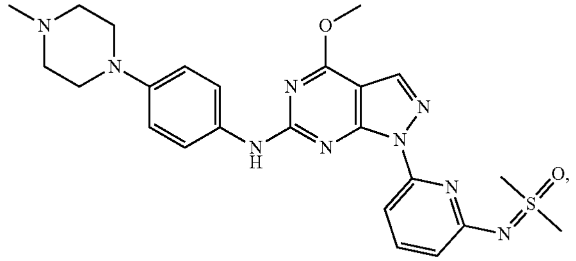
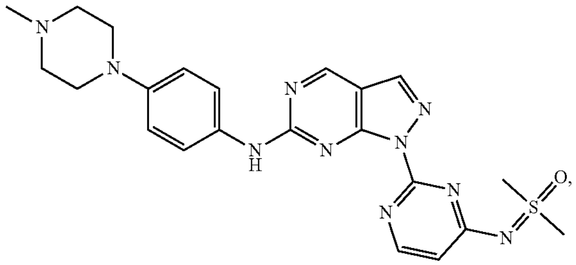
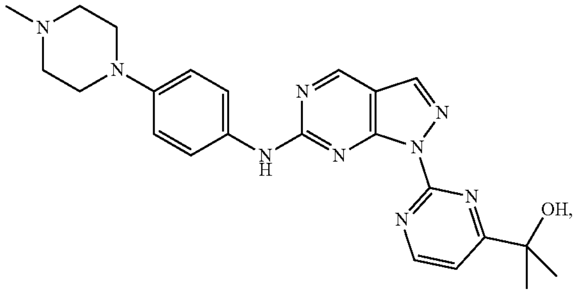
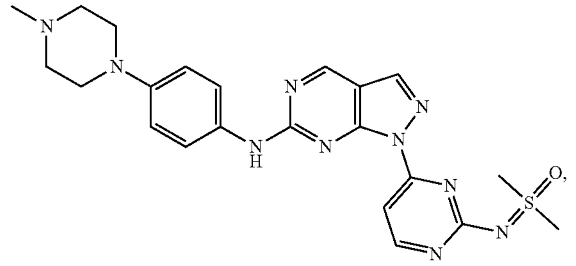
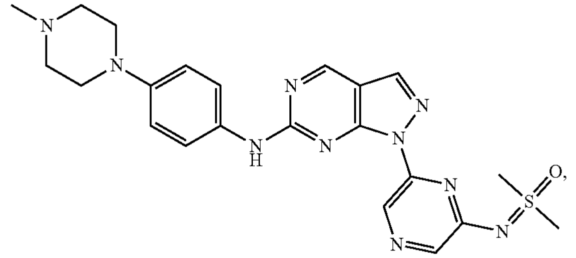

-continued
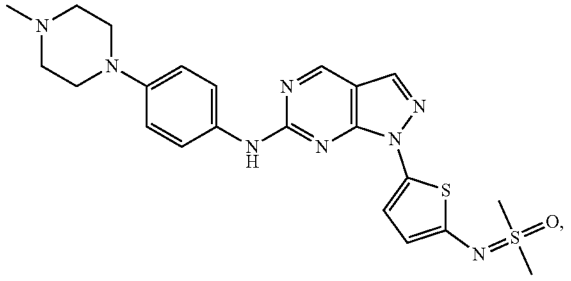
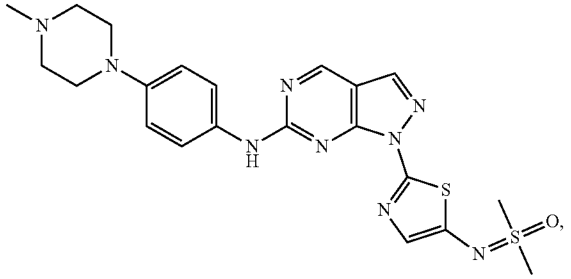
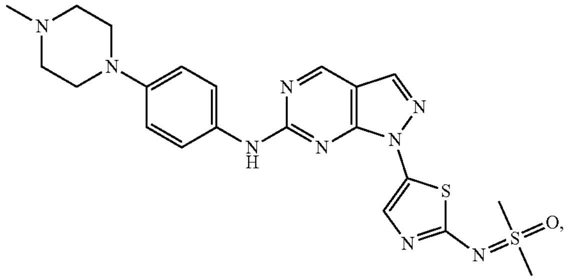
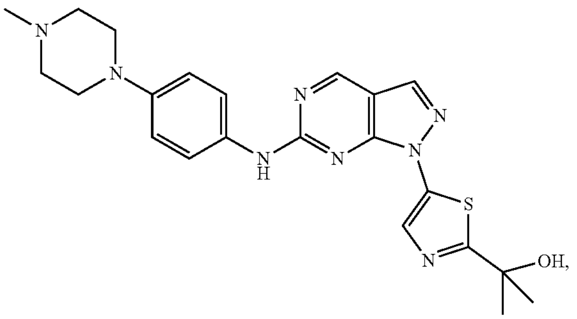
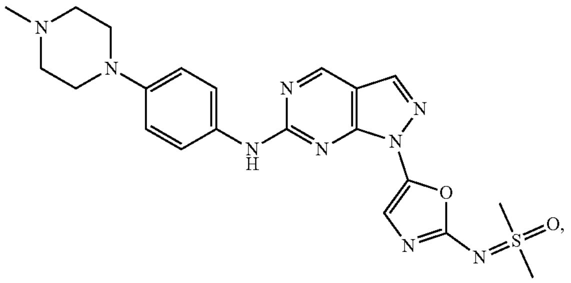
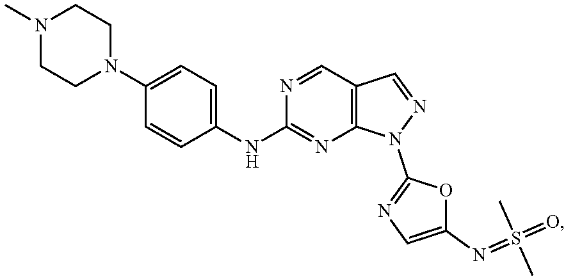
-continued
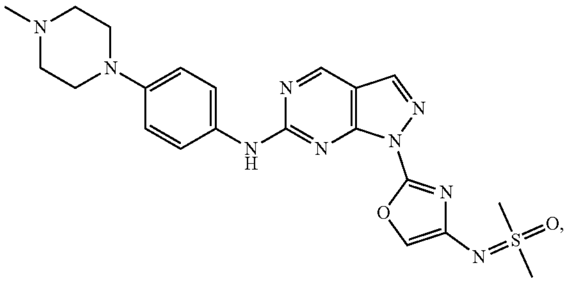
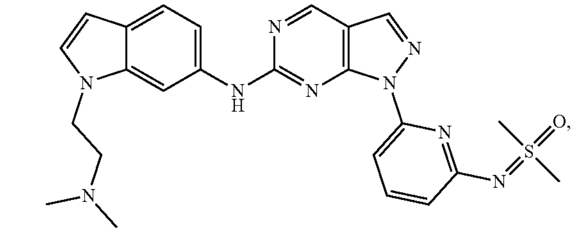
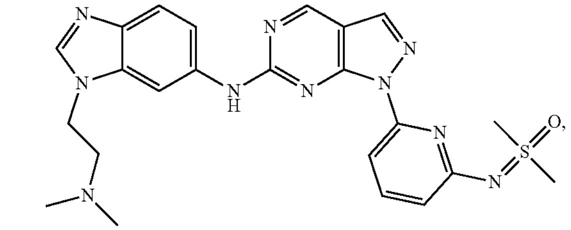
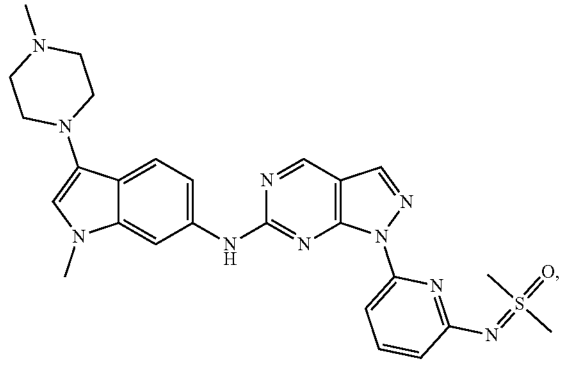
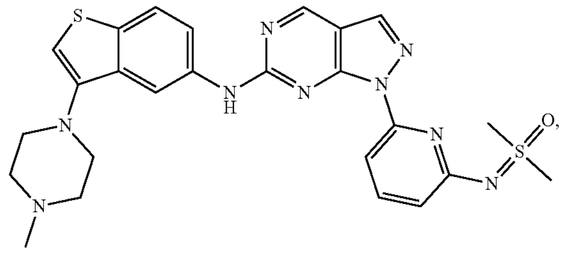
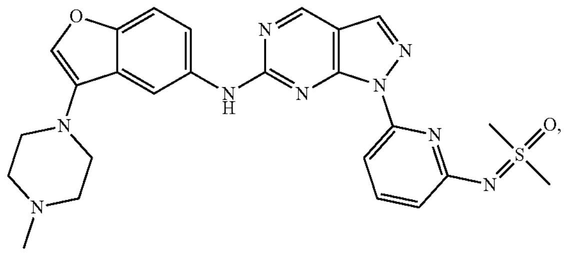

-continued
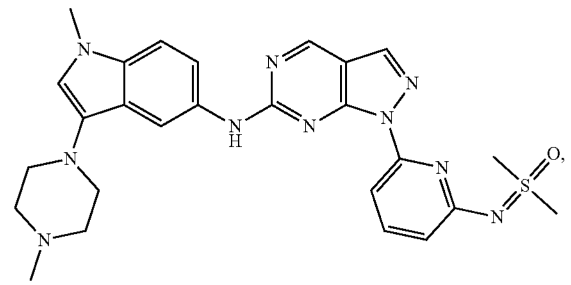
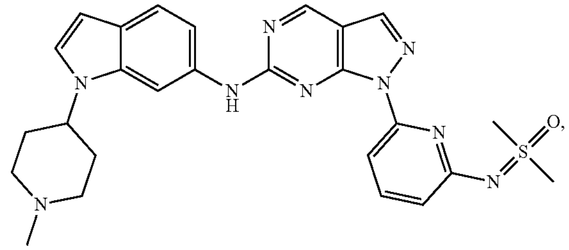
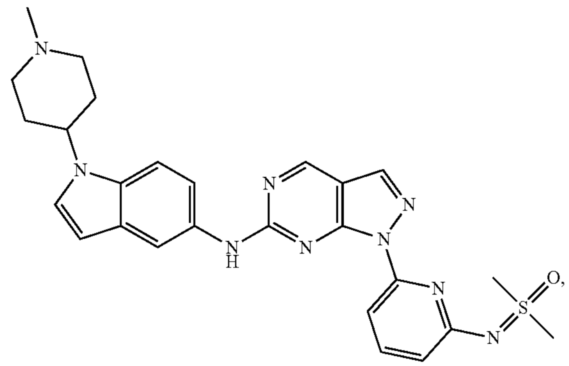
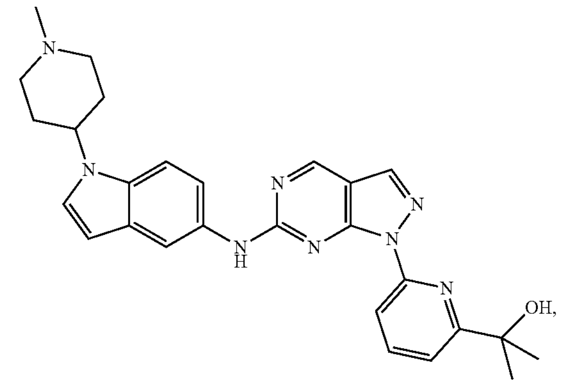
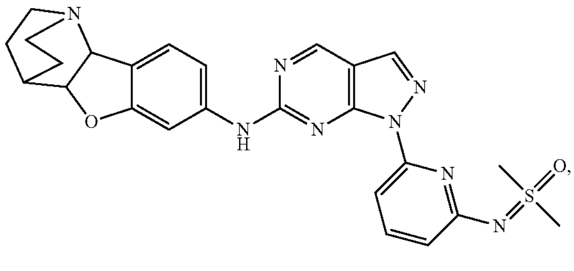
-continued
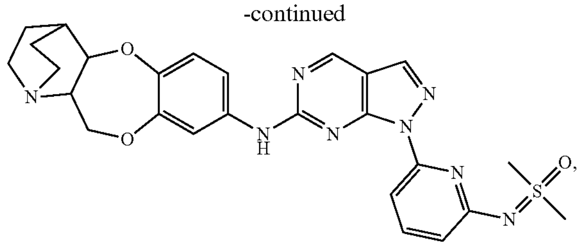
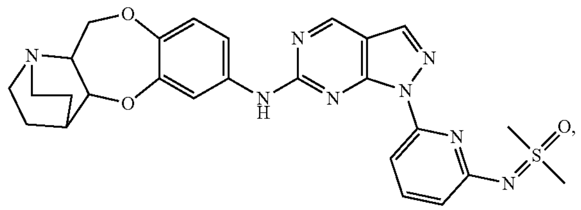
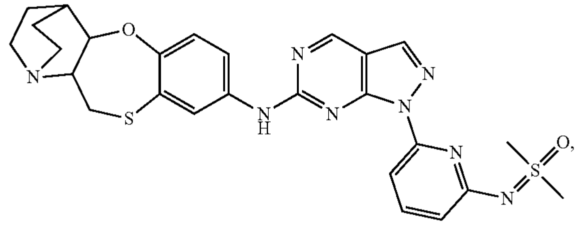
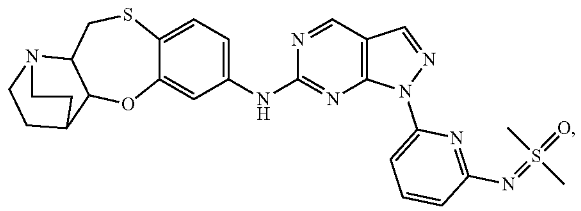
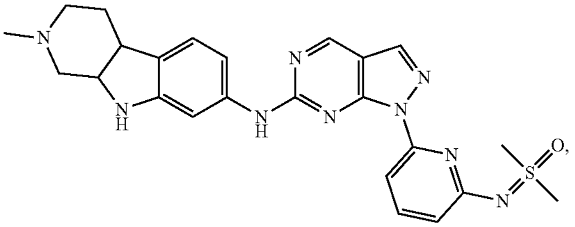
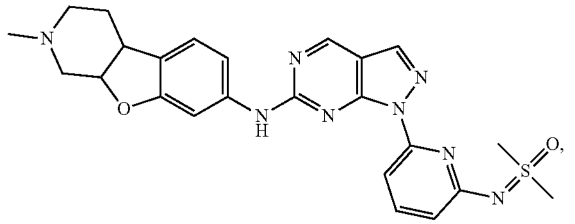
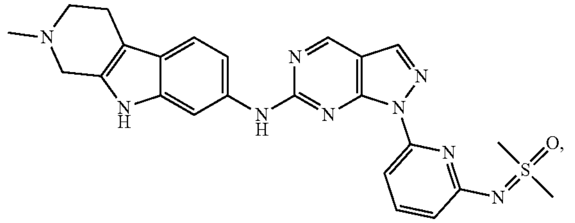

-continued
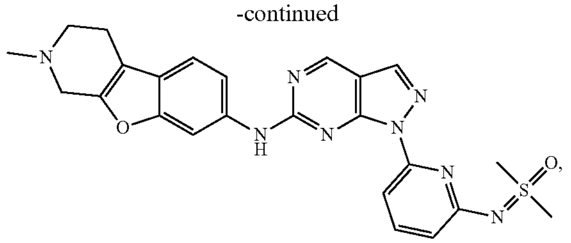
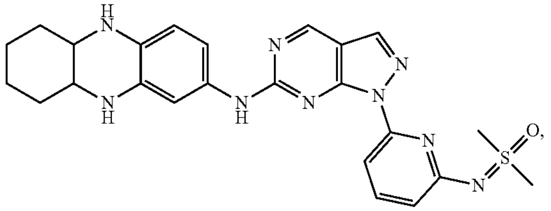
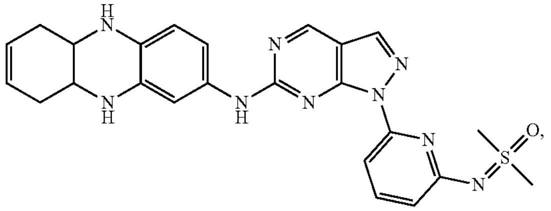
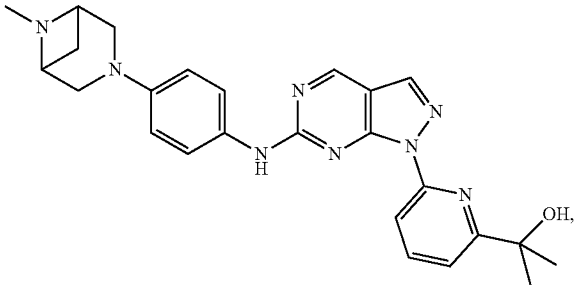
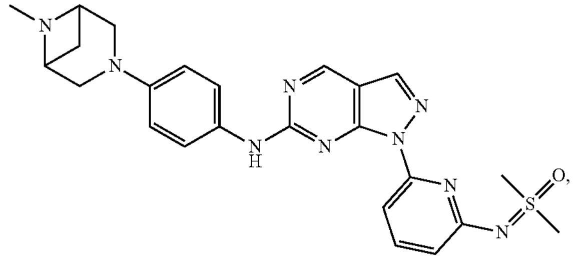
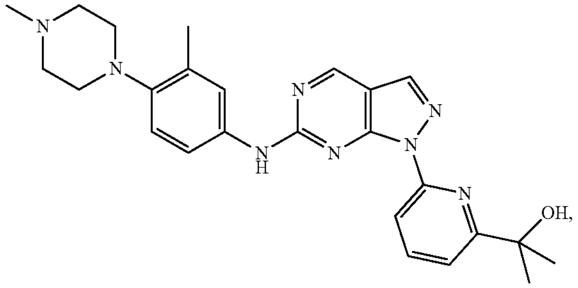
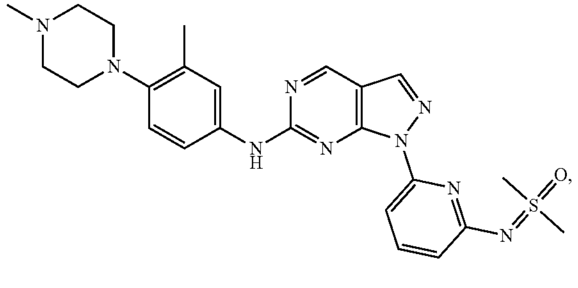
-continued
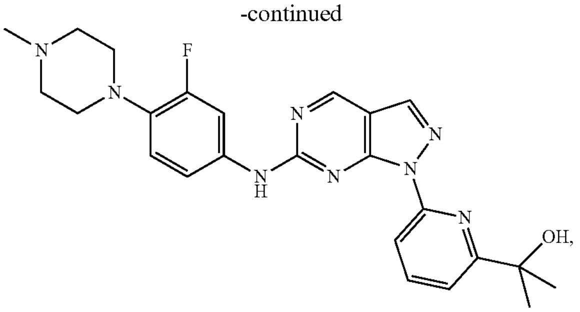
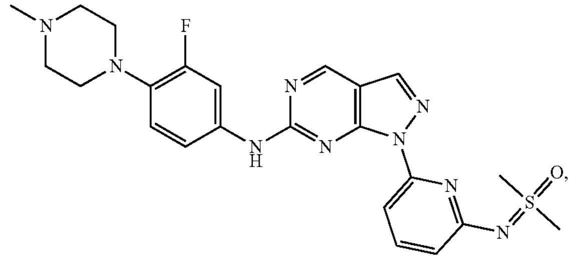
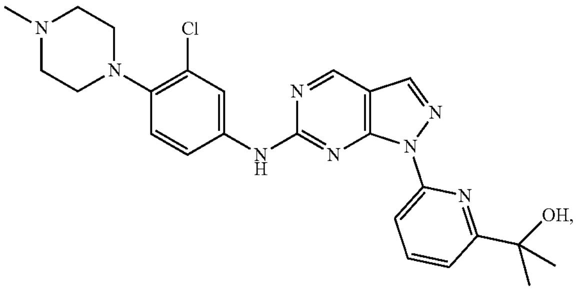
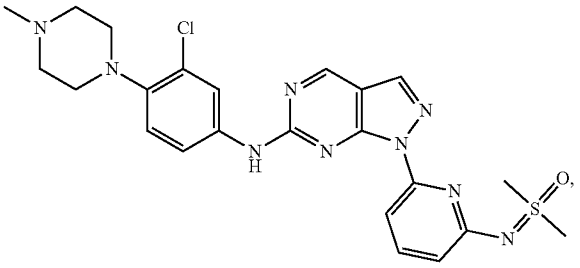
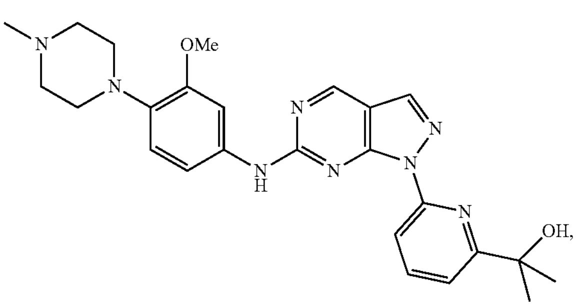
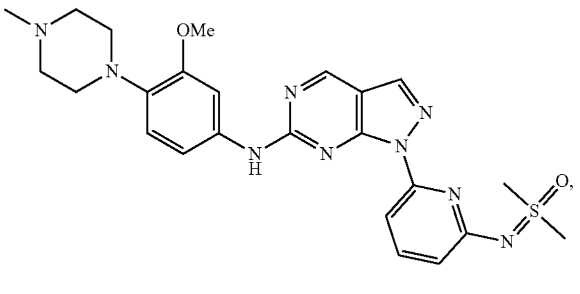

-continued
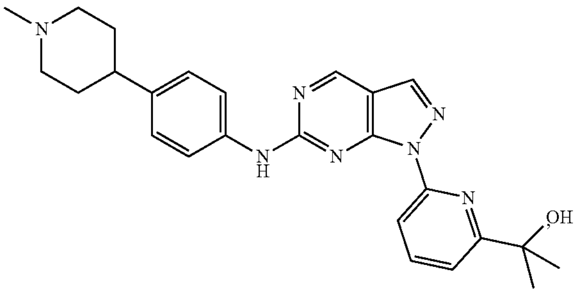
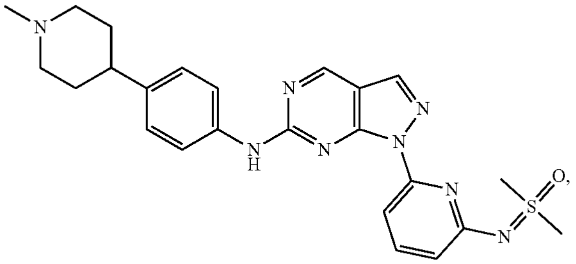
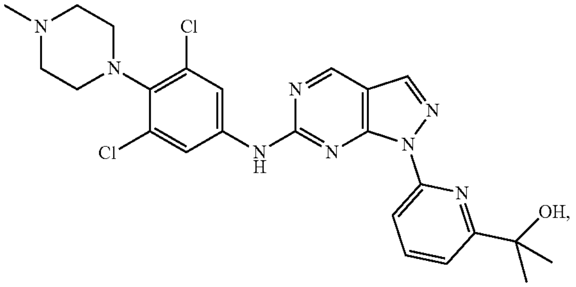
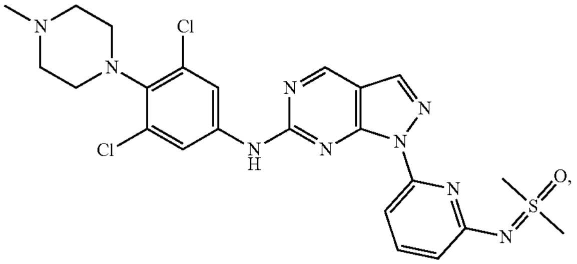
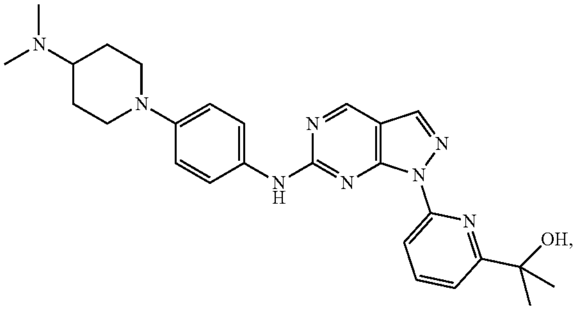
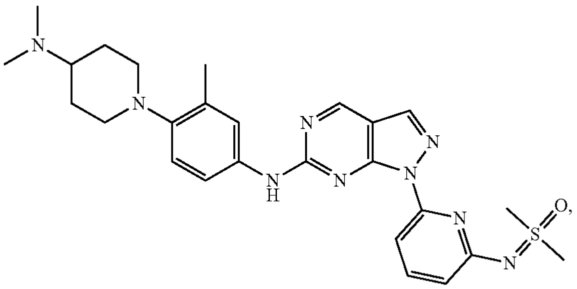
-continued
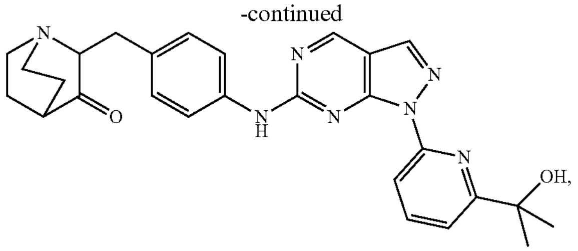
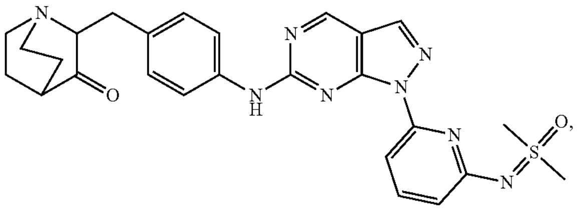
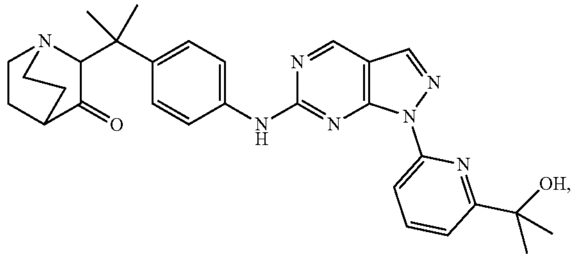
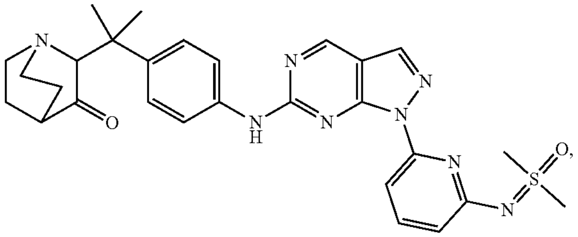
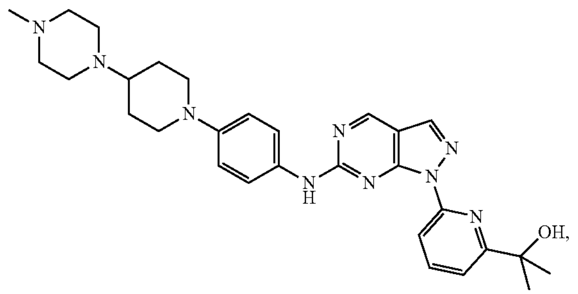
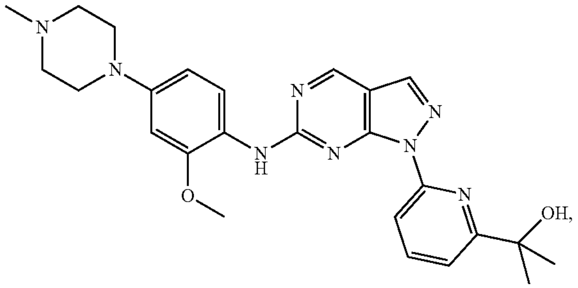

-continued
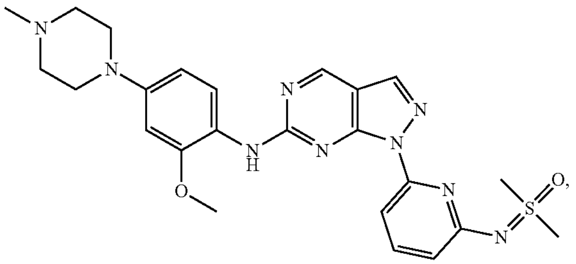
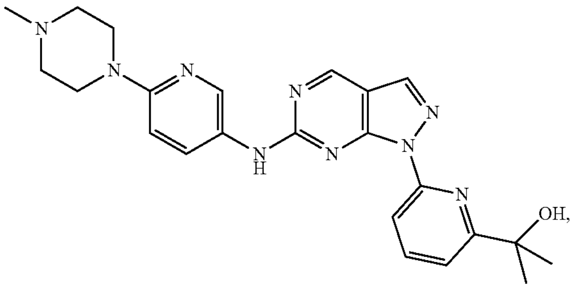
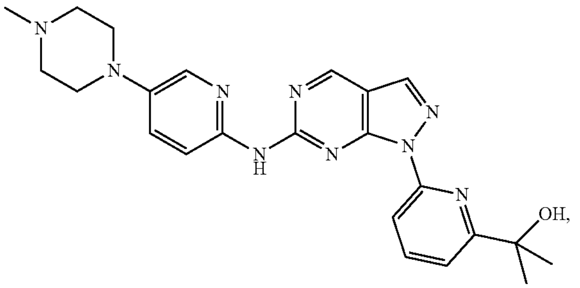
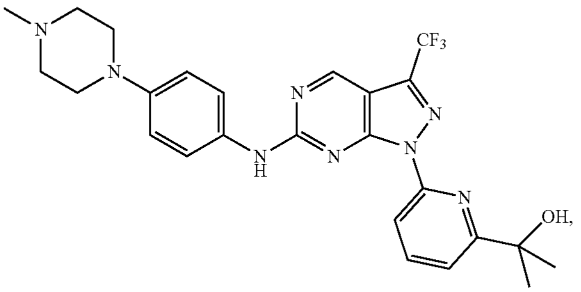
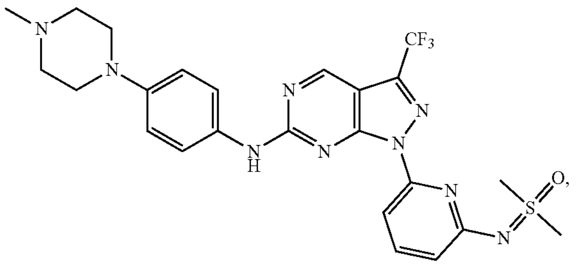
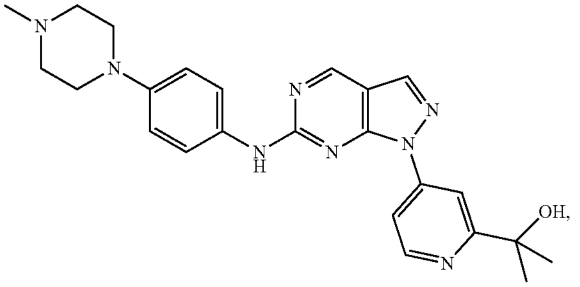
-continued
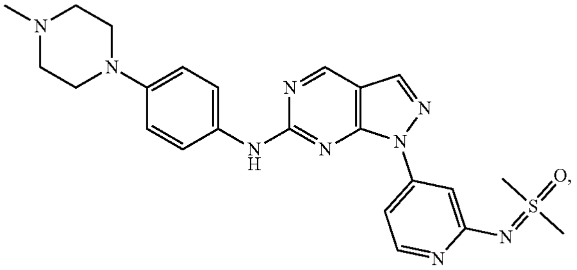
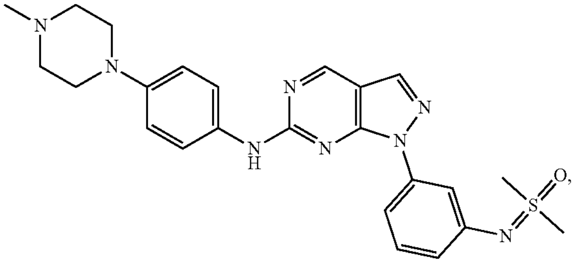
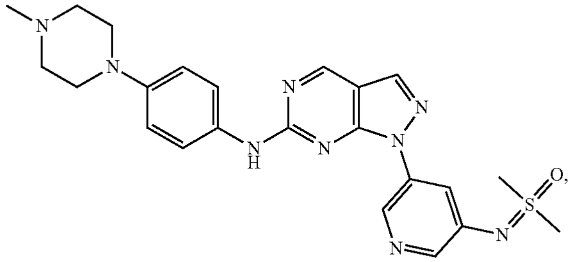
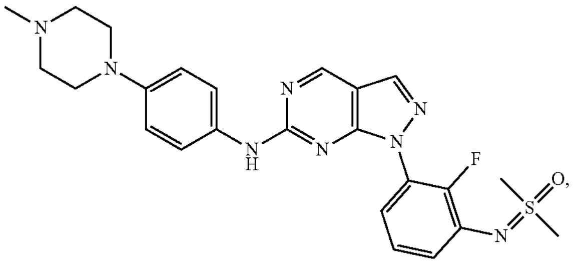
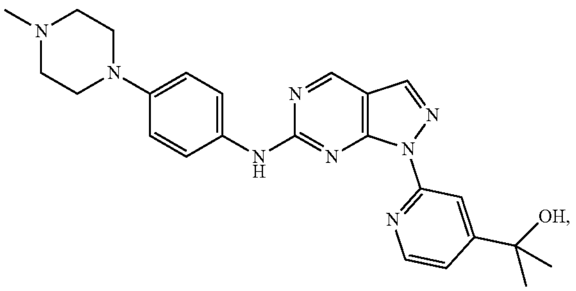
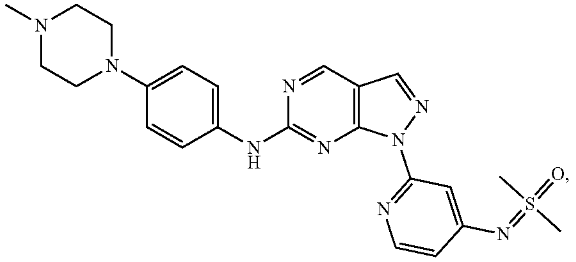

-continued
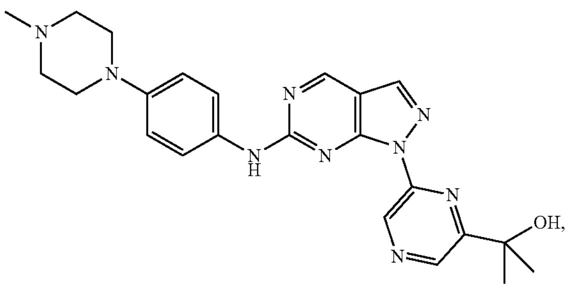
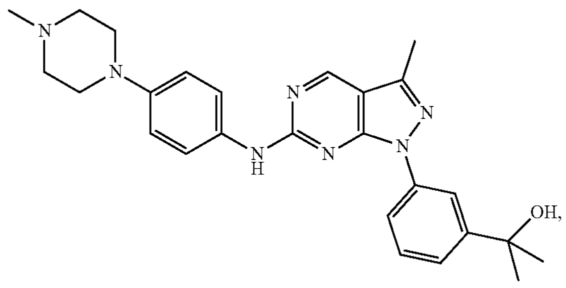
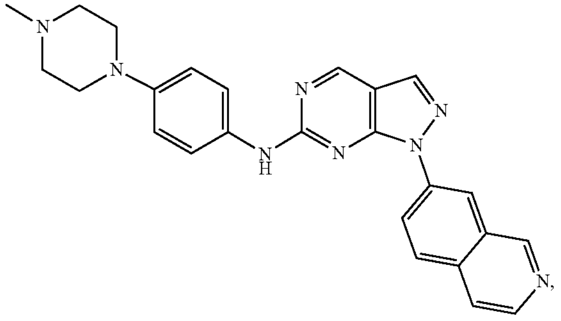
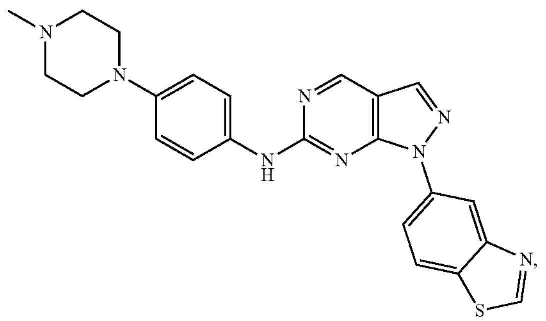
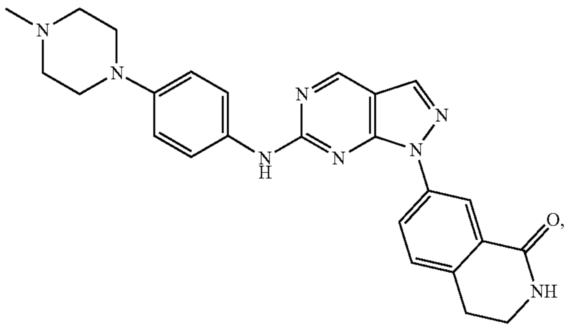
-continued
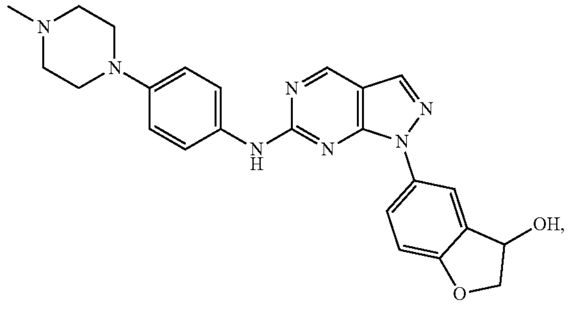
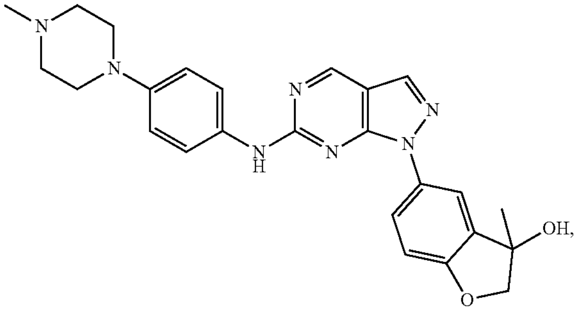
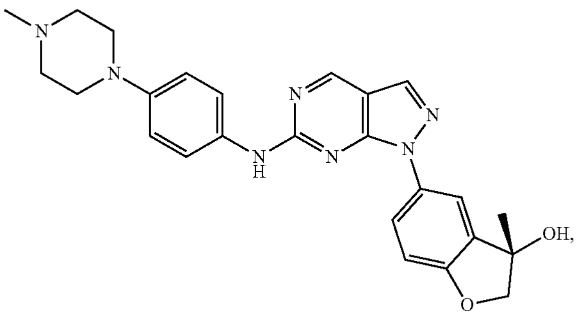
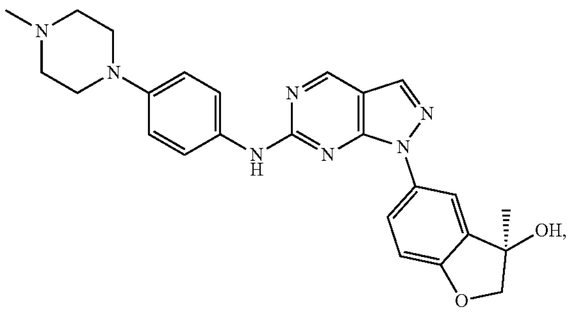
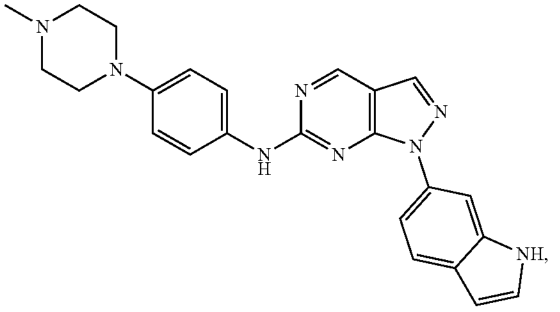

-continued
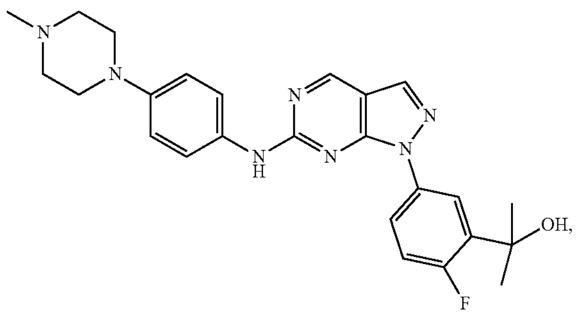
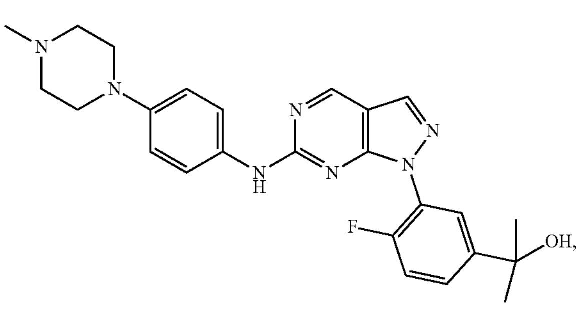
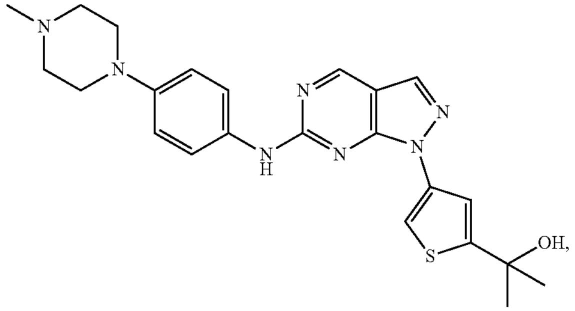
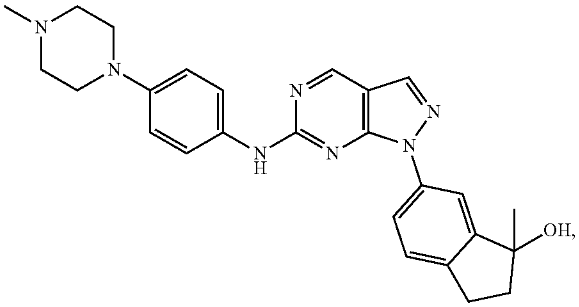
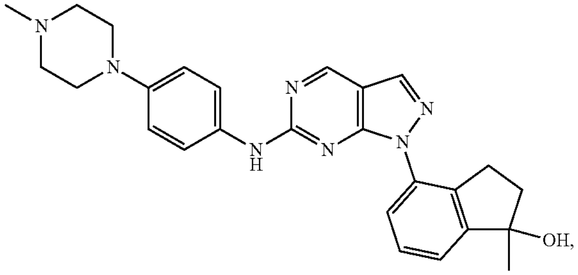
-continued
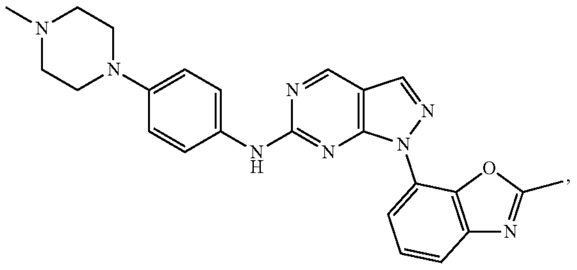
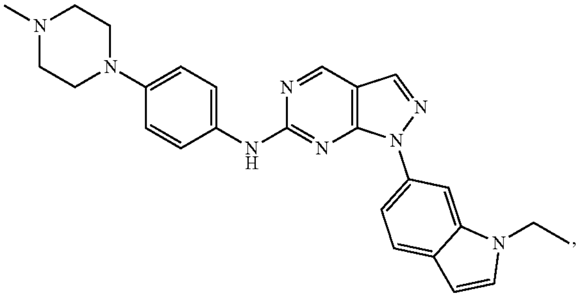
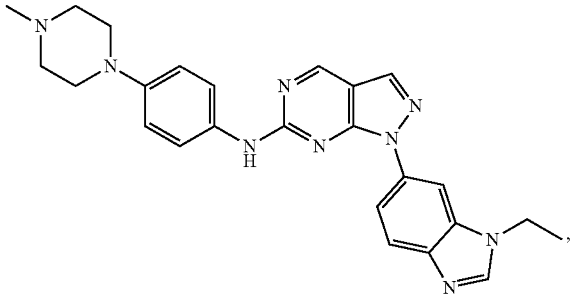
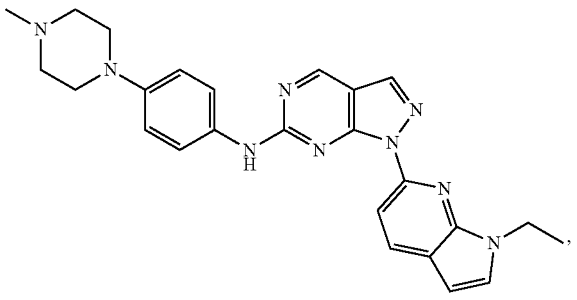
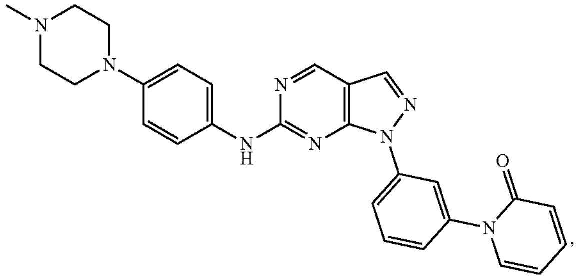

-continued
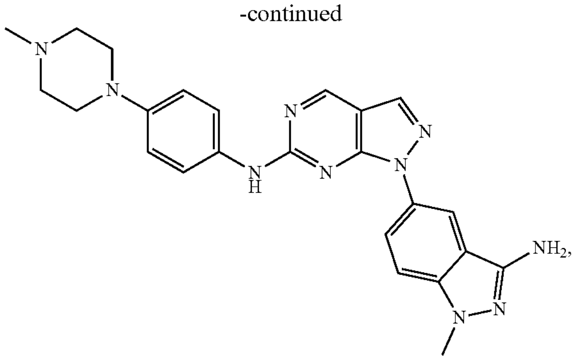
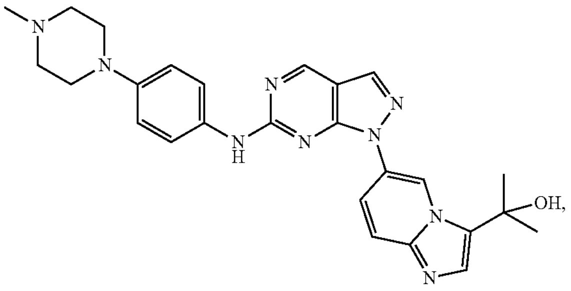
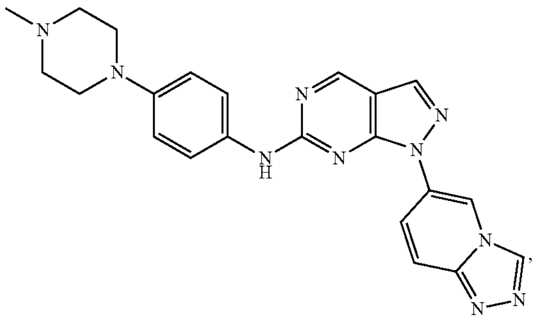
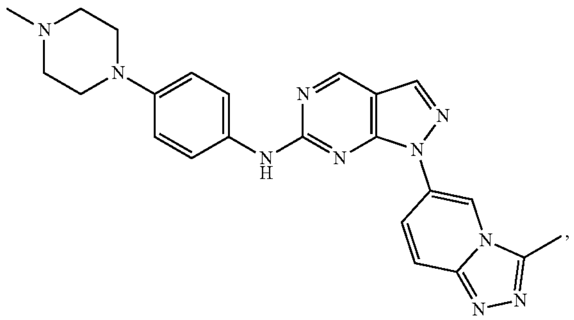
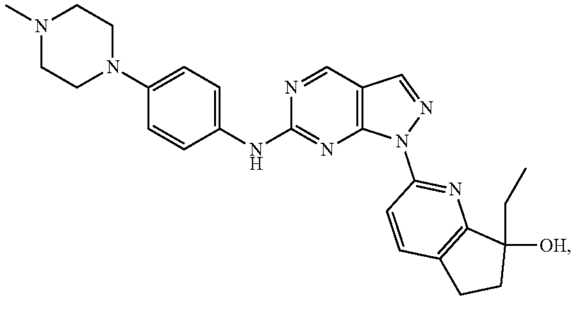
-continued
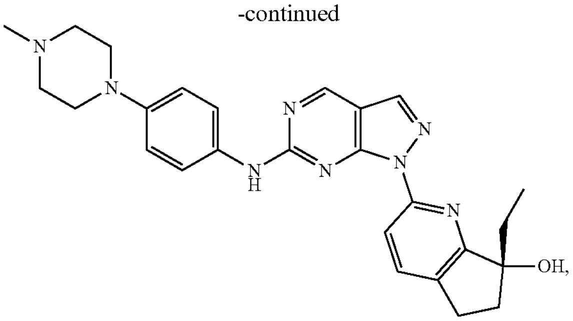
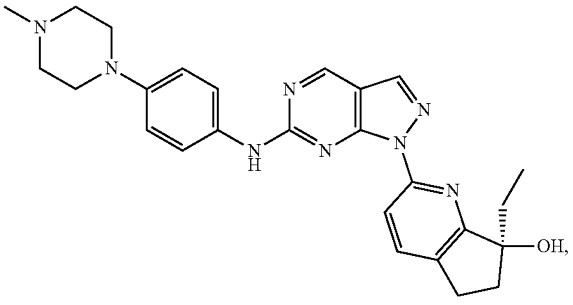
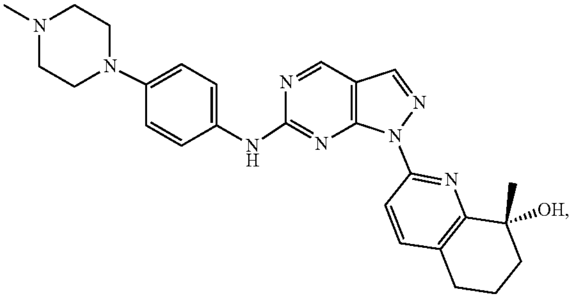
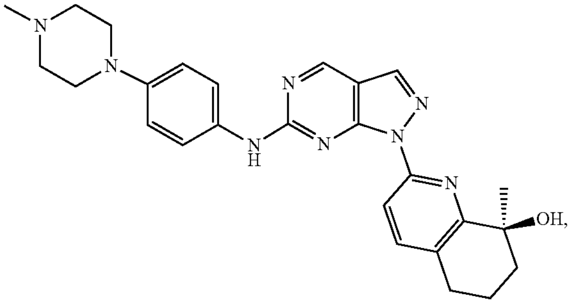
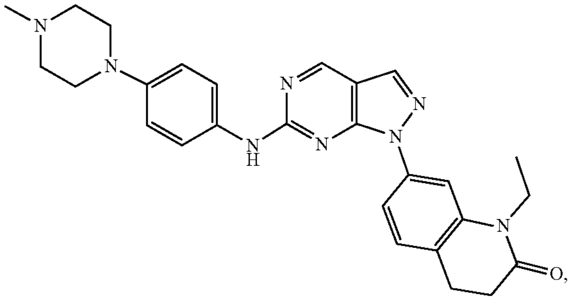

-continued
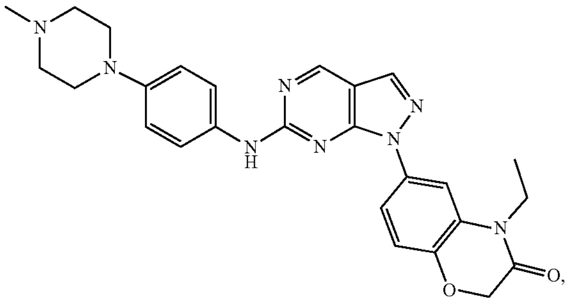
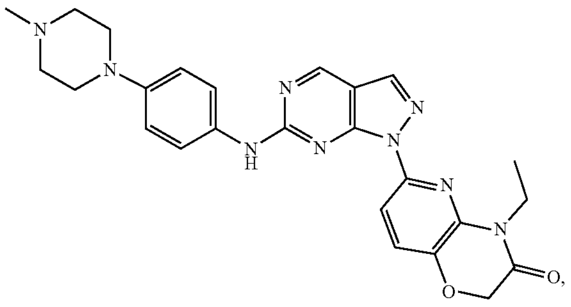
-continued
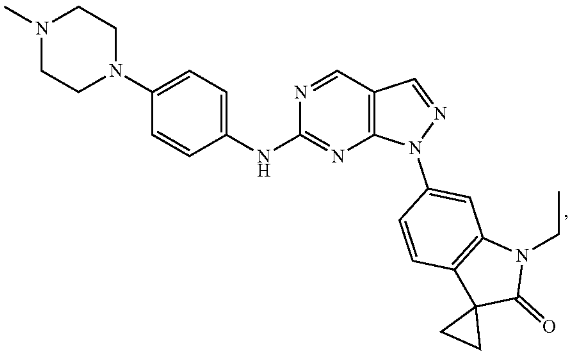
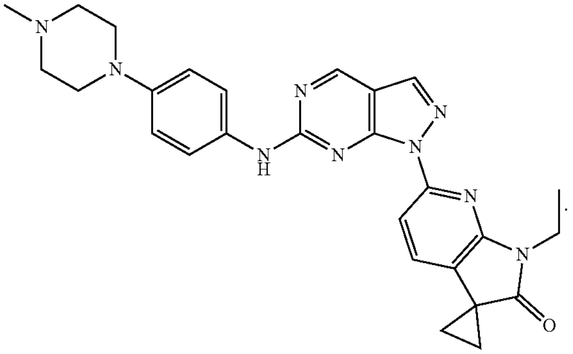
24. A method of treating cancer, comprising the step of administering an effective amount of the compound of claim 1, or a deuterated compound thereof, or a stereoisomer thereof, or a pharmaceutically acceptable salt thereof.
* * * * *